US012552785B2

(12) United States Patent
Cheng et al.

(10) Patent No.: US 12,552,785 B2
(45) Date of Patent: Feb. 17, 2026

(54) PYRAZOLO[1,5-α]PYRIDINE DERIVATIVE, PREPARATION METHOD THEREFOR, AND COMPOSITION AND USE THEREOF

(71) Applicant: SHENZHEN ZHONGGE BIOLOGICAL TECHNOLOGY CO., LTD., Guangdong (CN)

(72) Inventors: Huimin Cheng, Guangdong (CN); Xiaoming Wen, Guangdong (CN); Zhiqiang Liu, Guangdong (CN); Lei Fang, Guangdong (CN); Yu Chen, Guangdong (CN); Yong Wei, Guangdong (CN); Guogang Zhang, Guangdong (CN); Chuansheng Li, Guangdong (CN); Songling Ma, Guangdong (CN); Zhenzhen Qi, Guangdong (CN); Ping Chen, Guangdong (CN); Chunyi Niu, Guangdong (CN); Peiyu Zhang, Guangdong (CN); Lipeng Lai, Guangdong (CN); Jian Ma, Guangdong (CN); Shuhao Wen, Guangdong (CN)

(73) Assignee: SHENZHEN ZHONGGE BIOLOGICAL TECHNOLOGY CO., LTD., Guangdong (CN)

( * ) Notice: Subject to any disclaimer, the term of this patent is extended or adjusted under 35 U.S.C. 154(b) by 570 days.

(21) Appl. No.: 17/920,630

(22) PCT Filed: Apr. 22, 2021

(86) PCT No.: PCT/CN2021/089064

§ 371 (c)(1),
(2) Date: Oct. 21, 2022

(87) PCT Pub. No.: WO2021/213476

PCT Pub. Date: Oct. 28, 2021

(65) Prior Publication Data

US 2023/0159523 A1 May 25, 2023

(30) Foreign Application Priority Data

Apr. 22, 2020 (CN) ........................ 202010323409.2

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ................................................... C07D 471/04
USPC ................................................... 514/210.21
See application file for complete search history.

(56) References Cited

U.S. PATENT DOCUMENTS 8,546,403 B2 * 10/2013 Whitten .................. A61P 11/06 544/405
10,703,722 B2 * 7/2020 Whitten ................. A61K 47/02

FOREIGN PATENT DOCUMENTS

| | | | |
|---|---|---|---|
| CN | 103492386 | A | 1/2014 |
| CN | 111410662 | A | 7/2020 |
| CN | 112442050 | A | 3/2021 |
| CN | 112574235 | A | 3/2021 |
| CN | 112574236 | A | 3/2021 |
| WO | 2008/079909 | A1 | 7/2008 |
| WO | 2011/139489 | A2 | 11/2011 |
| WO | 2012/146657 | A1 | 11/2012 |
| WO | 2018/071454 | A1 | 4/2018 |
| WO | 2019/075108 | A1 | 4/2019 |
| WO | 2020/131627 | A1 | 6/2020 |

OTHER PUBLICATIONS

Zhong J., "Design, Synthesis and Biological Activity Evaluation of RET Fusion Kinase New Inhibitors", Chinese Doctoral Dissertations Full-text Database (Electronic Journal), No. 7 (Jul. 15, 2019), together with an English-language abstract.
International Search Report dated Jul. 20, 2021 received in International Application No. PCT/CN2021/089064, together with an English-language translation.

(Continued)

*Primary Examiner* — Niloofar Rahmani
(74) *Attorney, Agent, or Firm* — Scully, Scott, Murphy & Presser, P.C.

(57) ABSTRACT

The present invention relates to a pyrazolo[1,5-a]pyridine derivative, a preparation method therefor, and a composition and a use thereof. Specifically, the present invention relates to the compound of formula (I) and the use thereof for the treatment and/or prevention of wild type, gene-fusion type (including but not limited to KIF5B, CCDC6 and NCOA4) and mutant type (including but not limited to V804, G810 and M918) RET kinases-related diseases, including diseases or conditions mediated by RET kinase.

(I)

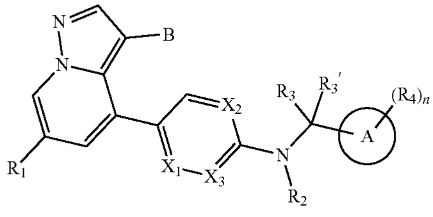

16 Claims, No Drawings

(56) References Cited

OTHER PUBLICATIONS

Extended European Search Report dated Apr. 11, 2024 received in European Application No. 21 792 970.2.
Eidam H S et al., "Discovery of a First-in-Class Gut-Restricted RET Kinase Inhibitor as a Clinical Candidate for the Treatment of IBS", ACS Med. Chem. Lett. 9:623-628 (2018).
Pasini B. et al., "RET Mutations in Human Disease", TIG 12(4):138-144 (Apr. 1996).
Plaza-Menacho I. et al., "Mechanisms of RET Signaling in Cancer: Current and Future Implications for Targeted Therapy", Cellular Signalling 26:1743-1752 (2014).

* cited by examiner

PYRAZOLO[1,5-α]PYRIDINE DERIVATIVE, PREPARATION METHOD THEREFOR, AND COMPOSITION AND USE THEREOF

TECHNICAL FIELD

This disclosure belongs to the field of medicine, and in particular to a pyrazolo[1,5-a]pyridine derivative, a pharmaceutically acceptable salt thereof, and a pharmaceutical composition using them as active ingredients. This disclosure also provides a preparation method of the compound and use of the compound as a medicine.

BACKGROUND

Cancer is caused by uncontrolled and unregulated cell proliferation, and the causes of uncontrolled and unregulated cell proliferation have always been the focus of drug researchers.

The human gene encoding the RET protein is located on the long arm of chromosome 10, and its abnormalities (gene fusions, mutations and amplifications) can cause a variety of diseases, including papillary thyroid carcinoma (PTC), medullary thyroid carcinoma (MTC), lung adenocarcinoma, Hirschsprung's disease, irritable bowel syndrome, etc. The chromosomal rearrangement where the RET gene is located may cause the RET gene to break. After the break, the 3' end of the RET gene can be fused with different genes such as KIF5B, TRIM33, CCDC6 or NCOA4 to form a fusion gene. The expressed fusion protein presents to be persistently activated, driving tumorigenesis.

RET is a single-pass transmembrane receptor belonging to the superfamily of tyrosine kinases and is required for the normal development, maturation, and maintenance of a variety of tissues and cells. RET signaling is mediated by the binding of soluble proteins of glial cell-derived neurotrophic factor (GDNF) and family ligand (GFL). The GDNF family does not directly bind to RET, but first forms a complex GFL-GFRu with the GDNF family receptor u (GFRu), and then catalyzes the homodimerization of RET to autophosphorylate the intracellular region of RET, and then recruits adaptor proteins and pathway proteins to activate various signaling pathways including MAPK, PI3K, JAK-STAT, PKA and PKC to participate in cell proliferation, nerve conduction, cell migration and cell differentiation (Alexander Drilon, Nature Reviews Clinical Oncology, 2018, 15:151-167), thus playing an important role in regulating cell survival, differentiation, proliferation, migration and chemotaxis.

Several multi-target kinase inhibitors, such as Cabozantinib, Vandetanib, Lenvatini and Ponatinib, have certain inhibitory activity against RET but they are all nonspecific RET inhibitors. In addition, since RET has a large number of homologies with the kinase domain of VEGFR2, these compounds have a certain inhibitory effect on multiple targets including VEGFR2 in addition to inhibiting RET, which leads to a high risk of off-target toxicity, making it difficult to achieve satisfactory efficacy.

Therefore, there is an urgent need in the field to develop drugs with high specificity and efficient inhibition against RET kinases.

SUMMARY

An objective of this disclosure is to provide a drug with high specificity and efficient inhibition for inhibiting RET kinase.

According to a first aspect of this disclosure, provided is a compound of formula (I) or a pharmaceutically acceptable salt, hydrate, solvate, stereoisomer, isotopic compound or prodrug thereof;

(I)

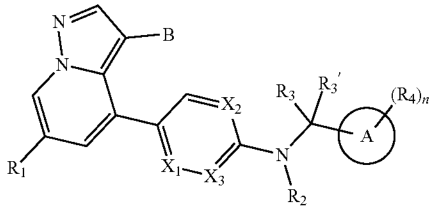

wherein, $R_1$ is selected from a group consisting of H, halogen, nitro, cyano, C1-C6 alkyl, C3-C8 cycloalkyl, 3- to 8-membered heterocyclyl, C1-C6 heteroalkyl, C2-C6 alkenyl, C2-C6 alkynyl, C6-C14 aryl, 5- to 14-membered heteroaryl, —$OR_5$, —O(C1-C6 alkylene)$R_5$, —$SR_5$, —$N(R_5)(R_6)$, —$S(O)_2R_5$, —$S(O)R_5$, —C(O)$R_5$, —OC(O)$R_5$, —C(O)O$R_5$, —OC(O)O—(C1-C6 alkylene)-C(O)$R_5$, —C(O)—$N(R_5)(R_6)$, —$N(R_5)$—C(O)$R_6$, —$N(R_5)$—C(O)O$R_6$, —$N(R_5)$—C(O)$N(R_5)(R_6)$, —(C1-C6 alkylene)-$N(R_5)$—C(O)$R_6$, —$N(R_5)S(O)_2R_6$, and —P(O)$(R_5)(R_6)$; wherein the heteroalkyl contains one or more carbon atoms on an alkyl carbon chain that is replaced a divalent linking group selected from a group consisting of —O—, —S—, —NH— and —C(O)—;

B is independently selected from a group consisting of H, halogen, cyano, $CHF_2$, $CF_3$, —C(O)O$R_5$, C1-C6 alkyl, and C3-C8 cycloalkyl;

$X_1$, $X_2$ and $X_3$ are each independently CR or N; wherein each R is independently selected from a group consisting of hydrogen, substituted or unsubstituted C1-C6 alkyl, halogen, and cyano, wherein the term "substituted" means "substituted with one or more groups independently selected from a group consisting of halogen, cyano, hydroxyl, and amino; and 0, 1, 2 or 3 of $X_1$, $X_2$ and $X_3$ are N";

$R_2$ is independently selected from a group consisting of hydrogen, C1-C6 alkyl, C3-C8 cycloalkyl, C1-C6 heteroalkyl, 3- to 8-membered cycloheteroalkyl; wherein the alkyl, cycloalkyl, heteroalkyl, or cycloheteroalkyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

$R_3$ and $R_3$' are each independently selected from a group consisting of H, halogen, cyano, hydroxyl, mercapto, amino, $CHF_2$, $CF_3$, C1-C6 alkyl, C1-C6 alkoxy, C3-C8 cycloalkyl, C1-C6 heteroalkyl, and 3- to 8-membered cycloheteroalkyl; wherein the alkyl, alkoxy, cycloalkyl, heteroalkyl, or cycloheteroalkyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

alternatively, $R_3$ and $R_3$' together with the C atom to which they are attached form C3-C8 cycloalkyl, 3- to 8-membered heterocyclyl, or carbonyl; wherein the cycloalkyl or heterocyclyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

A is independently selected from a group consisting of C3-C8 cycloalkyl, 3- to 8-membered heterocyclyl, C6-C14 aryl and 5- to 14-membered heteroarylene;

each $R_4$ is independently selected from a group consisting of H, halogen, nitro, cyano, hydroxyl, carboxyl, mercapto, C1-C6 alkyl, C3-C8 cycloalkyl, 3- to 8-membered heterocyclyl, C1-C6 heteroalkyl, C2-C6 alkenyl, C2-C6 alkynyl, C6-C14 aryl, 5- to 14-membered heteroaryl, $—OR_5$, $—SR_5$, $—N(R_5)(R_6)$, $—S(O)_2R_5$, $—S(O)R_5$, $—C(O)R_5$, $—OC(O)R_5$, $—C(O)R_5$, —OC(O)O—(C1-C6 alkylene)-$C(O)R_5$, $—C(O)—N(R_5)(R_6)$, $—N(R_5)—C(O)R_6$, $—N(R_5)—C(O)OR_6$, $—N(R_5)—C(O)N(R_5)(R_6)$, —(C1-C6 alkylene)-$N(R_5)—C(O)R_6$, $—N(R_5)S(O)_2R_6$, and $—P(O)(R_5)(R_6)$; wherein the alkyl, cycloalkyl, heteroalkyl, heterocyclyl, aryl, or heteroaryl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

$R_5$ and $R_6$ are each independently selected from a group consisting of substituted or unsubstituted groups: H, C1-C6 alkyl, C3-C8 cycloalkyl, 3- to 8-membered monoheterocyclyl, C6-C10 aryl, 5- to 10-membered heteroaryl, C5-C12 fused bicyclic group, 5- to 12-membered fused heterobicyclic group, C5-C12 spirobicyclic group and 5- to 12-membered spiro heterobicyclic group; wherein the term "substituted" means "substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl";

alternatively, $R_5$ and $R_6$ together with the N or P atom to which they are attached form 3- to 8-membered heterocyclyl;

unless otherwise specified, the alkyl, alkylene, cycloalkyl, heteroalkyl, alkenyl, alkynyl, aryl, heteroaryl, or heterocyclyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl;

n is 0, 1, 2 or 3.

In another preferred embodiment, $X_1$, $X_2$ and $X_3$ are each independently CH or N.

In another preferred embodiment, $X_2$ and $X_3$ are independently N.

In another preferred embodiment, $X_2$ is independently N.

In another preferred embodiment, B is independently selected from a group consisting of H, halogen, C1-C6 alkyl and cyano; the alkyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

In another preferred embodiment, B is independently cyano.

In another preferred embodiment, in the compound of formula (I) or a pharmaceutically acceptable salt, hydrate, solvate, stereoisomer, isotopic compound or prodrug thereof, $R_2$ is selected from a group consisting of H, C1-C6 alkyl, and C3-C8 cycloalkyl; wherein the alkyl or cycloalkyl is unsubstituted or substituted with one or more groups independently selected from a group consisting of C1-C6 alkyl, $CHF_2$, $CF_3$, halogen, cyano, hydroxyl, carboxyl, methyl ester group, amido, sulfonamido, carbonyl, mercapto, amino and dimethylphosphoryl.

In another preferred embodiment, in the compound of formula I or a pharmaceutically acceptable salt, hydrate, solvate, stereoisomer, isotopic compound or prodrug thereof, $R_3$ and $R_3$' are independently selected from a group consisting of H, halogen, cyano, hydroxyl, $CHF_2$, $CF_3$, C1-C6 alkyl, C1-C6 alkoxy, C3-C8 cycloalkyl, and C1-C6 heteroalkyl;

alternatively, $R_3$ and $R_3$' together with the C atom to which they are attached form C3-C8 cycloalkyl, 3- to 8-membered heterocyclyl, or carbonyl;

wherein the alkyl, alkoxy, cycloalkyl, heteroalkyl, or heterocyclyl is unsubstituted or substituted with one or more groups independently selected from a group consisting of C1-C6 alkyl, $CHF_2$, $CF_3$, halogen, cyano, hydroxyl, carboxyl, ester group, amido, sulfonamido, carbonyl, mercapto, amino and dimethylphosphoryl.

In another preferred embodiment, $R_3$ and $R_3$' are the same or different, and are independently selected from a group consisting of H, halogen, cyano, hydroxyl, C1-C6 alkyl, and C3-C6 cycloalkyl;

alternatively, $R_3$ and $R_3$' together with the C atom to which they are attached form C3-C6 cycloalkyl or carbonyl;

wherein the alkyl or cycloalkyl is unsubstituted or substituted with one or more groups independently selected from a group consisting of C1-C6 alkyl, $CHF_2$, $CF_3$, halogen, cyano, hydroxyl, carboxyl, ester group, amido, sulfonamido, carbonyl, mercapto, amino and dimethylphosphoryl.

In another preferred embodiment, in the compound of formula I or a pharmaceutically acceptable salt, hydrate, solvate, stereoisomer, isotopic compound or prodrug thereof, $R_1$ is independently selected from a group consisting of $—OR_5$, $—OC(O)R_5$, $—N(R_5)(R_6)$, $—C(O)—N(R_5)(R_6)$, $—N(R_5)—C(O)R_6$, $—N(R_5)—C(O)OR_6$, and $—N(R_5)S(O)_2R_6$; wherein $R_5$ and $R_6$ are each independently selected from a group consisting of substituted or unsubstituted groups: H, C1-C6 alkyl, C3-C8 cycloalkyl, 3- to 8-membered heterocyclyl, C6-C10 aryl, and 5- to 10-membered heteroaryl; wherein the term "substituted" means "substituted with one or more groups independently selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl".

In another preferred embodiment, $R_1$ is independently —$OR_5$, wherein $R_5$ is independently selected from a group consisting of substituted or unsubstituted groups of: C1-C6 alkyl, C3-C8 cycloalkyl, 3- to 8-membered heterocyclyl, C6-C10 aryl, and 5- to 10-membered heteroaryl, wherein the term "substituted" means "substituted with one or more groups independently selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl".

In another preferred embodiment, $R_1$ is independently selected from a group consisting of C3-C8 cycloalkyl, 3- to 8-membered heterocyclyl, C6-C14 aryl, 5- to 14-membered heteroaryl, and the cycloalkyl, aryl, heteroaryl, or heterocyclyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

In another preferred embodiment, the compound of formula I or a pharmaceutically acceptable salt, hydrate, solvate, stereoisomer, isotopic compound or prodrug thereof, A is independently selected from a group consisting of C6-C10 aryl or 5- to 10-membered heteroaryl, wherein the aryl or heteroaryl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, mercapto, amino and dimethylphosphoryl.

In another preferred embodiment, the compound of formula I or a pharmaceutically acceptable salt, hydrate, solvate, stereoisomer, isotopic compound or prodrug thereof, $R_4$ is independently selected from a group consisting of H, C1-C6 alkyl, C3-C8 cycloalkyl, C1-C6 heteroalkyl, C6-C10 aryl, 5- to 10-membered heteroaryl, 3- to 8-membered heterocyclyl, —$OR_5$, —$OC(O)R_5$, —$N(R_5)(R_6)$, —C(O)—$N(R_5)(R_6)$, —$N(R_5)$—$C(O)R_6$, —$N(R_5)$—$C(O)OR_6$, and —$N(R_5)S(O)_2R_6$;

wherein $R_5$ and $R_6$ are each independently selected from a group consisting of substituted or unsubstituted groups of: H, C1-C6 alkyl, C3-C8 cycloalkyl, 3- to 8-membered heterocyclyl, C6-C10 aryl, and 5- to 10-membered heteroaryl, wherein the term "substituted" means "substituted with one or more groups independently selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl";

Unless otherwise specified, the alkyl, cycloalkyl, heteroalkyl, heterocyclyl, aryl, or heteroaryl is unsubstituted or substituted with one or more groups independently selected from a group consisting of C1-C6 alkyl, $CHF_2$, $CF_3$, halogen, cyano, hydroxyl, carboxyl, ester group, amido, sulfonamido, carbonyl, mercapto, amino and dimethylphosphoryl.

In another preferred embodiment, each $R_4$ is independently selected from a group consisting of H, C1-C6 alkyl, C3-C8 cycloalkyl, 3- to 8-membered heterocyclyl, C6-C10 aryl, and 5- to 10-membered heteroaryl, and the alkyl, cycloalkyl, heterocyclyl, aryl, and heteroaryl can be optionally and independently substituted with one or more groups selected from C1-C6 alkyl, $CHF_2$, $CF_3$, halogen, cyano, hydroxyl, carboxyl, ester group, amido, sulfonamido, carbonyl, mercapto, amino, and dimethylphosphoryl.

In another preferred embodiment, the compound of formula I or a pharmaceutically acceptable salt, hydrate, solvate, stereoisomer, isotopic compound or prodrug thereof has one or more of the following features:

$R_1$ is selected from a group consisting of —$OR_5$, —$OC(O)R_5$, —$N(R_5)(R_6)$, —C(O)—$N(R_5)(R_6)$, —$N(R_5)$—$C(O)R_6$, —$N(R_5)$—$C(O)OR_6$, and —$N(R_5)S(O)_2R_6$, and preferably is —$OR_5$;

B is independently selected from a group consisting of H, halogen, C1-C6 alkyl and cyano, and preferably is cyano;

$X_1$, $X_2$ and $X_3$ are each independently CH or N;

$R_2$ is selected from a group consisting of H, C1-C6 alkyl, and C3-C8 cycloalkyl, and preferably is H or C1-C6 alkyl, more preferably C1-C6 alkyl;

$R_3$ and $R_3'$ are each independently selected from a group consisting of H, halogen, cyano, hydroxyl, $CHF_2$, $CF_3$, C1-C6 alkyl, C1-C6 alkoxy, C3-C8 cycloalkyl, C1-C6 heteroalkyl, and preferably is H or C1-C6 alkyl;

alternatively, $R_3$ and $R_3'$ together with the C atom to which they are attached form C3-C8 cycloalkyl, 3- to 8-membered heterocyclyl, or carbonyl;

A is independently selected from a group consisting of C6-C10 aryl and 5- to 10-membered heteroaryl;

each $R_4$ is independently selected from a group consisting of H, C1-C6 alkyl, C3-C8 cycloalkyl, C1-C6 heteroalkyl, C6-C10 aryl, 5- to 10-membered heteroaryl, 3- to 8-membered heterocyclyl, —$OR_5$, —$OC(O)R_5$, —$N(R_5)(R_6)$, —C(O)—$N(R_5)(R_6)$, —$N(R_5)$—$C(O)R_6$, —$N(R_5)$—$C(O)OR_6$, and —$N(R_5)S(O)_2R_6$, and preferably is C3-C8 cycloalkyl, C6-C10 aryl, 5- to 10-membered heteroaryl, or 3- to 8-membered heterocyclyl;

wherein $R_5$ and $R_6$ are each independently selected from a group consisting of substituted or unsubstituted groups of: H, C1-C6 alkyl, C3-C8 cycloalkyl, 3- to 8-membered heterocyclyl, C6-C10 aryl, and 5- to 10-membered heteroaryl, wherein the term "substituted" means "substituted with one or more groups selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl";

Unless otherwise specified, the alkyl, cycloalkyl, heteroalkyl, aryl, heteroaryl, and heterocyclyl can be optionally and independently substituted with one or more groups selected from C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

In another preferred embodiment, the compound of formula I has a structure shown as formula (II):

(II)

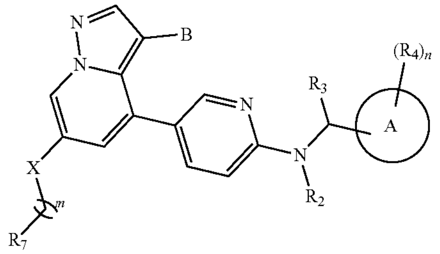

wherein

X is selected from a group consisting of O, S, and $NR_8$;

m is 0, 1, 2 or 3.

$R_7$ and $R_8$ are each a substituted or unsubstituted group selected from a group consisting of H, C1-C6 alkyl, C3-C8 cycloalkyl, 3- to 8-membered monoheterocyclyl, C6-C10 aryl, 5- to 10-membered heteroaryl, C5-C12 fused bicyclic group, 5- to 12-membered fused heterobicyclic group, C5-C12 spirobicyclic group, and 5- to 12-membered spiro heterobicyclic group;

wherein the term "substituted" means "substituted with one or more groups independently selected from a group consisting of C1-C6 alkyl, cyano, halogen, hydroxyl, C3-C8 cycloalkyl, 3- to 8-membered monoheterocyclyl, C6-C10 aryl, 5- to 10-membered heteroaryl, C5-C12 fused bicyclic group, 5- to 12-membered fused heterobicyclic group, C5-C12 spirobicyclic group, and 5- to 12-membered spiro heterobicyclic group";

B, $R_2$, $R_3$, A, $R_4$, and n are defined as above.

In another preferred embodiment, X is O.

In another preferred embodiment, $R_7$ is C1-C6 alkyl, and the alkyl can be optionally substituted with one or more groups independently selected from a group consisting of C1-C6 alkyl, cyano, halogen, and hydroxyl.

In another preferred embodiment, the compound of formula (I) has a structure shown as formula (III):

(III)

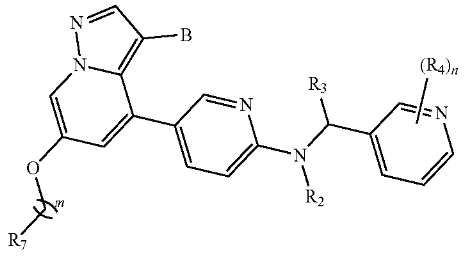

wherein B, $R_2$, $R_3$, $R_4$, $R_7$, m, and n are defined as above.

In another preferred embodiment, the compound of formula (I) has a structure shown as formula (IV):

(IV)

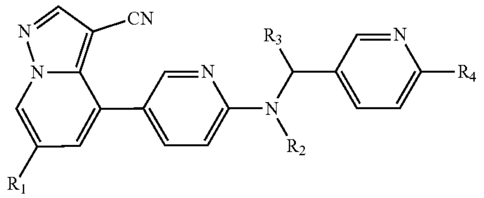

wherein $R_1$ is selected from a group consisting of —$OR_5$, —$N(R_5)(R_6)$, C3-C8 cycloalkyl, 3- to 8-membered heterocyclyl, C6-C14 aryl, and 5- to 14-membered heteroaryl;

$R_2$ is selected from a group consisting of H and C1-C6 alkyl;

$R_3$ is selected from a group consisting of H, halogen, cyano, hydroxyl, $CHF_2$, $CF_3$, C1-C6 alkyl, and C1-C6 alkoxy;

$R_4$ is independently selected from a group consisting of C3-C8 cycloalkyl, C6-C10 aryl, 5- to 10-membered heteroaryl, 3- to 8-membered heterocyclyl, —$OR_5$, —$OC(O)R_5$, —$N(R_5)(R_6)$, —$C(O)$—$N(R_5)(R_6)$, —$N(R_5)$—$C(O)R_6$, —$N(R_5)$—$C(O)OR_6$, and —$N(R_5)S(O)_2R_6$;

wherein $R_5$ and $R_6$ are each independently selected from a group consisting of substituted or unsubstituted groups of: H, C1-C6 alkyl, C3-C8 cycloalkyl, 3- to 8-membered heterocyclyl, C6-C10 aryl, and 5- to 10-membered heteroaryl, wherein the term "substituted" means "substituted with one or more groups independently selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl";

and unless otherwise specified, the alkyl, cycloalkyl, aryl, heteroaryl, or heterocyclyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

In another preferred embodiment, the prodrug of the compound or its pharmaceutically acceptable salt has a structure shown as formula (V):

(V)

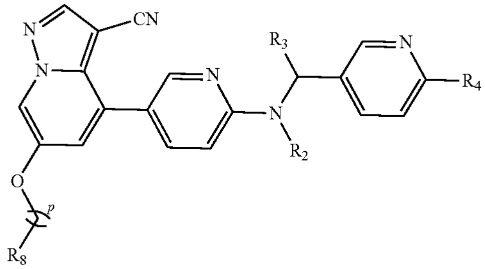

wherein $R_8$ is selected from a group consisting of

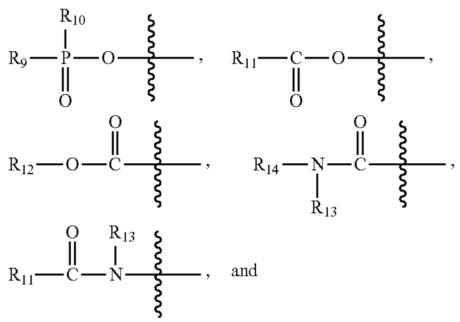

and

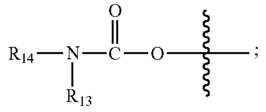

$R_9$ and $R_{10}$ are each independently selected from substituted or unsubstituted C1-C6 alkyl, hydroxyl, and —OM; M is Na or K;

$R_{11}$ and $R_{12}$ are each independently selected from substituted or unsubstituted C1-C6 alkyl, substituted or unsubstituted C6-C10 aryl, substituted or unsubstituted 5- to 10-membered heteroaryl;

$R_{13}$ and $R_{14}$ are each independently selected from substituted or unsubstituted C1-C6 alkyl, substituted or unsubstituted C6-C10 aryl, substituted or unsubstituted 5- to 10-membered heteroaryl;

p is 1, 2 or 3;

wherein the term "substituted" means "substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto and amino";

$R_2$, $R_3$ and $R_4$ are defined as above.

In another preferred embodiment, $R_4$ is a substituted or unsubstituted 5- to 6-membered heteroaryl; preferably, $R_4$ is a substituted or unsubstituted group selected from a group consisting of pyrrolyl, pyrazolyl, imidazolyl, oxazolyl, isoxazolyl, thiazolyl, thiadiazolyl, isothiazolyl, furyl, pyridyl, pyrazinyl, pyrimidinyl, pyridazinyl, triazinyl, triazolyl and tetrazolyl, wherein the term "substituted" means "substituted with one or more groups independently selected from a group consisting of C1-C6 alkyl, $CHF_2$, $CF_3$, halogen (preferably F), cyano, hydroxyl, carboxyl, ester group, amido, sulfonamido, carbonyl, mercapto, amino and dimethylphosphoryl".

In another preferred embodiment, $R_2$ and $R_3$ are each independently selected from a group consisting of H and C1-C6 alkyl.

In another preferred example, $X_1$, $X_2$, $X_3$, $R_1$, $R_2$, $R_3$, $R_3'$, $R_4$, n, p, A, X, $R_7$, $R_8$ and B are specific groups corresponding to respective specific compounds in the embodiments.

In another preferred embodiments, provided are the compound of formula (I) or a pharmaceutically acceptable salt, hydrate, solvate, stereoisomer, isotopic compound or prodrug thereof, and the compound is selected from:

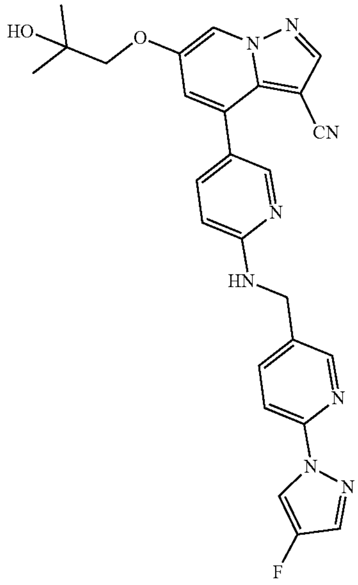

1

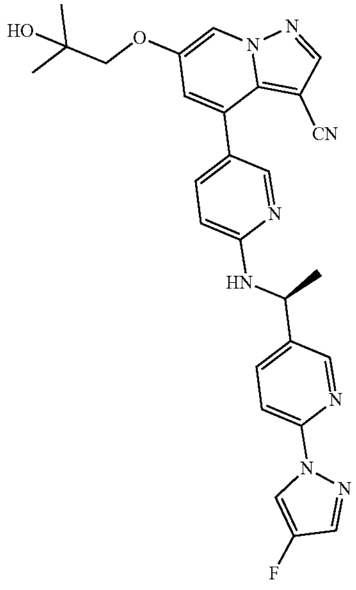

2

-continued
3
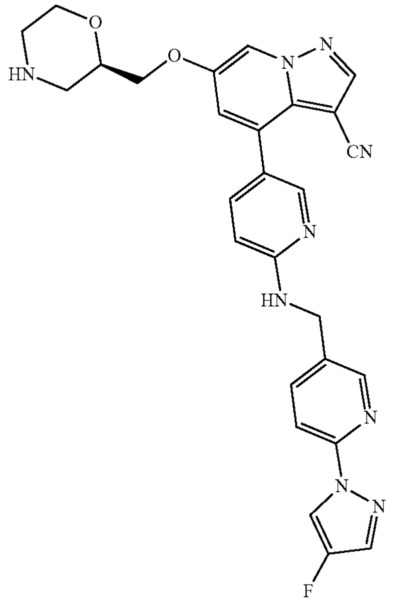
4
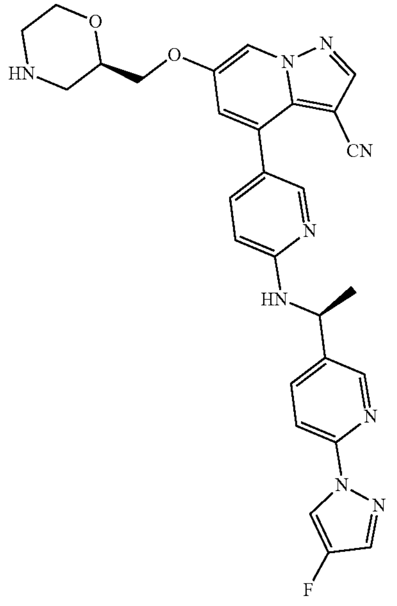
-continued
5
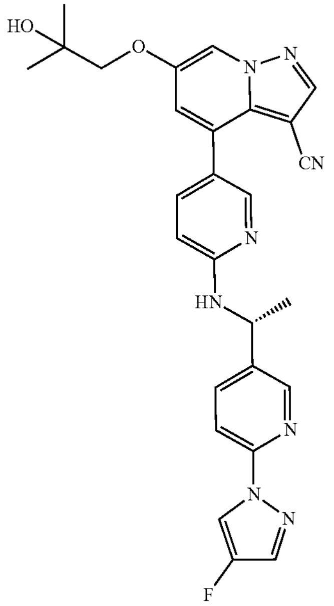
6
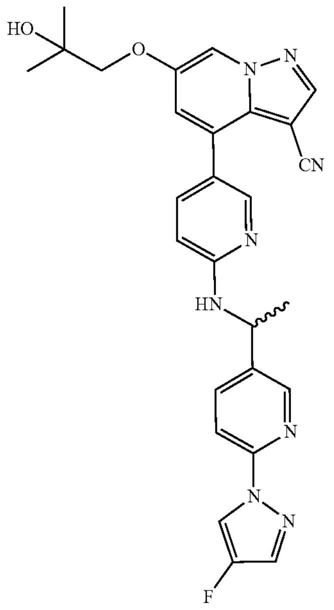

-continued
7
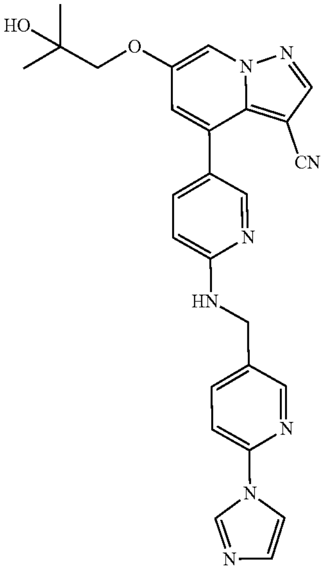
8
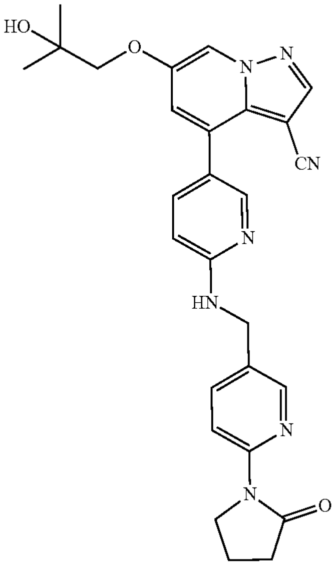
-continued
9
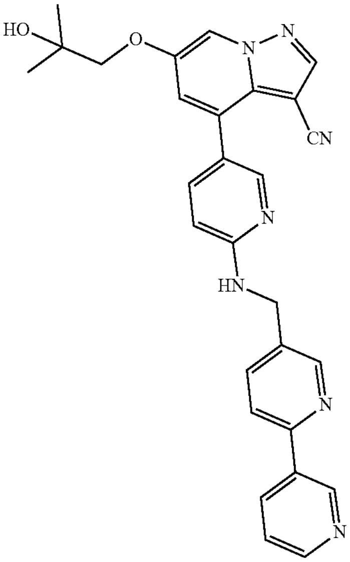
10
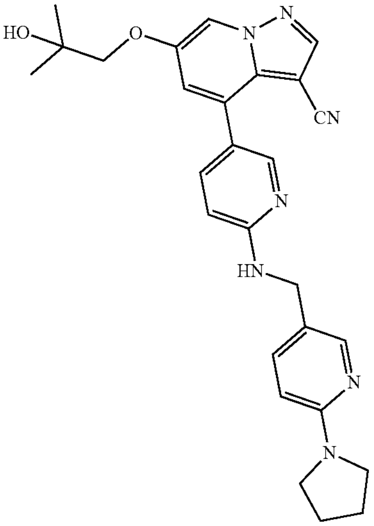
11
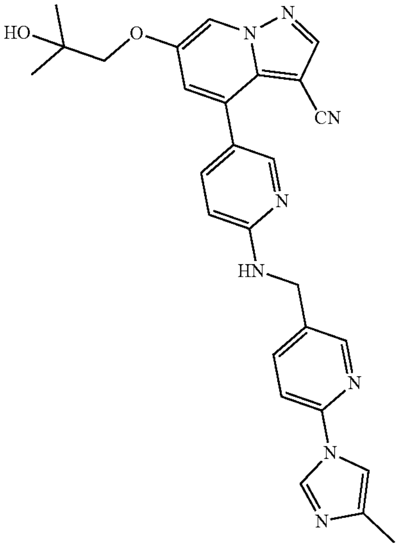

-continued
12
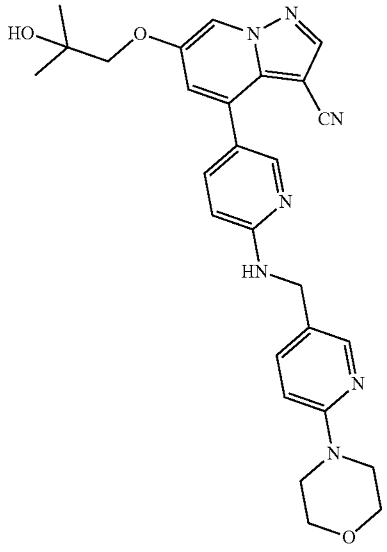
13
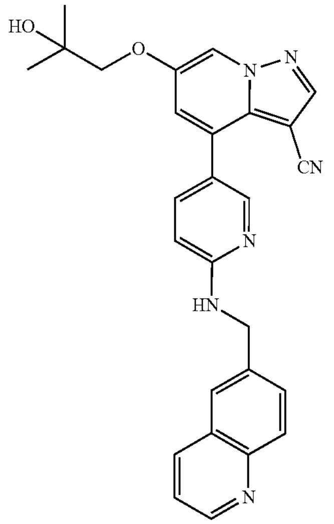
14
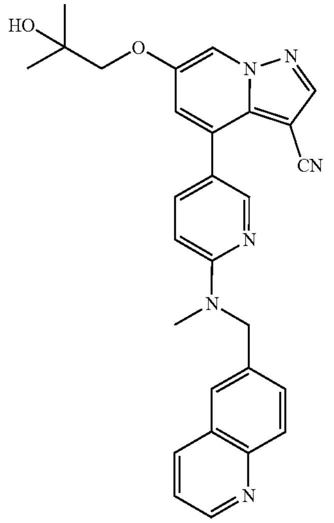
-continued
15
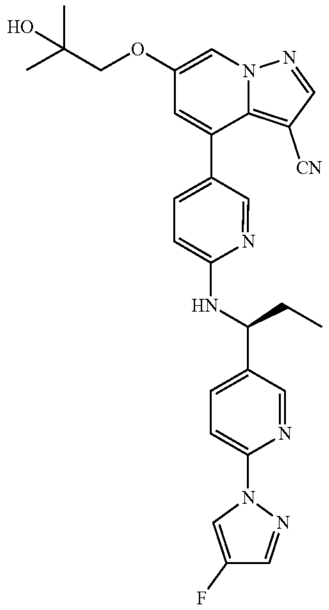
16
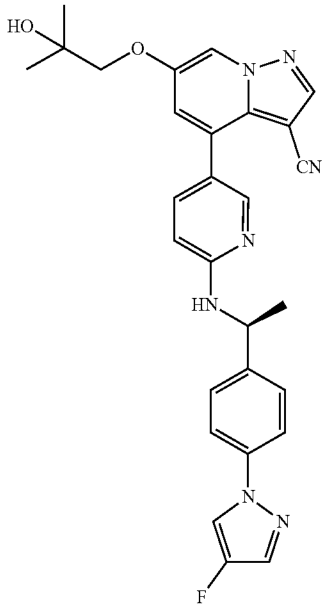

-continued
17
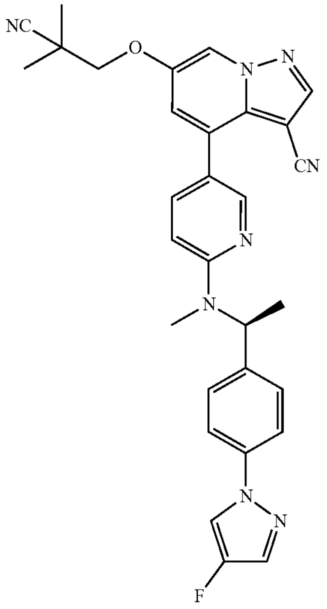
18
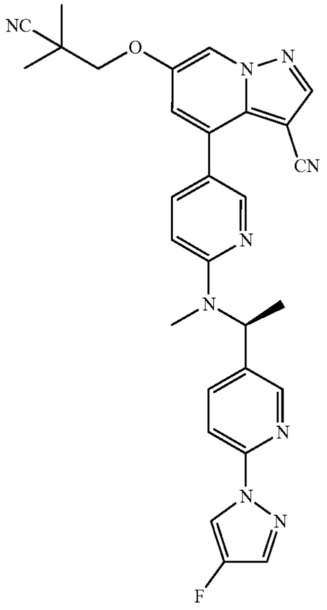
-continued
19
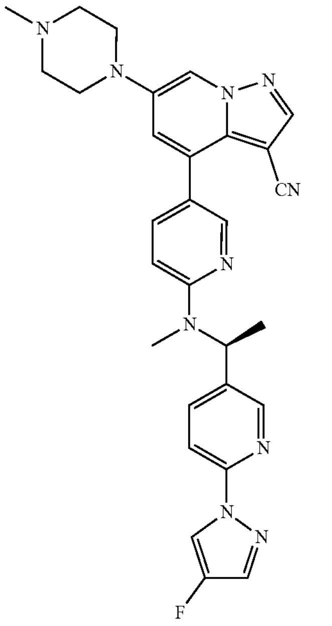
20
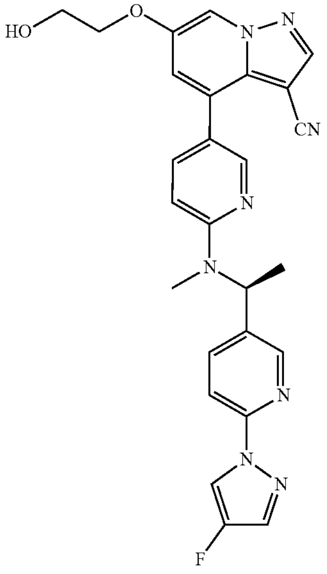

-continued
21
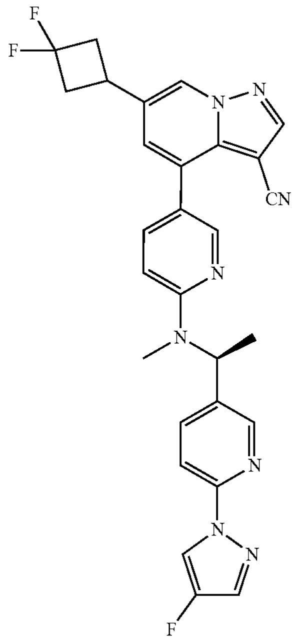
22
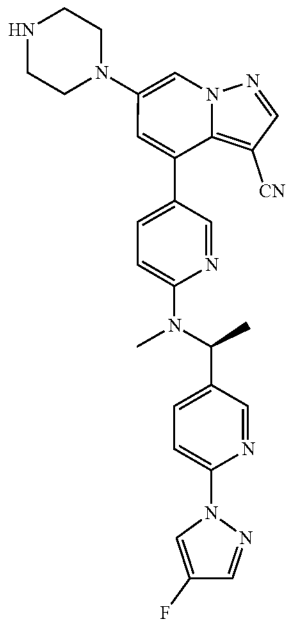
-continued
23
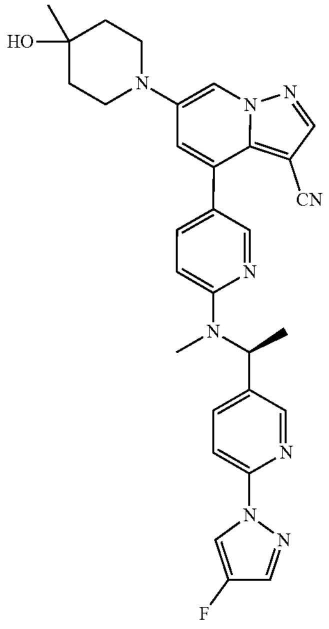
24
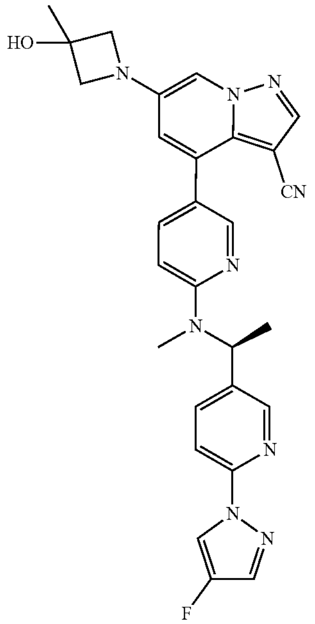

-continued
25
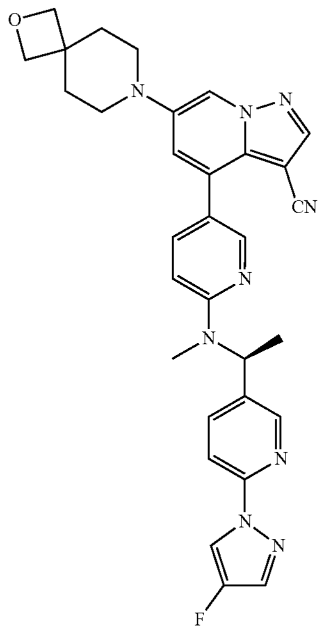
26
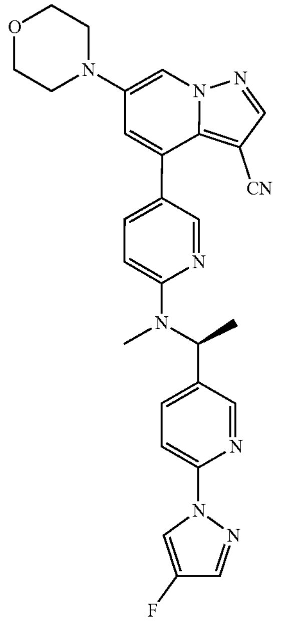
-continued
27
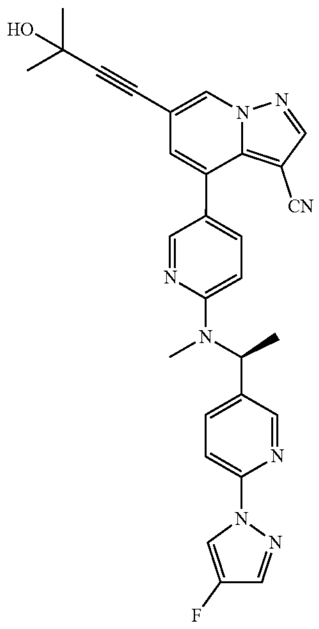
28
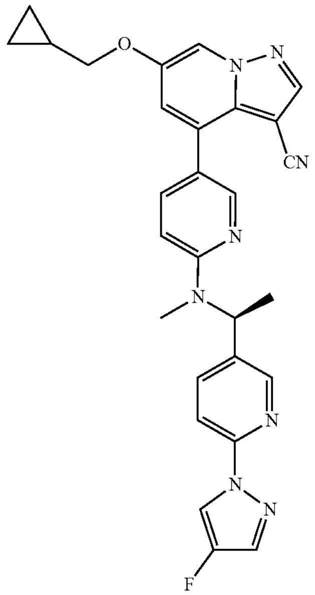

-continued
29
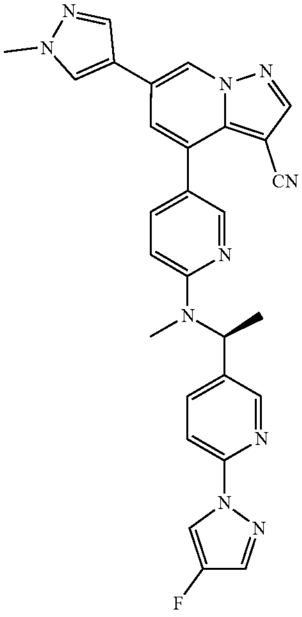
-continued
31
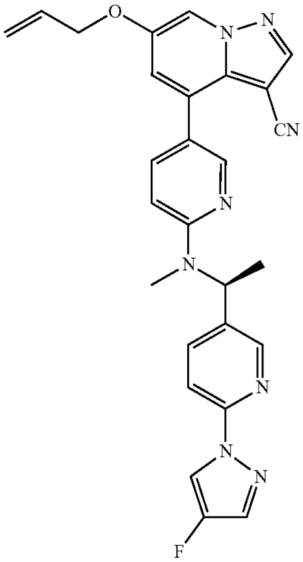
30
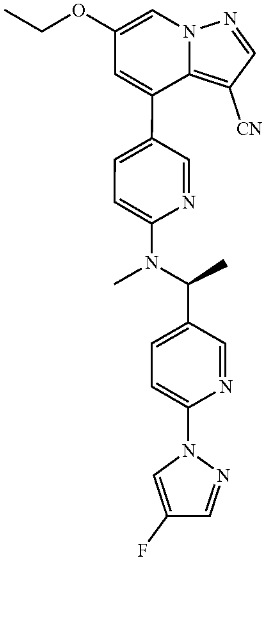
32
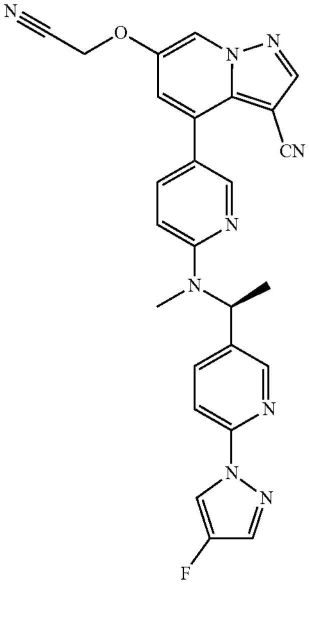

-continued
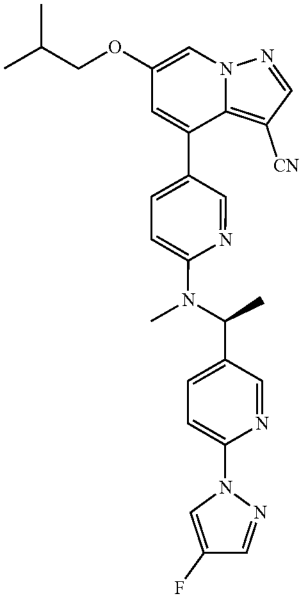
33
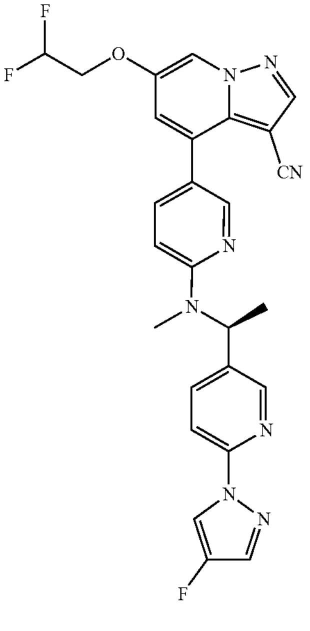
34
-continued
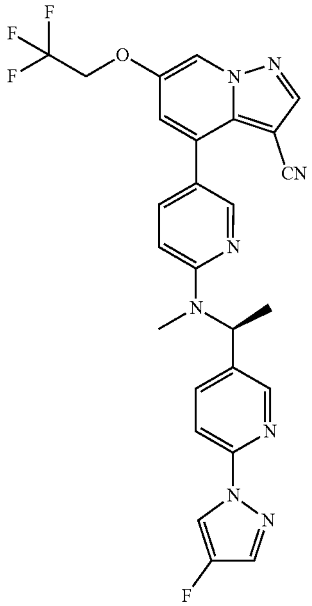
35
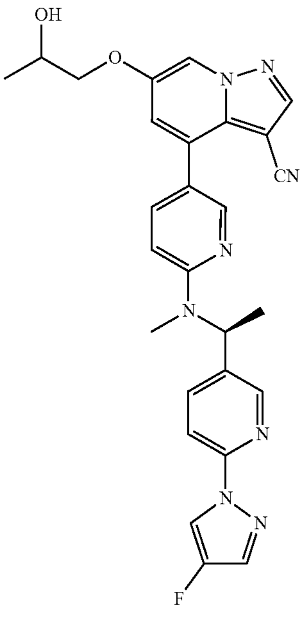
36

-continued
37
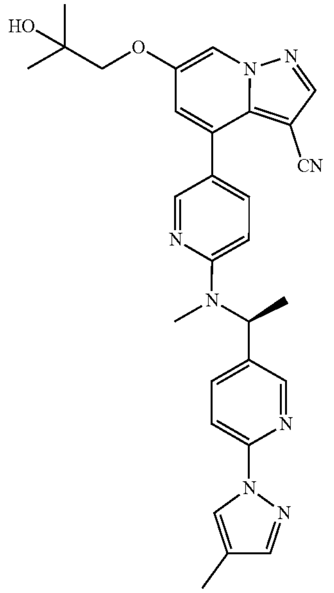
38
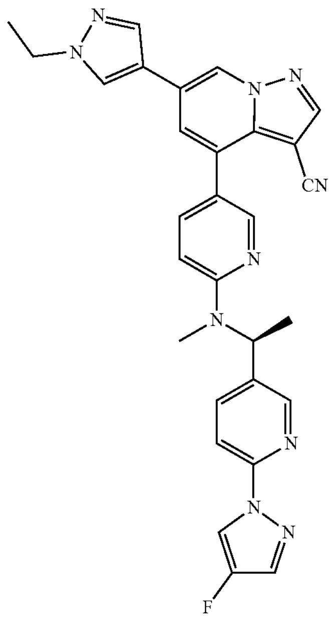
-continued
39
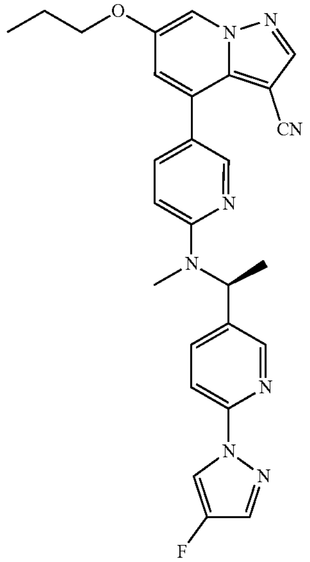
40
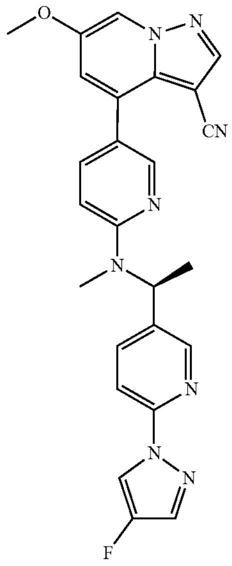

-continued
41
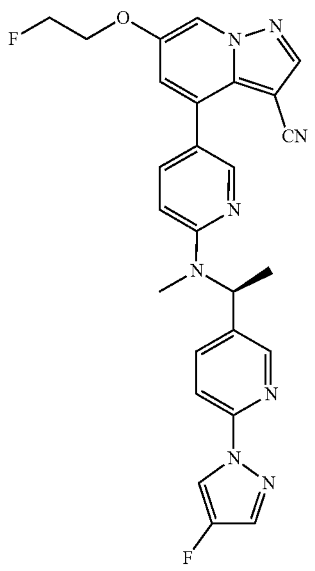
42
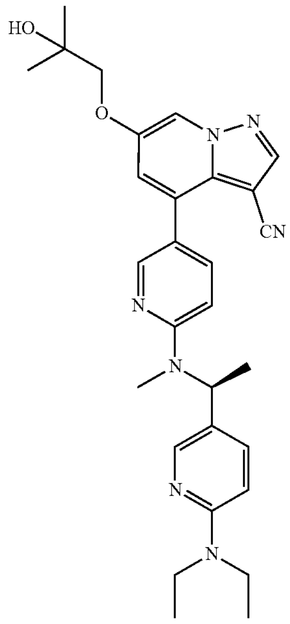
-continued
43
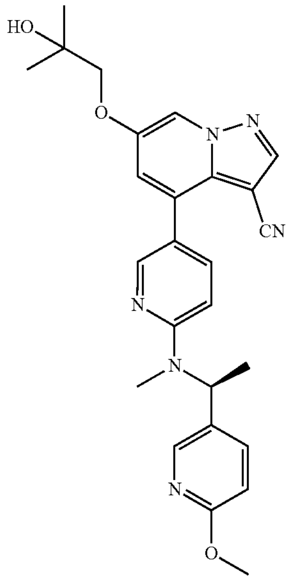
44
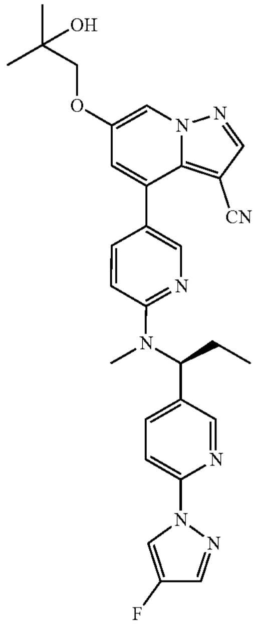

45
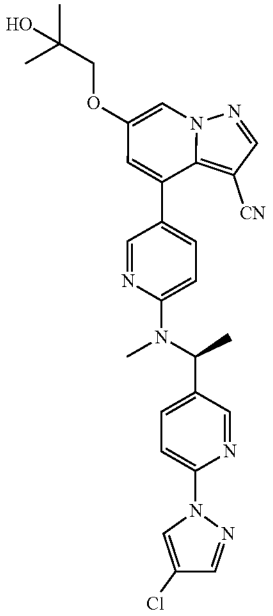
46
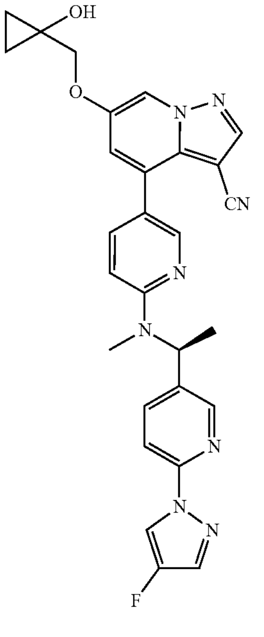
47
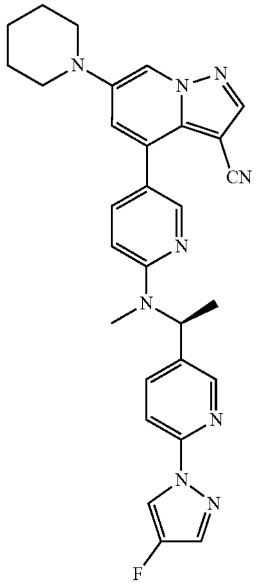
48
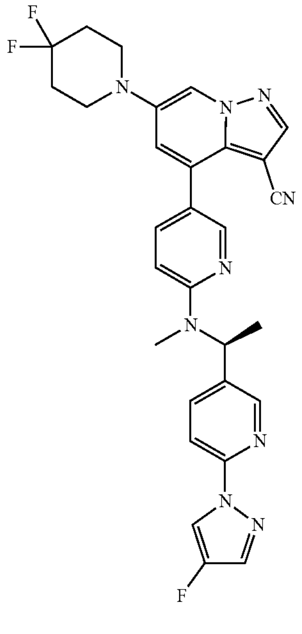

-continued
49
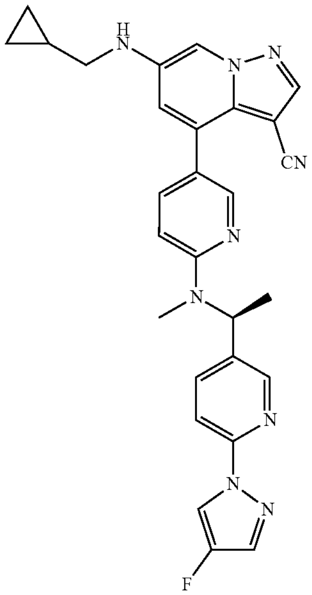
50
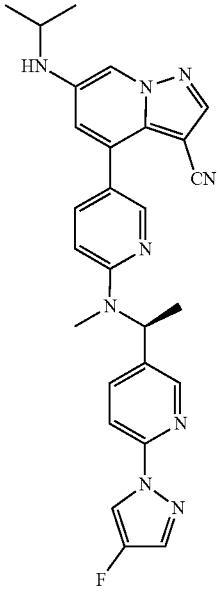
-continued
51
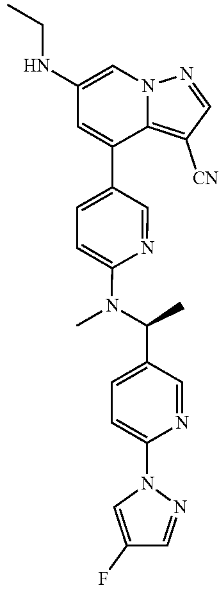
52
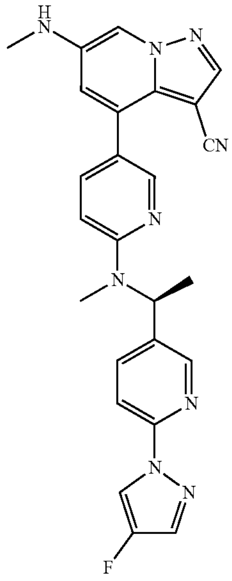

-continued
53
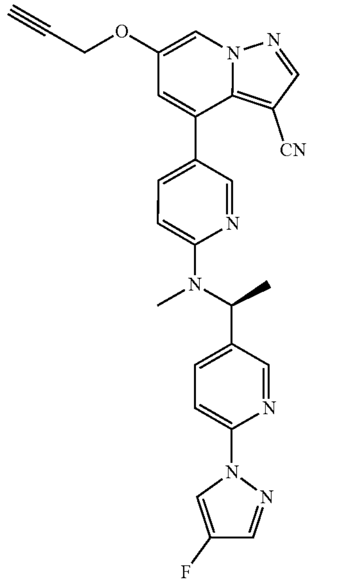
54
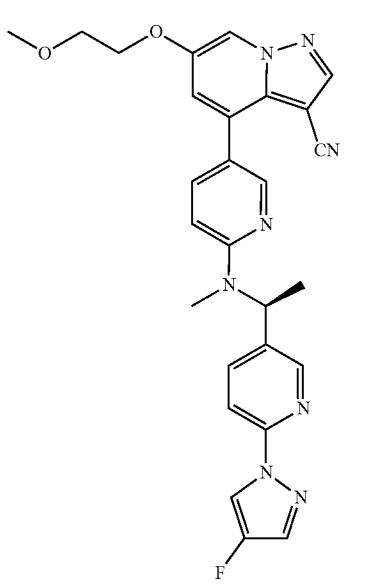
-continued
55
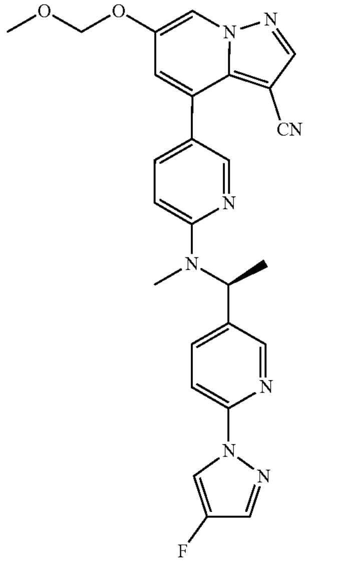
56
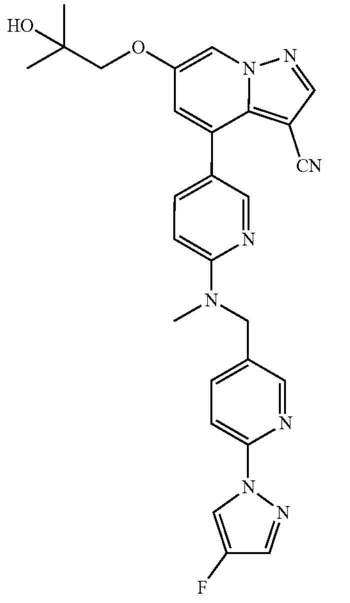

-continued
57
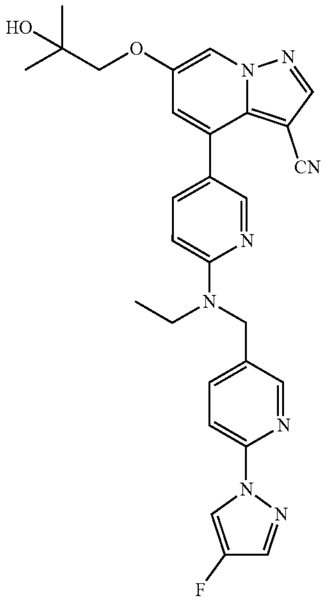
58
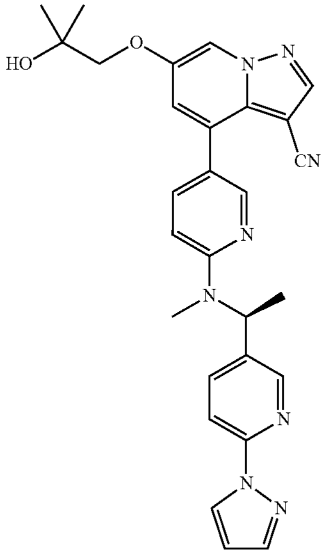
-continued
59
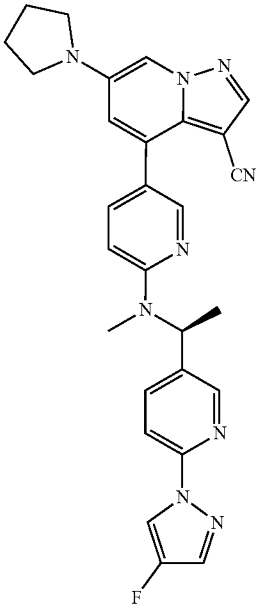
60
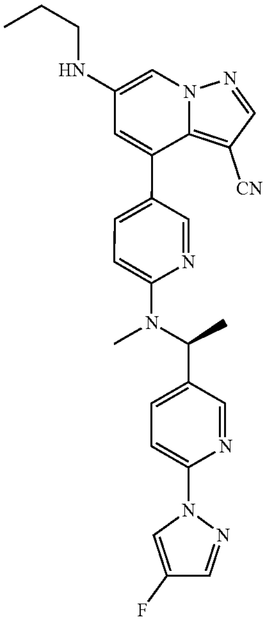

-continued
61
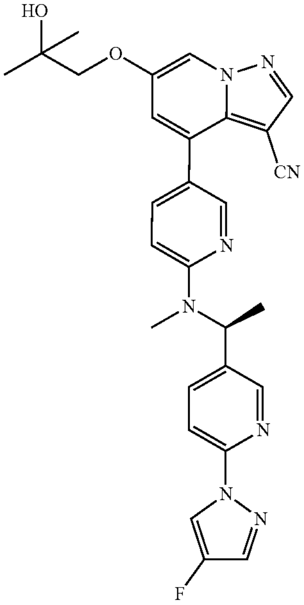
62
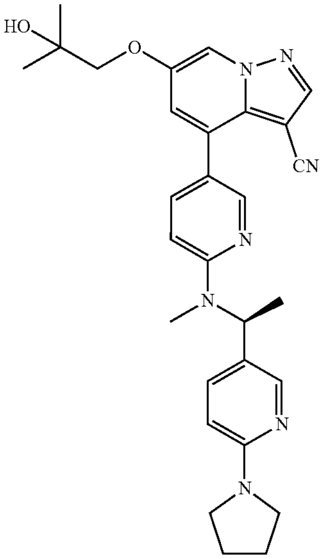
63
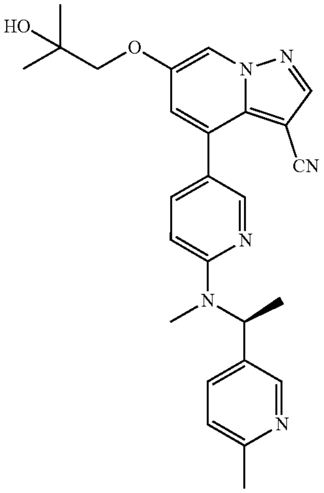
-continued
64
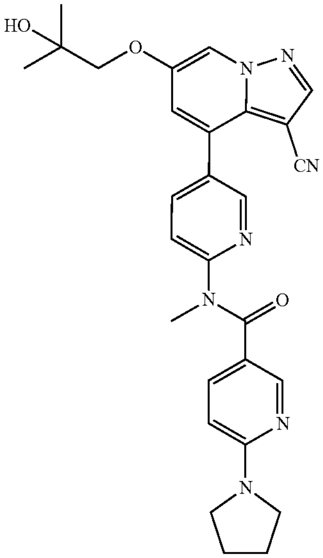
65
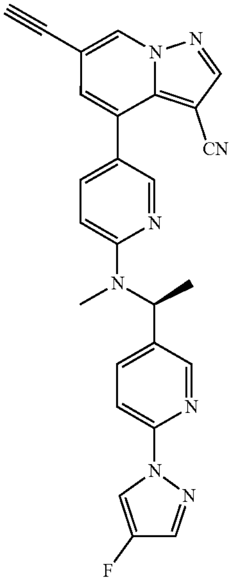

-continued

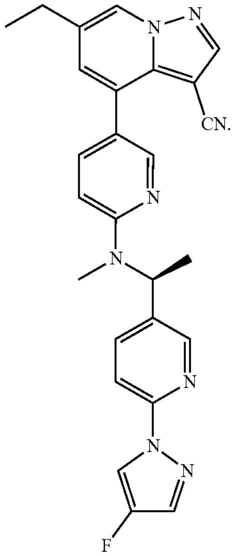

66

According to a second aspect of this disclosure, provided is a pharmaceutical composition comprising the compound described in the first aspect or a pharmaceutically acceptable salt, hydrate, solvate, stereoisomer, isotopic compound or prodrug thereof; and a pharmaceutically acceptable carrier or diluent.

In another preferred embodiment, the pharmaceutical composition further comprises a second therapeutic agent for a cancer.

In another preferred embodiment, the second therapeutic agent for a cancer comprises a radioactive agent, a cytotoxic agent, a kinase inhibitor, an immune targeting inhibitor or an angiogenesis inhibitor.

In another preferred embodiment, the second therapeutic agent for a cancer comprises one or more of:

a PD-1 inhibitor (such as Nivolumab, Pembrolizumab, JS-001, SHR-120, BGB-A317, IBI-308, GLS-010, GB-226, STW204, HX008, HLX10, BAT1306, AK105, LZM 009 or biosimilars thereof, etc.), a PD-L1 inhibitor (such as Durvalumab, Atezolizumab, CS1001, KN035, HLX20, SHR-1316, BGB-A333, JS003, CS1003, KL-A167, F520, GR1405, MSB2311 or biosimilars thereof, etc.), a CD20 antibody (such as Rituximab, Obinutuzumab, Ofatumumab, Tositumumab, Tiimumab, etc.), a CD47 antibody (such as Hu5F9-G4, CC-90002, TTI-621, TTI-622, OSE-172, SRF-231, ALX-148, NI-1701, SHR-1603, IBI188, IMMO1), an ALK inhibitor (such as Ceritinib, Alectinib, Brigatinib, Lorlatinib, and Oclatinib), a PI3K inhibitor (such as Ederatinib, Dactolisib, Taselisib, Buparlisib, etc.), a BTK Inhibitor (such as Ibrutinib, Tirabrutinib, Acalabrutinib, etc.), an EGFR inhibitor (such as Afatinib, Gefitinib, Erlotinib, Lapatinib, Dacomitinib, Icotinib, Canetinib, etc.), a VEGFR inhibitor (such as Sorafenib, Pazopanib, Rivatinib, Cabozantinib, Sunitinib, Donafenib, etc.), an HDAC inhibitor (such as Givinostat, Droxinostat, Entinostat, Darcylast, Tycodinaline, etc.), a CDK inhibitor (such as Palbociclib, Ribociclib, Abemaciclib, Lerociclib, etc.), a MEK inhibitor (such as Selumetinib (AZD6244), Trametinib (GSK1120212), PD0325901, U0126, AS-703026, PD184352 (CI-1040), etc.), an Akt inhibitor (such as MK-2206, Ipatasertib, Capivasertib, Afuresertib, Uprosertib, etc.), an mTOR inhibitor (such as Vistusertib, etc.), an SHP2 inhibitor (such as RMC-4630, JAB-3068, TNO155, etc.), an IGF-1R inhibitor (such as Ceritinib, Ocaltinib, Iinsitinib, BMS-754807, GSK1838705A, etc.), and a combination thereof.

According to a third aspect of this disclosure, provided is use of the compound as described in the first aspect or the pharmaceutical composition as described in the second aspect in preparation of a drug for inhibiting activity of an RET kinase in a cell or a subject.

In another preferred embodiment, an RET-related disease refers to a disease or condition related to or having a dysregulation of expression or activity or level of RET genes, RET kinases (also known as RET kinase proteins) or any (e.g., one or more) of them, for example, any type of dysregulation of expression or activity or level of the RET genes, RET kinases, RET kinase domains, or any of them described herein, wherein, the dysregulation of expression or activity or level of the RET genes is caused by RET gene mutation (such as point mutation and gene fusion).

In another preferred embodiment, the disease is selected from: irritable bowel syndrome, eye diseases, rheumatoid arthritis, pulmonary fibrosis, liver fibrosis, and tumors; the tumors include: bladder cancer, ovarian cancer, adenocarcinoma, gastric cancer, pancreatic cancer, prostate cancer, colon cancer, lung cancer, bone cancer, brain cancer, neurocytoma, rectal cancer, colon cancer, familial adenomatous polyposis cancer, hereditary non-polyposis colorectal cancer, esophageal cancer, lip cancer, laryngeal cancer, hypopharyngeal cancer, tongue cancer, salivary gland cancer, gastric cancer, adenocarcinoma, medullary thyroid cancer, papillary thyroid cancer, kidney cancer, renal parenchymal cancer, ovarian cancer, cervical cancer, endometrial adenocarcinoma, endometrial cancer, choriocarcinoma, pancreatic cancer, prostate cancer, testicular cancer, urinary cancer, melanoma, acute lymphocytic leukemia, chronic lymphocytic leukemia, acute myeloid leukemia, chronic myelocytic leukemia, hepatocellular carcinoma, gallbladder carcinoma, bronchial carcinoma, small cell lung cancer, non-small cell lung cancer, and multiple myeloma.

In another preferred embodiment, the dysregulation of expression or activity or level of RET genes, RET kinases, or any one of the RET genes and the RET kinases refers to one or more point mutations in the RET genes. One or more point mutations in the RET genes result in translation of an RET protein with one or more amino acid substitutions at one or more amino acid positions including but not limited to: 378, 385, 618, 620, 630, 631, 633, 804, 810, 883, or 918.

In another preferred embodiment, the dysregulation of expression or activity or level of the RET gene is an RET gene fusion, and the RET gene fusion comprises but is not limited to: KIF5B-RET, CDC6-RET, NCOA4-RET, CLIP1-RET, ERC1-RET, RUFY3-RET, TFG-RET, PRKAR1A-RET, or KTN1-RET.

In another preferred embodiment, the RET-related disease comprises but is not limited to a tumor or irritable bowel syndrome.

In another preferred embodiment, an RET-related tumor comprises but is not limited to: lung cancer, papillary thyroid cancer, medullary thyroid cancer, differentiated thyroid cancer, recurrent thyroid cancer, refractory differentiated thyroid cancer, type 2A or 2B multiple endocrine tumor (MEN2A or MEN2B, respectively), pheochromocytoma, parathyroid hyperplasia, breast cancer, colorectal cancer, papillary renal cell carcinoma, gangliomatosis of the gastrointestinal mucosa, or cervical cancer.

In another preferred embodiment, the lung cancer is RET fusion lung cancer, or the cancer is medullary thyroid cancer.

According to a fourth aspect, provided is a method of treating an RET-related disease, the method including administering to a subject identified or diagnosed as having an RET-related disease a therapeutically effective dose of a compound as described in the first aspect, or the pharmaceutically acceptable salt, hydrate, solvate, stereoisomer, isotopic compound or producing thereof, or the pharmaceutical composition as described in the second aspect.

According to a fifth aspect, provided is a method for inhibiting activity of an RET kinase in a cell or a subject, the method including a step of allowing the cell to contact the compound or the pharmaceutically acceptable salt, hydrate, solvate, stereoisomer, isotopic compound or producing thereof as described in the first aspect or the pharmaceutical composition as described in the second aspect or administering to the subject the compound as described in the first aspect or the pharmaceutical composition as described in the second aspect.

In another preferred embodiment, the cell is from a mammal.

In another preferred embodiment, the subject is a mammal, preferably a human.

It should be appreciated that, within the scope of this disclosure, the above-mentioned technical features of this disclosure and the technical features specifically described in the following (e.g., embodiments) can be combined with each other, thereby constituting new or preferred technical solutions. Due to space limitations, it is not described here.

DETAILED DESCRIPTION

After extensive and in-depth research, the inventors have unexpectedly found a compound with good inhibitory activity against RET kinase and good selectivity for VEGFR2 kinase. In addition, the compound has excellent inhibitory activity against RET kinase-sensitive cells and has good pharmacodynamic/pharmacokinetic properties. On this basis, this disclosure is implemented.

Definition of Terms

In this disclosure, unless otherwise specified, the terms used have the ordinary meanings known to those skilled in the art.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl", by itself or as part of another substituent, means a straight or branched alkyl having a specified number of carbon atoms (i.e., C1-C6 refers to 1, 2, 3, 4, 5 or 6 carbon atoms). Examples of alkyl include, but are not limited to, groups such as methyl, ethyl, n-propyl, isopropyl, n-butyl, tert-butyl, isobutyl, sec-butyl, n-pentyl, n-hexyl and the like. In the present application, alkyl is also intended to include substituted alkyls, i.e., one or more positions in the alkyl are substituted, and especially there are 1 to 4 substituents, which may be at any position.

The term "alkoxy" refers to a straight or branched chain or cyclic alkyl linked through an ether oxygen group from which its free valences originate. The alkoxy is preferably a C1-C6 alkoxy, more preferably a C1-C3 alkoxy. Its typical examples include (but not are limited to): methoxy, ethoxy, propoxy, isopropoxy, butoxy, and the like. Preferably it is C1-C3 alkoxy.

The term "heteroalkyl" refers to a group in which carbon atoms in an alkyl are substituted with 1, 2 or 3 heteroatoms selected from N, O, S, Si and P, wherein the N and S atoms are optionally oxidized. According to this disclosure, the term "C1-C6 heteroalkyl" refers to containing 1 to 6 (i.e., 1, 2, 3, 4, 5 or 6) carbon atoms and 1, 2, or 3 heteroatoms selected from N, O, Sand P, and its typical examples include (but not are limited to): $CH_3OCH_2—$, $CH_3SCH_2—$, $CH_3CH_2OCH_2—$ and the like.

The term "cycloalkyl" refers to a cyclic alkyl containing a saturated monocyclic ring (such as C3-C8 cycloalkyl), bicyclic ring (such as C5-C12 fused bicycle and 5- to 12-membered spirobicycle) or polycyclic ring. The "C3-C8 cycloalkyl" refers to a cyclic alkyl including 3, 4, 5, 6, 7, or 8 carbon atoms. The typical cycloalkyl groups of this disclosure include, but are not limited to: cyclopropyl, cyclobutyl, cyclopentyl, cyclohexyl, norbornyl,

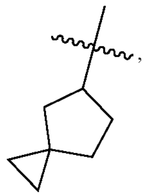,
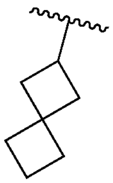,
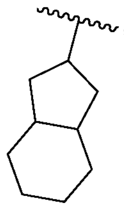,
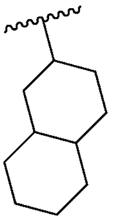

and the like. It should be appreciated that substituted or unsubstituted cycloalkyl groups, such as branched cycloalkyl groups (such as 1-methylcyclopropyl and 2-methylcyclopropyl), are included in the definition of "cycloalkyl".

The term "heterocycle", "heterocyclyl" or "heterocyclic group" usually refers to a stable monocyclic ring (such as 3- to 8-membered, i.e. 3-, 4-, 5-, 6-, 7- or 8-membered) or bicyclic (such as 5- to 12-membered, i.e. 5-, 6-, 7-, 8-, 9-, 10-, 11- or 12 membered), or polycyclic (such as 7- to 14-membered, i.e. 7-, 8-, 9-, 10-, 11-, 12-, 13- or 14-membered) heterocycle, including fused-ring, spiro and/or bridged structures, which are saturated or partially unsaturated, and contain carbon atoms and 1, 2, 3 or 4 heteroatoms independently selected from N, O and S. The term also includes polycyclic groups formed by the fusion of a heterocyclic ring with an aromatic ring such as a benzene ring. The "heterocycle" may be substituted or unsubstituted. N and S heteroatoms as ring atoms can be optionally oxidized. The N atom is substituted or unsubstituted (i.e., N or NR, wherein R is H or, if defined, another substituent). The heterocycle can be attached to its pendant group at any heteroatom or carbon atom that results in a stable structure. The heterocyclyl described herein may be substituted on a C or N atom if the resulting compound is stable. N in the heterocycle may be optionally quaternized. Preferably, when the total number of S and O atoms in the heterocycle exceeds 1, then these heteroatoms are not adjacent to each other. Preferably, the total number of S and O atoms in the heterocycle is not greater than 1. A heterocyclyl group can be attached to the residue of any heteroatom or carbon atom of a ring or cyclic molecule. Examples of heterocyclyl include, but are not limited to, typical monocyclic heterocyclyl groups, including, but not limited to, azetidinyl, pyrrolidinyl, oxetanyl, pyrazolidinyl, imidazolinyl, imidazolidinyl, oxazolidinyl, isoxazolidinyl, thiazolidinyl, isothiazolidinyl, tetrahydrofuranyl, piperidinyl, piperazinyl, 2-oxopiperazinyl, 2-oxopiperidyl, 2-oxopyrrolidinyl, hexahydroazepinyl, 4-piperidinyl, tetrahydropyranyl, morpholinyl, thiomorpholinyl, thiomorpholinosulfoxidyl, thiomorpholinylsulfonyl, 1,3-dioxanyl and tetrahydro-1,1-dioxothiophene. The "polycyclic heterocyclyl" includes spiro (e.g., 5- to 12-membered, preferably 7- to 9-membered), fused (e.g. 5- to 12-membered, preferably 8- to 10-membered) and bridged heterocyclyl.

Examples of spiro ring and fused ring include, but are not limited to

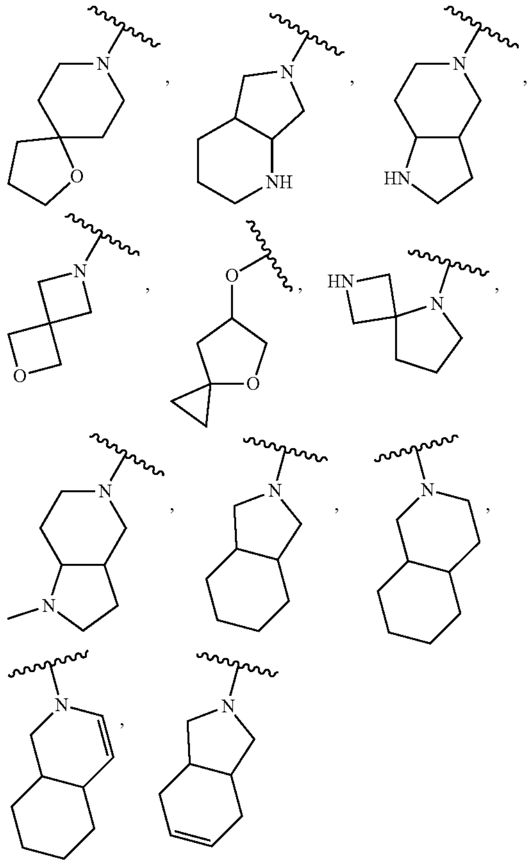

and the like. The spiro, fused and bridged heterocyclyl involved are optionally linked with other groups through single bonds, or are further in fused link with other cycloalkyls, heterocyclyls, aryls and heteroaryls through any two or more atoms on the ring.

A preferred class of heterocyclyl groups refers to a cycloalkyl ring having the specified number of ring vertices (or members) and having one to five heteroatoms selected from N, O, S and P, respectively substituted for carbon atoms in the ring skeleton and wherein N and S atoms are optionally oxidized and the N atom is optionally quaternized. The cycloheteroalkyl is usually a 3- to 12-membered ring, preferably a 3- to 8-membered ring in this disclosure, such as a 3- to 8-membered monocyclic ring, bicyclic (5- to 12-membered fused heterobicyclic, 5- to 12-membered spiro heterobicyclic) or polycyclic system (8- to 16-membered tricyclic ring). Examples of cycloheteroalkyl include, but are not limited to: pyrrolidinyl, imidazolidinyl, pyrazolidinyl, butyrolactam, valerolactam, imidazolidinone, hydantoin, dioxacyclopentyl, phthalimido, piperidinyl, 1,4-dioxanyl, morpholinyl, thiomorpholinyl, thiomorpholine-S-oxide, thiomorpholine-S,S-oxide, piperazinyl, pyranyl, pyridinone, 3-pyrrolidinyl, thiopyranyl, pyranone, tetrahydrofuran 1 tetrahydrothienyl, quinuclidine,

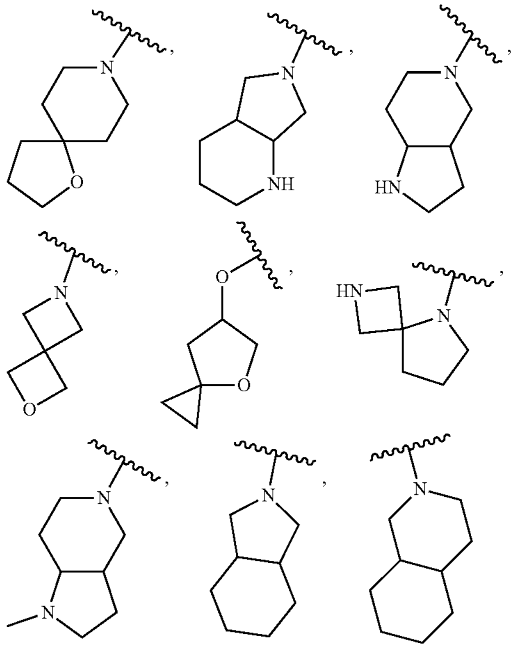

and their analogues.

The term "alkynyl" refers to a straight or branched hydrocarbon group containing one or more double bonds and usually 2 to 20 carbon atoms (or C2-C8) in length. For example, in this disclosure, "C2-C6 alkenyl" contains 2, 3, 4, 5 or 6 carbon atoms. Alkenyl groups include, but are not limited to, for example, vinyl, propenyl, butenyl, 1-methyl-2-buten-1-yl, and the like. In this disclosure, the "alkenyl" includes substituted alkenyl groups.

The term "alkenyl" refers to a straight or branched hydrocarbon group containing one or more triple bonds and usually 2 to 20 carbon atoms (or C2-C8) in length. In this disclosure, "C2-6 alkynyl" refers to a straight or branched alkynyl group having 2, 3, 4, 5 or 6 carbon atoms, including but not limited to ethynyl, propynyl or similar groups. In this disclosure, the alkynyl also includes substituted alkynyl groups, and substituents can be halo, hydroxyl, cyano, nitro and the like.

The term "aryl", alone or as part of a larger moiety such as "aralkyl", "aralkoxy" or "aryloxyalkyl", refers to a monocyclic, bicyclic or tricyclic ring system having a total of 5 to 15 ring members (preferably a 6-10 membered aromatic ring), wherein at least one ring in the system is aromatic and wherein each ring in the system contains 3 to 7 ring members. "Aryl" may be substituted or unsubstituted. In some embodiments of this disclosure, "aryl" refers to an aromatic ring system including, but not limited to, phenyl, biphenyl, indanyl, 1-naphthyl, 2-naphthyl, and tetrahydronaphthyl. The aryl can be fused to a heteroaryl, heterocyclyl or cycloalkyl ring, wherein the ring linked to the parent structure is an aryl ring. A fused aryl group can be attached to another group at a suitable position on the cycloalkyl or aromatic ring. The connecting lines drawn from the ring system indicate that the bond may be attached to any suitable ring atom. Aryl may be optionally substituted or unsubstituted.

The term "heteroaryl" refers to a heteroaromatic system containing 1 to 4 heteroatoms, 5 to 14 ring atoms, wherein the heteroatom is selected from O, N and S. Heteroaryl is preferably a 5- to 10-membered ring, more preferably 5- or 6-membered ring, such as pyrrolyl, pyrazolyl, imidazolyl, oxazolyl, isoxazolyl, thiazolyl, thiadiazolyl, isothiazolyl, furyl, pyridyl, pyrazinyl, pyrimidinyl, pyridazinyl, triazinyl, triazolyl, tetrazolyl, and the like. "Heteroaryl" may be substituted or unsubstituted, and in a case of a substituted heteroaryl, the substituent is preferably one or more of groups independently selected from: alkyl, deuterated alkyl, haloalkyl, alkoxy, haloalkoxy, alkenyl, alkynyl, alkylthio, alkylamino, halogen, amino, nitro, hydroxyl, mercapto, cyano, cycloalkyl, heterocyclyl, aryl, heteroaryl, cycloalkylthio, oxo, carboxyl, and carboxylate group.

In this disclosure, the term "amino" refers to a group having a structure of —N(R)(R'), wherein R and R' can independently represent H, alkyl or substituted alkyl (e.g., C1-C6 alkyl), cycloalkyl or substituted cycloalkyl, aryl or substituted aryl, heterocycle or substituted heterocycle, as defined above. R and R' can be the same or different in a dialkylamine moiety. Preferably, the amino is $NH_2$.

In this disclosure, the term "ester group" means a group having a structure of —C(O)—O—R or R—C(O)—O—, wherein R independently represents H, alkyl, cycloalkyl, aryl, heteroaryl, or heterocyclyl, as defined above.

In this disclosure, the term "amido" refers to a group having a structure of —CONRR', wherein R and R' can independently represent hydrogen, alkyl or substituted alkyl, cycloalkyl or substituted cycloalkyl, aryl or substituted aryl, heterocycle or substituted heterocycle, as defined above. R and R' can be the same or different in a dialkylamine moiety.

In this disclosure, the term "sulfonamido" refers to a group having a structure of —$SO_2$NRR', wherein R and R' can independently represent hydrogen, alkyl or substituted alkyl, cycloalkyl or substituted cycloalkyl, aryl or substituted aryl, heterocycle or substituted heterocycle, as defined above. R and R' can be the same or different in a dialkylamine moiety.

In this disclosure, each of the above-mentioned alkyl, alkoxy, cycloalkyl, heteroalkyl, aryl, heteroaryl, cycloheteroalkyl, alkenyl, alkyne, heterocyclyl, heterocyclic groups, and more may be substituted or unsubstituted.

Unless otherwise stated, it is assumed that any heteroatom that is not in a full valence state has enough hydrogen atoms to complement its valence.

When a substituent is a non-terminal substituent, it is a subunit of the corresponding group, for example, alkyl corresponds to alkylene, cycloalkyl corresponds to cycloalkylene, heterocyclyl corresponds to heterocyclylene, alkoxy corresponds to alkyleneoxy, and the like.

In this disclosure, the term "substituted" means one or more hydrogen atoms on a specific group are substituted with specific substituents. The specific substituents are the substituents correspondingly described above or the substituents that appear in the various examples. Unless otherwise specified, a substituted group may have a substituent, selected from a specific group of groups, at any substitutable position of the group, and the substituent may be the same or different at each position. That is, each substitution is independent of each other. It will be understood by those skilled in the art that combinations of substituents contemplated by this disclosure are those that are stable or chemically achievable. Typical substituents include, but are not limited to, one or more of the following groups: such as hydrogen, deuterium, halogen (e.g., mono- or poly-halogen substituents, the poly-halogen substituents are such as trifluoromethyl or alkyl containing $Cl_3$), cyano, nitrile, nitro, oxo (eg =O), trifluoromethyl, trifluoromethoxy, cycloalkyl, alkenyl, alkynyl, heterocyclyl, aromatic ring, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, and $NR_bP(=O)_2R_e$, wherein $R_a$ may independently represent hydrogen, deuterium, alkyl, cycloalkyl, alkenyl, alkynyl, heterocyclyl or aromatic ring, $R_b$, $R_c$, and $R_d$, may independently represent hydrogen, deuterium, alkyl, cycloalkyl, heterocyclyl or aromatic ring, or $R_b$ and $R_c$ together with the N atom may form a heterocyclyl; $R_e$ may independently represent hydrogen, alkyl, cycloalkyl, alkenyl, alkynyl, heterocyclyl or aromatic ring. The above-mentioned typical substituents such as alkyl, cycloalkyl, alkenyl, cycloalkenyl, alkynyl, heterocyclyl or aromatic ring may be optionally substituted. The substituents are for example (but not limited to): halogen, hydroxyl, cyano, carboxyl (—COOH), C1-C6 alkyl, C2-C6 alkenyl, C2-C6 alkynyl, C3-C8 cycloalkyl, 3- to 12-membered heterocyclyl, aryl, heteroaryl, C1-C8 aldehyde, C2-C10 acyl, C2-C10 ester, amido, C1-C6 alkoxy, C1-C10 sulfonyl, C1-C6 ureido, and the like.

The terms "halo" or "halogen" includes fluorine, chlorine, bromine, or iodine.

The term "cyano" refers to —CN.

The term "hydroxy" or "hydroxyl" refers to —OH.

The term "dimethylphosphoryl" refers to

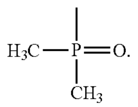

In this disclosure, the term "more" in "one or more" refers to 2, 3, 4 or 5 independently.

In this disclosure, the term "dysregulation of expression or activity or level of RET genes, RET kinases, or any one of the RET genes and the RET kinases" refers to or is caused by genetic mutations, including point mutation and gene fusion. For example, the dysregulation of expression or activity or level of RET genes, RET kinases, or any one of the RET genes and the RET kinases can be a mutation in an RET gene encoding an RET protein that is constitutively active or has increased activity compared to the protein encoded by the RET gene that does not include the mutation. For example, the dysregulation of expression or activity or level of RET genes, RET proteins, or any one of the RET genes and the RET kinases can be the result of a gene or chromosomal translocation that causes the expression of a fusion protein containing a first portion of RET comprising a functional kinase domain and a second portion of a chaperone (i.e., non-RET) protein.

Active Ingredient

As used herein, the terms "compound of this disclosure" and "active ingredient of this disclosure" are used interchangeably to refer to a compound of formula (I), or a pharmaceutically acceptable salt, hydrate, solvate, or isotopic compound (e.g., deuterated compound) or prodrug thereof (including but not limited to esters, amides, phosphate esters, phosphate sodium salt, amino acid esters, etc.). The terms also include racemates and optical isomers.

The compound of formula (I) has a structure shown as (I)

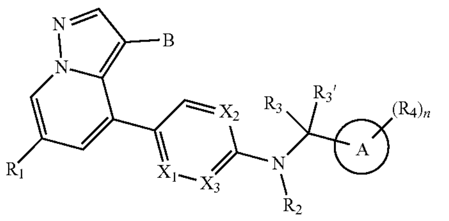

wherein, $X_1$, $X_2$, $X_3$, $R_1$, $R_2$, $R_3$, $R_3'$, $R_4$, n, A and B are defined as above.

Preferably, the compound of formula I has a structure of formula (II)

(II)

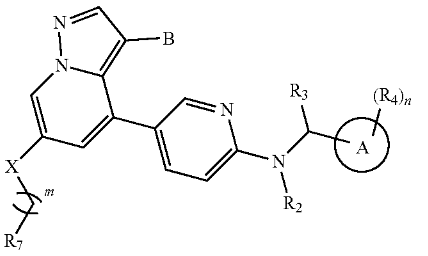

wherein $R_2$, $R_3$, $R_4$, $R_7$, m, n, A, B and X are defined as above.

Preferably, the compound of (I) has a structure of formula (III)

(III)

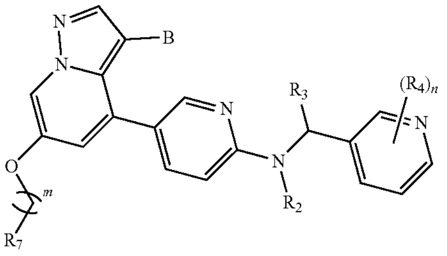

wherein B, $R_2$, $R_3$, $R_4$, $R_7$, m, and n are defined as above.

Preferably, the compound of formula (I) has a structure of formula (IV):

(IV)

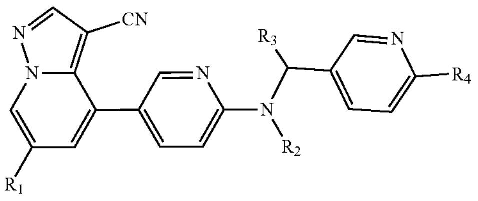

wherein $R_1$ is selected from a group consisting of —$OR_5$, —$N(R_5)(R_6)$, C3-C8 cycloalkyl, 3- to 8-membered heterocyclyl, C6-C14 aryl, and 5- to 14-membered heteroaryl;

$R_2$ is selected from a group consisting of H and C1-C6 alkyl;

$R_3$ is selected from a group consisting of H, halogen, cyano, hydroxyl, $CHF_2$, $CF_3$, C1-C6 alkyl, and C1-C6 alkoxy;

$R_4$ is independently selected from a group consisting of C3-C8 cycloalkyl, C6-C10 aryl, 5- to 10-membered heteroaryl, 3- to 8-membered heterocyclyl, —$OR_5$, —$OC(O)R_5$, —$N(R_5)(R_6)$, —$C(O)$—$N(R_5)(R_6)$, —$N(R_5)$—$C(O)R_6$, —$N(R_5)$—$C(O)OR_6$, and —$N(R_5)S(O)_2R_6$;

wherein $R_5$ and $R_6$ are each independently selected from substituted or unsubstituted groups selected from a group consisting of: H, C1-C6 alkyl, C3-C8 cycloalkyl, 3- to 8-membered heterocyclyl, C6-C10 aryl, and 5- to 10-membered heteroaryl, wherein the term “substituted” means “substituted with one or more groups selected from a group consisting of C1-C6 alkyl, cyano, halogen, hydroxyl, C3-C8 cycloalkyl, 3- to 8-membered heterocyclyl, C6-C10 aryl, and 5- to 10-membered heteroaryl”;

and the alkyl, cycloalkyl, aryl, heteroaryl, or heterocyclyl is unsubstituted or substituted with one or more groups selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

Preferably, the prodrugs of the compounds of formulas I to IV or their pharmaceutically acceptable salts have a structure of formula (V):

(V)

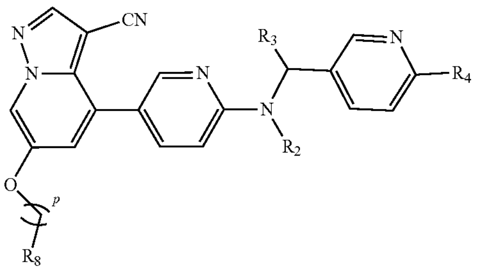

wherein $R_8$ is selected from a group consisting of

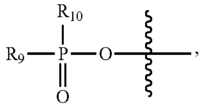, 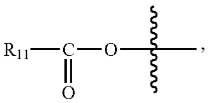, 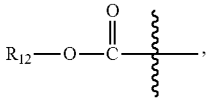, 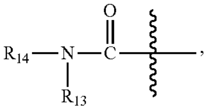, 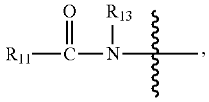, and 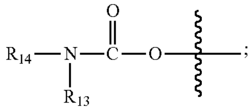;

$R_9$ and $R_{10}$ are each independently selected from substituted or unsubstituted C1-C6 alkyl, hydroxyl, and —OM; M is Na or K;

$R_{11}$ and $R_{12}$ are each independently selected from substituted or unsubstituted C1-C6 alkyl, substituted or unsubstituted C6-C10 aryl, substituted or unsubstituted 5- to 10-membered heteroaryl;

$R_{13}$ and $R_{14}$ are each independently selected from substituted or unsubstituted C1-C6 alkyl, substituted or unsubstituted C6-C10 aryl, substituted or unsubstituted 5- to 10-membered heteroaryl;

p is 1, 2 or 3;

wherein the term "substituted" means "substituted with one or more groups selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto and amino";

$R_2$, $R_3$ and $R_4$ are defined as above.

Preferably, in formulas I to IV, $R_4$ is a substituted or unsubstituted 5- to 6-membered heteroaryl; preferably, $R_4$ is a substituted or unsubstituted group selected from a group consisting of pyrrolyl, pyrazolyl, imidazolyl, oxazolyl, isoxazolyl, thiazolyl, thiadiazolyl, isothiazolyl, furyl, pyridyl, pyrazinyl, pyrimidinyl, pyridazinyl, triazinyl, triazolyl and tetrazolyl, wherein the term "substituted" means "substituted with one or more groups selected from a group consisting of C1-C6 alkyl, $CHF_2$, $CF_3$, halogen (preferably F), cyano, hydroxyl, carboxyl, ester group, amido, sulfonamido, carbonyl, mercapto, amino and dimethylphosphoryl";

$R_2$ and $R_3$ are each independently selected from a group consisting of H and C1-C6 alkyl.

The salts that the compounds of this disclosure may form are also within the scope of this disclosure. Unless otherwise specified, the compounds of this disclosure are understood to include their salts. The term "salt", as used herein, refers to salts in an acid or basic form formed using inorganic or organic acids and bases. In addition, when the compound of this disclosure contains a basic moiety, the compound includes, but is not limited to, pyridine or imidazole, and when it contains an acidic moiety, the compound includes, but is not limited to, a carboxylic acid, and the zwitterion ("inner salt") that may be formed is within the scope of the term "salt". Pharmaceutically acceptable (i.e., non-toxic, physiologically acceptable) salts are preferred, although other salts are also used, for example, in a separation or purification step in the preparation process. The compounds of this disclosure may form salts. For example, Compound I react with a certain amount, such as an equivalent amount, of an acid or base to produce a salt in a medium, or the compound is lyophilized in an aqueous solution to produce a salt.

The compounds of this disclosure contain basic moieties, including but not limited to amines or pyridine or imidazole rings, which may form salts with organic or inorganic acids. Typical acid-formed salts include acetates (e.g., formed with acetic acid or trihaloacetic acid, such as trifluoroacetic acid), adipates, alginates, ascorbates, aspartates, benzoates, besylates, bisulfates, borates, butyrates, citrates, camphorates, camphor sulfonates, cyclopentane propionates, diglycolates, dodecyl sulfates, ethanesulfonates, fumarates, glucoheptonates, glycerophosphates, hemisulfates, heptanoates, hexanoates, hydrochlorides, hydrobromides, hydroiodides, isethionates (e.g., 2-hydroxyethanesulfonate), lactates, maleates, mesylates, naphthalenesulfonates (e.g., 2-naphthalenesulfonate), nicotinates, nitrates, oxalates, pectates, persulfates, phenylpropionates (e.g., 3-phenylpropionate), phosphates, picrates, pivalates, propionates, salicylates, succinates, sulfates (e.g., formed with sulfuric acid), sulfonates, tartrates, thiocyanates, tosylates such as p-toluenesulfonates, dodecanoates, and the like.

Certain compounds of this disclosure may contain acidic moieties, including but not limited to carboxylic acids, which may form salts with various organic or inorganic bases. Typical base-formed salts include ammonium salts, alkali metal salts (such as sodium, lithium and potassium salts), alkaline earth metal salts such as calcium and magnesium salts and salts formed with organic bases (e.g., organic amines) such as benzathine, dicyclohexylamine, hepamine (salt formed with N,N-bis(dehydroabietyl)ethylenediamine), N-methyl-D-glucosamine, N-methyl-D-glucosamide, tert-butyl amines, and salts with amino acids such as arginine, lysine, and the like. Basic nitrogen-containing groups can form halide quaternary ammonium salts, such as small molecule alkyl halides (e.g., methyl, ethyl, propyl and butyl chlorides, bromides and iodides), dialkyl sulfates (e.g., dimethyl sulfate, diethyl, dibutyl and dipentyl), long-chain halides (e.g., decyl, dodecyl, tetradecyl and tetradecyl chlorides, bromides and iodides), aralkyl halides (such as benzyl and phenyl bromides), and the like.

Prodrugs and solvates of the compounds of this disclosure are also within the scope of this disclosure. The term "prodrug" as used herein refers to a compound that undergoes chemical transformation through metabolic or chemical processes to produce the compound of this disclosure, its salts or its solvates in the treatment of related diseases. The compounds of this disclosure include solvates, such as hydrates.

The compounds, salts or solvates of this disclosure, may exist in tautomeric forms (e.g., amides and imine ethers). All of these tautomers are part of this disclosure.

Stereoisomers of all the compounds (e.g., those due to asymmetric carbon atoms that may exist for various substitutions), including their enantiomeric and diastereomeric forms, are contemplated by this disclosure. Individual stereoisomers of the compounds of this disclosure may not exist concurrently with other isomers (e.g., as a pure or substantially pure optical isomer with specific activity), or may be mixtures, such as racemates, or mixtures with all other stereoisomers or a part thereof. The chiral center of this disclosure has two configurations, S and R, which are defined by the IUPAC Recommendation 1974. The racemic form can be resolved by physical methods, such as fractional crystallization, or by derivatization to diastereomers, separation crystallization, or separation by chiral column chromatography. Individual optical isomers can be obtained from racemates by suitable methods, including but not limited to conventional methods, such as salt formation with an optically active acid followed by crystallization.

For the compounds of this disclosure, the compounds obtained by successive preparation, separation and purification have a weight content equal to or greater than 90%, for example, equal to or greater than 95%, equal to or greater than 99% ("very pure" compounds), listed in the text description. Herein such "very pure" compounds of this disclosure are also intended to be part of this disclosure.

All configurational isomers of the compounds of this disclosure are contemplated, whether in an admixture, pure or very pure form. The definition of compounds of this disclosure includes both cis (Z) and trans (E) olefin isomers, as well as carbocyclic and heterocyclic cis and trans isomers.

Throughout the specification, groups and substituents may be selected to provide stable fragments and compounds.

Definitions of specific functional groups and chemical terms are detailed below. For purposes of this disclosure, chemical elements are as defined in the Periodic Table of the Elements, CAS version, Handbook of Chemistry and Physics, 75th Ed. Definitions of specific functional groups are also described therein. In addition, basic principles of organic chemistry and specific functional groups and reactivity are also stated in "Organic Chemistry", Thomas Sorrell, University Science Books, Sausalito: 1999, the entire contents of which are incorporated by reference.

Some compounds of this disclosure may exist in specific geometric or stereoisomeric forms. This disclosure covers all compounds, including their cis and trans isomers, R and S enantiomers, diastereomers, (D) isomers, (L) isomers, racemic mixtures and other mixtures. In addition, asymmetric carbon atoms may represent substituents such as alkyl. All isomers and their mixtures are incorporated herein.

According to this disclosure, the mixture of isomers may include isomers in various ratios. For example, mixture of only two isomers can have the combinations: 50:50, 60:40, 70:30, 80:20, 90:10, 95:5, 96:4, 97:3, 98:2, 99:1, and 100:0, and all ratios of isomers are within the scope of this disclosure. Similar ratios readily understood by those of ordinary skill in the art, as well as ratios that are mixtures of more complex isomers, are also within the scope of this disclosure.

This disclosure also includes isotopically labeled compounds that are equivalent to the original compounds disclosed herein. In practice, however, it usually occurs that one or more atoms are substituted with atoms with different atomic weights or mass numbers. Examples of isotopes that may be listed as compounds of this disclosure include hydrogen, carbon, nitrogen, oxygen, phosphorus, sulfur, fluorine and chlorine isotopes such as $^{2}H$, $^{3}H$, $^{13}C$, $^{11}C$, $^{14}C$ $^{15}N$, $^{18}O$, $^{17}O$, $^{31}P$, $^{32}P$, $^{35}S$, $^{18}F$ and $^{36}Cl$. The compounds of this disclosure, or enantiomers, diastereomers, isomers, or pharmaceutically acceptable salts or solvates, which contain isotopes or other isotopic atoms of the above compounds are within the scope of this disclosure. Some isotopically labeled compounds of this disclosure, such as radioisotopes of $^{3}H$ and $^{14}C$, are also included, and are useful in tissue distribution experiments of drugs and substrates. Tritium, i.e. $^{3}H$, and carbon-14, i.e. $^{14}C$, are relatively easy to prepare and detect. So, they are the first choice among isotopes. In addition, a heavier isotope substituent such as deuterium, i.e., $^{2}H$, may be preferred in some cases due to its good metabolic stability, which may have advantages in certain therapies, such as increased half-life or reduced dosage in vivo. Isotopically labeled compounds can be prepared using general methods by substituting readily available isotopically labeled reagents for non-isotopically labeled reagents using the solutions disclosed in the Examples.

If a specific enantiomer of a compound of this disclosure is to be engineered, it can be prepared by asymmetric synthesis, or by derivatization with a chiral auxiliary, separation of the resulting diastereomeric mixture, and removal of the chiral auxiliary to obtain a pure enantiomer. In addition, if the molecule contains a basic functional group, such as an amino acid, or an acidic functional group, such as a carboxyl group, it can, together with a suitable optically active acid or base, form diastereomeric salts, which can be separated by conventional means such as separation crystallization or chromatography, and then the pure enantiomers can be obtained.

As described herein, the compounds of this disclosure may be substituted with any number of substituents or functional groups to extend their scope. In general, whether the term "substituted" appears before or after the term "optional", the formulas that include substituents in the formulations of this disclosure refer to the replacement of hydrogen radicals with the specified structural substituents. When multiple positions in a particular structure are substituted with multiple specified substituents, the substituents may be the same or different at each position. The term "substituted" as used herein includes all allowable substitutions with organic compounds. Broadly speaking, the permissible substituents include acyclic, cyclic, branched, unbranched, carbocyclic, heterocyclic, aromatic and non-aromatic organic compounds. In this disclosure, for example, the heteroatom nitrogen may have hydrogen substituents or any permissible organic compound described above to complement its valence. Furthermore, this disclosure is not intended to limit in any way the permissible substituted organic compounds. This disclosure contemplates that the combination of substituents and variable groups is well suited for the treatment of diseases in the form of stable compounds. The term "stable" as used herein refers to a compound that is stable enough to be detected for a sufficient period of time to maintain the structural integrity of the compound, preferably for a sufficient period of time, and is used herein for the above-mentioned purposes.

The metabolites of the compounds of this disclosure and pharmaceutically acceptable salts of the compounds, as well as prodrugs that can be converted into the structures of the compounds of this disclosure and their pharmaceutically acceptable salts in vivo, are also included in the claims of this disclosure.

Preparation Method

Methods for preparing compounds of formula (I) are described in the following solutions and examples. Starting materials and intermediates were purchased from commercial sources, prepared by known procedures, or otherwise described. In some cases, the order in which the steps of the reaction solution are performed can be changed to facilitate the reaction or to avoid unwanted side reaction products.

The preparation method of the compound of formula (I) of this disclosure is described in more detail below, but these specific methods do not constitute any limitation to this disclosure. The compounds of this disclosure can also be optionally prepared by combining various synthesis methods described in this specification or known in the art, and such combinations can be easily performed by those skilled in the art to which this disclosure belongs.

Usually, in the preparation process, each reaction is usually carried out at 0° C. to 90° C. in a suitable solvent under the protection of inert gas, and the reaction time is usually 2 h to 24 h.

Method 1:

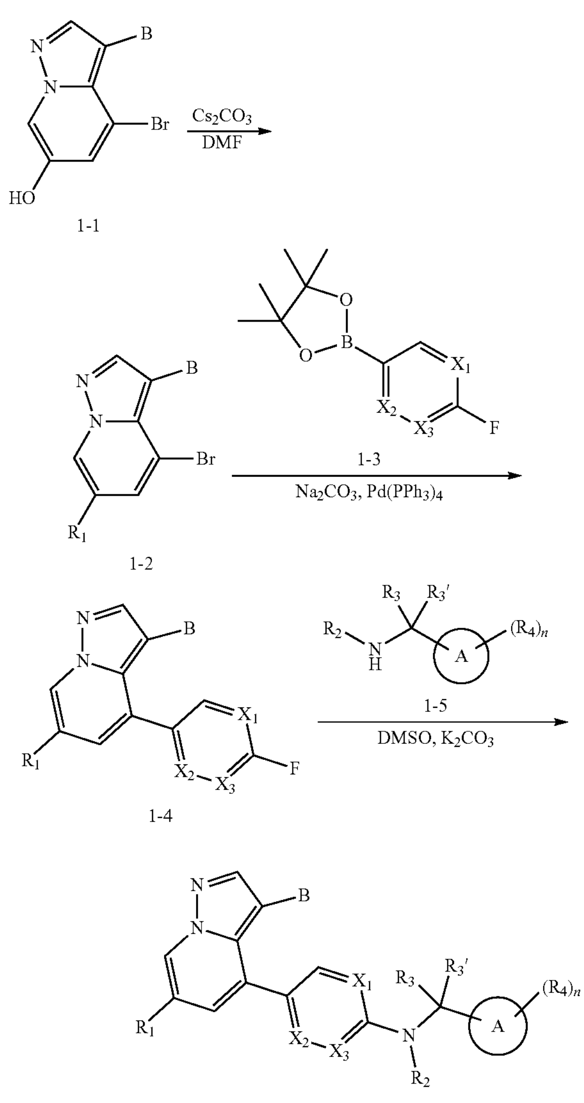

1-1, 1-2, 1-3, 1-4, 1-5, 1-6

$X_1$, $X_2$, $X_3$, A, B, $R_1$, $R_2$, $R_3$, $R_3'$, n and $R_4$ are defined as above.

The method includes the following steps:

(i) causing compound 1-1 to react in an inert solvent (e.g., DMF) under an alkaline condition (e.g., $Cs_2CO_3$) to obtain compound 1-2;

(ii) causing compound 1-2 to have a coupling reaction with compound 1-3 under an alkaline condition (e.g., $Na_2CO_3$) in the presence of a catalyst (e.g., a palladium catalyst), to obtain compound 1-4; and (iii) causing compound 1-4 to react with compound 1-5 in an inert solvent (e.g., DMSO) under an alkaline condition (e.g., $K_2CO_3$) at a high temperature to obtain compound 1-6.

Method 2:

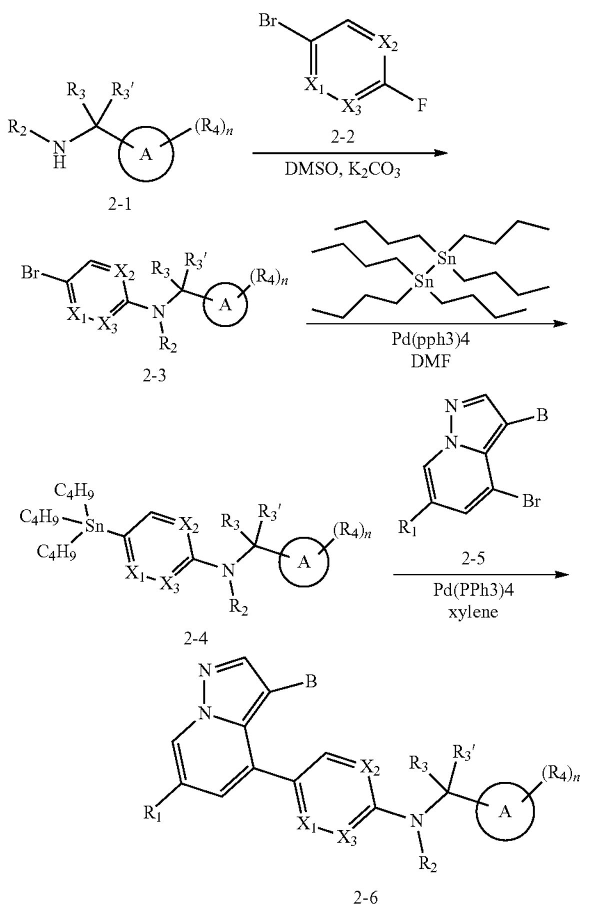

2-1, 2-2, 2-3, 2-4, 2-5, 2-6

$X_1$, $X_2$, $X_3$, A, B, $R_1$, $R_2$, $R_3$, $R_3'$, n and $R_4$ are defined as above.

The method includes the following steps:

(i') causing compound 2-1 to react with compound 2-2 in an inert solvent (e.g., DMSO) under an alkaline condition (e.g., $K_2CO_3$) at a high temperature to obtain compound 2-3;

(ii') causing compound 2-3 to react with $Sn_2(Bu\text{-}n)_6$ in an inert solvent (e.g., DMF) in the presence of a catalyst (e.g., a palladium catalyst) to obtain a tin reagent compound 2-4; and (iii') causing the tin reagent compound 2-4 to have a coupling reaction with compound 2-5 in an inert solvent (e.g., xylene) in the presence of a catalyst (e.g., a palladium catalyst) to obtain compound 2-6.

Method 3:

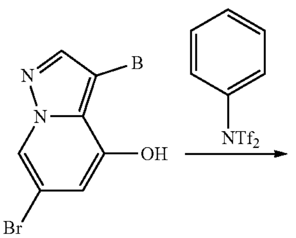

3-1

-continued

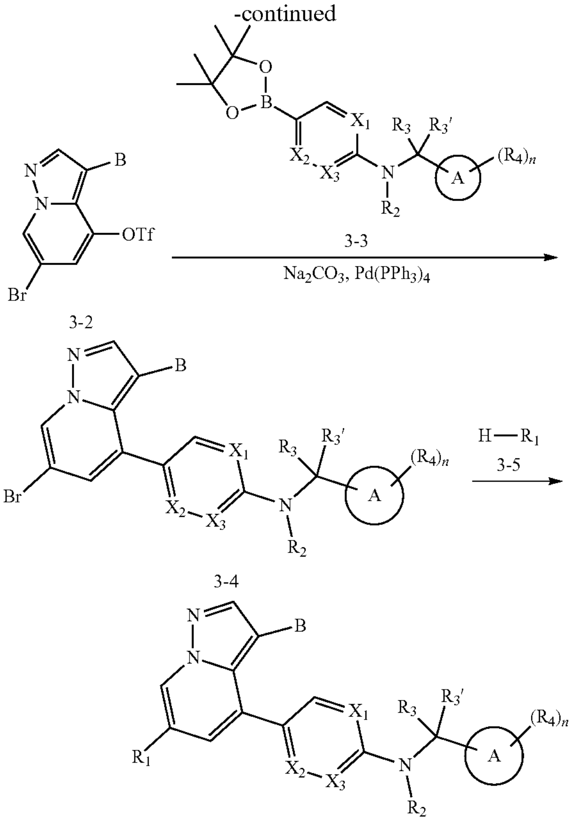

3-6

In the formulas, $X_1$, $X_2$, $X_3$, A, B, $R_1$, $R_2$, $R_3$, $R_3'$ and $R_4$ are defined as above.

The method includes the following steps:

(i) causing compound 3-1 to react with N-phenylbis (trifluoromethanesulfonyl)imide in an inert solvent (e.g., DMF) under an alkaline condition (e.g., DIPEA) to obtain compound 3-2;

(ii) causing the compound 3-2 to have a coupling reaction with compound 3-3 in a mixed solvent (e.g., dioxane/water) in the presence of a catalyst (e.g., a palladium catalyst) to obtain compound 3-4;

(iii) causing compound 3-4 to react with compound 3-5 under an alkaline condition (e.g., cesium carbonate) in the presence of a catalyst (e.g., a palladium catalyst) to obtain compound 3-6.

In the above reaction steps, the reaction solvents, reaction temperature, reaction time, catalysts, and the like can be selected according to the specific reactants.

Pharmaceutical Composition and its Application Method

The pharmaceutical composition of this disclosure is used for preventing and/or treating a disease selected from the following: inflammation, cancers, cardiovascular diseases, infection, immune diseases, and metabolic diseases.

The compound of general formula (I) may be used in combination with other drugs known to treat or ameliorate similar conditions. In a case of co-administration, the administration mode and dosage of the original drug may remain unchanged, while the compound of formula (I) is administered concurrently or subsequently. When the compound of formula (I) is administered concomitantly with one or more other drugs, a pharmaceutical composition containing one or more known drugs and the compound of formula (I) at the same time may be preferred. Combined pharmacotherapy also includes administration of a compound of formula (I) and one or more other known drugs at overlapping time periods. When a compound of formula (I) is used in combination with one or more other drugs, the doses of the compound of formula (I) or known drugs may be lower than their doses when they are used alone.

The drugs or active ingredients that can be used in combination with the compound of general formula (I) include but are not limited to: a PD-1 inhibitor (such as Nivolumab, Pembrolizumab, JS-001, SHR-120, BGB-A317, IBI-308, GLS-010, GB-226, STW204, HX008, HLX10, BAT1306, AK105, LZM 009 or biosimilars thereof, etc.), a PD-L1 inhibitor (such as Durvalumab, Atezolizumab, CS1001, KN035, HLX20, SHR-1316, BGB-A333, JS003, CS1003, KL-A167, F520, GR1405, MSB2311 or biosimilars thereof, etc.), a CD20 antibody (such as Rituximab, Obinutuzumab, Ofatumumab, Tositumumab, Tiimumab, etc.), a CD47 antibody (such as Hu5F9-G4, CC-90002, TTI-621, TTI-622, OSE-172, SRF-231, ALX-148, NI-1701, SHR-1603, IBI188, IMM01), an ALK inhibitor (such as Ceritinib, Alectinib, Brigatinib, Lorlatinib, and Oclatinib), a PI3K inhibitor (such as Ederatinib, Dactolisib, Taselisib, Buparlisib, etc.), a BTK Inhibitor (such as Ibrutinib, Tirabrutinib, Acalabrutinib, etc.), an EGFR inhibitor (such as Afatinib, Gefitinib, Erlotinib, Lapatinib, Dacomitinib, Icotinib, Canetinib, etc.), a VEGFR inhibitor (such as Sorafenib, Pazopanib, Rivatinib, Cabozantinib, Sunitinib, Donafenib, etc.), an HDAC inhibitor (such as Givinostat, Droxinostat, Entinostat, Darcylast, Tycodinaline, etc.), a CDK inhibitor (such as Palbociclib, Ribociclib, Abemaciclib, Lerociclib, etc.), a MEK inhibitor (such as Selumetinib (AZD6244), Trametinib (GSK1120212), PD0325901, U0126, AS-703026, PD184352 (CI-1040), etc.), an Akt inhibitor (such as MK-2206, Ipatasertib, Capivasertib, Afuresertib, Uprosertib, etc.), an mTOR inhibitor (such as Vistusertib, etc.), an SHP2 inhibitor (such as RMC-4630, JAB-3068, TNO155, etc.), an IGF-1R inhibitor (such as Ceritinib, Ocaltinib, Iinsitinib, BMS-754807, GSK1838705A, etc.), and a combination thereof.

The dosage forms of the pharmaceutical composition of this disclosure include (but are not limited to): injections, tablets, capsules, aerosol, suppository, films, drop pills, external liniments, controlled-release or sustained-release or nano preparations.

The pharmaceutical composition of this disclosure includes the compound of this disclosure or a pharmacologically acceptable salt thereof within a safe and effective dose and a pharmacologically acceptable excipient or carrier. The "safe and effective dose" means that the dose of the compound is sufficient to significantly improve the condition without causing serious side effects. Usually, the pharmaceutical composition contains 1 to 2000 mg of the compound of this disclosure/dose, more preferably 10 to 1000 mg of the compound of this disclosure/dose. Preferably, the "one dose" means a capsule or tablet.

The "pharmaceutically acceptable carrier" means: one or more compatible solid or liquid filler or gel substances, which are suitable for human use, and which must be of sufficient purity and sufficiently low toxicity. "Compatible" as used herein means that components in a composition can be blended with the compound of this disclosure and with each other without significantly reducing the efficacy of the compound. Part of examples of the pharmaceutically acceptable carrier include cellulose and its derivatives (such as sodium carboxymethyl cellulose, sodium ethyl cellulose, cellulose acetate, and the like), gelatin, talc, solid lubricants (such as stearic acid and magnesium stearate), calcium sulfate, vegetable oils (such as soybean oil, sesame oil, peanut oil, olive oil, and the like), polyols (such as propylene glycol, glycerin, mannitol, sorbitol, and the like), emulsifiers (such as Tween®), wetting agents (such as sodium lauryl sulfate), colorants, flavors, stabilizers, antioxidants, preservatives, pyrogen-free water, and the like.

The mode of administration of the compounds or pharmaceutical compositions of this disclosure is not particularly limited, and representative modes of administration include (but are not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compound is mixed with at least one conventional inert excipient (or carrier), such as sodium citrate or dicalcium phosphate, or with: (a) a filler or compatibilizer, such as starch, lactose, sucrose, glucose, mannitol and silicic acid; (b) a binder, such as hydroxymethylcellulose, alginate, gelatin, polyvinylpyrrolidone, sucrose and acacia; (c) a humectant, such as glycerol; (d) a disintegrant, such as agar, calcium carbonate, potato starch or tapioca starch, alginic acid, some complex silicates, and sodium carbonate; (e) a sustained-solubilization agent, such as paraffin; (f) an absorption accelerator, such as a quaternary ammonium compound; (g) a wetting agent, such as cetyl alcohol and glyceryl monostearate; (h) an adsorbent, such as kaolin; and (i) a lubricant, such as talc, calcium stearate, magnesium stearate, solid polyethylene glycol, sodium lauryl sulfate, or mixtures thereof. In capsules, tablets and pills, the dosage form may also include a buffering agent.

Solid dosage forms such as tablets, dragees, capsules, pills and granules can be prepared using coating and shell materials, such as enteric coatings and other materials well known in the art. They may contain an opacifying agent, and the release of the active compound or compounds in such compositions may be in a certain part of the digestive tract in a delayed manner. Examples of an embedding component that can be employed are polymeric substances and waxes. If desired, the active compound may also be in microencapsulated form with one or more of the above-mentioned excipients.

Liquid dosage forms for oral administration include pharmaceutically acceptable emulsions, solutions, suspensions, syrups or tinctures. In addition to the active compound, liquid dosage forms may contain inert diluents conventionally employed in the art, such as water or other solvents solubilizers and emulsifiers, such as ethanol, isopropanol, ethyl carbonate, ethyl acetate, propylene glycol, 1,3-butanediol, dimethylformamide and oils, especially cottonseed oil, peanut oil, corn germ oil, olive oil, castor oil and sesame oil or mixtures thereof.

Besides these inert diluents, the compositions can also contain adjuvants such as wetting agents, emulsifiers, suspensions, sweetening agents, flavoring agents and perfuming agents.

In addition to the active compounds, suspensions may contain suspending agents such as ethoxylated isostearyl alcohols, polyoxyethylene sorbitol and sorbitan esters, microcrystalline cellulose, aluminum methoxide and agar or mixtures thereof.

Compositions for parenteral injection may contain physiologically acceptable sterile aqueous or anhydrous solutions, dispersions, suspensions or emulsions and sterile powders for reconstitution into sterile injectable solutions or dispersions. Suitable aqueous and non-aqueous carriers, diluents, solvents or excipients include water, ethanol, polyols and suitable mixtures thereof.

Dosage forms for topical administration of the compounds of this disclosure include ointments, powders, patches, sprays and inhalants. The active ingredient is mixed under a sterile condition with a physiologically acceptable carrier and any preservatives, buffers, or propellants that may be required if necessary.

The treatment methods of this disclosure may be administered alone or in combination with other treatment means or treatment agents.

When the pharmaceutical composition is used, a safe and effective dose of the compound of this disclosure is applied to a mammal (such as a human) in need of treatment, wherein the dose is a pharmaceutically effective dose for administration, and for a person with a body weight of 60 kg, the daily dose is usually 1 mg to 2000 mg, preferably 50 mg to 1000 mg. Certainly, the specific dosage should also take into account the route of administration, the patient's health and other factors, which are all within the skill of the skilled physician.

This disclosure further provides a preparation method of a pharmaceutical composition, including the steps of: mixing a pharmaceutically acceptable carrier with the compound of the general formula (I) or its crystal form, pharmaceutically acceptable salt, hydrate or solvate according to this disclosure to form a pharmaceutical composition.

This disclosure further provides a treatment method, including the steps of: applying the compound of general formula (I), or its crystalline form, pharmaceutically acceptable salt, hydrate or solvate according to this disclosure to an object in need of treatment, or applying the pharmaceutical composition of this disclosure, for selectively inhibiting RET.

This disclosure has the following main advantages:

(1) The compounds of this disclosure have excellent inhibitory ability to RET kinase, and excellent selectivity to RET kinase, and have low inhibitory activity against other kinases such as VEGFR2.

(2) The compounds of this disclosure have lower toxic and side effects.

(3) The compounds of this disclosure have better pharmacodynamic and pharmacokinetic properties.

EXAMPLE

Universal Method

This disclosure will be further described below in conjunction with specific embodiments. It should be understood that these examples are only used to illustrate this disclosure and not to limit the scope of this disclosure. The experimental methods in the following examples where their specific conditions are not stated usually are implemented according to conventional conditions such as conditions stated by Sambrook et al., in Molecular Cloning: Laboratory Manual (New York: Cold Spring Harbor Laboratory Press, 1989), or according to conditions as suggested by manufacturers. Unless otherwise stated, percentages and parts are calculated by weight.

Unless otherwise defined, all professional and scientific terms used herein have the same meanings as those familiar to those skilled in the art. In addition, any methods and materials similar or equivalent to those described can be used in the methods of this disclosure. Methods and materials for preferred embodiments described herein are provided for illustrative purposes only.

The structures of the compounds of this disclosure were determined by nuclear magnetic resonance (NMR) and liquid chromatography-mass spectrometry (LC-MS).

NMR was performed using Bruker AVANCE-400 and Bruker AVANCE-500 NMR spectrometers; determination solvents include deuterated dimethyl sulfoxide (DMSO-$d_6$), deuterated acetone ($CD_3COCD_3$), deuterated chloroform ($CDCl_3$) and deuterated methanol ($CD_3OD$), and the like. The internal standard is tetramethylsilane (TMS). The chemical shift is measured in parts per million (ppm).

LC-MS was carried out using an Agilent 1260 mass spectrometer. The HPLC assay was performed using an Agilent 1100 high-pressure chromatograph (Microsorb 5 micron C18 100×3.0 mm column).

Qingdao GF254 silica gel plate was used for thin layer chromatography; 0.15-0.20 mm plate was used for TLC and 0.4 mm-0.5 mm plate was used for preparative thin layer chromatography. Column chromatography generally uses Qingdao 200-300 mesh silica gel as a carrier.

The starting materials in the examples of this disclosure are all known and commercially available, or can be synthesized by using or according to reference documents reported in the art.

Unless otherwise specified, all the reactions of this disclosure were carried out under the protection of dry inert gas (such as $N_2$ or Ar) by continuous magnetic stirring, and the reaction temperature was all in degrees Celsius.

The following abbreviations are used throughout this disclosure:

THF: tetrahydrofuran
DCM: dichloromethane
PE: petroleum ether
$Na_2CO_3$: sodium carbonate
MeOH: methanol
HCl: hydrochloric acid
$Pd(PPh_3)_4$: tetrakistriphenylphosphine palladium
$K_2CO_3$: potassium carbonate
$H_2O$: water
TEA: triethylamine
DIEA: N,N-diisopropylethylamine
DMF: N,N-dimethylformamide
DMSO: dimethyl sulfoxide
$NaBH_4$: sodium borohydride
$Sn_2(Bu-n)_6$: hexahexyl ditin
CuI: Cuprous iodide
$Cs_2CO_3$: cesium carbonate
$K_3PO_4$: potassium phosphate
$Pd_2(dba)_3$: tris(dibenzylideneacetone)dipalladium
Pd/C: palladium on carbon
Xantphos: 2-dicyclohexylphosphorus-2,4,6-triisopropylbiphenyl
EA: ethyl acetate
$Boc_2O$: di-tert-butyl dicarbonate
$Pd(dppf)_2Cl_2$: [1,1'-bis(diphenylphosphino)ferrocene] palladium dichloride
NaH: sodium hydrogen
$CH_3I$: iodomethane
L-Proline: L-Proline
L-Selectride: Lithium tri-sec-butyl borohydride Synthesis of Intermediate 1

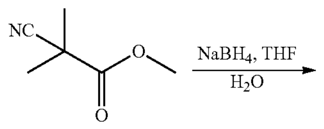

-continued

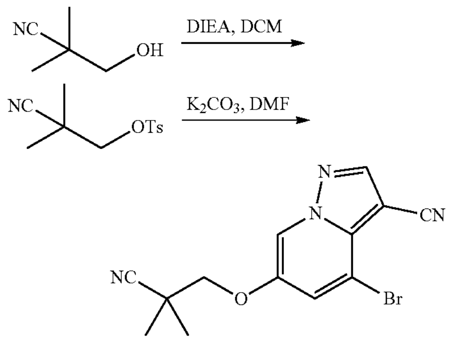

Step 1: 3-hydroxy-2,2-dimethylpropionitrile

At room temperature, methyl 2-cyano-2-methylpropanoate (2.0 g, 15.7 mmol) was dissolved in THF/$H_2O$=20/40 mL, and the resulting solution was cooled to 0° C. Sodium borohydride (1.78 g, 53.4 mmol) was added in batches, and then addition was completed. Reaction was carried out at room temperature for 4 h until the reaction was completed. Extraction with EA was carried out, and the organic phase was dried, filtered, concentrated, and subjected to column chromatography (PE:EA=1:1) to obtain 1.4 g of 3-hydroxy-2,2-dimethylpropionitrile with a yield of 90%. MS m/z (ESI): 100.2 $[M+H]^+$.

Step 2: 2-cyano-2-methylpropyl 4-methylbenzenesulfonate

At room temperature, 3-hydroxy-2,2-dimethylpropionitrile (1.4 g, 14.1 mmol) and DIEA (2.85 g, 28.28 mmol) were dissolved in dichloromethane (20 mL), and the resulting solution was cooled to 0° C. P-toluenesulfonyl chloride (2.6 g, 14.1 mmol) was added, and then addition was completed. Reaction was carried out at room temperature overnight until the reaction was completed. Extraction with DCM was carried out, and the organic phase was dried, filtered, concentrated, and subjected to column chromatography (PE:EA=3:1) to obtain 1.4 g of 2-cyano-2-methylpropyl 4-methylbenzenesulfonate with a yield of 36%. MS m/z (ESI): 254.1 $[M+H]^+$.

Step 3: 4-bromo-6-(2-cyano-2-methylpropoxy)pyrazolo[1,5-a]pyridine-3-carbonitrile At room temperature, 4-bromo-6-hydroxypyrazolo[1,5-a]pyridine-3-carbonitrile (350 mg, 1.37 mmol) and 2-cyano-2-methylpropyl 4-methylbenzenesulfonate (564 mg, 2.2 mmol) were dissolved in DMF (10 mL). Potassium carbonate (1.43 g, 4.44 mmol) was added, and then addition was completed. The mixed solution was stirred at 100° C. overnight to react until the reaction was completed. The resulting reaction solution was filtered, concentrated under reduced pressure to remove the solvent, and subjected to column chromatography (PE:EA=2:1) to obtain 170 mg of 4-bromo-6-(2-cyano-2-methylpropoxy)pyrazolo[1,5-a]pyridine-3-carbonitrile with a yield of 36%. MS m/z (ESI): 319.6 $[M+H]^+$.

Synthesis of Intermediate 2

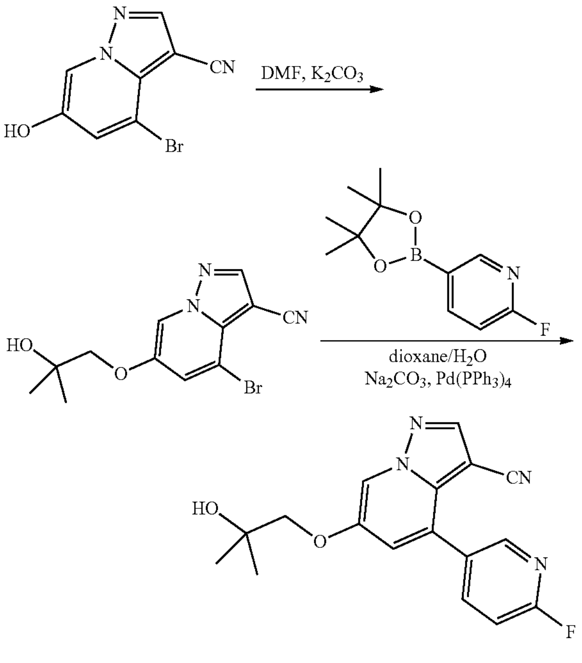 [SMILES: N#Cc1cnn2cc(O)cc(Br)c12 ; CC(C)(O)COc1cc(Br)c2c(C#N)cnn2c1 ; CC1(C)OB(c2ccc(F)nc2)OC1(C)C ; CC(C)(O)COc1cc(-c2ccc(F)nc2)c2c(C#N)cnn2c1]

Step 1: Synthesis of 4-bromo-6-(2-hydroxy-2-methylpropoxy)pyrazolo[1,5-a]pyridine-3-carbonitrile At room temperature, 4-bromo-6-hydroxypyrazolo[1,5-a]pyridine-3-carbonitrile (2.0 g, 8.4 mmol) and 2,2-dimethyloxirane (7.38 mL, 84 mmol) were dissolved in DMF (10 mL). Potassium carbonate (3.38 g, 25 mmol) was added, and then addition was completed. The mixed solution was stirred at 80° C. overnight to react in a sealed tube until the reaction was completed. The resulting reaction solution was filtered, concentrated under reduced pressure to remove the solvent, and subjected to column chromatography (PE:EA=2:1) to obtain 1.5 g of 4-bromo-6-(2-hydroxy-2-methylpropoxy)pyrazolo[1,5-a]pyridine-3-carbonitrile with a yield of 57%. MS m/z (ESI): 310.6 $[M+H]^+$.

Step 2: Synthesis of 4-(6-fluoropyridin-3-yl)-6-(2-hydroxy-2-methylpropoxy)pyrazolo[1,5-a]pyridine-3-carbonitrile 4-bromo-6-(2-hydroxy-2-methylpropoxy)pyrazolo[1,5-a]pyridine-3-carbonitrile (2.0 g, 6.4 mmol) and 2-fluoro-5-(4,4,5,5-tetramethyl-1,3,2-dioxaborolane-2-yl)pyridine (2.16 g, 9.9 mmol) were dissolved in dioxane:water=(4:1, 50 mL), and then $Pd(PPh_3)_4$ (747 mg, 0.64 mmol) and sodium carbonate (2.73 g, 25.7 mmol) were added to the resulting solution. The mixed solution was then stirred at 90° C. overnight under the protection of $N_2$. After the reaction was completed, water was added to quench the reaction, and the organic phase was separated, washed with water, dried, and subjected to column chromatography (DCM:MeOH=20:1) to obtain 1.7 g of 4-(6-fluoropyridin-3-yl)-6-(2-hydroxy-2-methylpropoxy)pyrazolo[1,5-a]pyridine-3-carbonitrile with a yield of 80%. MS m/z (ESI): 327.2 $[M+H]^+$.

Synthesis of Intermediate 3

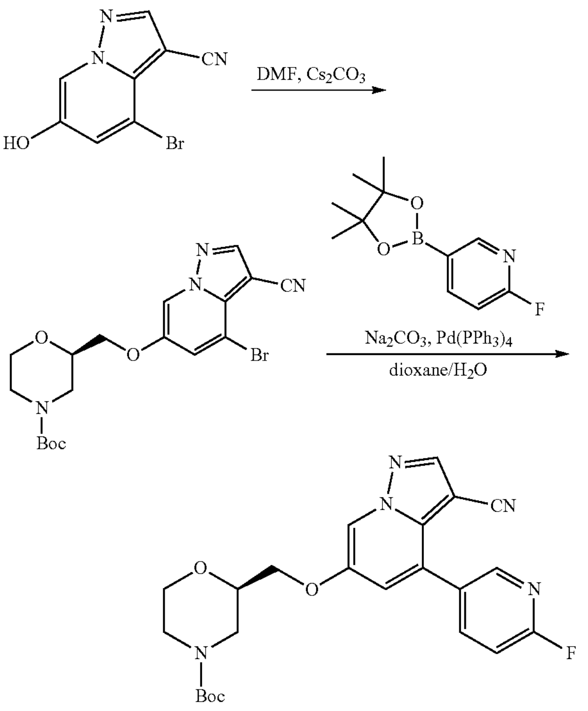 [SMILES: N#Cc1cnn2cc(O)cc(Br)c12 ; CC(C)(C)OC(=O)N1CCO[C@@H](COc2cc(Br)c3c(C#N)cnn3c2)C1 ; CC1(C)OB(c2ccc(F)nc2)OC1(C)C ; CC(C)(C)OC(=O)N1CCO[C@@H](COc2cc(-c3ccc(F)nc3)c3c(C#N)cnn3c2)C1]

Step 1: Synthesis of tert-butyl (R)-2-((4-bromo-3-cyanopyrazolo[1,5-a]pyridin-6-yl)oxy)methyl)morpholine-4-formate 4-bromo-6-hydroxypyrazolo[1,5-a]pyridine-3-carbonitrile (1.0 g, 4.2 mmol), tert-butyl (R)-2-bromomethylmorpholine-4-formate tert-butyl (1.6 g, 5.9 mmol) and cesium carbonate (4.1 g, 12.6 mmol) were dissolved in DMF (20 mL), and the mixed solution was stirred at 50° C. for 18 h to react until the reaction was completed. The resulting reaction solution was diluted with ethyl acetate, filtered, concentrated under reduced pressure to remove the solvent, and subjected to column chromatography (PE:EA=2:1) to obtain 1.13 g of tert-butyl (R)-2-((4-bromo-3-cyanopyrazolo[1,5-a]pyridin-6-yl)oxy)methyl)morpholine-4-formate with a yield of 61%. MS m/z (ESI): 438.6 $[M+H]^+$.

Step 2: Synthesis of tert-butyl (R)-2-((3-cyano-4-(6-fluoropyridin-3-yl)pyrazolo[1,5-a]pyridin-6-yl)oxy)methyl)morpholine-4-formate 2-fluoro-5-(4,4,5,5-tetramethyl-1,3,2-dioxaborolan-2-yl)pyridine (807 mg, 3.62 mmol) and tert-butyl (R)-2-((4-bromo-3-cyanopyrazolo[1,5-a]pyridin-6-yl)oxy)methyl)morpholine-4-formate (1.13 g, 2.59 mmol) were dissolved in dioxane:water=6:1 (30 mL), and then $Pd(PPh_3)_4$ (300 mg, 0.259 mmol) and sodium carbonate (823 mg, 7.78 mmol) were added respectively to the resulting solution. The mixed solution was stirred at 90° C. overnight under the protection of $N_2$. After the reaction was completed, water was added to quench the reaction, and the organic phase was separated, washed with water, dried, and subjected to column chromatography (DCM:MeOH=10:1) to obtain 0.9 g of tert-butyl (R)-2-((3-cyano-4-(6-fluoropyridin-3-yl)pyrazolo[1,5-a]pyridin-6-yl)oxy)methyl)morpholine-formate with a yield of 76%. MS m/z (ESI): 454.1 $[M+H]^+$.

Example 1: Preparation of 4-(6-(((6-(4-fluoro-1H-pyrazol-1-yl)pyridin-3-yl)methyl)amino)pyridin-3-yl)-6-(2-hydroxy-2-methylpropoxy)pyrazolo[1,5-a]pyridine-3-carbonitrile

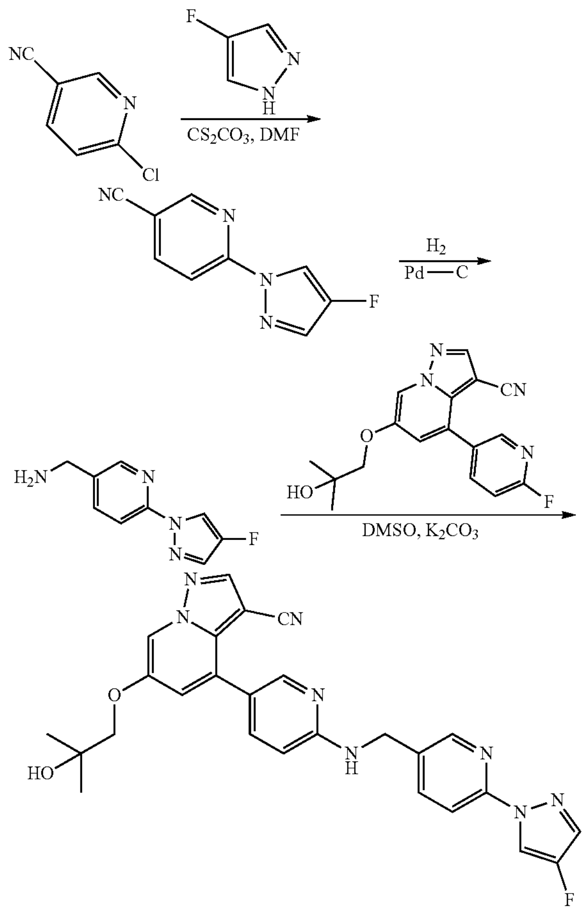

Step 1: Synthesis of 6-(4-fluoro-1H-pyrazol-1-yl)nicotinonitrile 6-chloronicotinonitrile (1.3 g, 9.4 mmol), 4-fluoro-1H-pyrazole (0.8 g, 9.4 mmol) and cesium carbonate (6.1 g, 18.8 mmol) were added to a single-mouth flask, and then DMF (10 mL) was added. The mixed solution was heated to 90° C. to react for 10 h. After the reaction was completed, water (10 mL) was added to quench the reaction, extraction with DCM (20 mL*2) was carried out, and the organic phase was washed with water, dried, spin-dried and subjected to column chromatography (PE:EA=10:1) to obtain 1.5 g of 6-(4-fluoro-1H-pyrazol-1-yl)nicotinonitrile. MS m/z (ESI): 189.3 $[M+H]^+$.

Step 2: Synthesis of (6-(4-fluoro-1H-pyrazol-1-yl) pyridin-3-yl)methanamine 6-(4-fluoro-1H-pyrazol-1-yl)nicotinonitrile (0.3 g, 1.6 mmol), Pd/C (0.05 g) was added to a single-mouth flask, and methanol (5 mL) was added; then, 3 drops of concentrated hydrochloric acid was added dropwise. The reaction was carried out at room temperature overnight in hydrogen atmosphere. After the reaction was completed, the reaction solution was filtered, and the mother solution was spin-dried to obtain 0.22 g of (6-(4-fluoro-1H-pyrazol-1-yl)pyridin-3-yl)methanamine. MS m/z (ESI): 193.1 $[M+H]^+$.

Step 3: Synthesis of 4-(6-(((6-(4-fluoro-1H-pyrazol-1-yl)pyridin-3-yl)methyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy) pyrazolo[1,5-a]pyridine-3-carbonitrile (0.2 g, 0.62 mmol), (6-(4-fluoro-1H-pyrazol-1-yl)pyridin-3-yl)methanamine (0.23 g, 1.2 mmol) and potassium carbonate (0.17 g, 1.2 mmol) were added to a single-mouth flask, and then DMSO (10 mL) was added. The mixed solution was heated to 130° C. to react for 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 30 mg of 4-(6-(((6-(4-fluoro-1H-pyrazol-1-yl)pyridin-3-yl)methyl) amino)pyridin-3-yl)-6-(2-hydroxy-2-methylpropoxy)pyrazolo[1,5-a]pyridine-3-carbonitrile (compound 1). MS m/z (ESI): 498.7 $[M+H]^+$. $^1H$ NMR (400 MHz, DMSO) δ 8.63 (dd, J=13.0, 3.2 Hz, 2H), 8.53 (s, 1H), 8.43 (d, J=1.8 Hz, 1H), 8.19 (d, J=2.3 Hz, 1H), 7.95 (dd, J=8.5, 2.2 Hz, 1H), 7.86 (dd, J=15.8, 6.3 Hz, 2H), 7.63 (dd, J=8.6, 2.4 Hz, 1H), 7.51 (t, J=5.9 Hz, 1H), 7.24 (d, J=2.0 Hz, 1H), 6.63 (d, J=8.7 Hz, 1H), 4.67 (s, 1H), 3.83 (s, 2H), 1.80 (d, J=13.5 Hz, 2H), 1.18 (s, 6H).

Example 2: Preparation of (S)-4-(6-((1-(6-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile

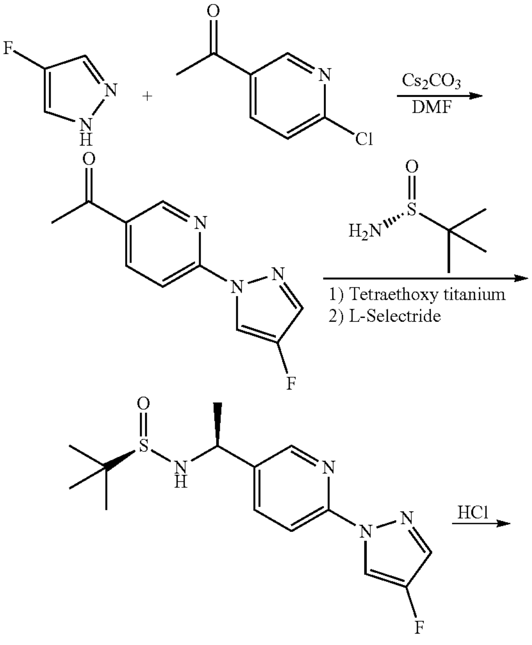

-continued

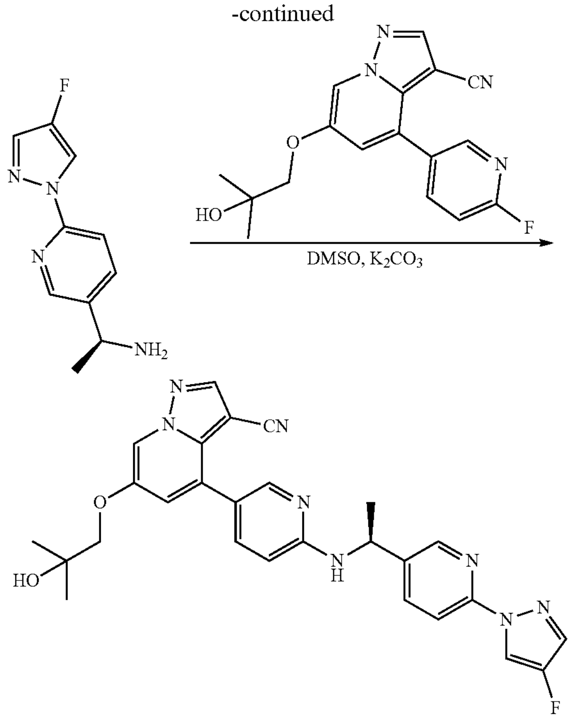

Step 1: Synthesis of 1-(6-(4-fluoro-1H-pyrazol-1-yl) pyridin-3-yl)ethan-1-one 2-chloro-5-acetylpyridine (2 g, 12.8 mmol), 4-fluoro-1H-pyrazole (1.1 g, 12.8 mmol) and cesium carbonate (8.4 g, 25.6 mmol) were added to a single-mouth flask, and then DMF (20 mL) was added. The mixed solution was heated to 90° C. to react for 10 h. After the reaction was completed, water (30 mL) was added to quench the reaction, extraction with DCM (40 mL*2) was carried out and the organic phase was washed with water, dried, spin-dried and subjected to column chromatography (PE:EA=10:1), to obtain 1.8 g of 1-(6-(4-fluoro-1H-pyrazol-1-yl)pyridin-3-yl)ethan-1-one. MS m/z (ESI): 206.2 $[M+H]^+$.

Step 2: Synthesis of (R)-N-((S)-1-(6-(4-fluoro-1H-pyrazol-1-yl)pyridin-3-yl)ethyl)-2-methylpropane-2-sulfinyl amide 1-(6-(4-fluoro-1H-pyrazol-1-yl)pyridin-3-yl)ethan-1-one (1.0 g, 4.8 mmol), R-(+)-tert-butylsulfinamide (0.58 g, 4.8 mmol) and titanium(IV) ethoxide (2.2 g, 9.6 mmol) were added to a double-mouth flask, and then THF (15 mL) was added. The reaction solution was refluxed to react overnight. After the reaction was completed, the reaction solution was cooled down to −75° C., and then L-selectride (14.4 mL, 1 N) was slowly added dropwise. After the addition was completed, the reaction solution was stirred at low temperature for 0.5 h, and then slowly warmed to room temperature to react for 2 h. After the reaction was completed, methanol was added at low temperature to quench the reaction, and water (20 mL) was added. Extraction with ethyl acetate (50 mL*2) was carried out, and the organic phase was dried, spin-dried and subjected to column chromatography (PE: EA=5:1) to obtain 0.9 g of (R)-N-((S)-1-(6-(4-fluoro-1H-pyrazol-1-yl)pyridin-3-yl)ethyl)-2-methylpropane-2-sulfinyl amide. MS m/z (ESI): 311.1 $[M+H]^+$.

Step 3: Synthesis of (S)-1-(6-(4-fluoro-1H-pyrazol-1-yl)pyridin-3-yl)ethan-1-amine (R)-N-((S)-1-(6-(4-fluoro-1H-pyrazol-1-yl)pyridin-3-yl) ethyl)-2-methylpropane-2-sulfinyl amide (0.9 g, 2.9 mmol) was dissolved in a small amount of methanol; then, 4N HCl/dioxane (6 mL) was added at low temperature, and the reaction solution was stirred at room temperature to react for 2 h. After the reaction was completed, diethyl ether was added to form a viscous solid, and the supernatant liquid was poured off. Petroleum ether was added and stirred to precipitate a solid, which was filtered, and then 0.45 g of (S)-1-(6-(4-fluoro-1H-pyrazol-1-yl)pyridin-3-yl)ethan-1-amine was obtained. MS m/z (ESI): 207.5 $[M+H]^+$.

Step 4: Synthesis of (S)-4-(6-((1-(6-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy) pyrazolo[1,5-a]pyridine-3-carbonitrile (0.2 g, 0.62 mmol), (S)-1-(6-(4-fluoro-1H-pyrazol-1-yl)pyridin-3-yl)ethan-1-amine (0.25 g, 1.2 mmol) and potassium carbonate (0.17 g, 1.2 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 25 mg of (S)-4-(6-((1-(6-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile (compound 2). MS m/z (ESI): 512.8 $[M+H]^+$. $^1$H NMR (400 MHz, DMSO) δ 8.65-8.58 (m, 2H), 8.51 (s, 1H), 8.47 (d, J=2.1 Hz, 1H), 8.12 (d, J=2.4 Hz, 1H), 7.98 (dd, J=8.5, 2.3 Hz, 1H), 7.85 (dd, J=13.4, 6.4 Hz, 2H), 7.60 (dd, J=8.7, 2.5 Hz, 1H), 7.48 (d, J=7.6 Hz, 1H), 7.21 (d, J=2.1 Hz, 1H), 6.62 (d, J=8.7 Hz, 1H), 4.65 (s, 1H), 3.81 (s, 2H), 1.50 (d, J=7.0 Hz, 3H), 1.17 (s, 6H).

Example 3: Preparation of (R)-4-(6-((((6-(4-fluoro-1H-pyrazol-1-yl)pyridin-3-yl)methyl)amino)pyridin-3-yl)-6-(morpholin-2-ylmethoxy)pyrazolo[1,5-a]pyridine-3-carbonitrile

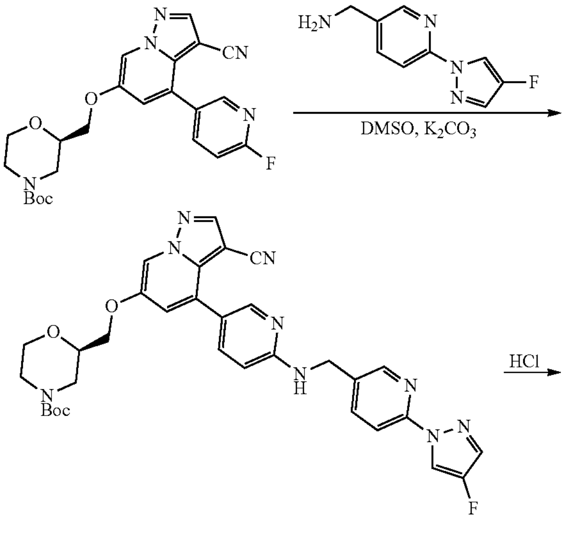

-continued

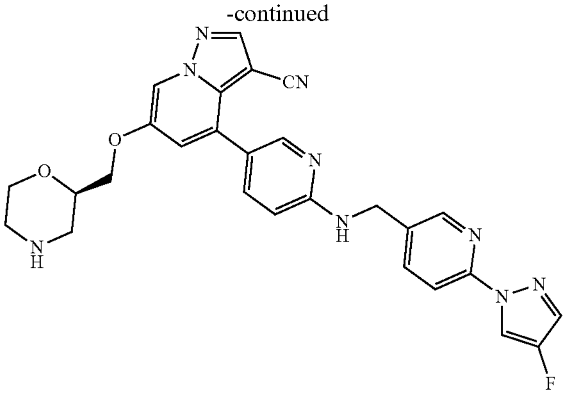

Step 1: Synthesis of tert-butyl (R)-2-(((3-cyano-4-(6-(((6-(4-fluoro-1H-pyrazol-1-yl)pyridin-3-yl)methyl)amino)pyridin-3-yl)pyrazolo[1,5-a]pyridinyl-6-yl)oxy)methyl)morpholine-4-carboxylate Tert-butyl (R)-2-(((3-cyano-4-(6-fluoropyridin-3-yl)pyrazolo[1,5-a]pyridin-6-yl)oxy)methyl)morpholine-4-carboxylate (0.25 g, 0.55 mmol), (6-(4-fluoro-1H-pyrazol-1-yl)pyridin-3-yl)methanamine (0.22 g, 1.1 mmol) and potassium carbonate (0.16 g, 1.1 mmol) were added to a single-mouth flask, and DMSO (10 mL) was then added. The mixed solution was heated to 130° C. to react for about 15 h. After the react ion was completed, water (10 mL) was added to quench the reaction, extraction with DCM (30 mL*2) was carried out and the organic phase was washed with water, dried, spin-dried and subjected to column chromatography (DCM:MeOH=10:1) to obtain 50 mg of tert-butyl (R)-2-(((3-cyano-4-(6-(((6-(4-fluoro-1H-pyrazol-1-yl)pyridin-3-yl)methyl)amino)pyridin-3-yl)pyrazolo[1,5-a]pyridinyl-6-yl)oxy)methyl)morpholine-4-carboxylate. MS m/z (ESI): 626.1 $[M+H]^+$.

Step 2: Synthesis of (R)-4-(6-((((6-(4-fluoro-1H-pyrazol-1-yl)pyridin-3-yl)methyl)amino)pyridin-3-yl)-6-(morpholin-2-ylmethoxy)pyrazolo[1,5-a]pyridine-3-carbonitrile Tert-butyl (R)-2-(((3-cyano-4-(6-(((6-(4-fluoro-1H-pyrazol-1-yl)pyridin-3-yl)methyl) amino)pyridin-3-yl)pyrazolo[1,5-a]pyridinyl-6-yl)oxy)methyl)morpholine-4-carboxylate (50 mg) was dissolved in a small amount of dichloromethane; then, 4N HCl/dioxane (1 mL) was added at low temperature, and the reaction solution was stirred at room temperature to react for 1 h. After the reaction was completed, an aqueous sodium bicarbonate solution was added to neutralize the reaction solution. Extraction with DCM (10 mL*2) was carried out, and the organic phase was dried, spin-dried and subjected to column chromatography (DCM:MeOH=10:1) to obtain 30 mg of (R)-4-(6-((((6-(4-fluoro-1H-pyrazol-1-yl)pyridin-3-yl)methyl)amino)pyridin-3-yl)-6-(morpholin-2-ylmethoxy)pyrazolo[1,5-a]pyridine-3-carbonitrile (compound 3). MS m/z (ESI): 525.9 $[M+H]^+$. $^1H$ NMR (500 MHz, DMSO) δ 8.69-8.62 (m, 2H), 8.55 (s, 1H), 8.45 (d, J=2.0 Hz, 1H), 8.21 (d, J=2.4 Hz, 1H), 7.97 (dd, J=8.5, 2.3 Hz, 1H), 7.90-7.82 (m, 2H), 7.64 (dd, J=8.6, 2.5 Hz, 1H), 7.52 (t, J=6.0 Hz, 1H), 7.27 (d, J=2.1 Hz, 1H), 6.65 (d, J=8.7 Hz, 1H), 4.60 (d, J=5.9 Hz, 2H), 4.05 (d, J=5.1 Hz, 2H), 3.78-3.68 (m, 2H), 3.46 (td, J=10.9, 3.3 Hz, 1H), 2.87 (dd, J=12.1, 2.1 Hz, 1H), 2.72-2.59 (m, 2H).

Example 4: Preparation of (R)-4-(6-((((S)-1-(6-(4-fluoro-1H-pyrazol-1-yl)pyridin-3-yl)ethan-1-yl)amino)pyridine-3-yl)-6-(morpholin-2-ylmethoxy)pyrazolo[1,5-a]pyridine-3-carbonitrile

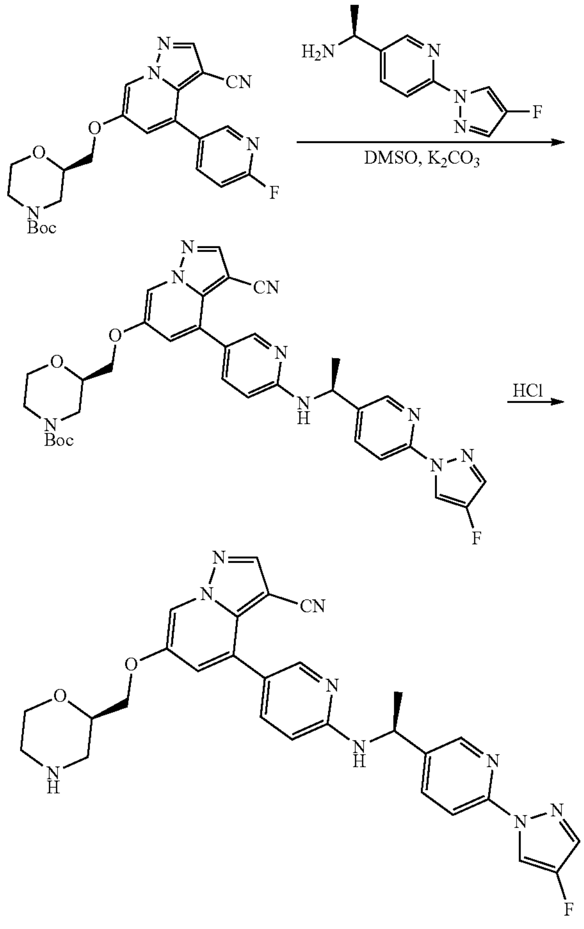 [SMILES: CC(C)(C)OC(=O)N1CCO[C@@H](COc2cc(-c3ccc(F)nc3)c3c(C#N)cnn3c2)C1 ; C[C@H](N)c1ccc(-n2cc(F)cn2)nc1 ; C[C@H](Nc1ccc(-c2cc(OC[C@H]3CN(C(=O)OC(C)(C)C)CCO3)cn3ncc(C#N)c23)cn1)c1ccc(-n2cc(F)cn2)nc1 ; Cl ; C[C@H](Nc1ccc(-c2cc(OC[C@H]3CNCCO3)cn3ncc(C#N)c23)cn1)c1ccc(-n2cc(F)cn2)nc1]

Step 1: Synthesis of tert-butyl (R)-2-(((3-cyano-4-(6-((((S)-1-6-(4-fluoro-1H-pyrazol-1-yl)pyridine-3-yl)ethan-1-yl)amino)pyridin-3-yl)pyrazolo[1,5-a]pyridin-6-yl)oxy)methyl)morpholine-4-carboxylate Tert-butyl (R)-2-(((3-cyano-4-(6-fluoropyridin-3-yl)pyrazolo[1,5-a]pyridin-6-yl)oxy)methyl)morpholine-4-carboxylate (0.30 g, 0.66 mmol), (S)-1-(6-(4-fluoro-1H-pyrazol-1-yl)pyridin-3-yl)ethan-1-amine (0.27 g, 1.3 mmol) and potassium carbonate (0.19 g 1.3 mmol) were added to a single-mouth flask, and then DMSO (10 mL) was added. The mixed solution was heated to 130° C. to react for about 15 h. After the reaction was completed, water (10 mL) was added to quench the reaction, extract ion with DCM (20 mL*2) was carried out and the organic phase was washed with water, dried, spin-dried and subjected to column chromatography (DCM:MeOH=10:1) to obtain 65 mg of tert-butyl (R)-2-(((3-cyano-4-(6-((((S)-1-6-(4-fluoro-1H-pyrazol-1-yl)pyridine-3-yl)ethan-1-yl)amino)pyridin-3-yl)pyrazolo[1,5-a]pyridin-6-yl)oxy)methyl)morpholine-4-carboxylate. MS m/z (ESI): 640.3 $[M+H]^+$.

Step 2: Synthesis of (R)-4-(6-((((S)-1-(6-(4-fluoro-1H-pyrazol-1-yl)pyridin-3-yl)ethan-1-yl)amino)pyridine-3-yl)-6-(morpholin-2-ylmethoxy)pyrazolo[1,5-a]pyridine-3-carbonitrile Tert-butyl (R)-2-(((3-cyano-4-(6-((((S)-1-6-(4-fluoro-1H-pyrazol-1-yl)pyridine-3-yl)ethan-1-yl)amino)pyridin-3-yl) pyrazolo[1,5-a]pyridin-6-yl)oxy)methyl)morpholine-4-carboxylate (65 mg) was dissolved in a small amount of dichloromethane; then, 4N HCl/dioxane (1 mL) was added at low temperature, and the reaction solution was stirred at room temperature to react for 1 h. After the reaction was completed, an aqueous sodium bicarbonate solution was added to neutralize the reaction solution. Extraction with DCM (10 mL*2) was carried out, and the organic phase was dried, spin-dried and subjected to column chromatography (DCM:MeOH=10:1) to obtain 40 mg of (R)-4-(6-((((S)-1-(6-(4-fluoro-1H-pyrazol-1-yl)pyridin-3-yl)ethan-1-yl) amino)pyridine-3-yl)-6-(morpholin-2-ylmethoxy)pyrazolo [1,5-a]pyridine-3-carbonitrile (compound 4). MS m/z (ESI): 540.2 $[M+H]^+$. $^1H$ NMR (500 MHz, DMSO) δ 8.64 (dd, J=4.6, 0.7 Hz, 2H), 8.53 (s, 1H), 8.49 (d, J=2.2 Hz, 1H), 8.14 (d, J=2.4 Hz, 1H), 8.00 (dd, J=8.5, 2.3 Hz, 1H), 7.89-7.83 (m, 2H), 7.61 (dd, J=8.7, 2.5 Hz, 1H), 7.48 (d, J=7.6 Hz, 1H), 7.23 (d, J=2.1 Hz, 1H), 6.63 (d, J=8.6 Hz, 1H), 5.24-5.15 (m, 1H), 4.03 (d, J=5.3 Hz, 2H), 3.77-3.66 (m, 2H), 3.45 (td, J=10.8, 3.3 Hz, 1H), 2.85 (dd, J=12.1, 2.1 Hz, 1H), 2.64 (dd, J=10.7, 3.2 Hz, 2H), 1.51 (d, J=7.0 Hz, 3H).

Example 5: Preparation of (R)-4-(6-((1-(6-(4-fluoro-1H-pyrazol-1-yl)pyridin-3-yl)ethyl)amino) pyridin-3-yl)-6-(2-hydroxy-2-methylpropoxy)pyrazolo[1,5-a]pyridine-3-carbonitrile

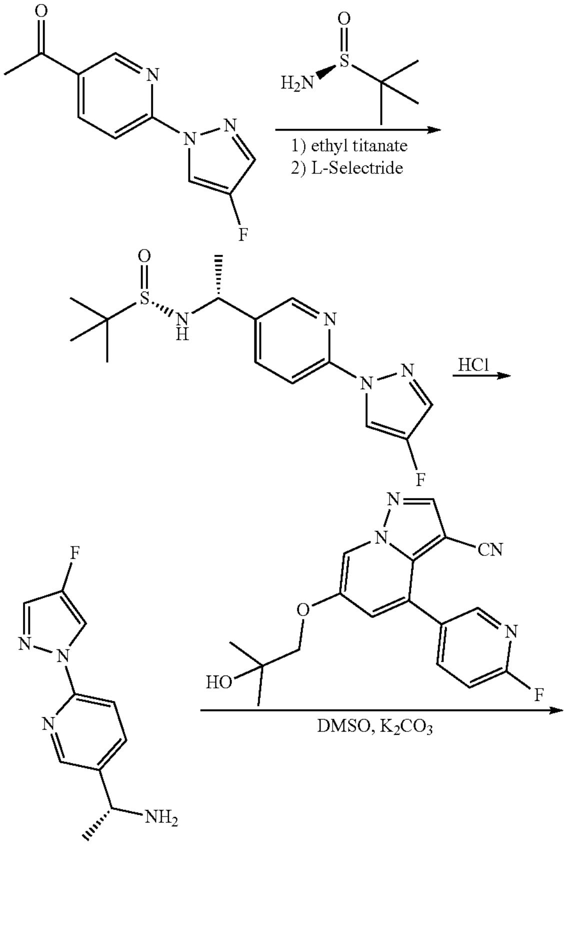

-continued

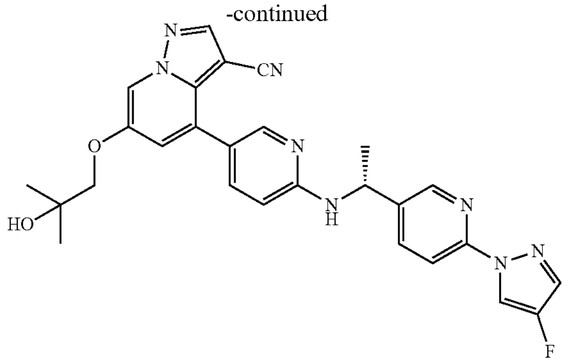

Step 1: Synthesis of (S)-N-((R)-1-(6-(4-fluoro-1H-pyrazol-1-yl)pyridin-3-yl)ethyl)-2-methylpropane-2-sulfinyl amide 1-(6-(4-fluoro-1H-pyrazol-1-yl)pyridin-3-yl)ethan-1-one (0.5 g, 2.4 mmol), S-(−)-tert-butylsulfinamide (0.3 g, 2.4 mmol) and titanium(IV) ethoxide (1.1 g, 4.8 mmol) were added to a double-mouth flask, and then THF (10 mL) was added. The reaction solution was refluxed to react overnight. After the reaction was completed, the reaction solution was cooled down to −75° C., and then L-selectride (7.2 mL, 1 N) was slowly added dropwise. After the addition was completed, the reaction solution was stirred at low temperature for 0.5 h, and then slowly warmed to room temperature to react for 2 h. After the reaction was completed, methanol was added at low temperature to quench the reaction, and water (20 mL) was added. Extraction with ethyl acetate (40 mL*2) was carried out, and the organic phase was dried, spin-dried and subjected to column chromatography (PE: EA=5:1) to obtain 0.5 g of (S)-N-((R)-1-(6-(4-fluoro-1H-pyrazol-1-yl)pyridin-3-yl)ethyl)-2-methylpropane-2-sulfinyl amide. MS m/z (ESI): 311.1 $[M+H]^+$.

Step 2: Synthesis of (R)-1-(6-(4-fluoro-1H-pyrazol-1-yl)pyridin-3-yl)ethan-1-amine (S)-N-((R)-1-(6-(4-fluoro-1H-pyrazol-1-yl)pyridin-3-yl) ethyl)-2-methylpropane-2-sulfinyl amide (0.5 g, 1.6 mmol) was dissolved in a small amount of methanol; then, 4N HCl/dioxane (4 mL) was added at low temperature, and the reaction solution was stirred at room temperature to react for 2 h. After the reaction was completed, diethyl ether was added to form a viscous solid, and the supernatant liquid was poured off. Petroleum ether was added and stirred to precipitate a solid, which was filtered, and then 0.25 g of (R)-1-(6-(4-fluoro-1H-pyrazol-1-yl)pyridin-3-yl)ethan-1-amine was obtained. MS m/z (ESI): 207.5 $[M+H]^+$.

Step 3: Synthesis of (R)-4-(6-((1-(6-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy) pyrazolo[1,5-a]pyridine-3-carbonitrile (0.2 g, 0.62 mmol), (R)-1-(6-(4-fluoro-1H-pyrazol-1-yl)pyridin-3-yl)ethan-1-amine (0.25 g, 1.2 mmol) and potassium carbonate (0.17 g, 1.2 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 15 mg of (R)-4-(6-((1-(6-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile (compound 5). MS m/z (ESI): 512.8 $[M+H]^+$. $^1H$ NMR (400 MHz, DMSO) δ 8.65-8.58 (m, 2H), 8.51 (s, 1H), 8.47 (d, J=2.1 Hz, 1H), 8.12 (d, J=2.4 Hz, 1H), 7.98 (dd, J=8.5, 2.3 Hz, 1H), 7.85 (dd, J=13.4, 6.4 Hz, 2H), 7.60 (dd, J=8.7, 2.5 Hz, 1H), 7.48 (d, J=7.6 Hz, 1H), 7.21 (d, J=2.1 Hz, 1H), 6.62 (d, J=8.7 Hz, 1H), 4.65 (s, 1H), 3.81 (s, 2H), 1.50 (d, J=7.0 Hz, 3H), 1.17 (s, 6H).

Example 6: Preparation of 4-(6-((1-(6-(4-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile

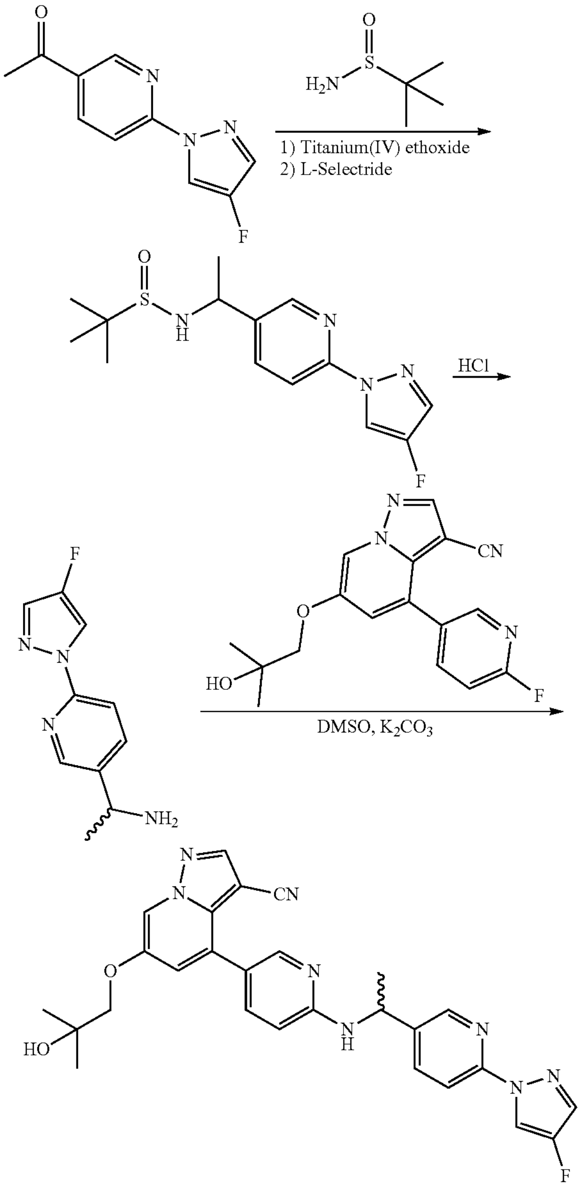

Step 1: Synthesis of N-(1-(1-(6-(4-fluoro-1H-pyrazol-1-yl)pyridin-3-yl)ethyl)-2-methylpropane-2-sulfinamide 1-(6-(4-fluoro-1H-pyrazol-1-yl)pyridin-3-yl)ethan-1-one (1.5 g, 7.2 mmol), tert-butylsulfinamide (0.9 g, 7.2 mmol) and titanium(IV) ethoxide (3.3 g, 14.4 mmol) were added to a double-mouth flask, and then THF (20 mL) was added. The reaction solution was refluxed to react overnight. After the reaction was completed, the reaction solution was cooled down to −75° C., and then L-selectride (21.6 mL, 1 N) was slowly added dropwise. After the addition was completed, the reaction solution was stirred at low temperature for 0.5 h, and then slowly warmed to room temperature to react for 2 h. After the reaction was completed, methanol was added at low temperature to quench the reaction, and water (30 mL) was added. Extraction with ethyl acetate (50 mL*2) was carried out, and the organic phase was dried, spin-dried and subjected to column chromatography (PE:EA=5:1) to obtain 1.2 g of N-(1-(1-(6-(4-fluoro-1H-pyrazol-1-yl)pyridin-3-yl)ethyl)-2-methylpropane-2-sulfinamide. MS m/z (ESI): 311.1 $[M+H]^+$.

Step 2: Synthesis of 1-(6-(4-fluoro-1H-pyrazol-1-yl)pyridin-3-yl)ethan-1-amine N-(1-(1-(6-(4-fluoro-1H-pyrazol-1-yl)pyridin-3-yl)ethyl)-2-methylpropane-2-sulfinamide (1.2 g, 3.9 mmol) was dissolved in a small amount of methanol; then, 4N HCl/dioxane (8 mL) was added at low temperature, and the reaction solution was stirred at room temperature to react for 2 h. After the reaction was completed, diethyl ether was added to form a viscous solid, and the supernatant liquid was poured off. Petroleum ether was added and stirred to precipitate a solid, which was filtered, and then 0.7 g of 1-(6-(4-fluoro-1H-pyrazol-1-yl)pyridin-3-yl)ethan-1-amine was obtained. MS m/z (ESI): 207.5 $[M+H]^+$.

Step 3: Synthesis of 4-(6-((1-(6-(4-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy)pyrazolo[1,5-a]pyridine-3-carbonitrile (0.4 g, 1.2 mmol), 1-(6-(4-fluoro-1H-pyrazol-1-yl)pyridin-3-yl)ethan-1-amine (0.5 g, 2.4 mmol) and potassium carbonate (0.4 g, 2.4 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 50 mg of 4-(6-((1-(6-(4-(4-fluoro-1H-pyrazol-1-yl)pyridin-3-yl)ethyl)amino)pyridin-3-yl)-6-(2-hydroxy-2-methylpropoxy)pyrazolo[1,5-a]pyridine-3-carbonitrile (compound 6). MS m/z (ESI): 512.8 $[M+H]^+$. $^1H$ NMR (400 MHz, DMSO) δ 8.65-8.58 (m, 2H), 8.51 (s, 1H), 8.47 (d, J=2.1 Hz, 1H), 8.12 (d, J=2.4 Hz, 1H), 7.98 (dd, J=8.5, 2.3 Hz, 1H), 7.85 (dd, J=13.4, 6.4 Hz, 2H), 7.60 (dd, J=8.7, 2.5 Hz, 1H), 7.48 (d, J=7.6 Hz, 1H), 7.21 (d, J=2.1 Hz, 1H), 6.62 (d, J=8.7 Hz, 1H), 4.65 (s, 1H), 3.81 (s, 2H), 1.50 (d, J=7.0 Hz, 3H), 1.17 (s, 6H).

Example 7: Preparation of 4-(6-(((6-(1H-imidazol-1-yl)pyridin-3-yl)methyl)amino)pyridin-3-yl)-6-(2-hydroxy-2-methylpropane)oxy)pyrazolo[1,5-a]pyridine-3-carbonitrile

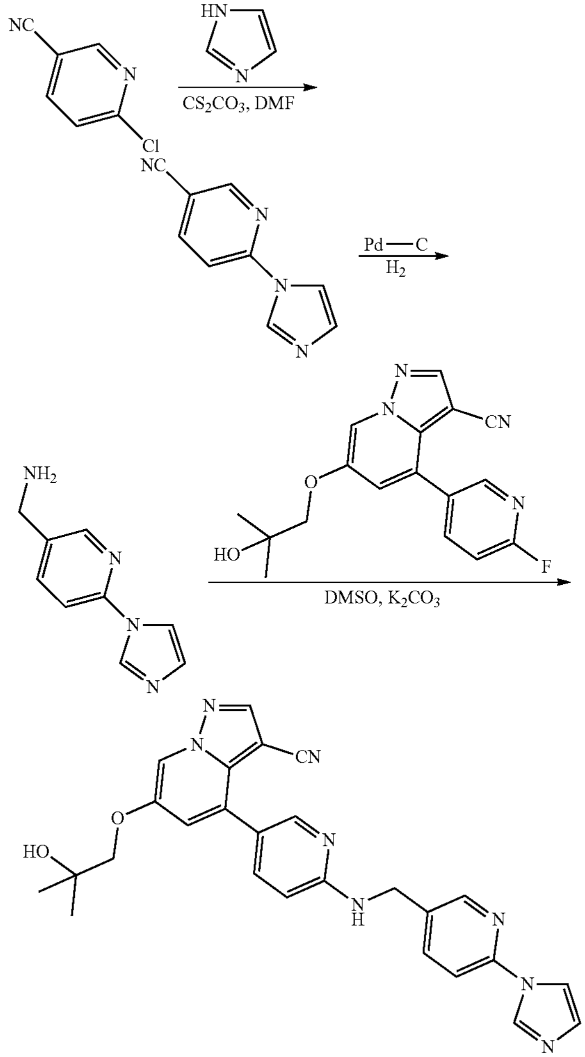

Step 1: Synthesis of 6-(1H-imidazol-1-yl)nicotinonitrile 6-chloronicotinonitrile (1.0 g, 7.3 mmol), 1H-pyrazole (0.5 g, 7.3 mmol) and cesium carbonate (4.7 g, 14.6 mmol) were added to a single-mouth flask, and then DMF (10 mL) was added. The mixed solution was heated to 90° C. to react for 10 h. After the reaction was completed, water (10 mL) was added to quench the reaction, extraction with DCM (30 mL*2) was carried out and the organic phase was washed with water, dried, spin-dried and subjected to column chromatography (PE:EA=6:1) to obtain 1.1 g of 6-(1H-imidazol-1-yl)nicotinonitrile. MS m/z (ESI): 171.2 $[M+H]^+$.

Step 2: Synthesis of (6-(1H-imidazol-1-yl)pyridin-3-yl)methanamine 6-(1H-imidazol-1-yl)nicotinonitrile (0.5 g, 2.9 mmol) and Pd/C (0.06 g) were added to a single-mouth flask, and methanol (5 mL) was then added to the mixed solution; next, 3 drops of concentrated hydrochloric acid was added dropwise. The reaction was carried out overnight at room temperature in hydrogen atmosphere. After the reaction was completed, the reaction solution was filtered, and the mother solution was spin-dried to obtain 0.4 g of (6-(1H-imidazol-1-yl)pyridin-3-yl)methanamine. MS m/z (ESI): 175.2 $[M+H]^+$.

Step 3: Synthesis of 4-(6-(((6-(1H-imidazol-1-yl)pyridin-3-yl)methyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy)pyrazolo[1,5-a]pyridine-3-carbonitrile (0.3 g, 0.92 mmol), (6-(1H-imidazol-1-yl)pyridin-3-yl)methanamine (0.33 g, 1.84 mmol) and potassium carbonate (0.26 g, 1.84 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (30 mL*2) was carried out and the organic phase was washed with water, dried, spin-dried and subjected to column chromatography (DCM:MeOH=10:1) to obtain 45 mg of 4-(6-(((6-(1H-imidazol-1-yl)pyridin-3-yl)methyl)amino)pyridin-3-yl)-6-(2-hydroxy-2-methylpropane)oxy)pyrazolo[1,5-a]pyridine-3-carbonitrile (compound 7). MS m/z (ESI): 481.6 $[M+H]^+$. $^1H$ NMR (400 MHz, DMSO) δ 8.63 (d, J=2.0 Hz, 1H), 8.55 (s, 2H), 8.49 (d, J=1.9 Hz, 1H), 8.21 (d, J=2.3 Hz, 1H), 8.00-7.92 (m, 2H), 7.77 (d, J=8.4 Hz, 1H), 7.65 (dd, J=8.6, 2.4 Hz, 1H), 7.54 (t, J=5.9 Hz, 1H), 7.25 (d, J=2.0 Hz, 1H), 7.13 (s, 1H), 6.66 (d, J=8.6 Hz, 1H), 4.69 (s, 1H), 4.60 (d, J=5.8 Hz, 2H), 3.84 (s, 2H), 1.20 (s, 6H).

Example 8: Preparation of 6-(2-hydroxy-2-methylpropoxy)-4-(6-((6-(2-oxopyrrolidin-1-yl)pyridin-3-yl)methylamino)pyridine-3-yl)pyrazolo[1,5-a]pyridine-3-carbonitrile

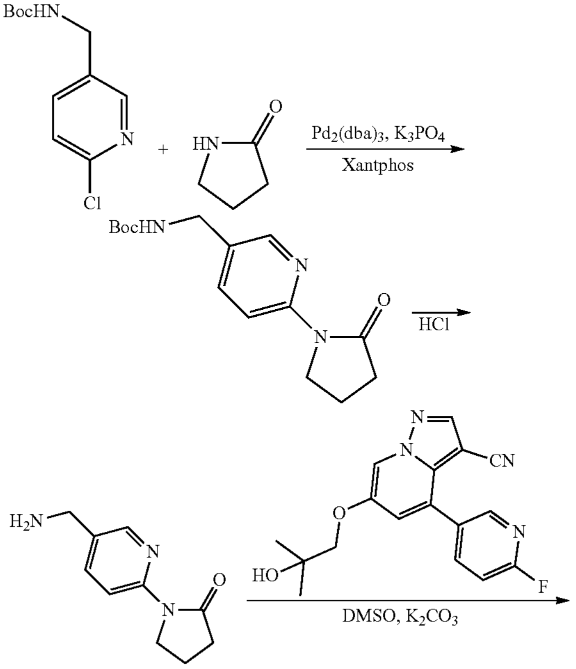

-continued

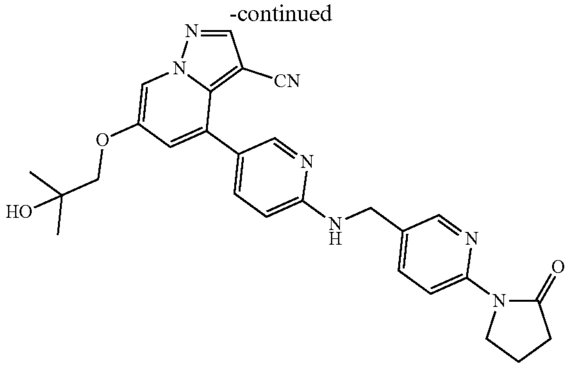

Step 1: Synthesis of tert-butyl ((6-(2-(2-oxypyrrolidin-1-yl)pyridin-3-yl)methy 1)carbamate Tert-butyl ((6-chloropyridin-3-yl)methyl)carbamate (0.3 g, 1.3 mmol), pyrrolidin-2-one (0.42 g, 5.2 mmol), potassium phosphate (1.3 g, 6.5 mmol), tris(dibenzylideneacetone)dipalladium (0.22 g, 0.26 mmol) and xantphos (0.15 g, 0.3 mmol) were dissolved in toluene (15 ml). The mixed solution was stirred at 80° C. to react for 6 h under the protection of $N_2$. After the reaction was found to be completed from the monitoring, the reaction solution was cooled, and water was added to quench the reaction, extraction with EA (30 mL*2) was then carried out, and the organic phase was washed with water and then dried, concentrated and subjected to column chromatography (PE:EA=3:1) to obtain 0.3 g of tert-butyl ((6-(2-(2-oxypyrrolidin-1-yl)pyridin-3-yl)methyl)carbamate. MS m/z (ESI): 292.3 $[M+H]^+$.

Step 2: Synthesis of 1-(5-(methylamino)pyridin-2-yl)pyrrolidin-2-one

Tert-butyl ((6-(2-(2-oxypyrrolidin-1-yl)pyridin-3-yl)methyl)carbamate (0.4 g, 1.4 mmol) was dissolved in a small amount of dichloromethane; then, 4N HCl/dioxane (2 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.2 g of 1-(5-(methylamino)pyridin-2-yl)pyrrolidin-2-one was obtained. MS m/z (ESI): 192.3 $[M+H]^+$.

Step 3: Synthesis of 6-(2-hydroxy-2-methylpropoxy)-4-(6-((((6-(2-oxopyrrolidin-1-yl)pyridin-3-yl)methylamine)pyridine-3-yl)pyrazolo[1,5-a]pyridine-3-carbonitrile 4-(6-fluoropyridin-3-yl)-6-(2-hydroxy-2-methylpropoxy)pyrazolo[1,5-a]pyridine-3-carbonitrile (0.2 g, 0.62 mmol), 1-(5-(methylamino)pyridin-2-yl)pyrrolidin-2-one (0.23 g, 1.24 mmol) and potassium carbonate (0.17 g, 1.24 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 35 mg of 6-(2-hydroxy-2-methylpropoxy)-4-(6-(((((6-(2-oxopyrrolidin-1-yl)pyridin-3-yl)methyl)amino)pyridin-3-yl)pyrazolo[1,5-a]pyridine-3-carbonitrile (compound 8). MS m/z (ESI): 498.6 $[M+H]^+$. $^1H$ NMR (400 MHz, DMSO) δ 8.65 (s, 1H), 8.62 (s, 1H), 8.20 (d, 1H), 8.15 (s, 1H), 7.59-7.61 (m, 1H), 7.48-7.51 (m, 1H), 7.24 (s, 1H), 6.56 (d, 1H), 6.48 (d, 1H), 4.69 (s, 1H), 3.84 (s, 1H), 2.30 (s, 4H), 1.60 (s, 6H).

Example 9: Preparation of 4-(6-(([2,3'-bipyridyl]-5-ylmethyl)amino)pyridin-3-yl)-6-(2-hydroxy-2-methylpropoxy)pyrazole[1,5-a]pyridine-3-carbonitrile

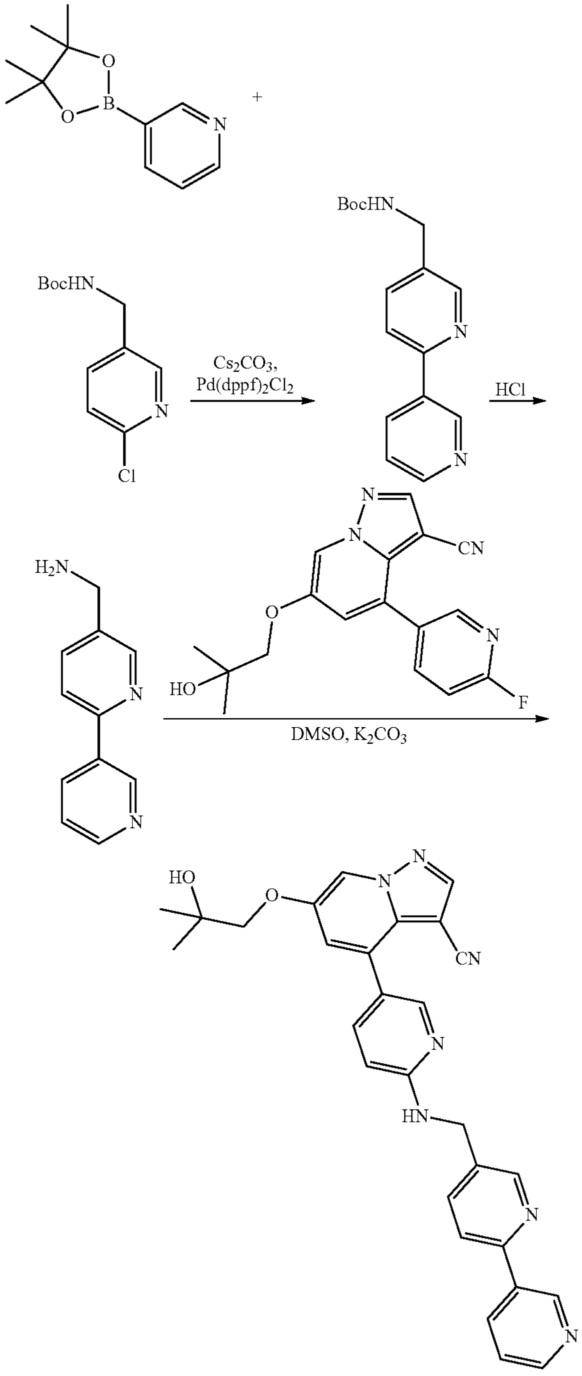

Step 1: Synthesis of tert-butyl ([2,3'-bipyridyl]-5-ylmethyl)carbamate 3-(4,4,5,5-tetramethyl-1,3,2-dioxaboroboran-2-yl)pyridine (0.5 g, 2.43 mmol), tert-butyl ((6-chloropyridin-3-yl) methyl)carbamate (0.6 g, 2.43 mmol), Pd(dppf)$_2$Cl$_2$ (0.19 g, 0.24 mmol) and cesium carbonate (1.6 g, 4.86 mmol) were dissolved in dioxane (15 mL) and water (5 mL). The resulting reaction solution was stirred at 80° C. for 16 h to react. After the reaction was found to be completed from the monitoring, the reaction solution was cooled, extracted with EA (20 mL*2), and the organic phase was washed with water and then dried, concentrated and subjected to column chromatography (PE:EA=5:1) to obtain 0.45 g of tert-butyl ([2,3'-bipyridyl]-5-ylmethyl)carbamate. MS m/z (ESI): 286.5 $[M+H]^+$.

Step 2: Synthesis of [2,3'-bipyridyl]-5-ylmethanamine

Tert-butyl ([2,3'-bipyridyl]-5-ylmethyl)carbamate (0.4 g, 1.4 mmol) was dissolved in a small amount of dichloromethane; then, 4N HCl/dioxane (2 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.25 g of [2,3'-bipyridyl]-5-ylmethanamine was obtained. MS m/z (ESI): 186.4.3 $[M+H]^+$.

Step 3: Synthesis of 4-(6-(([[2,3'-bipyridyl]-5-ylmethyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy) pyrazolo[1,5-a]pyridine-3-carbonitrile (0.2 g, 0.62 mmol), [2,3'-bipyridyl]-5-ylmethanamine (0.17 g, 0.92 mmol) and potassium carbonate (0.17 g, 1.24 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (20 mL*2) was carried out and the organic phase was washed with water, dried, spin-dried and subjected to column chromatography (DCM:MeOH=10:1) to obtain 35 mg of 4-(6-(([[2,3'-bipyridyl]-5-ylmethyl)amino)pyridin-3-yl)-6-(2-hydroxy-2-methylpropoxy)pyrazolo[1,5-a]pyridine-3-carbonitrile (compound 9). MS m/z (ESI): 492.8 $[M+H]^+$. $^1$H NMR (400 MHz, DMSO) δ 8.63 (m, 1H), 8.55 (s, 2H), 8.49 (d, J=1.9 Hz, 1H), 8.21 (d, J=2.3 Hz, 1H), 7.92 (m, 2H), 7.77 (m, 1H), 7.65 (dd, J=8.6, 2.4 Hz, 1H), 7.45 (m 1H), 7.34 (m, 2H), 7.13 (s, 1H), 6.96 (d, J=8.8 Hz, 1H), 4.69 (s, 1H), 4.60 (d, J=5.8 Hz, 2H), 3.84 (s, 2H), 1.20 (s, 6H).

Example 10: Preparation of 6-(2-hydroxy-2-methylpropoxy)-4-(6-(((6-(pyrrolidin-1-yl)pyridin-3-yl) methyl)amino)pyridine-3-yl)pyrazo[1,5-a]pyridine-3-carbonitrile

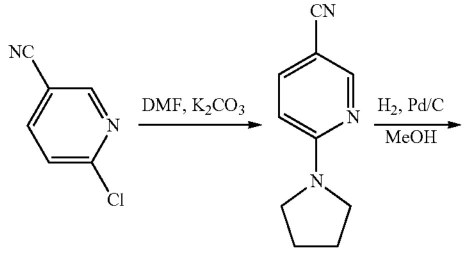

-continued

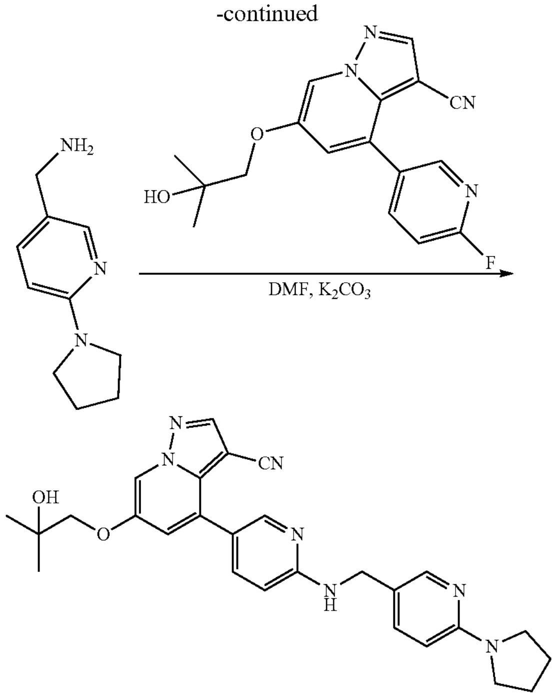

Step 1: Synthesis of 6-(pyrrolidin-1-yl)nicotine nitrile

At room temperature, tetrahydropyrrole (0.5 g, 7.2 mmol) and 6-chloronicotinonitrile (0.5 g, 3.6 mmol) were dissolved in 10 mL of DMF, and then potassium carbonate (1.5 g, 10.8 mmol) was added, and addition was completed. The mixed solution was stirred at 90° C. overnight to react. After the reaction was completed, it was quenched. Extraction was carried out, and the organic phase was washed, concentrated and subjected to column chromatography (PE:EA=2:1) to obtain 600 mg of 6-(pyrrolidin-1-yl)nicotine nitrile. MS m/z (ESI): 174.1 $[M+H]^+$.

Step 2: Synthesis of (6-(pyrrolidin-1-yl)pyridin-3-yl)methylamine 6-(pyrrolidin-1-yl)nicotine nitrile (0.3 g, 1.7 mmol) was dissolved in methanol (10 mL), and then Pd/C (30 mg) was added; then, hydrogen replacement was carried out three times. The reaction solution was stirred at room temperature for 4 h until the reaction was completed. Extraction was carried out, and the organic phase was concentrated, and subjected to column chromatography (DCM:MeOH=10:1) to obtain 165 mg of (6-(pyrrolidin-1-yl)pyridin-3-yl)methylamine. MS m/z (ESI): 178.3 $[M+H]^+$.

Step 3: Synthesis of 6-(2-hydroxy-2-methylpropoxy)-4-(6-((6-(pyrrolidin-1-yl)pyridin-3-yl) methyl)amino)pyridin-3-yl)pyrazo[1,5-a]pyridine-3-carbonitrile At room temperature, (6-(pyrrolidin-1-yl)pyridin-3-yl) methylamine (0.15 g, 0.84 mmol) and 4-(6-fluoropyridin-3-yl)-6-(2-hydroxy-2-methylpropoxy)pyrazolo[1,5-a]pyridine-3-carbonitrile (0.14 g, 0.42 mmol) were dissolved in DMSO (5 mL), and then potassium carbonate (0.18 g, 1.26 mmol) was added to the resulting solution. The mixed solution was then stirred at 135° C. overnight to react under the protection of $N_2$ until the reaction was completed. Extraction was carried out, and the organic phase was washed, and subjected to column chromatography (DCM: MeOH=10:1) to obtain 16 mg of 6-(2-hydroxy-2-methylpropoxy)-4-(6-((6-(pyrrolidin-1-yl)pyridin-3-yl)methyl)amino)pyridin-3-yl)pyrazo[1,5-a]pyridine-3-carbonitrile (compound 10) with a yield of 8%. MS m/z (ESI): 484.5 $[M+H]^+$. $^1H$ NMR (400 MHz, DMSO) δ 8.63 (s, 1H), 8.62 (s, 1H), 8.20 (d, 1H), 8.05 (s, 1H), 7.59-7.61 (m, 1H), 7.48-7.51 (m, 1H), 7.24 (s, 1H), 6.56 (d, 1H), 6.38 (d, 1H), 4.69 (s, 1H), 4.34 (d, 2H), 3.84 (s, 1H), 1.90 (s, 4H), 1.20 (s, 6H).

Example 11: Preparation of 6-(2-hydroxy-2-methylpropoxy)-4-(6-((6-(4-methyl-1H-imidazol-1-yl)pyridin-3-yl)methyl)amino)pyridin-3-yl)pyrazolo[1,5-a]pyridine-3-carbonitrile

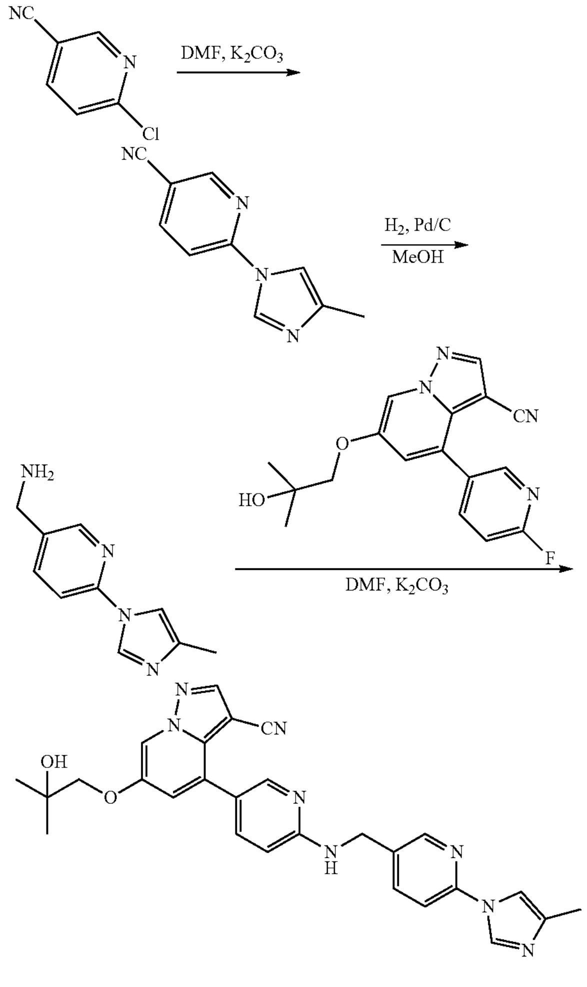

Step 1: Synthesis of 6-(4-methyl-1H-imidazol-1-yl)nicotine nitrile

At room temperature, 4-methyl-1H-imidazole (0.6 g, 2.3 mmol) and 6-chloronicotinonitrile (0.5 g, 3.6 mmol) were dissolved in 10 mL of DMF, and potassium carbonate (2.5 g, 18 mmol) was added. The mixed solution was stirred at 90° C. overnight to react. After the reaction was completed, it was quenched. Extraction was carried out, and the organic phase was washed, concentrated and subjected to column chromatography (PE:EA=2:1) to obtain 650 mg of 6-(4-methyl-1H-imidazol-1-yl)nicotine nitrile. MS m/z (ESI): 184.5 $[M+H]^+$.

Step 2: Synthesis of 6-(4-methyl-1H-imidazol-1-yl) pyridin-3-yl)methylamine 6-(4-methyl-1H-imidazol-1-yl)nicotine nitrile (0.65 g, 3 mmol) was dissolved in methanol (10 mL), and then Pd/C (65 mg) was added; then, hydrogen replacement was carried out three times. The reaction solution was stirred at room temperature for 4 h until the reaction was completed. Extraction was carried out and the organic phase was concentrated and subjected to column chromatography (DCM: MeOH=10:1) to obtain 200 mg of 6-(4-methyl-1H-imidazol-1-yl)pyridin-3-yl)methylamine. MS m/z (ESI): 189.1 $[M+H]^+$.

Step 3: Synthesis of 6-(2-hydroxy-2-methylpropoxy)-4-(6-((6-(4-methyl-1H-imidazol-1-yl)pyridin-3-yl)methyl)amino)pyridin-3-yl)pyrazolo[1,5-a]pyridine-3-carbonitrile At room temperature, 4-(6-fluoropyridin-3-yl)-6-(2-hydroxy-2-methylpropoxy)pyrazolo[1,5-a]pyridine-3-carbonitrile (0.12 g, 0.36 mmol) and 6-(4-methyl-1H-imidazol-1-yl)pyridin-3-yl)methylamine (0.2 g, 0.73 mmol) were dissolved in DMSO (5 mL), and then potassium carbonate (0.25 g, 1.8 mmol) was added. The mixed solution was then stirred at 135° C. overnight to react under the protection of $N_2$. After the reaction was completed, the reaction solution was extracted, washed, and subjected to column chromatography (DCM:MeOH=10:1) to obtain 16 mg of 6-(2-hydroxy-2-methylpropoxy)-4-(6-((6-(4-methyl-1H-imidazol-1-yl)pyridin-3-yl)methyl)amino)pyridin-3-yl)pyrazolo[1,5-a]pyridine-3-carbonitrile (compound 11). MS m/z (ESI): 495.2 $[M+H]^+$. $^1H$ NMR (400 MHz, DMSO) δ 8.63 (s, 1H), 8.54 (s, 1H), 8.45 (s, 1H), 8.38 (s, 1H), 8.20 (d, 1H), 7.62-7.69 (m, 3H), 7.50 (m, 1H), 7.25 (s, 1H), 6.63 (s, 1H), 4.68 (s, 1H), 4.57 (d, 2H), 3.84 (s, 2H), 2.15 (m, 3H), 1.20 (s, 6H).

Example 12: Preparation of 6-(2-hydroxy-2-methylpropoxy)-4-(6-((((6-morpholinopyridin-3-yl)methyl)amino)pyridin-3-yl)pyrazole[1,5-a]pyridine-3-carbonitrile

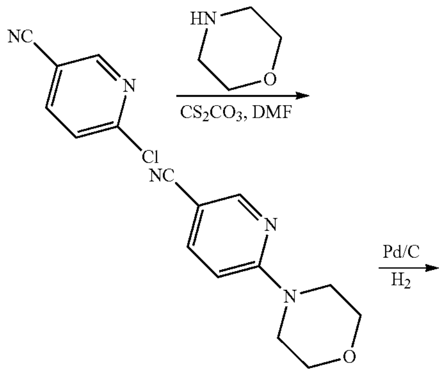

-continued

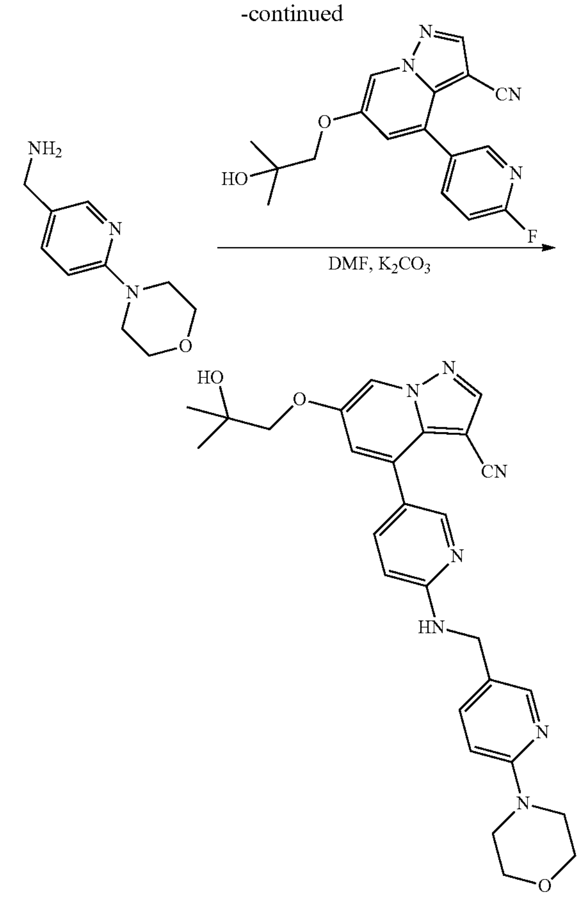

Step 1: Synthesis of 6-morpholinonicotinonitrile

At room temperature, morpholine (0.32 g, 3.6 mmol) and 6-chloronicotinonitrile (0.5 g, 3.6 mmol) were dissolved in DMF (10 mL), and then cesium carbonate (1.0 g, 7.2 mmol) was added. The mixed solution was heated to 90° C. to react for 10 h. After the reaction was completed, water (10 mL) was added to quench the reaction, extraction with DCM (30 mL*2) was carried out and the organic phase was washed with water, dried, spin-dried and subjected to column chromatography (PE:EA=6:1) to obtain 0.55 g of 6-morpholinonicotinonitrile. MS m/z (ESI): 190.2 $[M+H]^+$.

Step 2: Synthesis of (6-morpholinopyridin-3-yl)methanamine 6-morpholinonicotinonitrile (0.5 g, 2.6 mmol) and Pd/C (0.05 g) were added to a single-mouth flask, and then methanol (5 mL) was added; next 3 drops of concentrated hydrochloric acid was added dropwise. The reaction was carried out overnight at room temperature in hydrogen atmosphere. After the reaction was completed, the reaction solution was filtered, and the mother solution was spin-dried to obtain 0.3 g of (6-morpholinopyridin-3-yl)methanamine. MS m/z (ESI): 193.8 $[M+H]^+$.

Step 3: Synthesis of 6-(2-hydroxy-2-methylpropoxy)-4-(6-((((6-morpholinopyridin-3-yl)methyl)amino)pyridin-3-yl)pyrazole[1,5-a]pyridine-3-carbonitrile 4-(6-fluoropyridin-3-yl)-6-(2-hydroxy-2-methylpropoxy)pyrazolo[1,5-a]pyridine-3-carbonitrile (0.3 g, 0.92 mmol), (6-morpholinopyridin-3-yl)methanamine (0.35 g, 1.8 mmol) and potassium carbonate (0.26 g, 1.8 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (30 mL*2) was carried out and the organic phase was washed with water, dried, spin-dried and subjected to column chromatography (DCM:MeOH=10:1) to obtain 45 mg of 6-(2-hydroxy-2-methylpropoxy)-4-(6-((((6-morpholinopyridin-3-yl)methyl)amino)pyridin-3-yl)pyrazole[1,5-a]pyridine-3-carbonitrile (compound 12). MS m/z (ESI): 500.3 $[M+H]^+$. $^1$H NMR (400 MHz, DMSO) δ 8.63 (d, J=2.0 Hz, 1H), 8.54 (s, 1H), 8.20 (d, J=2.4 Hz, 1H), 8.14 (d, J=2.2 Hz, 1H), 7.59 (ddd, J=15.5, 8.7, 2.4 Hz, 2H), 7.30 (t, J=5.8 Hz, 1H), 7.24 (d, J=2.0 Hz, 1H), 6.79 (d, J=8.7 Hz, 1H), 6.59 (d, J=8.7 Hz, 1H), 4.69 (s, 1H), 4.39 (d, J=5.7 Hz, 2H), 3.85 (s, 2H), 3.70-3.61 (m, 4H), 3.41-3.34 (m, 4H), 1.20 (s, 6H).

Example 13: Preparation of 6-(2-hydroxy-2-methylpropoxy)-4-(6-(quinolin-7-methyl)amino)pyridin-3-yl)pyrazolo[1,5-a]pyridine-3-carbonitrile

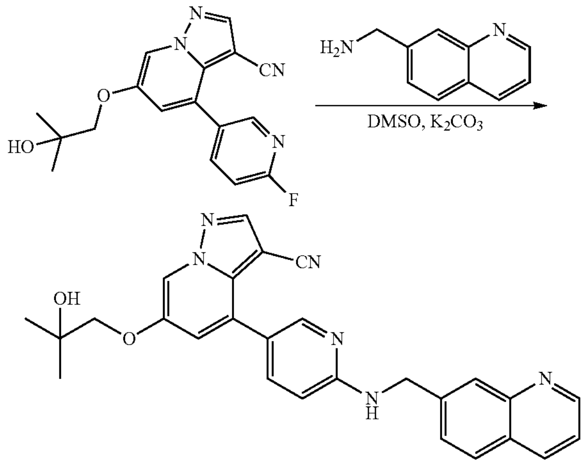

At room temperature, 4-(6-fluoropyridin-3-yl)-6-(2-hydroxy-2-methylpropoxy)pyrazolo[1,5-a]pyridine-3-carbonitrile (0.15 g, 0.46 mmol) and quinolin-7-ylmethanamine (0.15 g, 0.92 mmol) were dissolved in DMSO (5 mL), and then potassium carbonate (0.13 g, 0.92 mmol) was added. The mixed solution was heated to 130° C. and stirred overnight to react. After the reaction was completed, Extraction was carried out and the organic phase was washed with water, and subjected to column chromatography (DCM: MeOH=10:1) to obtain 30 mg of 6-(2-hydroxy-2-methylpropoxy)-4-(6-(quinolin-7-methyl)amino)pyridin-3-yl)pyrazolo[1,5-a]pyridine-3-carbonitrile (compound 13). MS m/z (ESI): 465.1 $[M+H]^+$. $^1$H NMR (500 MHz, DMSO) δ 8.84 (dd, J=4.2, 1.6 Hz, 1H), 8.64 (d, J=2.0 Hz, 1H), 8.55 (s, 1H), 8.32 (dd, J=29.6, 5.1 Hz, 2H), 7.96 (d, J=8.7 Hz, 1H), 7.76 (dd, J=9.0, 2.5 Hz, 2H), 7.67 (dd, J=8.7, 1.7 Hz, 1H), 7.49 (dd, J=8.3, 4.2 Hz, 1H), 7.29 (d, J=2.0 Hz, 1H), 6.82 (d, J=8.9 Hz, 1H), 5.06 (s, 2H), 3.85 (s, 2H), 1.20 (s, 6H).

Example 14: Preparation of 6-(2-hydroxy-2-methyl-propoxy)-4-(6-(methyl(quinolin-6-ylmethyl)amino) pyridin-3-yl)pyrazolo[1,5-a]pyridine-3-carbonitrile

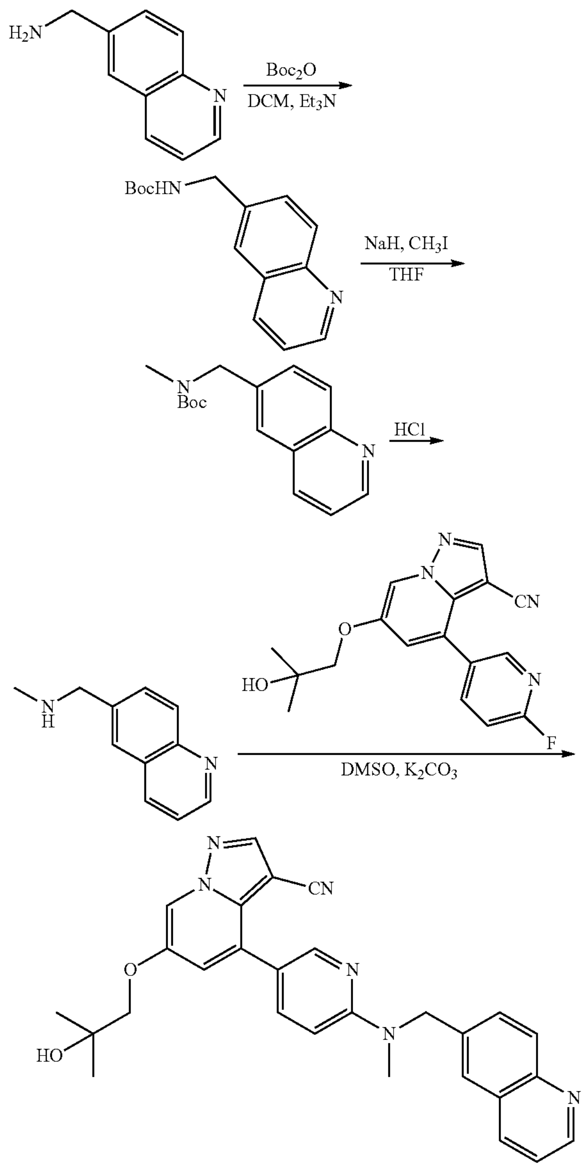

Step 1: Synthesis of tert-butyl (quinolin-6-ylmethyl)carbamate

At room temperature, quinolin-6ylmethanamine (0.5 g, 3.2 mmol) and triethylamine (0.96 g, 9.6 mmol) were dissolved in DCM (20 mL), and then $Boc_2O$ (0.7 g, 3.2 mmol) was added. The mixed solution was stirred at room temperature for 3 h to react. After the reaction was completed, water (10 mL) was added to quench the reaction, extraction with DCM (20 mL*2) was then carried out, and the organic phase was washed with water, dried and spin-dried to obtain 0.6 g of tert-butyl (quinolin-6-ylmethyl) carbamate. MS m/z (ESI): 259.5 $[M+H]^+$.

Step 2: Synthesis of tert-butyl (quinolin-6-ylmethyl)methylcarbamate

At room temperature, tert-butyl (quinolin-6-ylmethyl)carbamate (0.6 g, 2.3 mmol) was dissolved in THF (10 mL), and the mixed solution was cooled to 0° C., and then NaH (0.1 g, 4.6 mmol) was slowly added. The reaction solution was stirred at low temperature to react for 0.5 h, and then iodomethane (0.33 g, 2.3 mmol) was added. After the addition was completed, the reaction was further carried out at low temperature for 6 h. After the reaction was completed, methanol was added at low temperature to quench the reaction, extraction with EA (20 mL*2) was carried out, and the organic phase was washed, dried, and spin-dried to obtain 0.55 g of tert-butyl (quinolin-6-ylmethyl)methylcarbamate. MS m/z (ESI): 272.9 $[M+H]^+$.

Step 3: Synthesis of N-methyl-1-(quinolin-6-yl)methanamine

Tert-butyl (quinolin-6-ylmethyl)methylcarbamate (0.55 g, 2.0 mmol) was dissolved in a small amount of dichloromethane; then, 4N HCl/dioxane (3 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.3 g of N-methyl-1-(quinolin-6-yl)methanamine was obtained. MS m/z (ESI): 172.7 $[M+H]^+$.

Step 4: Synthesis of 6-(2-hydroxy-2-methyl-propoxy)-4-(6-(methyl(quinolin-6-ylmethyl)amino) pyridin-3-yl)pyrazolo[1,5-a]pyridine-3-carbonitrile 4-(6-fluoropyridin-3-yl)-6-(2-hydroxy-2-methylpropoxy) pyrazolo[1,5-a]pyridine-3-carbonitrile (0.3 g, 0.92 mmol), N-methyl-1-(quinolin-6-yl)methanamine (0.31 g, 1.8 mmol) and potassium carbonate (0.26 g, 1.8 mmol) were added to a single-mouth flask, and then DMSO (10 mL) was added. The mixed solution was heated to 130° C. to react for about 15 h to react. After the reaction was completed, water (10 mL) was added to quench the reaction, extraction with DCM (30 mL*2) was carried out and the organic phase was washed with water, dried, spin-dried and subjected to column chromatography (DCM:MeOH=10:1) to obtain 60 mg of 6-(2-hydroxy-2-methylpropoxy)-4-(6-(methyl(quinolin-6-ylmethyl)amino)pyridin-3-yl)pyrazolo[1,5-a]pyridine-3-carbonitrile (compound 14). MS m/z (ESI): 479.3 $[M+H]^+$. $^1H$ NMR (500 MHz, DMSO) δ 8.84 (dd, J=4.2, 1.6 Hz, 1H), 8.64 (d, J=2.0 Hz, 1H), 8.55 (s, 1H), 8.32 (dd, J=29.6, 5.1 Hz, 2H), 7.96 (d, J=8.7 Hz, 1H), 7.76 (dd, J=9.0, 2.5 Hz, 2H), 7.67 (dd, J=8.7, 1.7 Hz, 1H), 7.49 (dd, J=8.3, 4.2 Hz, 1H), 7.29 (d, J=2.0 Hz, 1H), 6.82 (d, J=8.9 Hz, 1H), 5.06 (s, 2H), 3.85 (s, 2H), 3.14 (s, 3H), 1.20 (s, 6H).

Example 15: Preparation of (S)-4-(6-((1-(6-(4-fluoro-1H-pyrazol-1-yl)pyridin-3-yl)propyl)amino) pyridin-3-yl)-6-(2-hydroxy-2-methylpropoxy)pyrazolo[1,5-a]pyridine-3-carbonitrile

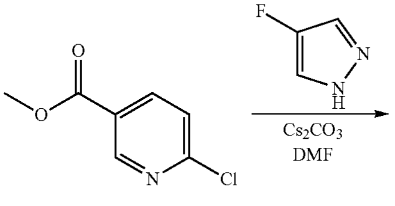

-continued

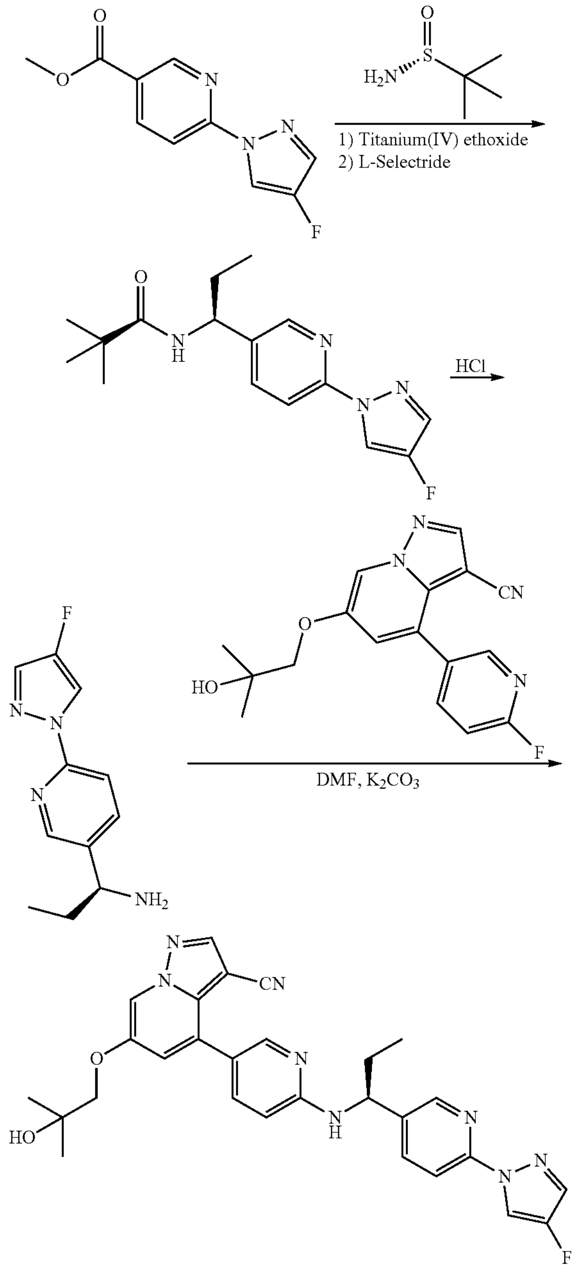

Step 1: Synthesis of 1-(6-(4-fluoro-1H-pyrazol-1-yl) pyridin-3-yl)propan-1-one 1-(6-chloropyridin-3-yl)-1-propanone (1.5 g, 8.88 mmol), 4-fluoro-1H-pyrazole (0.76 g, 8.88 mmol) and cesium carbonate (5.8 g, 17.6 mmol) were added to a single-mouth flask, and then DMF (20 mL) was added. The mixed solution was heated to 90° C. to react for 10 h. After the reaction was completed, water (20 mL) was added to quench the reaction, extraction with DCM (30 mL*2) was carried out and the organic phase was washed with water, dried, spin-dried and subjected to column chromatography (PE:EA=10:1) to obtain 1.4 g of 1-(6-(4-fluoro-1H-pyrazol-1-yl)pyridin-3-yl) propan-1-one. MS m/z (ESI): 220.2 $[M+H]^+$.

Step 2: Synthesis of (R)-N-((S)-1-(6-(4-fluoro-1H-pyrazol-1-yl)pyridin-3-yl)propyl)-2-methylpropane-2-sulfinyl amide 1-(6-(4-fluoro-1H-pyrazol-1-yl)pyridin-3-yl)propan-1-one (1.4 g, 6.4 mmol), R-(+)-tert-butylsulfinamide (0.77 g, 6.4 mmol) and titanium(IV) ethoxide (2.9 g, 12.8 mmol) were added to a double-mouth flask, and then THF (20 mL) was added. The reaction solution was refluxed to react overnight. After the reaction was completed, the reaction solution was cooled down to −75° C., and then L-selectride (19.2 mL, 1 N) was slowly added dropwise. After the addition was completed, the reaction solution was stirred at low temperature for 0.5 h, and then slowly warmed to room temperature to react for 2 h. After the reaction was completed, methanol was added at low temperature to quench the reaction, and water (20 mL) was added. Extraction with ethyl acetate (60 mL*2) was carried out, and the organic phase was dried, spin-dried and subjected to column chromatography (PE:EA=5:1) to obtain 1.0 g of (R)-N-((S)-1-(6-(4-fluoro-1H-pyrazol-1-yl)pyridin-3-yl)propyl)-2-methylpropane-2-sulfinyl amide. MS m/z (ESI): 325.5 $[M+H]^+$.

Step 3: Synthesis of (S)-1-(6-(4-fluoro-1H-pyrazol-1-yl)pyridin-3-yl)propan-1-amine (R)-N-((S)-1-(6-(4-fluoro-1H-pyrazol-1-yl)pyridin-3-yl) propyl)-2-methylpropane-2-sulfinyl amide (1.0 g, 3.0 mmol) was dissolved in a small amount of methanol; then, 4N HCl/dioxane (4 mL) was added at low temperature, and the reaction solution was stirred at room temperature to react for 2 h. After the reaction was completed, diethyl ether was added to form a viscous solid, and the supernatant liquid was poured off. Petroleum ether was added and stirred to precipitate a solid, which was filtered, and then 0.5 g of (S)-1-(6-(4-fluoro-1H-pyrazol-1-yl)pyridin-3-yl)propan-1-amine was obtained. MS m/z (ESI): 221.3 $[M+H]^+$.

Step 4: Synthesis of (S)-4-(6-((1-(6-(4-fluoro-1H-pyrazol-1-yl)pyridin-3-yl)propyl)amino)pyridin-3-yl)-6-(2-hydroxy-2-methylpropoxy)pyrazolo[1,5-a] pyridine-3-carbonitrile 4-(6-fluoropyridin-3-yl)-6-(2-hydroxy-2-methylpropoxy) pyrazolo[1,5-a]pyridine-3-carbonitrile (0.35 g, 1.1 mmol), (S)-1-(6-(4-fluoro-1H-pyrazol-1-yl)pyridin-3-yl)propan-1-amine (0.47 g, 2.2 mmol) and potassium carbonate (0.31 g, 2.2 mmol) were added to a single-mouth flask, and then DMSO (15 mL) was added. The mixed solution was heated to 130° C. to react for about 15 h. After the reaction was completed, water (10 mL) was added to quench the reaction, extraction with DCM (30 mL*2) was carried out and the organic phase was washed with water, dried, spin-dried and subjected to column chromatography (DCM:MeOH=10:1) to obtain 50 mg of (S)-4-(6-((1-(6-(4-fluoro-1H-pyrazol-1-yl)pyridin-3-yl)propyl)amino)pyridin-3-yl)-6-(2-hydroxy-2-methylpropoxy)pyrazolo[1,5-a]pyridine-3-carbonitrile (compound 15). MS m/z (ESI): 527.6 $[M+H]^+$. $^1H$ NMR (400 MHz, DMSO) δ 8.65-8.58 (m, 2H), 8.51 (s, 1H), 8.47 (d, J=2.1 Hz, 1H), 8.12 (d, J=2.4 Hz, 1H), 7.98 (dd, J=8.5, 2.3 Hz, 1H), 7.85 (dd, J=13.4, 6.4 Hz, 2H), 7.60 (dd, J=8.7, 2.5 Hz, 1H), 7.48 (d, J=7.6 Hz, 1H), 7.21 (d, J=2.1 Hz, 1H), 6.62 (d, J=8.7 Hz, 1H), 4.65 (s, 1H), 3.81 (s, 2H), 2.61 (s, 2H), 1.50 (d, J=7.0 Hz, 3H), 1.17 (s, 6H).

Example 16: Preparation of (S)-4-(6-((1-(4-(4-fluoro-1H-pyrazol-1-yl)phenyl)ethyl)amino)pyridin-3-yl)-6-(2-hydroxy-2-methylpropoxy)pyrazolo[1,5-a]pyridine-3-carbonitrile

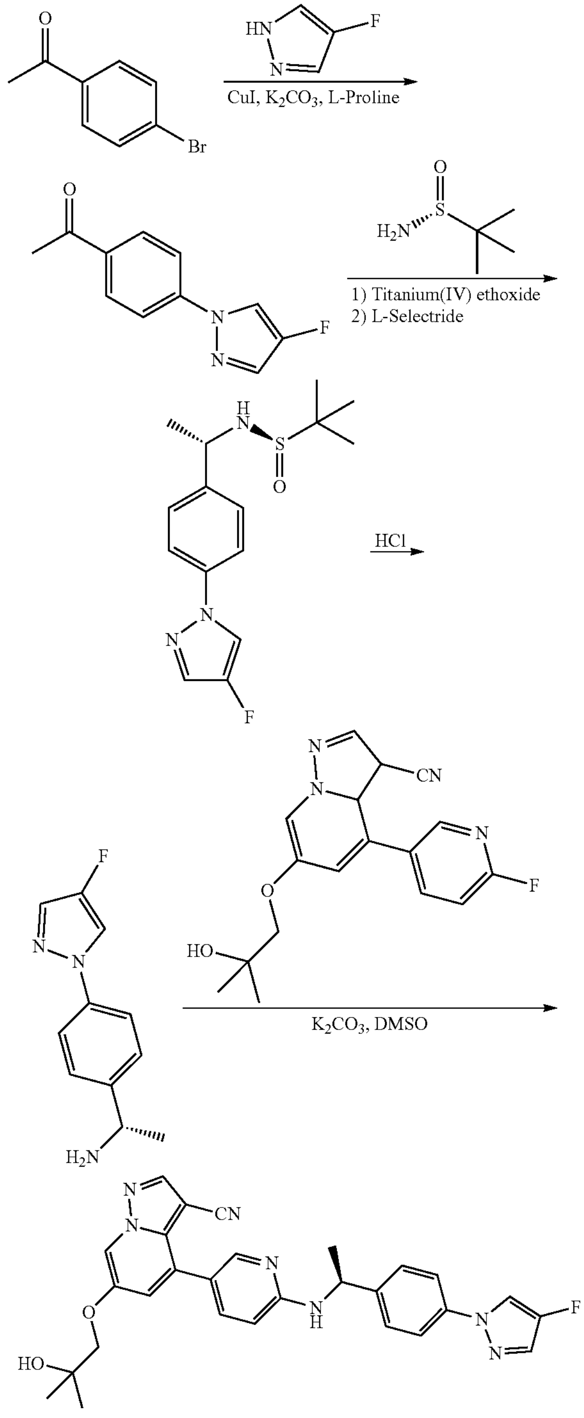

Step 1: Synthesis of 1-(4-(4-fluoro-1H-pyrazol-1-yl)phenyl)ethan-1-one 1-(4-bromophenyl)ethan-1-one (2.5 g, 12.6 mmol), 4-fluoro-1H-pyrazole (1.1 g, 12.6 mmol) and potassium carbonate (3.5 g, 25.2 mmol), CuI (0.22 g, 1.26 mmol) and L-Proline (0.27 g, 2.52 mmol) were added to a double-mouth flask, and then DMSO (20 mL) was added. The mixed solution was heated to 130° C. for 5 h to react under the protection of $N_2$. After the reaction was found to be completed from the monitoring, water (30 mL) was added to quench the reaction, extraction with DCM (50 mL*2) was then carried out, and the organic phase was washed with water, dried, spin-dried and subjected to column chromatography (PE:EA=10:1) to obtain 1.1 g of 1-(4-(4-fluoro-1H-pyrazol-1-yl)phenyl)ethan-1-one. MS m/z (ESI): 205.2 $[M+H]^+$.

Step 2: Synthesis of (R)-N-((S)-1-(4-(4-fluoro-1H-pyrazol-1-yl)phenyl)ethyl)-2-methylpropane-2-sulfinamide 1-(4-(4-fluoro-1H-pyrazol-1-yl)phenyl)ethan-1-one (1.1 g, 5.4 mmol), R-(+)-tert-butylsulfinamide (0.65 g, 5.4 mmol) and titanium(IV) ethoxide (2.4 g, 10.8 mmol) were added to a double-mouth flask, and then THF (15 mL) was added. The reaction solution was refluxed to react overnight. After the reaction was completed, the reaction solution was cooled down to −75° C., and then L-selectride (16.2 mL, 1 N) was slowly added dropwise. After the addition was completed, the reaction solution was stirred at low temperature for 0.5 h, and then slowly warmed to room temperature to react for 2 h. After the reaction was completed, methanol was added at low temperature to quench the reaction, and water (20 mL) was added. Extraction with ethyl acetate (60 mL*2) was carried out, and the organic phase was dried, spin-dried and subjected to column chromatography (PE:EA=5:1) to obtain 0.8 g of (R)-N-((S)-1-(4-(4-fluoro-1H-pyrazol-1-yl)phenyl)ethyl)-2-methylpropane-2-sulfinamide. MS m/z (ESI): 310.7 $[M+H]^+$.

Step 3: Synthesis of (S)-1-(4-(4-(4-fluoro-1H-pyrazol-1-yl)phenyl)ethan-1-amine (R)-N-((S)-1-(4-(4-fluoro-1H-pyrazol-1-yl)phenyl)ethyl)-2-methylpropane-2-sulfinamide (0.8 g, 2.6 mmol) was dissolved in a small amount of methanol; then, 4N HCl/dioxane (4 mL) was added at low temperature, and the reaction solution was stirred at room temperature to react for 2 h. After the reaction was completed, diethyl ether was added to form a viscous solid, and the supernatant liquid was poured off. Petroleum ether was added and stirred to precipitate a solid, which was filtered, and then 0.35 g of (S)-1-(4-(4-(4-fluoro-1H-pyrazol-1-yl)phenyl)ethan-1-amine was obtained. MS m/z (ESI): 206.3 $[M+H]^+$.

Step 4: Synthesis of (S)-4-(6-((1-(4-(4-fluoro-1H-pyrazol-1-yl)phenyl)ethyl)amino)pyridin-3-yl)-6-(2-hydroxy-2-methylpropoxy)pyrazolo[1,5-a]pyridine-3-carbonitrile 4-(6-fluoropyridin-3-yl)-6-(2-hydroxy-2-methylpropoxy)pyrazolo[1,5-a]pyridine-3-carbonitrile (0.2 g, 0.62 mmol), (S)-1-(4-(4-(4-fluoro-1H-pyrazol-1-yl)phenyl)ethan-1-amine (0.19 g, 0.92 mmol) and potassium carbonate (0.17 g, 1.24 mmol) were added to a single-mouth flask, and then DMSO (10 mL) was added. The mixed solution was heated to 130° C. to react for about 15 h. After the reaction was completed, water (10 mL) was added to quench the reaction, extraction with DCM (30 mL*2) was carried out and the organic phase was washed with water, dried, spin-dried and subjected to column chromatography (DCM:MeOH=10:1)

to obtain 30 mg of (S)-4-(6-((1-(4-(4-fluoro-1H-pyrazol-1-yl)phenyl)ethyl)amino)pyridin-3-yl)-6-(2-hydroxy-2-methylpropoxy)pyrazolo[1,5-a]pyridine-3-carbonitrile (compound 16). MS m/z (ESI): 512.7 $[M+H]^+$. $^1H$ NMR (500 MHz, DMSO) δ 8.61 (dd, J=6.0, 3.3 Hz, 2H), 8.53 (s, 1H), 8.13 (d, J=2.4 Hz, 1H), 7.78 (d, J=4.2 Hz, 1H), 7.69 (d, J=8.6 Hz, 2H), 7.60 (dd, J=8.7, 2.4 Hz, 1H), 7.50 (d, J=8.6 Hz, 2H), 7.43 (d, J=7.5 Hz, 1H), 7.21 (d, J=2.0 Hz, 1H), 6.60 (d, J=8.7 Hz, 1H), 5.16-5.08 (m, 1H), 4.67 (s, 1H), 3.82 (s, 2H), 1.47 (d, J=6.9 Hz, 3H), 1.18 (s, 6H).

Example 17: Preparation of (S)-6-(2-cyano-2-methylpropoxy)-4-(6-((1-(4-(4-fluoro-1H-pyrazol-1-yl)phenyl)ethyl)(methyl)amino)pyridin-3-yl)pyrazolo[1,5-a]pyridine-3-carbonitrile

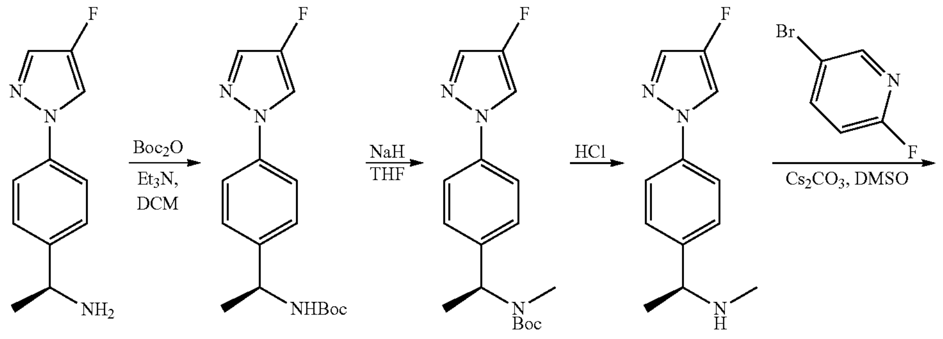

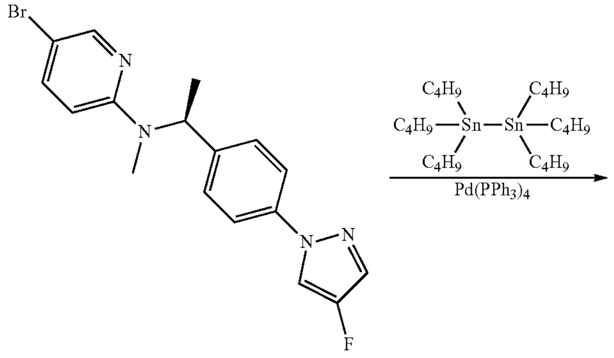

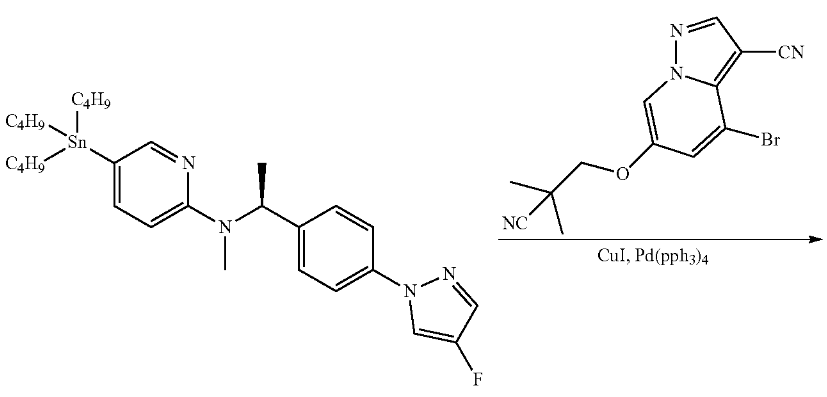

-continued

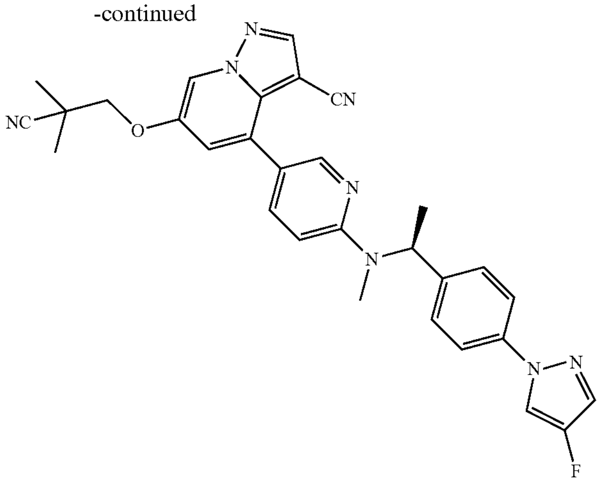

Step 1: Synthesis of tert-butyl (S)-(1-(1-(4-(4-fluoro-1H-pyrazol-1-yl)phenyl)ethyl)carbamate At room temperature, (S)-1-(4-(4-(4-fluoro-1H-pyrazol-1-yl)phenyl)ethan-1-amine (1.0 g, 4.88 mmol) and triethylamine (0.98 g, 9.8 mmol) were dissolved in DCM (20 mL), and then $Boc_2O$ (1.07 g, 4.88 mmol) was added. The mixed solution was stirred at room temperature for 4 h to react. After the reaction was completed, water (10 mL) was added to quench the reaction, extraction with DCM (20 mL*2) was then carried out, and the organic phase was washed with water, dried and spin-dried to obtain 1.2 g of tert-butyl (S)-(1-(1-(4-(4-fluoro-1H-pyrazol-1-yl)phenyl)ethyl)carbamate. MS m/z (ESI): 306.5 $[M+H]^+$.

Step 2: Synthesis of tert-butyl (S)-(1-(4-(4-fluoro-1H-pyrazol-1-yl)phenyl)ethyl)(methyl)carbamate At room temperature, (S)-(1-(1-(4-(4-fluoro-1H-pyrazol-1-yl)phenyl)ethyl)carbamate tert-butyl (1.2 g, 3.9 mmol) was dissolved in THF (15 mL); then, the mixed solution was cooled to 0° C., and NaH (0.19 g, 7.8 mmol) was slowly added. The reaction solution was stirred at low temperature to react for 0.5 h, and then iodomethane (0.56 g, 3.9 mmol) was added. After the addition was completed, the reaction was further carried out at low temperature for 5 h. After the reaction was completed, methanol was added at low temperature to quench the reaction, extraction with EA (20 mL*2) was carried out, and the organic phase was washed, dried, spin-dried and subjected to column chromatography to obtain (PE:DCM=1:1) to obtain 1.1 g of tert-butyl (S)-(1-(4-(4-fluoro-1H-pyrazol-1-yl)phenyl)ethyl)(methyl)carbamate. MS m/z (ESI): 319.9 $[M+H]^+$.

Step 3: Synthesis of (S)-1-(4-(4-fluoro-1H-pyrazol-1-yl)phenyl)-N-methyl-1-amine Tert-butyl (S)-(1-(4-(4-fluoro-1H-pyrazol-1-yl)phenyl)ethyl)(methyl)carbamate (1.1 g, 3.5 mmol) was dissolved in a small amount of dichloromethane; then, 4N HCl/dioxane (4 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.6 g of (S)-1-(4-(4-fluoro-1H-pyrazol-1-yl)phenyl)-N-methyl-1-amine was obtained. MS m/z (ESI): 219.7 $[M+H]^+$.

Step 4: Synthesis of (S)-5-bromo-N-(1-(4-(4-fluoro-1H-pyrazol-1-yl)phenyl)ethyl)-N-methylpyridin-2-amine (S)-1-(4-(4-fluoro-1H-pyrazol-1-yl)phenyl)-N-methyl-1-amine (0.6 g, 2.73 mmol), 2-fluoro-5-bromopyridine (4.8 g, 27.3 mmol) and cesium carbonate (1.78 g, 5.46 mmol) were added to a single-mouth flask, and then DMSO (15 mL) was added. The mixed solution was heated to 130° C. to react for about 40 h. After the reaction was completed, water (10 mL) was added to quench the reaction, extraction with DCM (30 mL*2) was carried out and the organic phase was washed with water, dried, spin-dried and subjected to column chromatography (PE:DCM=1:1) to obtain 0.5 g of (S)-5-bromo-N-(1-(4-(4-fluoro-1H-pyrazol-1-yl)phenyl)ethyl)-N-methylpyridin-2-amine. MS m/z (ESI): 376.3 $[M+H]^+$.

Step 5: Synthesis of (S)—N-(1-(4-(4-fluoro-1H-pyrazol-1-yl)phenyl)ethyl)-N-methyl-5-(tributylstannyl)pyridine-2-amine (S)-5-bromo-N-(1-(4-(4-fluoro-1H-pyrazol-1-yl)phenyl)ethyl)-N-methylpyridin-2-amine (0.5 g, 1.33 mmol) was dissolved in DMF (10 mL), and then hexabutyltin (1.1 g, 2.0 mmol) and tetrakistriphenylphosphine (0.15 g, 0.13 mmol) were added. The resulting solution was stirred at 140° C. for 2 h to react. After the reaction was found to be completed from the monitoring, the reaction was quenched with an ammonium chloride solution (10 mL), extraction with ethyl acetate (10 mL*2) was then carried out, and the organic phase was washed with water, dried, concentrated, and subjected to column chromatography (PE:EA=10:1) to obtain 0.2 g of (S)—N-(1-(4-(4-fluoro-1H-pyrazol-1-yl)phenyl)ethyl)-N-methyl-5-(tributylstannyl)pyridine-2-amine. MS m/z (ESI): 586.3 $[M+H]^+$.

Step 6: Synthesis of (S)-6-(2-cyano-2-methylpropoxy)-4-(6-((1-(4-(4-fluoro-1H-pyrazol-1-yl)phenyl)ethyl)(methyl)amino)pyridin-3-yl)pyrazolo[1,5-a]pyridine-3-carbonitrile 4-bromo-6-(2-cyano-2-methylpropoxy)pyrazolo[1,5-a]pyridine-3-carbonitrile (0.15 g, 0.47 mmol), (S)—N-(1-(4-

(4-fluoro-1H-pyrazol-1-yl)phenyl)ethyl)-N-methyl-5-(tributylstannyl)pyridine-2-amine (0.27 g, 0.47 mmol), CuI (9 mg, 0.047 mmol) and tetrakistriphenylphosphine palladium (54 mg, 0.047 mmol) were dissolved in xylene (15 mL). The mixed solution was stirred at 130° C. for 4 h to react. After the reaction was found to be completed from the monitoring, water (10 mL) was added to quench the reaction, extraction with EA (20 mL*3) was then carried out, and the organic phase was washed with water and then dried, concentrated and subjected to column chromatography (DCM:MeOH=10:1) to obtain 40 mg of (S)-6-(2-cyano-2-methylpropoxy)-4-(6-((1-(4-(4-fluoro-1H-pyrazol-1-yl)phenyl)ethyl)(methyl)amino)pyridin-3-yl)pyrazolo[1,5-a]pyridine-3-carbonitrile (compound 17). MS m/z (ESI): 535.1 $[M+H]^+$. $^1H$ NMR (500 MHz, DMSO) δ 8.71 (d, J=1.9 Hz, 1H), 8.56 (d, J=4.5 Hz, 1H), 8.41 (s, 2H), 8.30 (s, 2H), 7.92 (dd, J=6.4, 3.3 Hz, 2H), 7.87 (d, J=8.5 Hz, 1H), 7.80 (dd, J=8.8, 2.7 Hz, 1H), 7.40 (d, J=2.9 Hz, 1H), 6.83 (d, J=8.9 Hz, 1H), 4.45 (s, 1H), 3.47 (d, J=6.9 Hz, 2H), 2.83 (s, 3H), 1.81 (d, J=7.0 Hz, 3H), 1.46 (s, 6H).

Example 18: Preparation of (S)-6-(2-cyano-2-methylpropoxy)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile

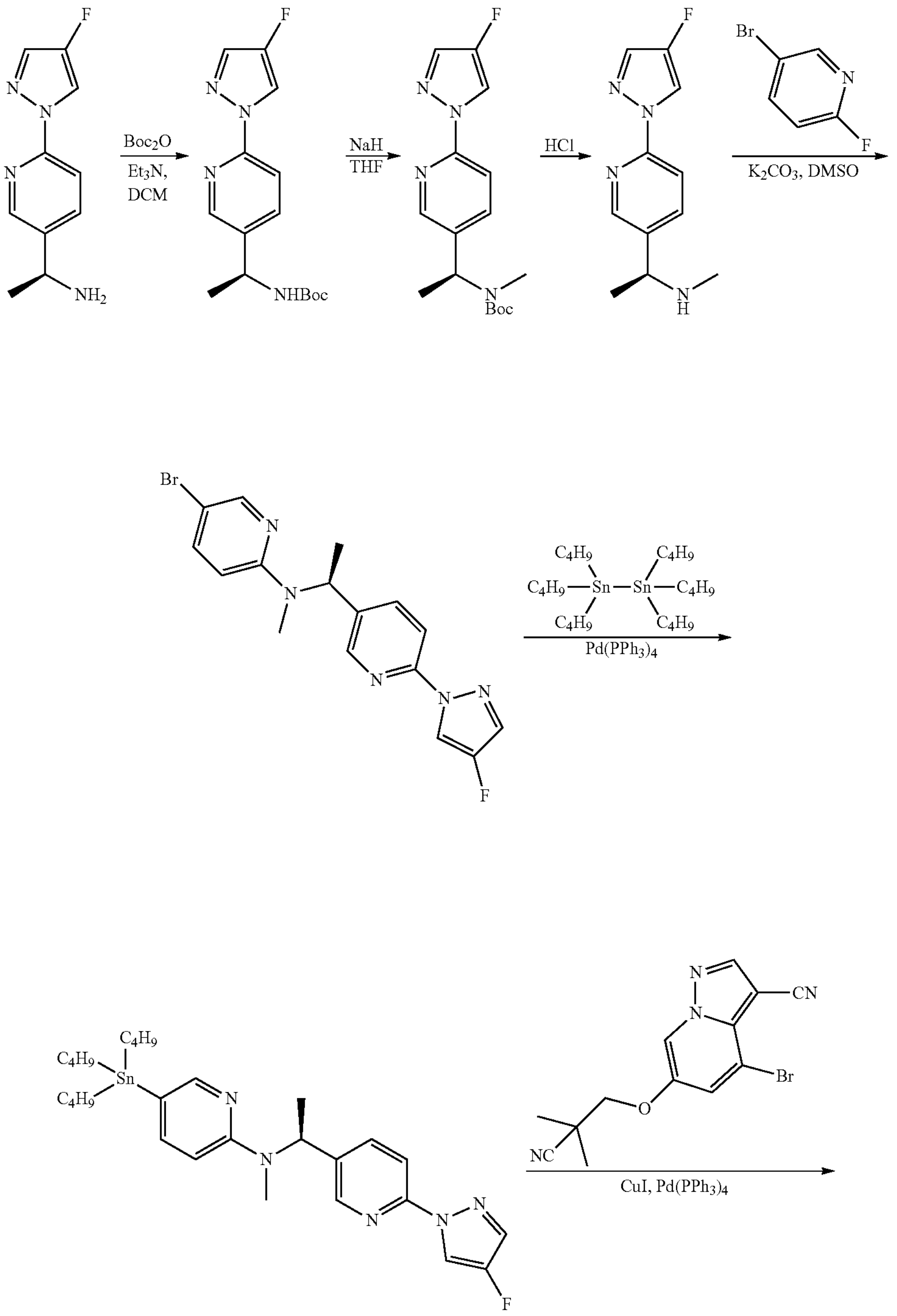

-continued

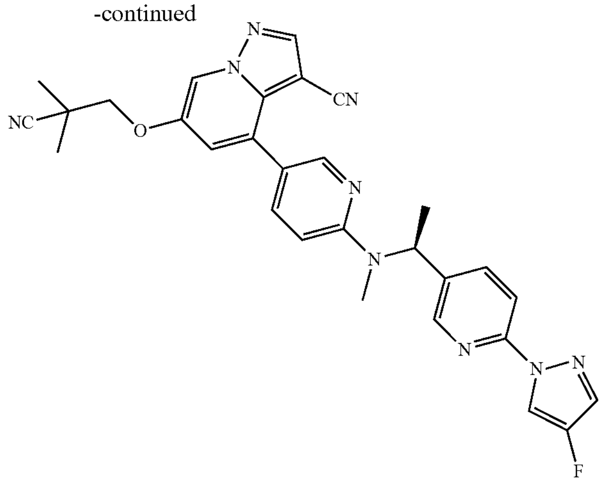

Step 1: Synthesis of tert-butyl (S)-(1-(6-(4-(4-fluoro-1H-pyrazol-1-yl)pyridin-3-yl)ethyl)carbamate At room temperature, (S)-1-(6-(4-fluoro-1H-pyrazol-1-yl)pyridin-3-yl)ethan-1-amine (1.5 g, 7.28 mmol) and triethylamine (1.48 g, 14.5 mmol) were dissolved in DCM (20 mL), and then $Boc_2O$ (1.59 g, 7.28 mmol) was added. The mixed solution was stirred at room temperature for 4 h to react. After the reaction was completed, water (10 mL) was added to quench the reaction, extraction with DCM (20 mL*2) was then carried out, and the organic phase was washed with water, dried, and spin-dried to obtain 1.8 g of tert-butyl (S)-(1-(6-(4-(4-fluoro-1H-pyrazol-1-yl)pyridin-3-yl)ethyl)carbamate. MS m/z (ESI): 307.4 $[M+H]^+$.

Step 2: Synthesis of tert-butyl (S)-(1-(6-(4-fluoro-1H-pyrazol-1-yl)pyridin-3-yl)ethyl)(methyl)carbamate At room temperature, tert-butyl (S)-(1-(6-(4-(4-fluoro-1H-pyrazol-1-yl)pyridin-3-yl)ethyl)carbamate (1.8 g, 5.9 mmol) was dissolved in THF (20 mL); then, the mixed solution was cooled to 0° C., and NaH (0.29 g, 11.8 mmol) was slowly added. The reaction solution was stirred at low temperature to react for 0.5 h, and then iodomethane (0.84 g, 3.9 mmol) was added. After the addition was completed, the reaction was further carried out at low temperature for 5 h. After the reaction was completed, methanol was added at low temperature to quench the reaction, extraction with EA (30 mL*2) was carried out, and the organic phase was washed, dried, spin-dried and subjected to column chromatography (PE:DCM=1:1) to obtain 1.7 g of tert-butyl (S)-(1-(6-(4-fluoro-1H-pyrazol-1-yl)pyridin-3-yl)ethyl)(methyl)carbamate. MS m/z (ESI): 321.3 $[M+H]^+$.

Step 3: Synthesis of (S)-1-(6-(4-fluoro-1H-pyrazol-1-yl)pyridin-3-yl)-N-methyl-1-amine Tert-butyl (S)-(1-(6-(4-fluoro-1H-pyrazol-1-yl)pyridin-3-yl)ethyl)(methyl)carbamate (1.7 g, 5.3 mmol) was dissolved in a small amount of dichloromethane; then, 4N HCl/dioxane (6 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.8 g of (S)-1-(6-(4-fluoro-1H-pyrazol-1-yl)pyridin-3-yl)-N-methyl-1-amine was obtained. MS m/z (ESI): 221.2 $[M+H]^+$.

Step 4: Synthesis of (S)-5-bromo-N-(1-(6-(4-fluoro-1H-pyrazol-1-yl)pyridin-3-yl)ethyl)-N-methylpyridin-2-amine (S)-1-(6-(4-fluoro-1H-pyrazol-1-yl)pyridin-3-yl)-N-methyl-1-amine (0.8 g, 3.62 mmol), 2-fluoro-5-bromopyridine (6.3 g, 36.2 mmol) and potassium carbonate (2.4 g, 7.24 mmol) were added to a single-mouth flask, and then DMSO (15 mL) was added. The mixed solution was heated to 130° C. to react for about 40 h. After the reaction was completed, water (10 mL) was added to quench the reaction, extraction with DCM (30 mL*2) was carried out and the organic phase was washed with water, dried, spin-dried and subjected to column chromatography (PE:DCM=1:1) to obtain 0.7 g of (S)-5-bromo-N-(1-(6-(4-fluoro-1H-pyrazol-1-yl)pyridin-3-yl)ethyl)-N-methylpyridin-2-amine. MS m/z (ESI): 377.2 $[M+H]^+$.

Step 5: Synthesis of (S)—N-(1-(6-(6-(4-fluoro-1H-pyrazol-1-yl)pyridin-3-yl)ethyl)-N-methyl-5-(tributylstannane)yl)pyridin-2-amine (S)-5-bromo-N-(1-(6-(4-fluoro-1H-pyrazol-1-yl)pyridin-3-yl)ethyl)-N-methylpyridin-2-amine (0.7 g, 1.86 mmol) was dissolved in DMF (10 mL); then, hexabutyltin (1.6 g, 2.79 mmol) and tetrakistriphenylphosphine palladium (0.21 g, 0.186 mmol) were added, and the resulting solution was stirred at 140° C. for 2 h to react. After the reaction was found to be completed from the monitoring, the reaction was quenched with an ammonium chloride solution (10 mL), extraction with ethyl acetate (10 mL*2) was carried out, and the organic phase was washed with water, dried, concentrated, and subjected to column chromatography (PE:EA=10:1) to obtain 0.3 g of (S)—N-(1-(6-(6-(4-fluoro-1H-pyrazol-1-yl)pyridin-3-yl)ethyl)-N-methyl-5-(tributylstannane)yl)pyridin-2-amine. MS m/z (ESI): 587.4 $[M+H]^+$.

Step 6: Synthesis of (S)-6-(2-cyano-2-methylpropoxy)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile 4-bromo-6-(2-cyano-2-methylpropoxy)pyrazolo[1,5-a]pyridine-3-carbonitrile (0.2 g, 0.63 mmol), (S)—N-(1-(6-(6-

(4-fluoro-1H-pyrazol-1-yl)pyridin-3-yl)ethyl)-N-methyl-5-(tributylstannane)yl)pyridin-2-amine (0.37 g, 0.63 mmol), CuI (12 mg, 0.063 mmol) and tetrakistriphenylphosphine palladium (73 mg, 0.063 mmol) were dissolved in xylene (15 mL). The mixed solution was stirred at 130° C. for 4 h to react. After the reaction was found to be completed from the monitoring, water (10 mL) was added to quench the reaction, extraction with EA (20 mL*3) was then carried out, and the organic phase was washed with water and then dried, concentrated and subjected to column chromatography (DCM:MeOH=10:1) to obtain 50 mg of (S)-6-(2-cyano-2-methylpropoxy)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile (compound 18). MS m/z (ESI): 536.6 $[M+H]^+$. $^1H$ NMR (500 MHz, DMSO) δ 8.76 (d, J=1.9 Hz, 1H), 8.66 (d, J=4.5 Hz, 1H), 8.61 (s, 1H), 8.40 (s, 2H), 7.92 (dd, J=6.4, 3.3 Hz, 2H), 7.87 (d, J=8.5 Hz, 1H), 7.83 (dd, J=8.8, 2.5 Hz, 1H), 7.40 (d, J=1.9 Hz, 1H), 6.83 (d, J=8.9 Hz, 1H), 4.35 (s, 1H), 3.43 (d, J=6.9 Hz, 2H), 2.83 (s, 3H), 1.61 (d, J=7.0 Hz, 3H), 1.44 (s, 6H).

Example 19: Preparation of (S)-4-(6-((1-(6-(4-fluoro-1H-pyrazol-1-yl)pyridin-3-yl)ethyl)(methyl)amino)pyridine-3-yl)-6-(4-methylpiperazin-1-yl)pyrazolo[1,5-a]pyridine-3-carbonitrile

Step 1: Synthesis of 6-bromo-3-cyanopyrazolo[1,5-a]pyridin-4-yl trifluoromethanesulfonate 6-bromo-4-hydroxypyrazolo[1,5-a]pyridine-3-carbonitrile (4 g, 16.88 mmol), N-phenylbis(trifluoromethanesulfonyl)imide (7.3 g, 20.25 mmol) and N,N-diisopropylethylamine (4.35 g, 33.76 mmol) were dissolved in 40 mL of DMA. The mixed solution was stirred at room temperature for 16 h to react. After the reaction was found to be completed from the monitoring, water was added to quench the reaction, extraction with EA (50 mL*2) was then carried out, and the organic phase was washed with a NaCl solution and then dried, concentrated and subjected to column chromatography to obtain 6-bromo-3-cyanopyrazolo[1,5-a]pyridin-4-yl trifluoromethanesulfonate (4.5 g). MS m/z (ESI): 370 $[M+H]^+$.

Step 2: Synthesis of (S)-6-bromo-4-(6-((1-(6-(4-(4-fluoro-1H-pyrazol-1-yl)pyridin)-3-yl)ethyl)(methyl)amino)pyridinyl-3-yl)pyrazolo[1,5-a]pyridine-3-carbonitrile 6-bromo-3-cyanopyrazolo[1,5-a]pyridin-4-yl trifluoromethanesulfonate (2 g, 5.42 mmol), sodium carbonate (1.56 g, 14.75 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (2.08 g, 4.93 mmol) and [1,1'-bis(diphenylphosphino)ferrocene]palla-

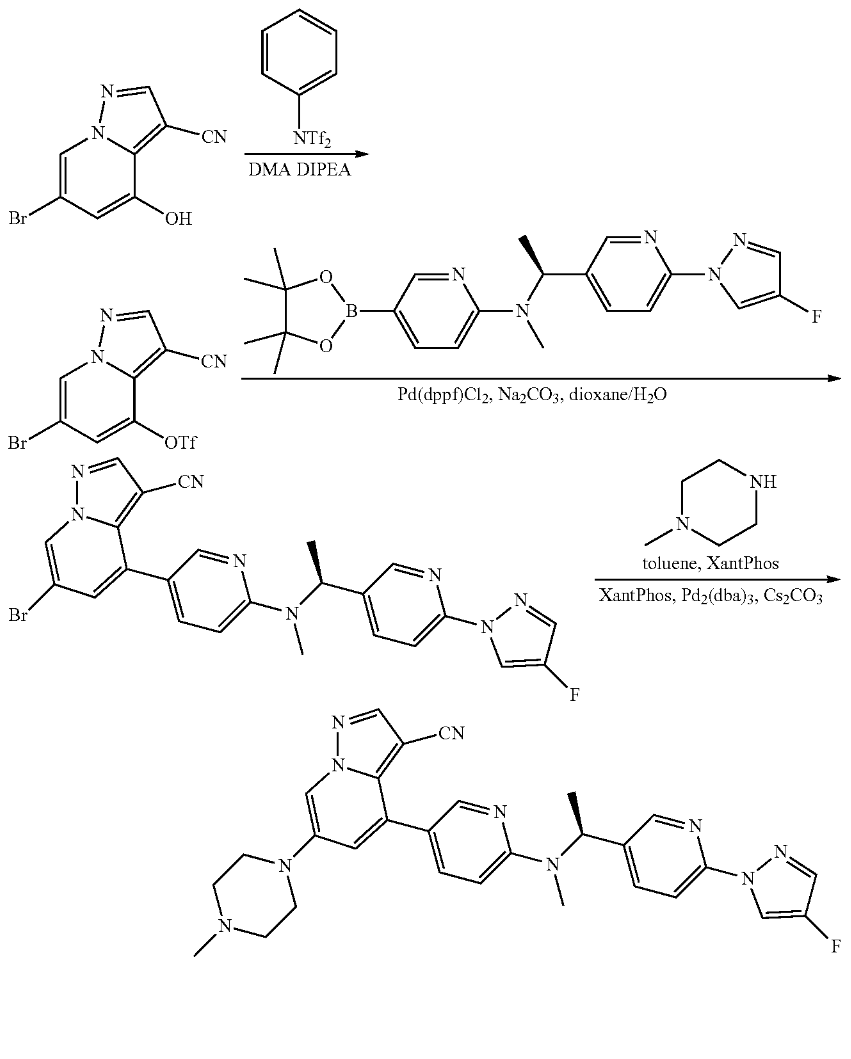

dium dichloride (403 mg, 0.542 mmol) were dissolved in a mixed solution of dioxane:water=45 mL:15 mL. The mixed solution reacted at 80° C. for 16 h. After the reaction was found to be completed from the monitoring, water was added to quench the reaction, extraction with EA (30 mL*3) was then carried out, and the organic phase was washed with water and then dried, concentrated and subjected to column chromatography to obtain 510 mg of (S)-6-bromo-4-(6-((1-(6-(4-(4-fluoro-1H-pyrazol-1-yl)pyridin)-3-yl)ethyl)(methyl)amino)pyridinyl-3-yl)pyrazolo[1,5-a]pyridine-3-carbonitrile. MS m/z (ESI): 517 [M+H]+.

Step 3: Synthesis of (S)-4-(6-((1-(6-(4-fluoro-1H-pyrazol-1-yl)pyridin-3-yl)ethyl)(methyl)amino)pyridine-3-yl)-6-(4-methylpiperazin-1-yl)pyrazolo[1,5-a]pyridine-3-carbonitrile (S)-6-bromo-4-(6-((1-(6-(4-(4-fluoro-1H-pyrazol-1-yl)pyridin)-3-yl)ethyl)(methyl)amino)pyridinyl-3-yl)pyrazolo[1,5-a]pyridine-3-carbonitrile (50 mg, 0.097 mmol), cesium carbonate (94.9 mg, 0.291 mmol), N-methylpiperazine (39.1 mg, 0.291 mmol), 4,5-bisdiphenylphosphine-9,9-dimethylxanthene (5.6 mg, 0.0097 mmol) and tris(dibenzylideneacetone)dipalladium (8.9 mg, 0.0097 mmol) were dissolved in toluene (10 ml). The mixed solution reacted at 120° C. for 16 h. After the reaction was found to be completed from the monitoring, water was added to quench the reaction, extraction with EA (20 m L*3) was then carried out, and the organic phase was washed with water and the n dried, concentrated and subjected to column chromatography to obtain 13 mg of (S)-4-(6-((1-(6-(4-fluoro-1H-pyrazol-1-yl)pyridin-3-yl)ethyl)(methyl)amino)pyridine-3-yl)-6-(4-methylpiperazin-1-yl)pyrazolo[1,5-a]pyridine-3-carbonitrile (compound 19). MS m/z (ESI): 537 [M+H]+. $^1$H NMR (500 MHz, DMSO-d6) δ 8.65 (d, J=4.6 Hz, 1H), 8.50 (s, 1H) 8.39 (d, J=2.2 Hz, 1H), 8.36 (d, J=2.6 Hz, 1H), 8.28 (d, J=2.1 Hz, 1H), 7.92-7.85 (m, 3H), 7.79 (dd, J=8.8, 2.6 Hz, 1H), 7.49 (d, J=2.1 Hz, 1H), 6.80 (d, J=8.9 Hz, 1H), 6.29 (t, J=7.2 Hz, 1H), 3.19 (t, J=4.9 Hz, 4H), 2.81 (s, 3H), 2.47 (d, J=4.8 Hz, 4H), 2.22 (s, 3H), 1.60 (d, J=7.1 Hz, 3H).

Example 20: Preparation of ((S)-4-(6-((1-(6-(4-fluoro-1H-pyrazol-1-yl)pyridin-3-yl)ethyl)(methyl)amino)pyridine-3-yl)-6-(2-hydroxyethoxy)pyrazolo[1,5-a]pyridine-3-carbonitrile

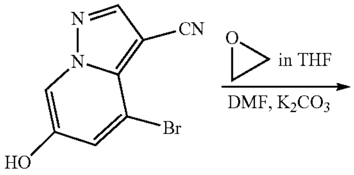

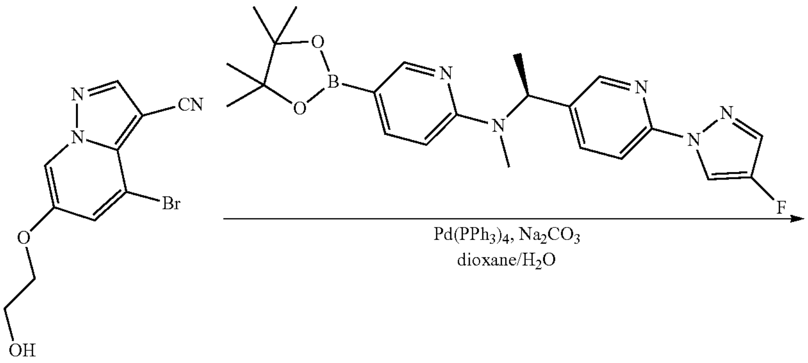

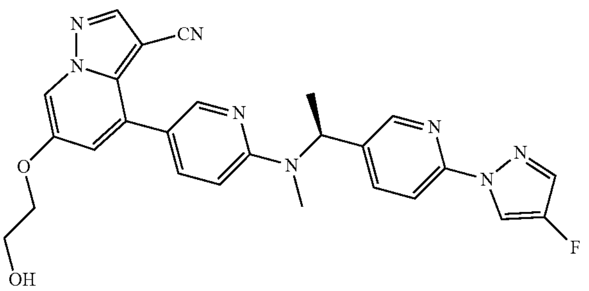

Step 1: Synthesis of 4-bromo-6-(2-hydroxyethoxy) pyrazolo[1,5-a]pyridine-3-carbonitrile 4-bromo-6-hydroxypyrazolo[1,5-a]pyridine-3-carbonitrile (500 mg, 2.11 mmol), potassium carbonate (582.3 mg, 4.22 mmol) and ethylene oxide solution in tetrahydrofuran (3M) (2.1 ml, 6.33 mmol) were dissolved in DMF (10 mL). The mixed solution reacted at 70° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 305 mg of 4-bromo-6-(2-hydroxyethoxy) pyrazolo[1,5-a]pyridine-3-carbonitrile. MS m/z (ESI): 281 $[M+H]^+$.

Step 2: ((S)-4-(6-((1-(6-(4-fluoro-1H-pyrazol-1-yl) pyridin-3-yl)ethyl)(methyl)amino)pyridine-3-yl)-6-(2-hydroxyethoxy)pyrazolo[1,5-a]pyridine-3-carbonitrile 4-bromo-6-(2-hydroxyethoxy)pyrazolo[1,5-a]pyridine-3-carbonitrile (305 mg, 1.08 mmol), sodium carbonate (345 mg, 3.25 mmol), (S)—N-(1-(6-(4-fluoro-1H-pyrazol-1-yl) pyridin-3-yl)ethyl)-N-methyl-5-(4,4,5,5-tetramethyl-1,3,2-dioxaborolane-2-yl)pyridin-2-amine (456.8 mg, 1.08 mmol) and tetrakis(triphenylphosphine)palladium (124.7 mg, 0.108 mmol) were dissolved in dioxane:water=15 mL:5 ml. The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 150 mg of (S)-4-(6-((1-(6-(4-fluoro-1H-pyrazol-1-yl) pyridin-3-yl)ethyl)(methyl)amino)pyridine-3-yl)-6-(2-hydroxyethoxy)pyrazolo[1,5-a]pyridine-3-carbonitrile (compound 20). MS m/z (ESI): 498 $[M+H]^+$. $^1$H NMR (400 MHz, DMSO-d6) δ 8.67-8.61 (m, 2H), 8.55 (s, 1H), 8.37 (d, J=2.3 Hz, 1H), 8.35 (d, J=2.5 Hz, 1H), 7.92-7.87 (m, 2H), 7.84 (dd, J=8.6, 0.8 Hz, 1H), 7.78 (dd, J=8.8, 2.6 Hz, 1H), 7.28 (d, J=2.1 Hz, 1H), 6.80 (d, J=8.8 Hz, 1H), 6.25 (t, J=7.1 Hz, 1H), 4.93 (t, J=5.4 Hz, 1H), 4.10 (t, J=4.8 Hz, 2H), 3.73 (q, J=5.1 Hz, 2H), 2.80 (s, 3H), 1.58 (d, J=7.0 Hz, 3H).

Example 21: Preparation of 6-(3,3-difluoroazetidine-1-yl)-4-(4-((3R)-3-(4-(4-fluoro-1H-pyrazol-1-yl)phenyl butan-2-yl)phenyl pyrazolo[1,5-a]pyridine-3-carbonitrile

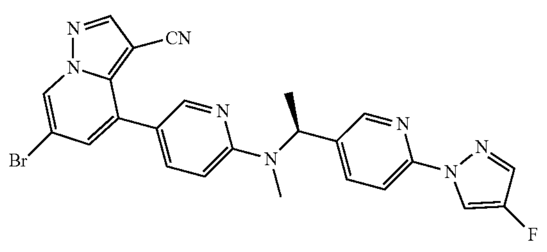

+

-continued

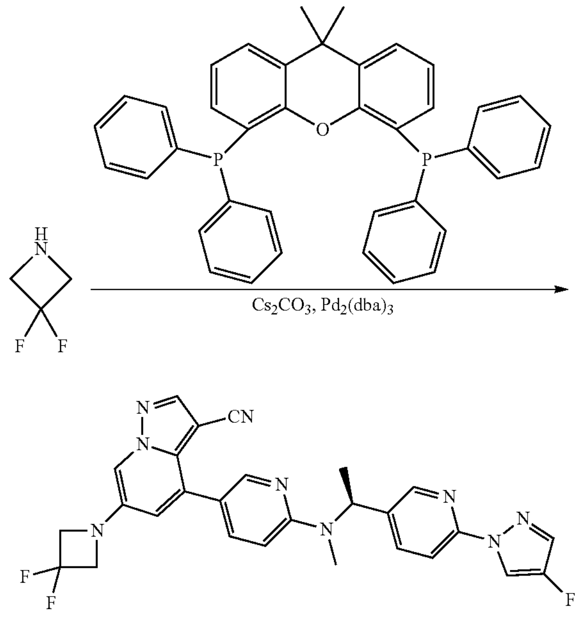

Step 1: Synthesis of 6-(3,3-difluoroazetidine-1-yl)-4-(4-((3R)-3-(4-(4-fluoro-1H-pyrazol-1-yl)phenyl) butan-2-yl)phenyl)pyrazolo[1,5-a]pyridine-3-carbonitrile (S)-6-bromo-4-(6-((1-(6-(4-fluoro-1H-pyrazol-1-yl)pyridin-3-yl)ethyl)methylamine)pyridine-3-yl)-pyrazolo[1,5-a] pyridine-3-carbonitrile (50 mg, 0.097 mmol), 3,3-difluoroazetidine (38 mg, 0.293 mmol), cesium carbonate (126.4 mg, 0.388 mmol), tris(dibenzylideneacetone)dipalladium (9 mg, 0.0097 mmol) and (9,9-dimethyl-9H-oxanthene-4,5-diyl)bis(diphenylphosphine) (60 mg, 0.097 mmol) were dissolved in 5 mL of toluene. The mixed solution was stirred at 130° C. overnight to react under the protection of $N_2$. After the reaction was found to be completed from the monitoring, the reaction solution was cooled, and water was added to quench the reaction, extraction with EA (30 mL*2) was then carried out, and the organic phase was washed with water and then dried, concentrated and subjected to column chromatography to obtain 42 mg 6-(3,3-difluoroazetidine-1-yl)-4-(4-((3R)-3-(4-(4-fluoro-1H-pyrazol-1-yl)phenyl)butan-2-yl)phenyl)pyrazolo[1,5-a]pyridine-3-carbonitrile (compound 21). MS m/z (ESI): 527.2 $[M+H]^+$. $^1$H NMR (400 MHz, DMSO) δ 8.66 (d, J=4.5 Hz, 1H), 8.53 (s, 1H), 8.38 (dd, J=7.5, 2.2 Hz, 2H), 8.28 (d, J=1.9 Hz, 1H), 7.90 (dt, J=15.1, 5.6 Hz, 3H), 7.81 (dd, J=8.8, 2.5 Hz, 1H), 7.11 (d, J=1.9 Hz, 1H), 6.83 (d, J=8.9 Hz, 1H), 6.28 (d, J=7.1 Hz, 1H), 4.39 (t, J=12.3 Hz, 4H), 2.83 (s, 3H), 1.62 (t, J=7.7 Hz, 4H), 1.26-1.17 (m, 2H), 1.06 (s, 2H), 0.83 (d, J=7.2 Hz, 1H).

Example 22: Preparation of (S)-4-(6-((1-(6-(4-fluoro-1H-pyrazol-1-yl)pyridin-3-yl)ethyl)(methyl)amino)pyridine-3-yl)-6-(piperidin-4-yl)pyrazolo[1,5-a]pyridine-3-carbonitrile

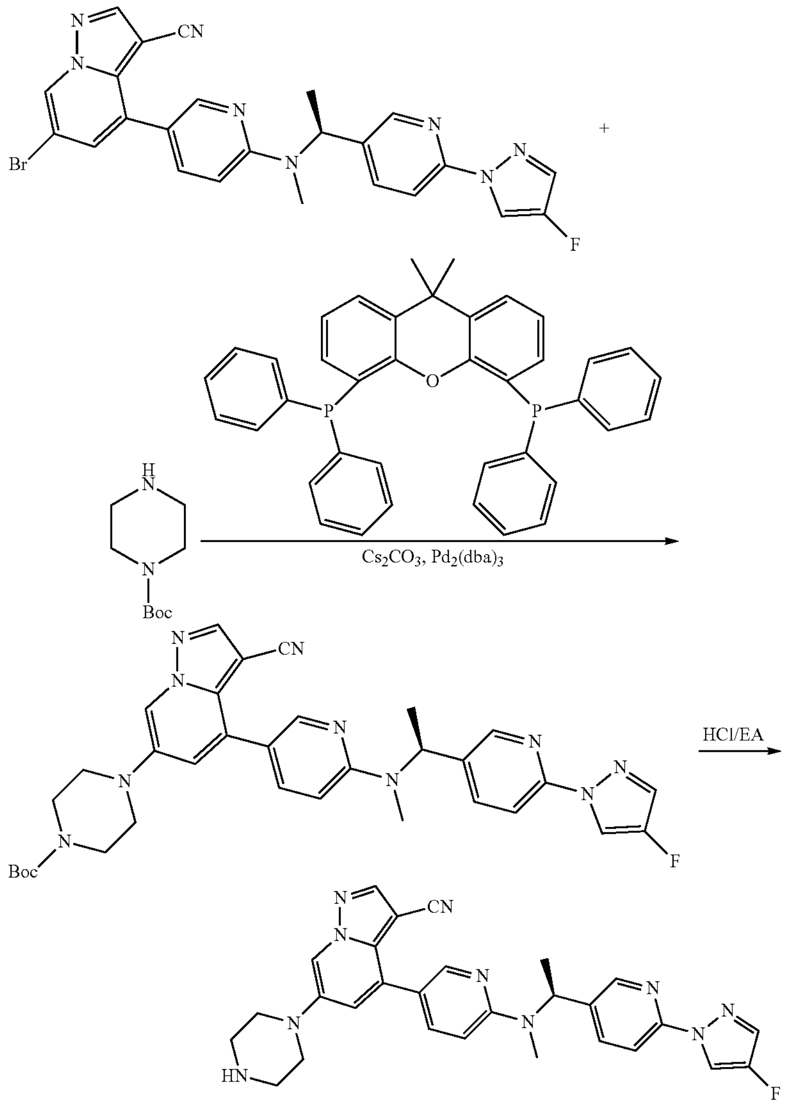

Step 1: Synthesis of tert-butyl (S)-4-(3-cyano-4-(6-((1-(6-(4-fluoro-1H-pyrazol-1-yl)pyridin-3-yl)ethyl)(methyl)amino)pyridin-3-yl)pyrazolo[1,5-a]pyridin-6-yl)piperidine-1-carboxylate (S)-6-Bromo-4-(6-((1-(6-(4-fluoro-1H-pyrazol-1-yl)pyridin-3-yl)ethyl)(methyl)amino)pyridine)pyrazolo[1,5-a]pyridine-3-carbonitrile (50 mg, 0.097 mmol), tert-butyl piperazine-1-carboxylate (55 mg, 0.293 mmol), cesium carbonate (126.4 mg, 0.388 mmol), tris(dibenzylideneacetone)dipalladium (9 mg, 0.0097 mmol) and (9,9-dimethyl-9H-oxanthene-4,5-diyl)bis(diphenylphosphine) (60 mg, 0.097 mmol) were dissolved in 5 mL of toluene. The mixed solution was stirred at 130° C. overnight to react under the protection of $N_2$. After the reaction was found to be completed from the monitoring, the reaction solution was cooled, and water was added to quench the reaction, extraction with EA (30 mL*2) was then carried out, and the organic phase was washed with water and then dried, concentrated and subjected to column chromatography to obtain 52 mg of tert-butyl (S)-4-(3-cyano-4-(6-((1-(6-(4-fluoro-1H-pyrazol-1-yl)pyridin-3-yl)ethyl)(methyl)amino)pyridin-3-yl)pyrazolo[1,5-a]pyridin-6-yl)piperidine-1-carboxylate. MS m/z (ESI): 621.3 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(piperidin-4-yl)pyrazolo[1,5-a]pyridine-3-carbonitrile Tert-butyl (S)-4-(3-cyano-4-(6-((1-(6-(4-fluoro-1H-pyrazol-1-yl)pyridin-3-yl)ethyl)(methyl)amino)pyridin-3-yl)pyrazolo[1,5-a]pyridin-6-yl)piperidine-1-carboxylic acid (52 mg, 0.083 mmol) was dissolved in 3 mL of hydrochloric acid/ethyl acetate. The reaction solution was stirred at 0° C. for 30 min. After the reaction was found to be completed from the monitoring, the reaction solution was concentrated to dryness, adjusted to pH 7-8 with a sodium carbonate solution. Extraction with EA (30 mL*2) was carried out, and the organic phase was washed with water, dried, concentrated and subjected to column chromatography to obtain 42 mg of (S)-4-(6-((1-(6-(4-fluoro-1H-pyrazol-1-yl)pyridin-3-yl)ethyl)(methyl)amino)pyridine-3-yl)-6-(piperidin-4-yl) pyrazolo[1,5-a]pyridine-3-carbonitrile ((compound 22). MS m/z (ESI): 521.25 $[M+H]^+$. $^1H$ NMR (400 MHz, DMSO) δ 8.66 (d, J=4.5 Hz, 1H), 8.51 (s, 1H), 8.38 (dd, J=12.0, 2.2 Hz, 2H), 8.27 (d, J=1.8 Hz, 1H), 7.95-7.83 (m, 3H), 7.80 (dd, J=8.8, 2.5 Hz, 1H), 7.48 (d, J=1.9 Hz, 1H), 6.81 (d, J=8.9 Hz, 1H), 6.29 (q, J=6.7 Hz, 1H), 3.18-3.04 (m, 4H), 2.92-2.73 (m, 7H), 1.89 (s, 1H), 1.61 (d, J=7.0 Hz, 3H), 1.23 (d, J=11.5 Hz, 2H), 0.83 (d, J=7.3 Hz, 1H).

Example 23: Preparation of (S)-4-(6-((1-(6-(4-fluoro-1H-pyrazol-1-yl)pyridin-3-yl)ethyl)(methyl)amino)pyridine-3-yl)-6-(4-hydroxy-4-methylpiperidin-1-yl)pyrazolo[1,5-a]pyridine-3-carbonitrile

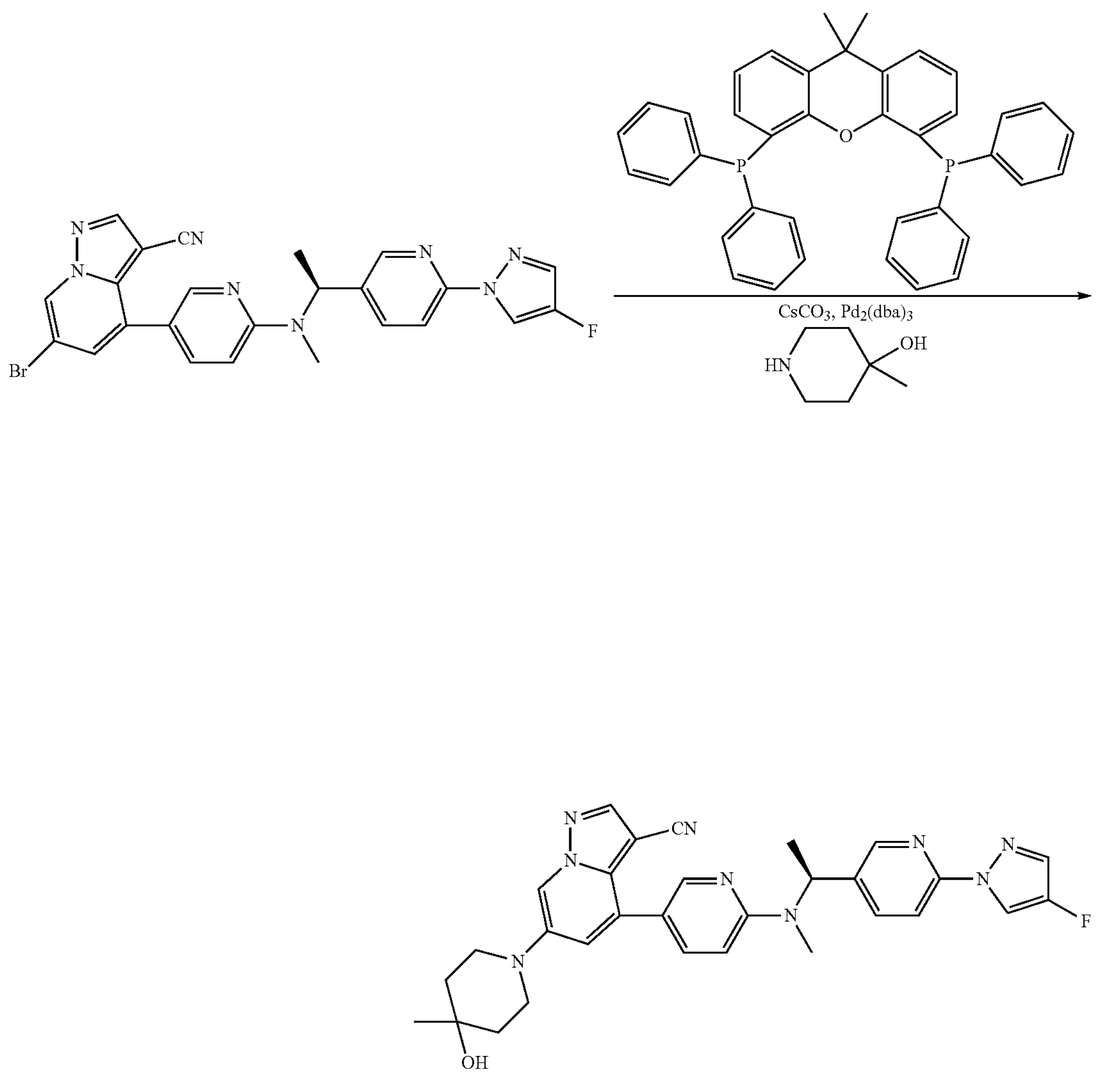

Step 1: Synthesis of (S)-4-(6-((1-(6-(4-fluoro-1H-pyrazol-1-yl)pyridin-3-yl)ethyl)(methyl)amino)pyridine-3-yl)-6-(4-hydroxy-4-methylpiperidin-1-yl) pyrazolo[1,5-a]pyridine-3-carbonitrile (S)-6-bromo-4-(6-((1-(6-(4-fluoro-1H-pyrazol-1-yl)pyridin-3-yl)ethyl)(methyl)amino)pyridin-3-yl)pyrazolo[1,5-a] pyridine-3-carbonitrile (150 mg, 0.29 mmol) was dissolved in toluene (5 mL), and then 4-methylpiperidin-4-ol (100 mg, 0.87 mmol), (9,9-dimethyl-9H-oxanthene-4,5-diyl)bis(diphenylphosphine) (168 mg, 0.29 mmol), cesium carbonate (378 mg, 1.16 mmol) and $Pd_2(dba)_3$ (27 mg, 0.03 mmol) were added. The reaction solution was heated to 130° C. to react overnight under the protection of $N_2$. After all the raw materials were consumed, the reaction system was lowered to room temperature. The reaction solution was washed with water, extracted with EA, and the organic phases were combined, dried, spin-dried and subjected to column chromatography to obtain 104 mg of (S)-4-(6-((1-(6-(4-fluoro-1H-pyrazol-1-yl)pyridin-3-yl)ethyl)(methyl)amino)pyridine-3-yl)-6-(4-hydroxy-4-methylpiperidin-1-yl)pyrazolo [1,5-a]pyridine-3-carbonitrile (compound 23). MS m/z (ESI): 552.6 $[M+H]^+$. $^1H$ NMR (500 MHz, DMSO) δ 8.65 (d, J=3.9 Hz, 1H), 8.48 (s, 1H), 8.39 (d, J=2.1 Hz, 1H), 8.36 (d, J=2.3 Hz, 1H), 8.28 (d, J=1.9 Hz, 1H), 7.92 (d, J=3.4 Hz, 1H), 7.90 (d, J=2.3 Hz, 1H), 7.86 (d, J=8.4 Hz, 1H), 7.79 (dd, J=8.8, 2.5 Hz 1H), 7.46 (d, J=1.9 Hz, 1H), 6.80 (d, J=8.8 Hz, 1H), 4.33 (s, 1H), 2.81 (s, 3H), 1.59 (m, 6H), 1.21 (s, 1H), 1.15 (s, 3H).

J=8.6 Hz, 1H), 7.78 (dd, J=8.8, 2.5 Hz 1H), 7.02 (d, J=1.9 Hz, 1H), 6.81 (d, J=8.9 Hz, 1H), 4.25 (d, J=7.7 Hz, 2H), 3.89 (d, J=7.7 Hz, 2H) 2.82 (d, J=5.5 Hz, 3H), 2.48 (m, 5H), 1.64 (s, 3H), 1.59 (d, J=7.0 Hz, 3H).

Example 24: Preparation of (S)-6-(3-cyano-3-methylazetidine-1-yl)-4-(6-((1-(6-(4-fluoro-1H-pyrazole-1)-yl)pyridin-3-yl)ethyl)(methyl)amino)pyridin-3-yl)pyrazolo[1,5-a]pyridine-3-carbonitrile

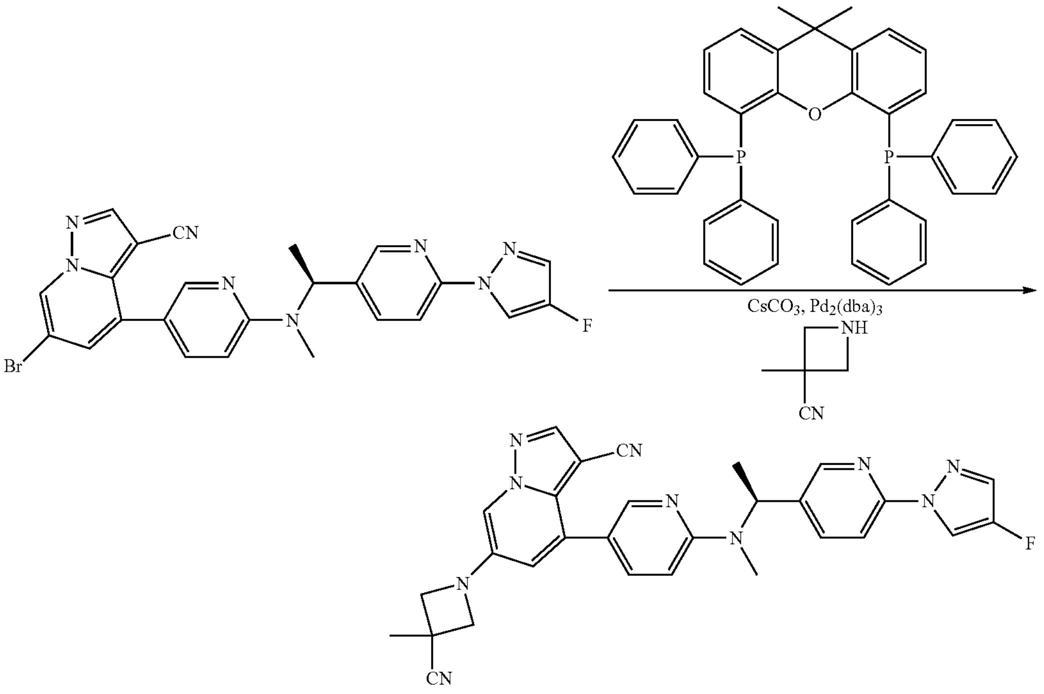

Step 1: Synthesis of (S)-6-(3-cyano-3-methylazetidine-1-yl)-4-(6-((1-(6-(4-fluoro-1H-pyrazole-1-yl)pyridin-3-yl)ethyl)(methyl)amino)pyridin-3-yl)pyrazolo[1,5-a]pyridine-3-carbonitrile (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (150 mg, 0.29 mmol) was dissolved in toluene (5 mL), and then 3-methylazetidine-3-carbonitrile (84 mg, 0.87 mmol), (9,9-dimethyl-9H-oxanthene-4,5-diyl) bis(diphenylphosphine) (168 mg, 0.29 mmol), cesium carbonate (378 mg, 1.16 mmol) and $Pd_2(dba)_3$ (27 mg, 0.03 mmol) were added to the mixed solution. The reaction solution was heated to 130° C. to react overnight under the protection of $N_2$. After all the raw materials were consumed, the reaction system was lowered to room temperature. The reaction solution was washed with water, extracted with EA, and the organic phases were combined, dried, spin-dried and subjected to column chromatography to obtain 105 mg of (S)-6-(3-cyano-3-methylazetidine-1-yl)-4-(6-((1-(6-(4-fluoro-1H-pyrazole-1-yl)pyridin-3-yl)ethyl)(methyl)amino)pyridin-3-yl)pyrazolo[1,5-a]pyridine-3-carbonitrile (compound 24). MS m/z (ESI): 533.6 $[M+H]^+$. $^1H$ NMR (500 MHz, DMSO) δ 8.65 (d, J=4.5 Hz, 1H), 8.50 (s, 1H), 8.38 (d, J=2.0 Hz, 1H), 8.35 (d, J=2.4 Hz, 1H), 8.17 (d, J=1.8 Hz, 1H), 7.91 (d, J=2.4 Hz, 1H), 7.89 (d, J=3.6 Hz, 1H), 7.86 (d,

Example 25: Preparation of (S)-4-(6-((1-(6-(4-fluoro-1H-pyrazol-1-yl)pyridin-3-yl)ethyl)(methyl)amino)pyridine-3-yl)-6-(2-oxo-7-azaspiro[3.5]nonan-7-yl)pyrazolo[1,5-a]pyridine-3-carbonitrile

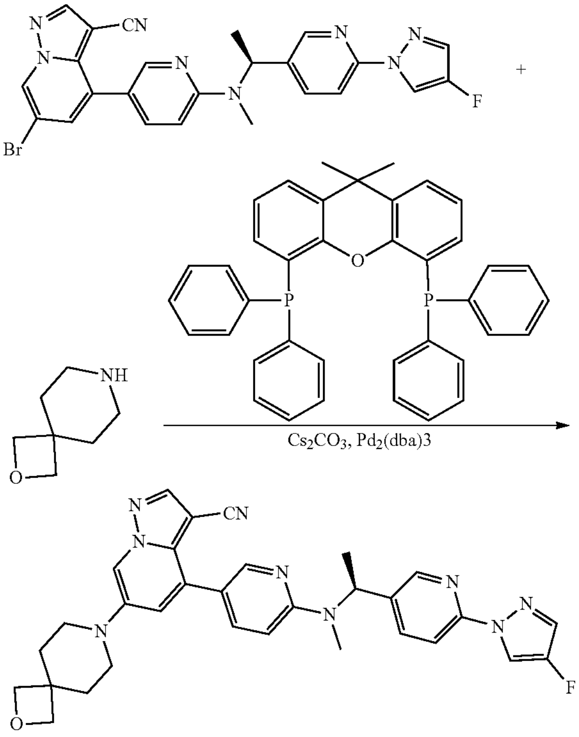

Step 1: Synthesis of (S)-4-(6-((1-(6-(4-fluoro-1H-pyrazol-1-yl)pyridin-3-yl)ethyl)(methyl)amino)pyridine-3-yl)-6-(2-oxo-7-azaspiro[3.5]nonan-7-yl)pyrazolo[1,5-a]pyridine-3-carbonitrile (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (150 mg, 0.29 mmol) was dissolved in toluene (5 mL), and then 2-oxo-7-azaspiro[3.5]nonane (110 mg, 0.87 mmol), (9,9-dimethyl-9H-oxanthene-4,5-diyl)bis(diphenylphosphine) (168 mg, 0.29 mmol), cesium carbonate (378 mg, 1.16 mmol) and $Pd_2(dba)_3$ (27 mg, 0.03 mmol) were added. The reaction solution was heated to reflux to react overnight under the protection of $N_2$. After all the raw materials were consumed, the reaction system was lowered to room temperature. The reaction solution was washed with water, extracted with EA, and the organic phases were combined, dried, spin-dried and subjected to column chromatography to obtain 55 mg of (S)-4-(6-((1-(6-(4-fluoro-1H-pyrazol-1-yl)pyridin-3-yl)ethyl)(methyl)amino)pyridine-3-yl)-6-(2-oxo-7-azaspiro[3.5]nonan-7-yl)pyrazolo[1,5-a]pyridine-3-carbonitrile (compound 25). MS m/z (ESI): 564.3 $[M+H]^+$. $^1H$ NMR (400 MHz, DMSO) δ 8.65 (dd, J=4.6, 0.8 Hz, 1H), 8.49 (s, 1H), 8.38 (dd, J=14.1, 2.2 Hz, 2H), 8.28 (d, J=2.0 Hz, 1H), 7.90 (dd, J=3.0, 1.2 Hz, 1H), 7.87 (d, J=8.4 Hz, 1H), 7.80 (dd, J=8.8, 2.5 Hz, 1H), 7.48 (d, J=2.0 Hz, 1H), 6.81 (d, J=8.8 Hz, 1H), 6.28 (d, J=7.1 Hz, 1H), 4.34 (s, 3H), 3.15-3.11 (m, 3H), 2.83 (s, 3H), 1.98-1.83 (m, 4H), 1.61 (d, J=7.0 Hz, 2H), 1.22 (s, 4H).

Example 26: Preparation of (S)-4-(6-((1-(6-(4-fluoro-1H-pyrazol-1-yl)pyridin-3-yl)ethyl)(methyl)amino)pyridine-3-yl)-6-morpholinopyrazolo[1,5-a]pyridine-3-carbonitrile

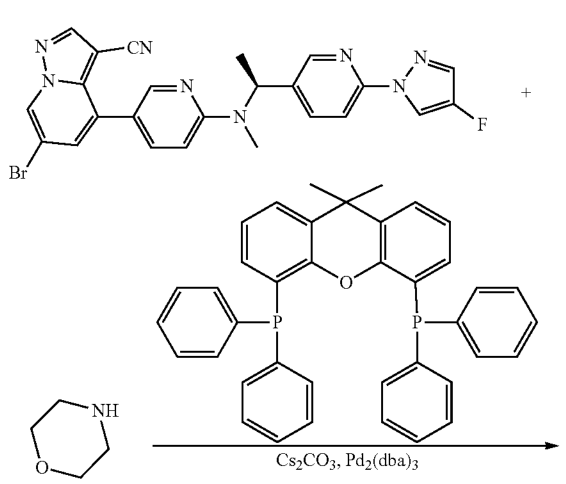

-continued

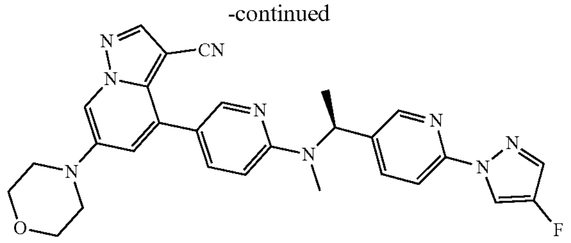

Step 1: Synthesis of (S)-4-(6-((1-(6-(4-fluoro-1H-pyrazol-1-yl)pyridin-3-yl)ethyl)(methyl)amino)pyridine-3-yl)-6-morpholinopyrazolo[1,5-a]pyridine-3-carbonitrile (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (150 mg, 0.29 mmol) was dissolved in toluene (5 mL), and then morpholine (76 mg, 0.87 mmol), (9,9-dimethyl-9H-oxanthene-4,5-diyl)bis(diphenylphosphine) (168 mg, 0.29 mmol), cesium carbonate (378 mg, 1.16 mmol) and $Pd_2(dba)_3$ (27 mg, 0.03 mmol) were added. The reaction solution was heated to reflux to react overnight under the protection of $N_2$. After all the raw materials were consumed, the reaction system was lowered to room temperature. The reaction solution was washed with water, extracted with EA, and the organic phases were combined, dried, spin-dried and subjected to column chromatography to obtain 69 mg of (S)-4-(6-((1-(6-(4-fluoro-1H-pyrazol-1-yl)pyridin-3-yl)ethyl)(methyl)amino)pyridine-3-yl)-6-morpholinopyrazolo[1,5-a]pyridine-3-carbonitrile (compound 26). MS m/z (ESI): 524.1 $[M+H]^+$. $^1H$ NMR (400 MHz, DMSO) δ 8.63 (dd, J=4.5, 0.7 Hz, 1H), 8.50 (s, 1H), 8.36 (dd, J=10.2, 2.2 Hz, 2H), 8.29 (d, J=2.0 Hz, 1H), 7.93-7.82 (m, 3H), 7.78 (dd, J=8.8, 2.5 Hz, 1H), 7.49 (d J=2.0 Hz, 1H), 6.79 (d, J=8.8 Hz, 1H), 6.26 (q, J=6.7 Hz, 1H), 3.76-3.67 (m, 4H), 3.20-3.10 (m, 4H), 2.80 (s, 3H), 1.58 (d, J=7.0 Hz, 3H).

Example 27: Preparation of (S)-4-(6-((1-(6-(4-fluoro-1H-pyrazol-1-yl)pyridin-3-yl)ethyl)(methyl)amino)pyridine-3-yl)-6-(3-hydroxy-3-methyl-1-yn-1-yl)pyrazolo[1,5-a]pyridine-3-carbonitrile

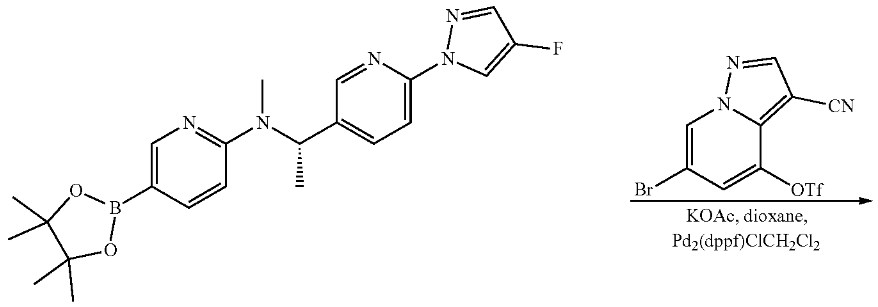

-continued

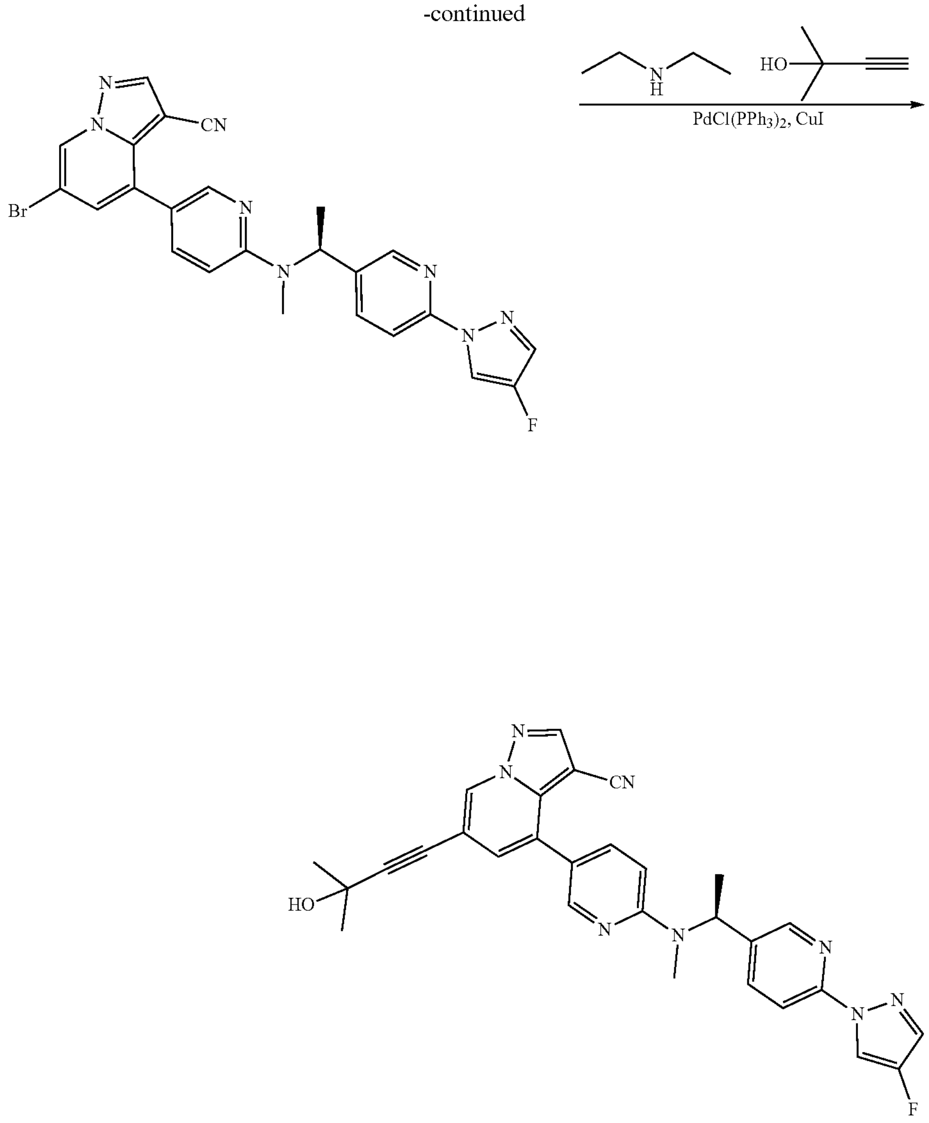

Step 1: Synthesis of (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile 6-bromo-3-cyanopyrazolo[1,5-a]pyridin-4-yl trifluoromethanesulfonate (452 mg, 1.22 mmol), (S)—N-(1-(6-(4-fluoro-1H-pyrazol-1-yl)pyridin-3-yl)ethyl)-N-methyl-5-(4,4,5,5-tetramethyl-1,3,2-di oxaborin-2-yl)pyridin-2-amine (400 mg, 0.94 mmol) and Pd(dppf)$Cl_2CH_2Cl_2$ (76 mg, 0.0114 mmol) were dissolved in 1,4-dioxane:$H_2O$=5:1 (24 mL), and then KOAc (277 mg, 2.82 mmol) was added. The mixed solution was stirred at 50° C. overnight under the protection of $N_2$. The reaction solution was cooled to room temperature, and water was added to quench the reaction, extraction was carried out, and the organic phase was washed with water, dried, and subjected to column chromatography to obtain 93 mg of (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile with a yield of 30%. MS m/z (ESI): 517 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(3-hydroxy-3-methyl-1-yn-1-yl)pyrazolo[1,5-a]pyridine-3-carbonitrile (S)-6-bromo-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (186 mg, 0.36 mmol), 2-methyl-3-yn-2-ol (30 mg, 0.36 mmol), $PdCl(PPh_3)_2$ (13 mg, 0.08 mmol) and CuI (7 mg, 0.036 mmol) were dissolved in diethylamine (10 mL). The mixed solution was stirred at 50° C. to react for 5 h. After the reaction was completed, water was added to quench the reaction, extraction was carried out, and the organic phase was washed, dried, concentrated and subjected to column chromatography to obtain 37 mg of (S)-4-(6-((1-(6-(4-fluoro-1H-pyrazolyl)pyridin-3-yl)ethyl)(methyl)amino)pyridin-3-yl)-6-(3-hydroxy-3-methyl-1-yn-1-yl)pyrazolo[1,5-a]pyridine-3-carbonitrile (compound 27) with a yield of 20%, as a white solid. MS m/z (ESI): 521 $[M+H]^+$. $^1H$ NMR (400 MHz, DMSO) δ 9.06 (s, 1H), 8.72 (s, 1H), 8.65-8.66 (m, 1H), 8.37-8.40 (m, 1H), 7.80-7.91 (m, 4H), 7.40 (s, 1H), 6.81 (d, 1H), 6.26-6.36 (m, 1H), 5.56 (s, 1H), 2.82 (s, 3H), 1.60-1.62 (d, 3H), 1.48 (s, 6H).

Example 28: Preparation of (S)-6-(cyclopropylmethoxy)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile

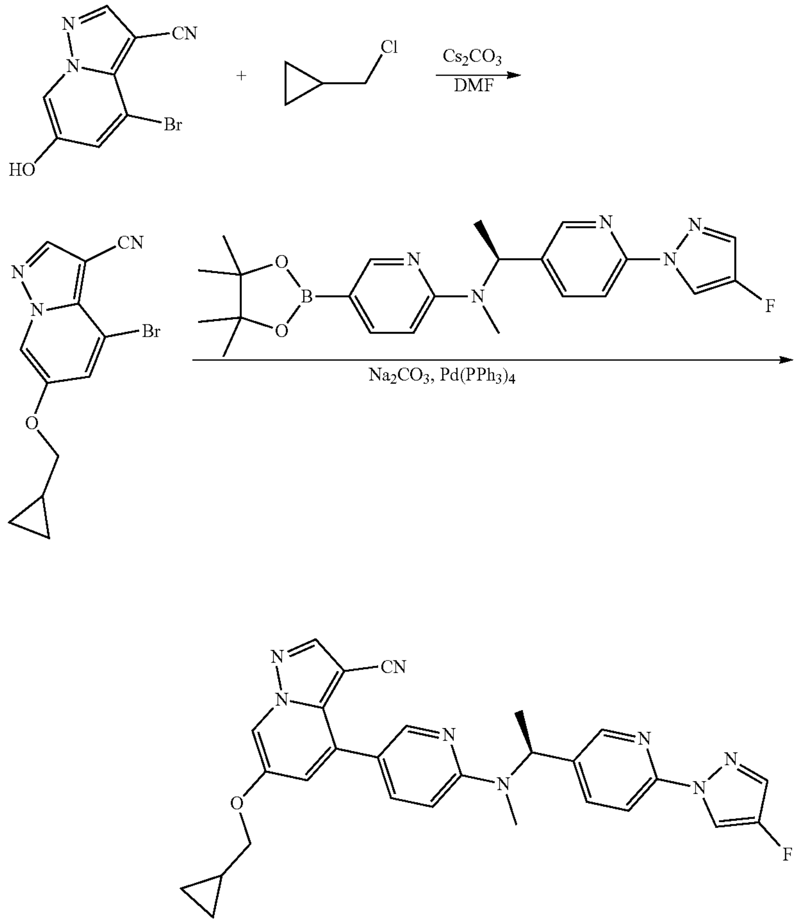

Step 1: Synthesis of 4-bromo-6-(cyclopropylmethoxy)pyrazolo[1,5-a]pyridine-3-carbonitrile 4-bromo-6-hydroxypyrazolo[1,5-a]pyridine-3-carbonitrile (200 mg, 0.84 mmol), (chloromethyl)cyclopropane (0.17 ml, 1.68 mmol) and cesium carbonate (554.4 mg, 1.68 mmol) were dissolved in 3 mL of DMF, and then the mixed solution was stirred at 60° C. overnight to react. After the reaction was found to be completed from the monitoring, the reaction solution was cooled, and water was added to quench the reaction, extraction with EA (30 mL*2) was then carried out, and the organic phase was washed with water, dried, concentrated and subjected to column chromatography to obtain 170 mg of 4-bromo-6-(cyclopropylmethoxy)pyrazolo[1,5-a]pyridine-3-carbonitrile. MS m/z (ESI): 291.00 $[M+H]^+$.

Step 2: Synthesis of (S)-6-(cyclopropylmethoxy)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile 4-bromo-6-(cyclopropylmethoxy)pyrazolo[1,5-a]pyridine-3-carbonitrile (170 mg, 0.58 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (247 mg, 0.58 mmol), sodium carbonate (186 mg, 1.75 mmol) and tetrakistriphenylphosphine palladium (68 mg, 0.058 mmol) were dissolved in 3 mL of dioxane and 1 mL of water. The mixed solution was stirred at 90° C. overnight to react under the protection of $N_2$. After the reaction was found to be completed from the monitoring, the reaction solution was cooled, and water was added to quench the reaction, extraction with EA (30 mL*2) was then carried out, and the organic phase was washed with water and then dried, concentrated and subjected to column chromatography to obtain 48 mg of (S)-6-(cyclopropylmethoxy)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (compound 28). MS m/z (ESI): 507.22 $[M+H]^+$. $^1H$ NMR (400 MHz, DMSO) δ 8.66 (dd, J=4.6, 0.7 Hz, 1H), 8.61-8.51 (m, 2H), 8.38 (dd, J=10.9, 2.2 Hz, 2H), 7.96-7.83 (m, 3H), 7.80 (dd, J=8.8, 2.5 Hz, 1H), 7.32 (d, J=2.1 Hz, 1H), 6.82 (d, J=8.8 Hz, 1H), 6.28 (d, J=7.0 Hz, 1H), 5.75 (s, 1H), 4.34 (t, J=5.1 Hz, 1H), 3.94 (d, J=7.1 Hz, 2H), 3.43 (ddd, J=14.0, 7.0, 5.1 Hz, 2H), 1.61 (d, J=7.0 Hz, 3H), 1.32-1.19 (m, 2H), 1.05 (t, J=7.0 Hz, 2H), 0.64-0.56 (m, 2H), 0.40-0.28 (m, 2H).

Example 29: Preparation of (S)-6-(1-methyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile

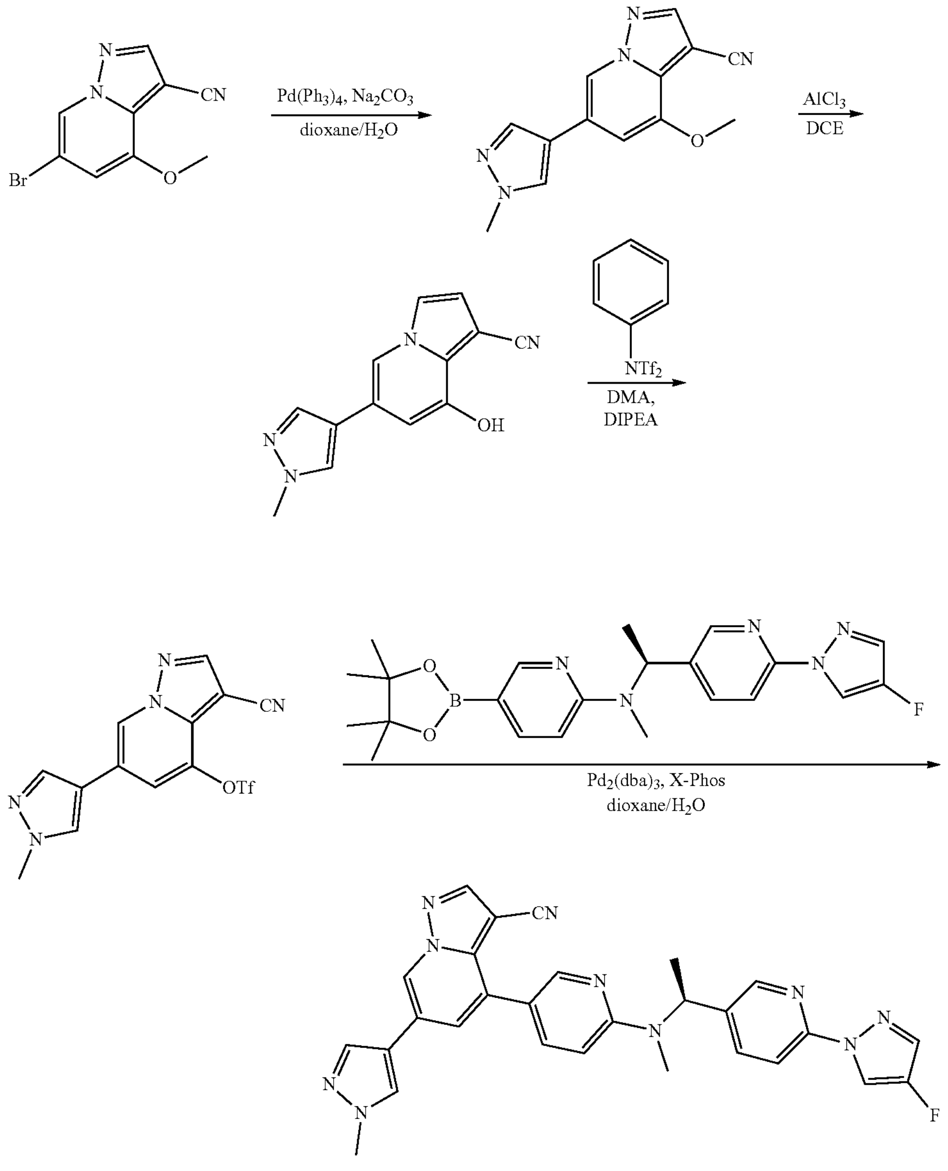

Step 1: Synthesis of 4-methoxy-6-(1-methyl-1H-pyrazol-4-yl)pyrazolo[1,5-a]pyridine-3-carbonitrile 6-bromo-4-methoxypyrazolo[1,5-a]pyridine-3-carbonitrile (510 mg, 2.03 mmol), sodium carbonate (646 mg, 6.09 mmol), 1-methyl-1H-pyrazole-4-boronic acid pinacol ester (507 mg, 2.44 mmol) and tetrakis(triphenylphosphine)palladium (234.2 mg, 0.203 mmol) were dissolved in dioxane: water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 400 mg of 4-methoxy-6-(1-methyl-1H-pyrazol-4-yl)pyrazol[1,5-a]pyridine-3-carbonitrile. MS m/z (ESI): 254 $[M+H]^+$.

Step 2: Synthesis of 4-hydroxy-6-(1-methyl-1H-pyrazol-4-yl)pyrazolo[1,5-a]pyridine-3-carbonitrile 4-methoxy-6-(1-methyl-1H-pyrazol-4-yl)pyrazol[1,5-a]pyridine-3-carbonitrile (430 mg, 1.70 mmol) and aluminum trichloride (678 mg, 5.10 mmol) were dissolved in 30 mL of DCE. The mixed solution reacted at room temperature for 16 h. After the reaction was found to be completed from the monitoring, water was added to quench the reaction, extraction with EA (30 mL*2) was then carried out, and the organic phase was washed with a NaCl solution and then dried, concentrated and subjected to column chromatography to obtain 160 mg of 4-hydroxy-6-(1-methyl-1H-pyrazol-4-yl)pyrazol[1,5-a]pyridine-3-carbonitrile. MS m/z (ESI): 240 $[M+H]^+$.

Step 3: Synthesis of 3-cyano-6-(1-methyl-1H-pyrazol-4-yl)pyrazol[1,5-a]pyridin-4-yl trifluoromethanesulfonate 4-hydroxy-6-(1-methyl-1H-pyrazol-4-yl)pyrazol[1,5-a]pyridine-3-carbonitrile (160 mg, 0.669 mmol), N-phenylbis(trifluoromethanesulfonyl)imide (287 mg, 0.803 mmol) and N,N-diisopropylethylamine (173 mg, 1.34 mmol) were dissolved in 20 mL of DMA. The mixed solution reacted at room temperature for 16 h. After the reaction was found to be completed from the monitoring, water was added to quench the reaction, extraction with EA (30 mL*2) was then carried out, and the organic phase was washed with a NaCl solution and then dried, concentrated and subjected to column chromatography to obtain 120 mg of 3-cyano-6-(1-methyl-1H-pyrazol-4-yl)pyrazol[1,5-a]pyridin-4-yl trifluoromethanesulfonate. MS m/z (ESI): 372 $[M+H]^+$.

Step 4: Synthesis of (S)-6-(1-methyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile 3-cyano-6-(1-methyl-1H-pyrazol-4-yl)pyrazol[1,5-a]pyridin-4-yl trifluoromethanesulfonate (120 mg, 0.323 mmol), tris(dibenzylideneacetone)dipalladium (29.3 mg, 0.032 mmol), 2-dicyclohexylphosphorus-2,4,6-triisopropylbiphenyl (30.9 mg, 0.065 mmol) and (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (164.2 mg, 0.388 mmol) were dissolved in dioxane:water (15 ml:5 ml). The mixed solution was stirred at 85° C. for 16 h to react. After the reaction was found to be completed from the monitoring, 10 mL of water was added to quench the reaction, extraction with EA (20 m L*3) was then carried out, and the organic phase was washed with water and the n dried, concentrated and subjected to column chromatography to obtain 30 mg of (S)-6-(1-methyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile (compound 29). MS m/z (ESI): 519 $[M+H]^+$. $^1H$ NMR (400 MHz, DMSO-d6) δ 9.22 (d, J=1.5 Hz, 1H), 8.68-8.63 (m, 2H), 8.44-8.37 (m, 3H), 8.12 (d, J=0.8 Hz, 1H), 7.94-7.84 (m, 4H), 7.80 (d, J=1.5 Hz, 1H), 6.85 (d, J=8.8 Hz, 1H), 6.30 (d, J=7.0 Hz, 1H), 3.87 (s, 3H), 2.84 (s, 3H), 1.62 (d, J=7.0 Hz, 3H).

Example 30: Preparation of (S)-4-(6-((1-(6-(4-fluoro-1H-pyrazol-1-yl)pyridin-3-yl)ethyl)(methyl)amino)pyridine-3-yl)-6-ethoxypyrazolo[1,5-a]pyridine-3-carbonitrile

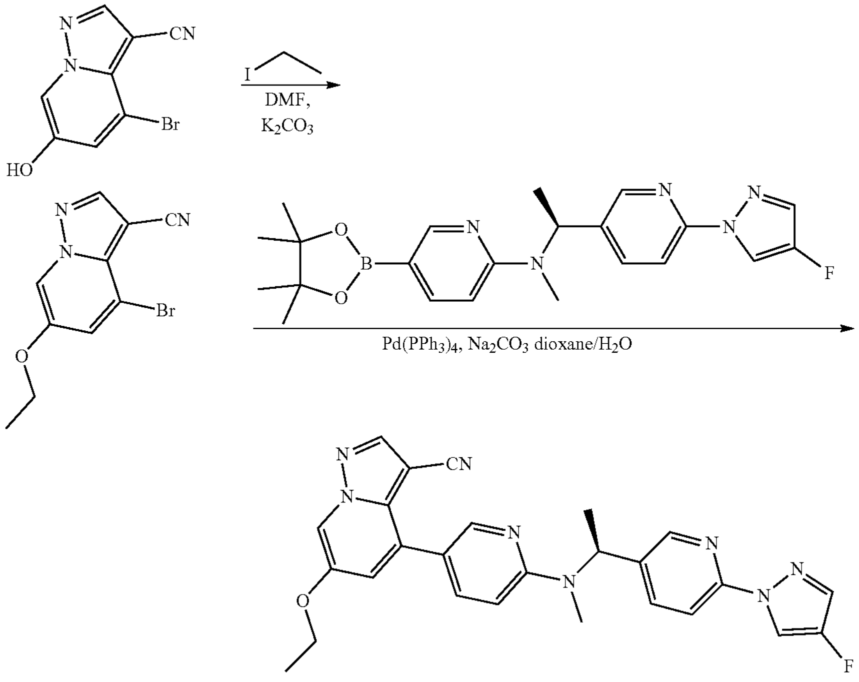

Step 1: Synthesis of 4-bromo-6-ethoxypyrazolo[1,5-a]pyridine-3-carbonitrile 4-bromo-6-hydroxypyrazolo[1,5-a]pyridine-3-carbonitrile (200 mg, 0.844 mmol), potassium carbonate (256 mg, 1.857 mmol) and iodoethane (263 mg, 1.688 mmol) were dissolved in DMF (20 mL). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 190 mg of 4-bromo-6-ethoxypyrazolo[1,5-a]pyridine-3-carbonitrile. MS m/z (ESI): 266 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-ethoxypyrazolo[1,5-a]pyridine-3-carbonitrile 4-bromo-6-ethoxypyrazolo[1,5-a]pyridine-3-carbonitrile (190 mg, 0.717 mmol), s odium carbonate (228 mg, 2.15 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (363 mg, 0.86 mmol) and tetrakis (triphenylphosphine)palladium (83 mg, 0.0717 mm ol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 65 mg of (S)-4-(6-((1-(6-(4-fluoro-1H-pyrazol-1-yl) pyridin-3-yl)ethyl)(methyl)amino)pyridine-3-yl)-6-ethoxy-pyrazolo[1,5-a]pyridine-3-carbonitrile (compound 30). MS m/z (ESI): 483 $[M+H]^+$. $^1$H NMR (400 MHz, DMSO-d6) δ 8.68-8.61 (m, 2H), 8.56 (s, 1H), 8.41-8.35 (m, 2H), 7.94-7.84 (m, 3H), 7.79 (dd, J=8.8, 2.6 Hz, 1H), 7.28 (d, J=2.1 Hz, 1H), 6.84-6.78 (m, 1H), 6.28 (q, J=6.9 Hz, 1H), 4.14 (q, J=6.9 Hz, 2H), 2.82 (s, 3H), 1.60 (d, J=7.0 Hz, 3H), 1.37 (t, J=6.9 Hz, 3H).

Example 31: (S)-4-(6-((1-(6-(4-fluoro-1H-pyrazol-1-yl)pyridin-3-yl)ethyl)(methyl)amino)pyridine-3-yl)-6-allyloxypyrazolo[1,5-a]pyridine-3-carbonitrile

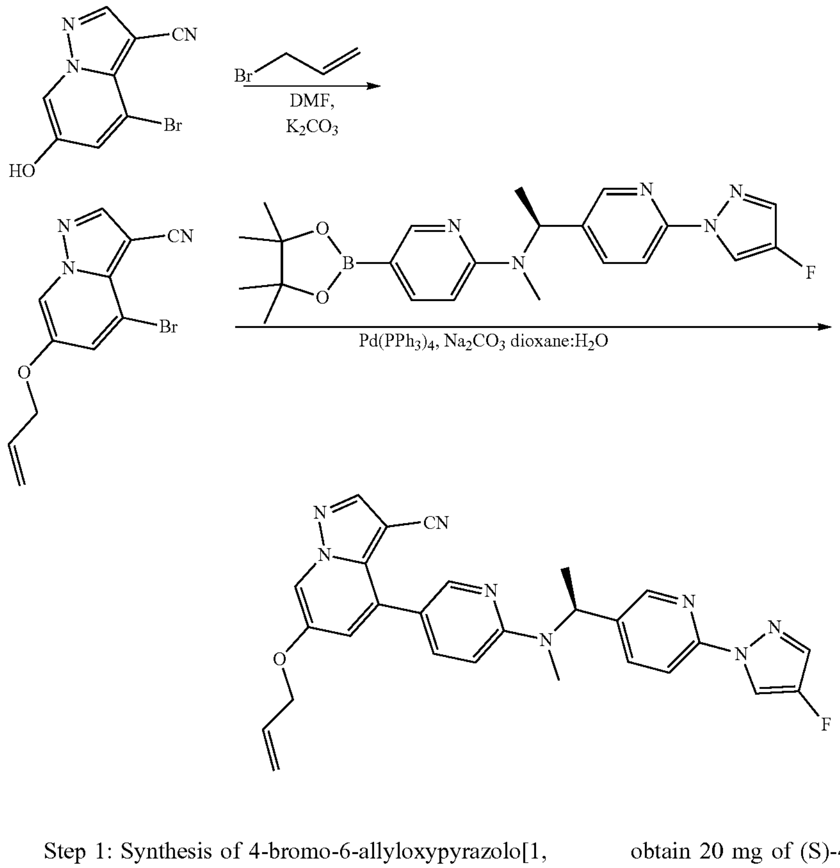

Step 1: Synthesis of 4-bromo-6-allyloxypyrazolo[1,5-a]pyridine-3-carbonitrile 4-bromo-6-hydroxypyrazolo[1,5-a]pyridine-3-carbonitrile (200 mg, 0.844 mmol), potassium carbonate (256 mg, 1.857 mmol) and allyl bromide (112 mg, 0.928 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 120 mg of 4-bromo-6-allyloxypyrazolo[1,5-a]pyridine-3-carbonitrile. MS m/z (ESI): 278 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-allyloxypyrazolo[1,5-a]pyridine-3-carbonitrile 4-bromo-6-allyloxypyrazolo[1,5-a]pyridine-3-carbonitrile (120 mg, 0.433 mmol), sodium carbonate (138 mg, 1.299 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (220 mg, 0.520 mmol) and tetrakis(triphenylphosphine)palladium (50 mg, 0.0433 m mol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 20 mg of (S)-4-(6-((1-(6-(4-fluoro-1H-pyrazol-1-yl) pyridin-3-yl)ethyl)(methyl)amino)pyridine-3-yl)-6-allyloxypyrazolo[1,5-a]pyridine-3-carbonitrile (compound 31). MS m/z (ESI): 495 $[M+H]^+$. $^1$H NMR (400 MHz, DMSO-d6) δ 10.14 (s, 1H), 8.66 (dd, J=4.5, 0.9 Hz, 1H), 8.55 (s, 1H), 8.40 (dt, J=1.7, 0.8 Hz, 1H), 8.33 (dd, J=2.6, 0.7 Hz, 1H), 7.94-7.85 (m, 3H), 7.76 (dd, J=8.8, 2.5 Hz 1H), 7.22 (s, 1H), 6.82 (dd, J=8.9, 0.8 Hz, 1H), 6.28 (q, J=6.9 Hz, 1H), 6.04-5.94 (m, 1H), 5.15-5.03 (m, 2H), 3.92 (d, J=6.2 Hz, 2H), 2.82 (s, 3H), 1.61 (d, J=7.0 Hz, 3H).

Example 32: Preparation of (S)-4-(6-((1-(6-(4-fluoro-1H-pyrazol-1-yl)pyridin-3-yl)ethyl)(methyl)amino)pyridine-3-yl)-6-cyanomethoxypyrazolo[1,5-a]pyridine-3-carbonitrile

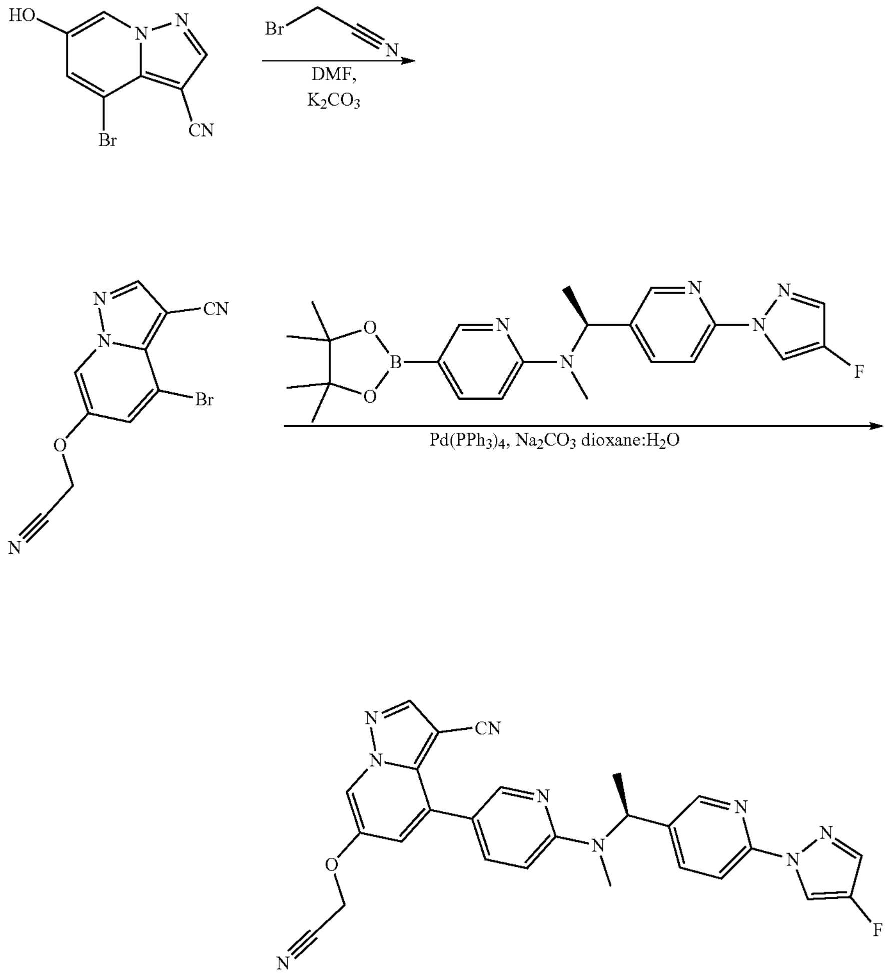

Step 1: Synthesis of 4-bromo-6-cyanomethoxypyrazolo[1,5-a]pyridine-3-carbonitrile 4-bromo-6-hydroxypyrazolo[1,5-a]pyridine-3-carbonitrile (200 mg, 0.844 mmol), potassium carbonate (256 mg, 1.857 mmol) and bromoacetonitrile (112 mg, 0.928 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 190 mg of 4-bromo-6-cyanomethoxypyrazolo[1,5-a]pyridine-3-carbonitrile. MS m/z (ESI): 277 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-cyanomethoxypyrazolo[1,5-a]pyridine-3-carbonitrile 4-bromo-6-cyanomethoxypyrazolo[1,5-a]pyridine-3-carbonitrile (190 mg, 0.688 m mol), sodium carbonate (219 mg, 2.065 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (350 mg, 0.826 mmol) and tetrakis(triphenylphosphine)palladium (79 mg, 0.0688 mmol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 32 mg of (S)-4-(6-((1-(6-(4-fluoro-1H-pyrazol-1-yl)pyridin-3-yl)ethyl)(methyl)amino)pyridine-3-yl)-6-cyanomethoxypyrazolo[1,5-a]pyridine-3-carbonitrile (compound 32). MS m/z (ESI): 494 $[M+H]^+$. $^1H$ NMR (400 MHz, DMSO-d6) δ 8.93 (d, J=2.1 Hz, 1H), 8.71-8.64 (m, 2H), 8.43-8.38 (m, 2H), 7.95-7.86 (m, 3H), 7.83 (dd, J=8.8, 2.6 Hz, 1H), 7.47 (d, J=2.2 Hz, 1H), 6.86-6.81 (m, 1H), 6.29 (q, J=7.0 Hz, 1H), 5.34 (s, 2H), 2.83 (s, 3H), 1.61 (d, J=7.0 Hz, 3H).

Example 33: Preparation of (S)-4-(6-((1-(6-(4-fluoro-1H-pyrazol-1-yl)pyridin-3-yl)ethyl)(methyl)amino)pyridine-3-yl)-6-isobutoxypyrazolo[1,5-a]pyridine-3-carbonitrile

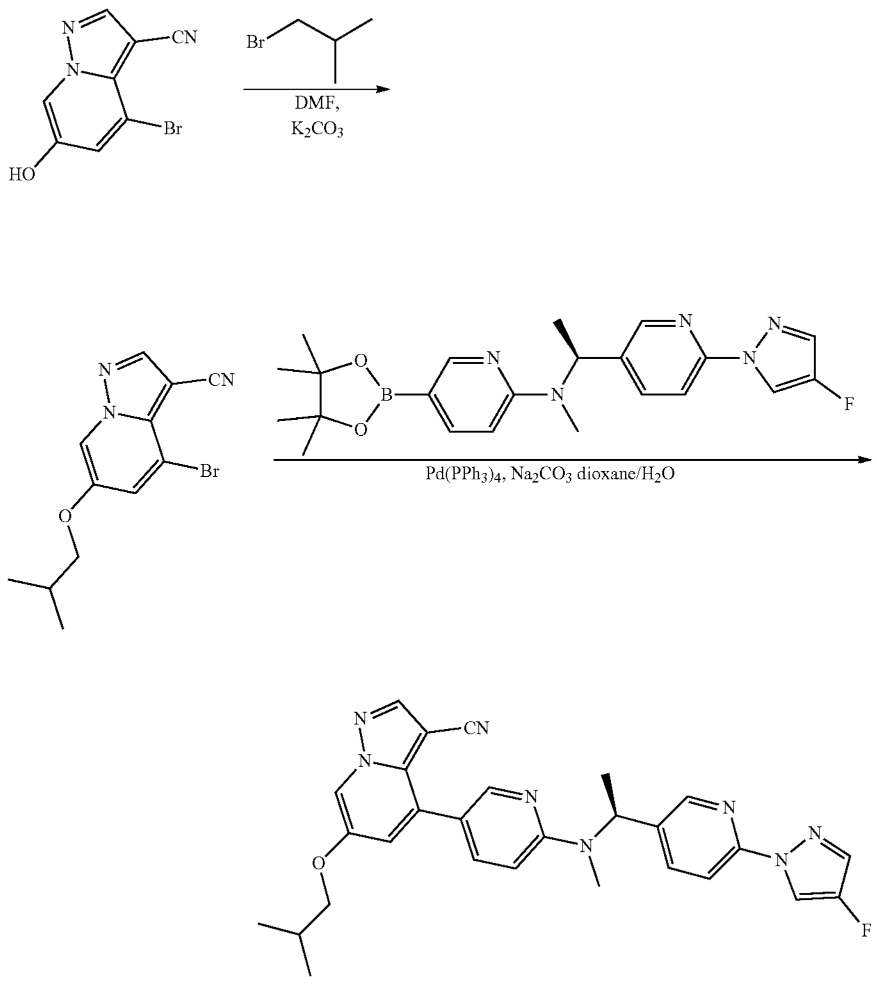

Step 1: Synthesis of 4-bromo-6-isobutoxypyrazolo[1,5-a]pyridine-3-carbonitrile 4-bromo-6-hydroxypyrazolo[1,5-a]pyridine-3-carbonitrile (200 mg, 0.844 mmol), potassium carbonate (256 mg, 1.857 mmol) and isobutyl bromide (127 mg, 0.928 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 110 mg of 4-bromo-6-isobutoxypyrazolo[1,5-a]pyridine-3-carbonitrile. MS m/z (ESI): 294 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-isobutoxypyrazolo[1,5-a]pyridine-3-carbonitrile 4-bromo-6-isobutoxypyrazolo[1,5-a]pyridine-3-carbonitrile (110 mg, 0.375 mmol), sodium carbonate (120 mg, 1.126 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (190 mg, 0.451 mmol) and tetrakis(triphenylphosphine)palladium (43 mg, 0.0375 mmol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 50 mg of (S)-4-(6-((1-(6-(4-fluoro-1H-pyrazol-1-yl)pyridin-3-yl)ethyl)(methyl)amino)pyridine-3-yl)-6-isobutoxypyrazolo[1,5-a]pyridine-3-carbonitrile (compound 33). MS m/z (ESI): 511 $[M+H]^+$. $^1H$ NMR (400 MHz, DMSO-d6) δ 8.69-8.63 (m, 2H), 8.57 (s, 1H), 8.39 (ddd, J=9.3, 2.7, 0.8 Hz, 2H), 7.95-7.84 (m, 3H), 7.81 (dd, J=8.8, 2.6 Hz, 1H), 7.31 (d, J=2.1 Hz, 1H), 6.82 (d, J=8.9 Hz, 1H), 6.29 (q, J=6.9 Hz, 1H), 3.88 (d, J=6.5 Hz, 2H), 2.82 (s, 3H), 2.06 (dt, J=13.2, 6.6 Hz, 1H), 1.61 (d, J=7.0 Hz, 3H), 1.00 (d, J=6.7 Hz, 6H).

Example 34: Preparation of (S)-4-(6-((1-(6-(4-fluoro-1H-pyrazol-1-yl)pyridin-3-yl)ethyl)(methyl)amino)pyridine-3-yl)-6-(2,2-difluoroethoxy)pyrazolo[1,5-a]pyridine-3-carbonitrile

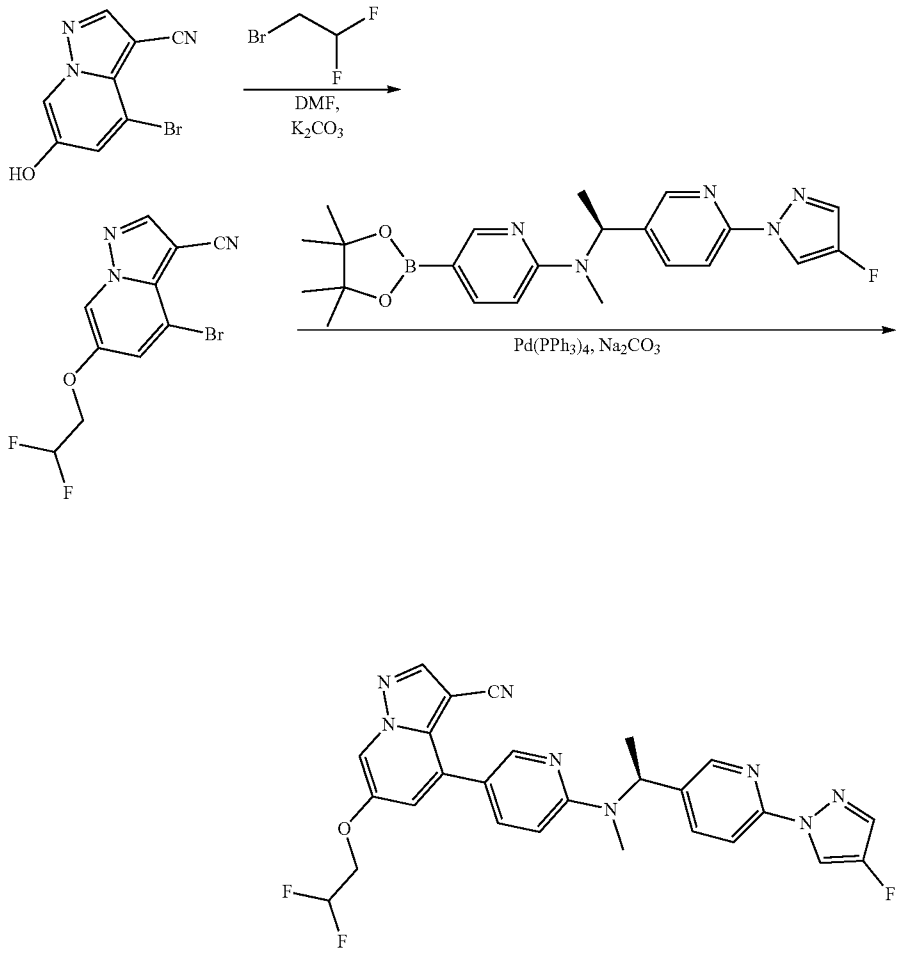

Step 1: Synthesis of 4-bromo-6-(2,2-difluoroethoxy)pyrazolo[1,5-a]pyridine-3-carbonitrile 4-bromo-6-hydroxypyrazolo[1,5-a]pyridine-3-carbonitrile (200 mg, 0.844 mmol), potassium carbonate (233 mg, 1.688 mmol) and 1-bromo-2,2-difluoroethane (184 mg, 1.266 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 150 mg of 4-bromo-6-(2,2-difluoroethoxy)pyrazolo[1,5-a]pyridine-3-carbonitrile. MS m/z (ESI): 302 $[M+H]^+$.

Step 2: (S)-4-(6-((1-(6-(4-fluoro-1H-pyrazol-1-yl)pyridin-3-yl)ethyl)(methyl)amino)pyridine-3-yl)-6-(2,2-difluoroethoxy)pyrazolo[1,5-a]pyridine-3-carbonitrile 4-bromo-6-(2,2-difluoroethoxy)pyrazolo[1,5-a]pyridine-3-carbonitrile (150 mg, 0.498 mmol), sodium carbonate (158 mg, 1.49 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (253 mg, 0.598 mmol) and tetrakis(triphenylphosphine)palladium (58 mg, 0.0498 mmol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 60 mg of (S)-4-(6-((1-(6-(4-fluoro-1H-pyrazol-1-yl)pyridin-3-yl)ethyl)(methyl)amino)pyridine-3-yl)-6-(2,2-difluoroethoxy)pyrazolo[1,5-a]pyridine-3-carbonitrile (compound 34). MS m/z (ESI): 519 $[M+H]^+$. $^1H$ NMR (400 MHz, DMSO-d6) δ 8.82 (d, J=2.1 Hz, 1H), 8.66 (dd, J=4.5, 0.9 Hz, 1H), 8.61 (s, 1H), 8.39 (dd, J=5.5, 2.4 Hz, 2H), 7.94-7.85 (m, 3H), 7.82 (dd, J=8.8, 2.6 Hz, 1H), 7.40 (d, J=2.1 Hz, 1H), 6.83 (d, J=8.9 Hz, 1H), 6.46 (tt, J=54.1, 3.5 Hz, 1H), 6.28 (t, J=7.1 Hz, 1H), 4.49 (td, J=14.6, 3.5 Hz, 2H), 2.83 (s, 3H), 1.61 (d, J=7.0 Hz, 3H).

Example 35: Preparation of (S)-4-(6-((1-(6-(4-fluoro-1H-pyrazol-1-yl)pyridin-3-yl)ethyl)(methyl)amino)pyridine-3-yl)-6-(2,2,2-trifluoroethoxy)pyrazolo[1,5-a]pyridine-3-carbonitrile

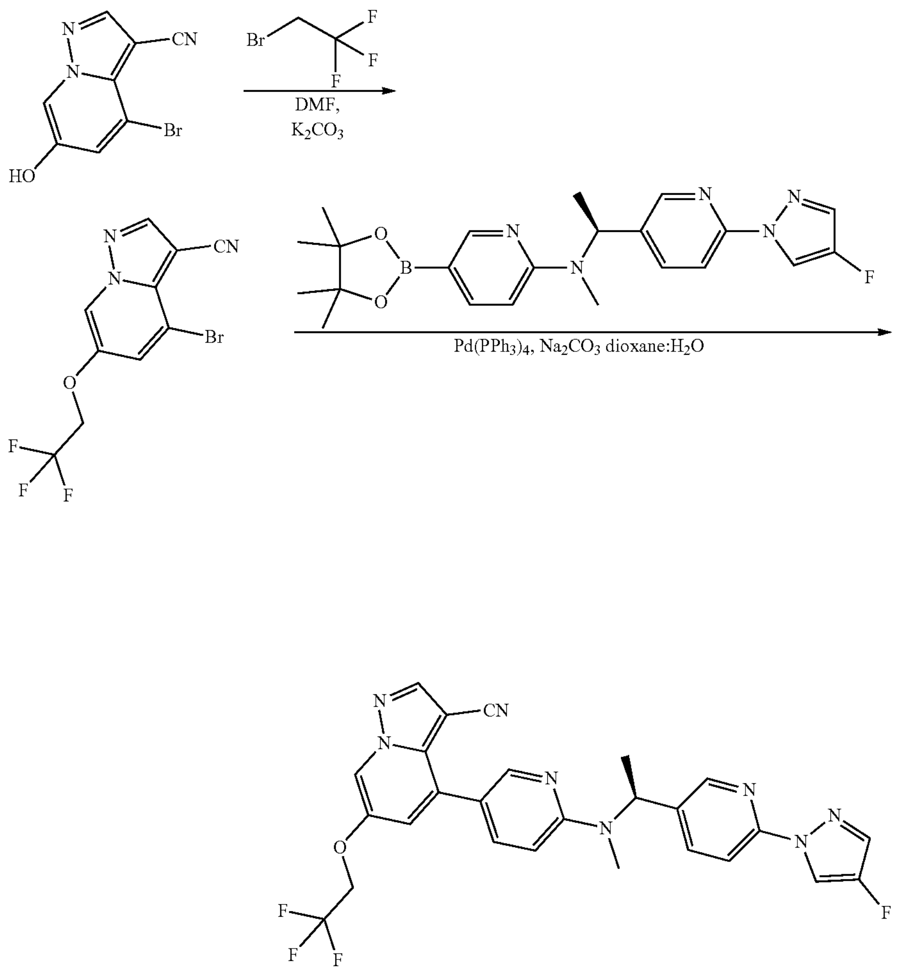

Step 1: Synthesis of 4-bromo-6-(2,2,2-trifluoroethoxy)pyrazolo[1,5-a]pyridine-3-carbonitrile 4-bromo-6-hydroxypyrazolo[1,5-a]pyridine-3-carbonitrile (200 mg, 0.844 mmol), potassium carbonate (233 mg, 1.688 mmol) and 1-bromo-2,2,2-trifluoroethane (206 mg, 1.266 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 120 mg of 4-bromo-6-(2,2,2-trifluoroethoxy)pyrazolo[1,5-a]pyridine-3-carbonitrile. MS m/z (ESI): 320 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(2,2,2-trifluoroethoxy)pyrazolo[1,5-a]pyridine-3-carbonitrile 4-bromo-6-(2,2,2-trifluoroethoxy)pyrazolo[1,5-a]pyridine-3-carbonitrile (120 mg, 0.376 mmol), sodium carbonate (120 mg, 1.129 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (191 mg, 0.451 mmol) and tetrakis(triphenylphosphine)palladium (43 mg, 0.0376 mmol) were dissolved in dioxane: water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 55 mg of (S)-4-(6-((1-(6-(4-fluoro-1H-pyrazol-1-yl)pyridin-3-yl)ethyl)(methyl)amino)pyridine-3-yl)-6-(2,2,2-trifluoroethoxy)pyrazolo[1,5-a]pyridine-3-carbonitrile (compound 35). MS m/z (ESI): 537 $[M+H]^+$. $^{1}H$ NMR (400 M Hz, DMSO-$d^6$) δ 8.88 (d, J=2.1 Hz, 1H), 8.65 (dd, J=4.5, 0.9 Hz, 1H), 8.63 (s, 1H), 8.41-8.36 (m, 2H), 7.94-7.80 (m, 4H), 7.46 (d, J=2.1 Hz, 1H), 6.82 (d, J=8.9 Hz, 1H), 6.28 (t, J=7.0 Hz, 1H), 4.94 (q, J=8.8 Hz, 2H), 2.83 (s, 3H), 1.61 (d, J=7.0 Hz, 3H).

Example 36: Preparation of (S)-4-(6-((1-(6-(4-fluoro-1H-pyrazol-1-yl)pyridin-3-yl)ethyl)(methyl)amino)pyridine-3-yl)-6-(2-hydroxypropoxy)pyrazolo[1,5-a]pyridine-3-carbonitrile

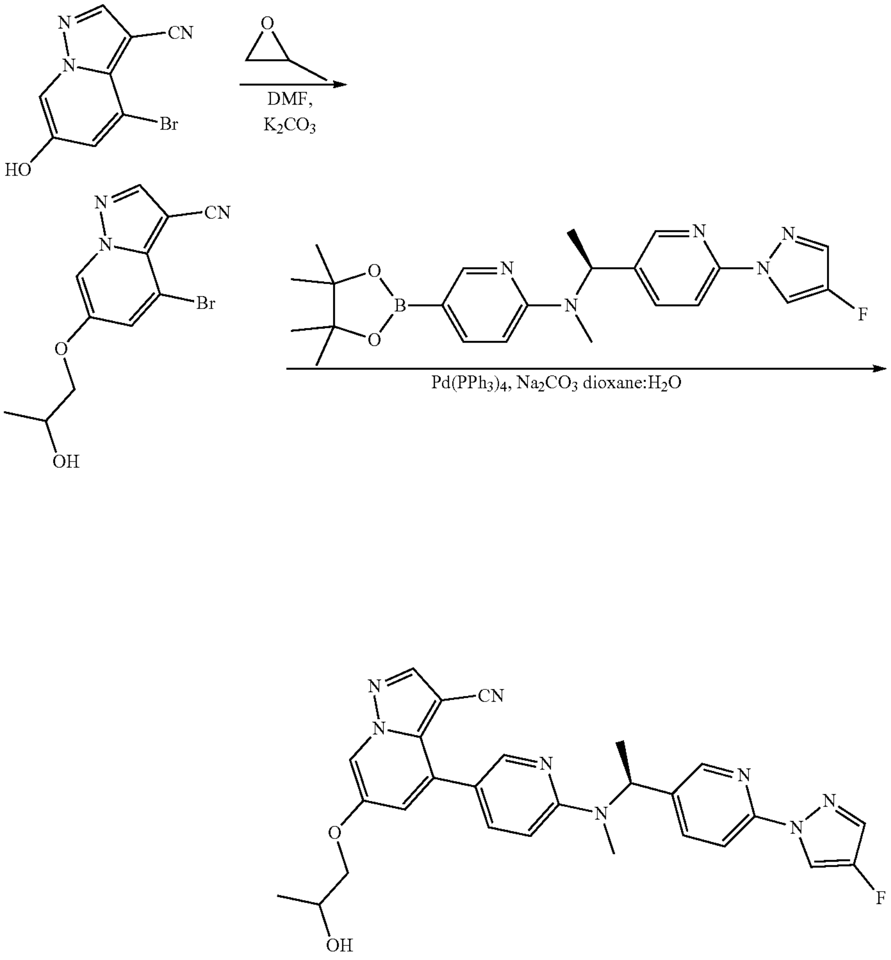

Step 1: Synthesis of 4-bromo-6-(2-hydroxypropoxy)pyrazolo[1,5-a]pyridine-3-carbonitrile 4-bromo-6-hydroxypyrazolo[1,5-a]pyridine-3-carbonitrile (300 mg, 1.27 mmol), potassium carbonate (524 mg, 3.80 mmol) and propylene oxide (220 mg, 3.80 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 150 mg of 4-bromo-6-(2-hydroxypropoxy)pyrazolo[1,5-a]pyridine-3-carbonitrile. MS m/z (ESI): 296 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(2-hydroxypropoxy)pyrazolo[1,5-a]pyridine-3-carbonitrile 4-bromo-6-(2-hydroxypropoxy)pyrazolo[1,5-a]pyridine-3-carbonitrile (150 mg, 0.508 mmol), sodium carbonate (162 mg, 1.525 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (237 mg, 0.559 mmol) and tetrakis(triphenylphosphine)palladium (59 mg, 0.0508 mmol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 30 mg of (S)-4-(6-((1-(6-(4-fluoro-1H-pyrazol-1-yl)pyridin-3-yl)ethyl)(methyl)amino)pyridine-3-yl)-6-(2-hydroxypropoxy)pyrazolo[1,5-a]pyridine-3-carbonitrile (compound 36). MS m/z (ESI): 513 $[M+H]^+$. $^1H$ NMR (400 MHz, DMSO-d6) δ 8.73-8.65 (m, 2H), 8.57 (s, 1H), 8.42-8.35 (m, 2H), 7.94-7.84 (m, 3H), 7.80 (ddd, J=8.8, 2.6, 1.4 Hz, 1H), 7.30 (d, J=2.1 Hz, 1H), 6.82 (d, J=8.8 Hz, 1H), 6.29 (q, J=7.0 Hz, 1H), 4.94 (dd, J=11.8, 5.1 Hz, 1H), 3.96 (hept, J=3.2, 2.8 Hz, 2H), 3.57-3.40 (m, 1H), 2.82 (s, 3H), 1.61 (d, J=7.0 Hz, 3H), 1.16 (d, J=6.1 Hz, 3H).

Example 37: Preparation of (S)-6-(2-hydroxy-2-methylpropoxy)-4-(6-(methyl(1-(6-(4-methyl-1H-pyrazol-1-yl)pyridine)-3-yl)ethyl)amino)pyridin-3-yl)pyrazolo[1,5-a]pyridine-3-carbonitrile
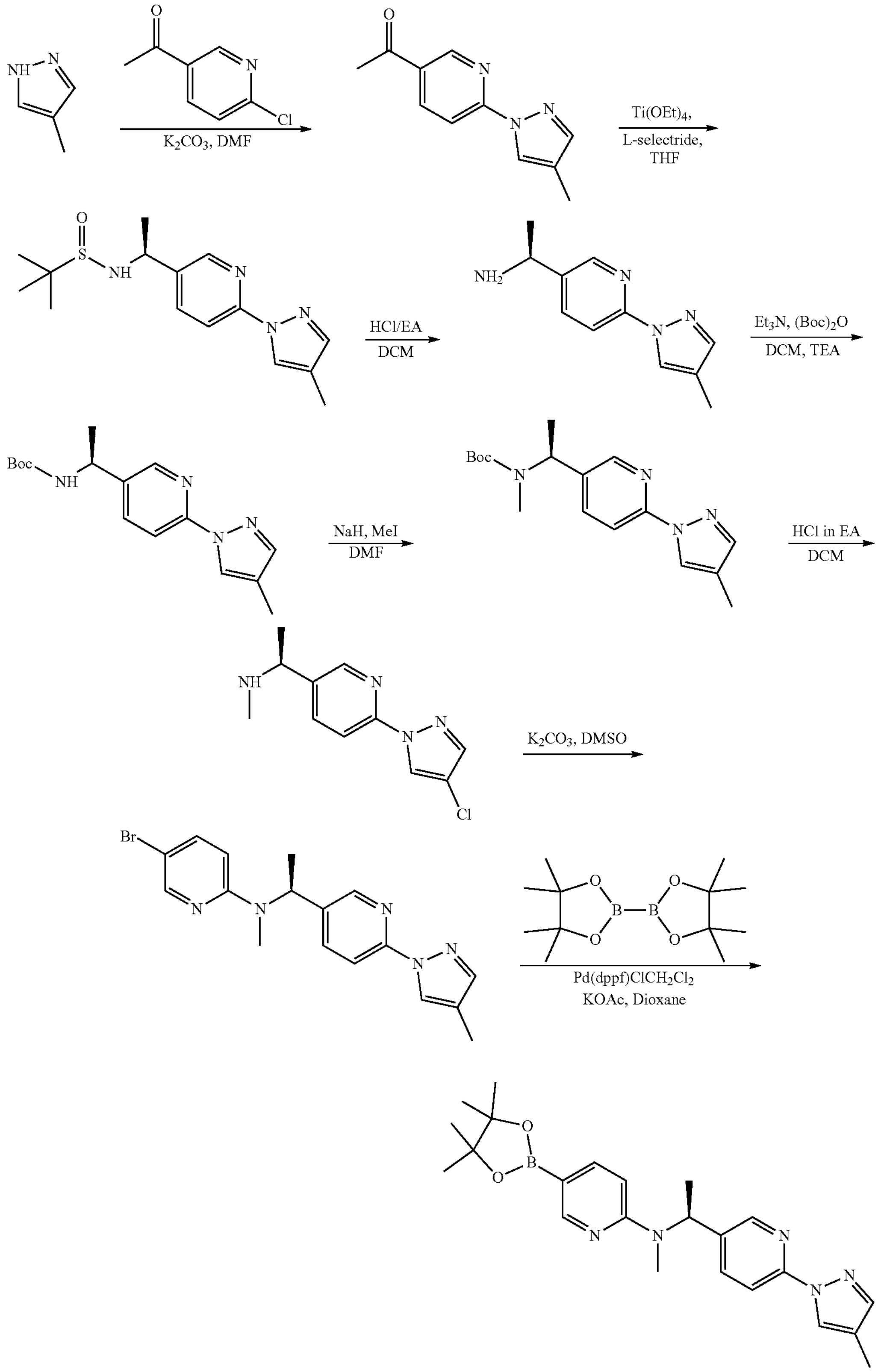

-continued

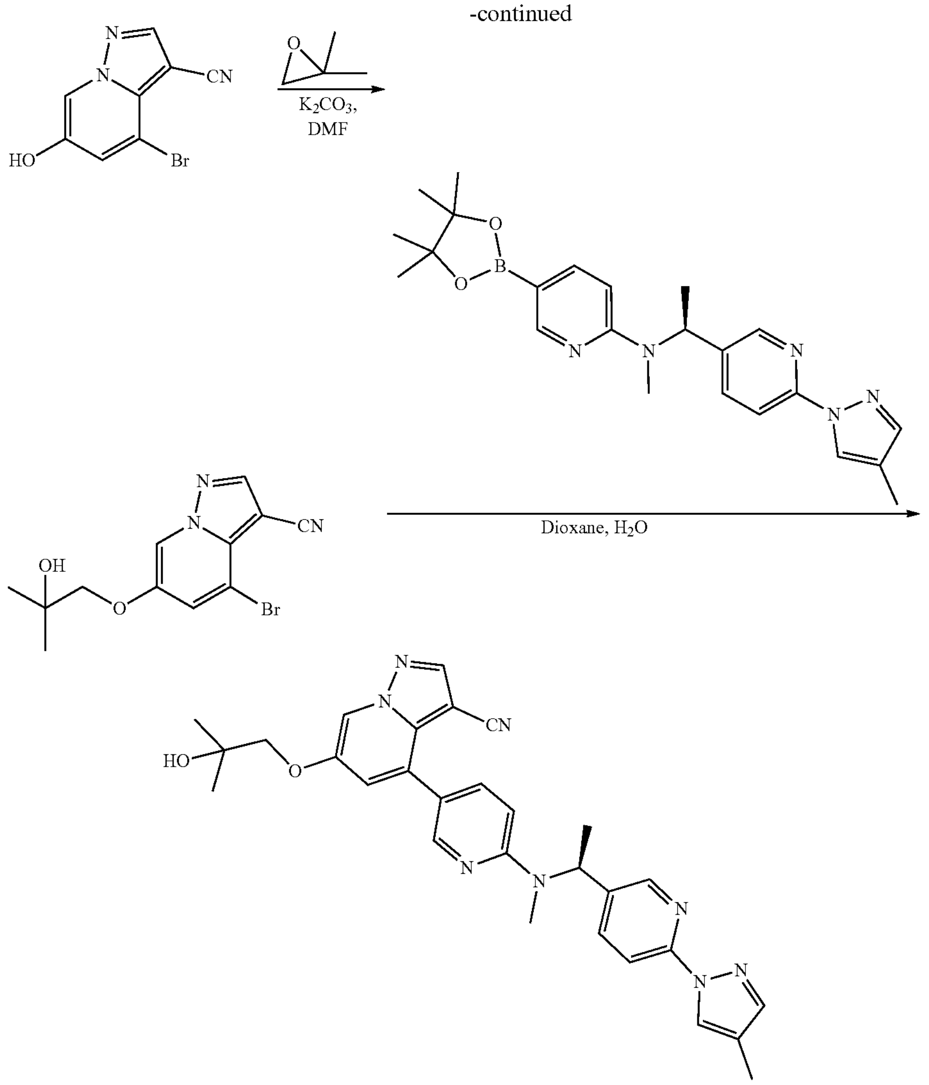

Step 1: Synthesis of 1-(6-(4-methyl-1H-pyrazol-1-yl)pyridin-3-yl)ethan-1-one 4-methyl-1H-pyrazole (5 g, 24.4 mmol), 1-(6-chloropyridin-3-yl)ethan-1-one (9.5 g, 24.4 mmol) and potassium carbonate (16.8 g, 48.8 mmol) were dissolved in 60 mL of DMF. The mixed solution was stirred at 110° C. for 16 h to react. After the reaction was found to be completed from the monitoring, water was added to quench the reaction, extraction with EA (50 mL*2) was then carried out, and the organic phase was washed with a NaCl solution and then dried, concentrated and subjected to column chromatography to obtain 6.8 g of 1-(6-(4-methyl-1H-pyrazol-1-yl) pyridin-3-yl)ethan-1-one. MS m/z (ESI): 206 $[M+H]^+$.

Step 2: Synthesis of 2-methyl-N-((S)-1-(6-(4-methyl-1H-pyrazol-1-yl)pyridin-3-yl)ethyl)propane-2-sulfinamide 1-(6-(4-methyl-1H-pyrazol-1-yl)pyridin-3-yl)ethan-1-one (3.5 g, 17.4 mmol), tetraethyl titanate (7.9 g, 34.8 mmol) and (S)-2-methylpropane-2-sulfinamide (2.7 g, 22.64 mmol) were dissolved in tetrahydrofuran (50 mL). The mixed solution reacted at 75° C. for 16 h. After the reaction was found to be completed from the monitoring, the reaction solution was cooled to −78° C., and 2M of lithium tri-sec-butyl borohydride (34.8 ml, 34.8 mmol) was added dropwise. After the reaction was found to be completed from the monitoring, water was added to quench the reaction, extraction with EA (70 mL*3) was then carried out, and the organic phase was washed with water and then dried, concentrated and subjected to column chromatography to obtain 5.3 g of 2-methyl-N-((S)-1-(6-(4-methyl-1H-pyrazol-1-yl)pyridin-3-yl)ethyl)propane-2-sulfinamide. MS m/z (ESI): 307 $[M+H]^+$.

Step 3: Synthesis of (S)-1-(6-(4-(4-methyl-1H-pyrazol-1-yl)pyridin-3-yl)ethan-1-amine 2-methyl-N-((S)-1-(6-(4-methyl-1H-pyrazol-1-yl)pyridin-3-yl)ethyl)propane-2-sulfinamide (3 g, 9.80 mmol) was dissolved in 50 mL of dichloromethane, and then 2M hydrochloric acid in ethyl acetate (29.4 ml, 58.8 mmol) was added dropwise. The mixed solution reacted at room temperature for 2 h. After the reaction was found to be completed from the monitoring, the reaction solution was extracted with EA (50 mL*3), and the organic phase was washed with water and then dried, concentrated and subjected to column chromatography to obtain 1.8 g of (S)-1-(6-(4-(4-methyl-1H-pyrazol-1-yl)pyridin-3-yl)ethan-1-amine. MS m/z (ESI): 203 $[M+H]^+$.

Step 4: Synthesis of tert-butyl (S)-(1-(6-(4-(4-methyl-1H-pyrazol-1-yl)pyridin-3-yl)ethyl)carbamate (S)-1-(6-(4-(4-methyl-1H-pyrazol-1-yl)pyridin-3-yl)ethan-1-amine (1.8 g, 8.91 mmol), boc anhydride (2.1 g, 9.8 mmol) and triethylamine (4.5 g, 44.55 mmol) were dissolved in 50 mL of dichloromethane. The mixed solution was stirred at room temperature for 3 h to react. After the reaction was found to be completed from the monitoring, water was added to quench the reaction, extraction with EA (50 mL*2) was then carried out, and the organic phase was washed with a NaCl solution and then dried, concentrated and subjected to column chromatography to obtain 2.5 g of tert-butyl (S)-(1-(6-(4-(4-methyl-1H-pyrazol-1-yl)pyridin-3-yl)ethyl)carbamate. MS m/z (ESI): 303 $[M+H]^+$.

Step 5: Synthesis of tert-butyl (S)-methyl(1-(6-(4-methyl-1H-pyrazol-1-yl)pyridin-3-yl)ethyl)carbamate Tert-butyl (S)-(1-(6-(4-(4-methyl-1H-pyrazol-1-yl)pyridin-3-yl)ethyl)carbamate (2.5 g, 8.28 mmol) was dissolved in tetrahydrofuran (50 mL), and then sodium hydride (0.5 g, 12.4 mmol) was added. The mixed solution reacted at room temperature for 30 min, and iodomethane (1.2 g, 8.3 mmol) was added dropwise. After the reaction was found to be completed from the monitoring, water was added to quench the reaction, extraction with EA (20 mL*3) was then carried out, and the organic phase was washed with water and then dried, concentrated and subjected to column chromatography to obtain 2.5 g of tert-butyl (S)-methyl(1-(6-(4-methyl-1H-pyrazol-1-yl)pyridin-3-yl)ethyl)carbamate. MS m/z (ESI): 317 $[M+H]^+$.

Step 6: Synthesis of (S)—N-methyl-1-(6-(4-methyl-1H-pyrazol-1-yl)pyridin-3-yl)ethan-1-amine Tert-butyl (S)-methyl(1-(6-(4-methyl-1H-pyrazol-1-yl)pyridin-3-yl)ethyl)carbamate (2.5 g, 7.91 mmol) was dissolved in 50 mL of dichloromethane, and then 2M hydrochloric acid in ethyl acetate (23.7 ml, 47.47 mmol) was added dropwise. The mixed solution reacted at room temperature for 2 h. After the reaction was found to be completed from the monitoring, the reaction solution was extracted with EA (50 mL*3), and the organic phase was washed with water and then dried, concentrated and subjected to column chromatography to obtain 1.6 g of (S)—N-methyl-1-(6-(4-methyl-1H-pyrazol-1-yl)pyridin-3-yl)ethan-1-amine. MS m/z (ESI): 217 $[M+H]^+$.

Step 7: Synthesis of (S)-5-bromo-N-methyl-N-(1-(6-(4-methyl-1H-pyrazol-1-yl)pyridin-3-yl)ethyl)pyridin-2-amine (S)—N-methyl-1-(6-(4-methyl-1H-pyrazol-1-yl)pyridin-3-yl)ethan-1-amine (1.6 g, 7.4 mmol), potassium carbonate (5.1 g, 37.03 mmol) and 2-fluoro-5-bromopyridine (6.5 g, 37.03 mmol) were dissolved in DMSO (50 ml). The mixed solution reacted at 140° C. for 24 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 2.1 g of (S)-5-bromo-N-methyl-N-(1-(6-(4-methyl-1H-pyrazol-1-yl)pyridin-3-yl)ethyl)pyridin-2-amine. MS m/z (ESI): 372 $[M+H]^+$.

Step 8: Synthesis of ((S)—N-methyl-N-(1-(6-(4-methyl-1H-pyrazol-1-yl)pyridin-3-yl)ethyl)-5-(4,4,5,5-tetramethyl-1,3,2-dioxaborolane-2-yl)pyridin-2-amine (S)-5-bromo-N-methyl-N-(1-(6-(4-methyl-1H-pyrazol-1-yl)pyridin-3-yl)ethyl)pyridin-2-amine (1 g, 2.70 mmol), potassium acetate (796 mg, 8.09 mmol), biboron pinacol ester (2.05 g, 8.09 mmol) and [1,1'-bis(diphenylphosphino)ferrocene]palladium dichloride (220 mg, 0.27 mmol) were dissolved in dioxane (50 mL), and the resulting reaction solution was stirred at 80° C. for 16 h to react. After the reaction was found to be completed from the monitoring, the reaction solution was cooled, water was added to quench the reaction, extraction with EA (30 mL*3) was then carried out, and the organic phase was washed with water and then dried, concentrated and subjected to column chromatography to obtain 500 mg of (S)—N-methyl-N-(1-(6-(4-methyl-1H-pyrazol-1-yl)pyridin-3-yl)ethyl)-5-(4,4,5,5-tetramethyl-1,3,2-dioxaborolane-2-yl)pyridin-2-amine. MS m/z (ESI): 420 $[M+H]^+$.

Step 9: Synthesis of 4-bromo-6-(2-hydroxy-2-methylpropoxy)pyrazolo[1,5-a]pyridine-3-carbonitrile 4-bromo-6-hydroxypyrazolo[1,5-a]pyridine-3-carbonitrile (300 mg, 1.27 mmol), potassium carbonate (524 mg, 3.80 mmol) and 2,2-dimethyloxirane (273 mg, 3.80 mmol) were dissolved in DMF (20 mL). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 248 mg of 4-bromo-6-(2-hydroxy-2-methylpropoxy)pyrazolo[1,5-a]pyridine-3-carbonitrile. MS m/z (ESI): 310 $[M+H]^+$.

Step 10: Synthesis of (S)-6-(2-hydroxy-2-methylpropoxy)-4-(6-(methyl(1-(6-(4-methyl-1H-pyrazol-1-yl)pyridine)-3-yl)ethyl)amino)pyridin-3-yl)pyrazolo[1,5-a]pyridine-3-carbonitrile 4-bromo-6-(2-hydroxy-2-methylpropoxy)pyrazolo[1,5-a]pyridine-3-carbonitrile (248 mg, 0.803 mmol), sodium carbonate (255 mg, 2.409 mmol), (S)—N-methyl-N-(1-(6-(4-methyl-1H-pyrazol-1-yl)pyridin-3-yl)ethyl)-5-(4,4,5,5-tetramethyl-1,3,2-dioxaborolane-2-yl)pyridin-2-amine (370 mg, 0.883 mmol) and tetrakis(triphenylphosphine)palladium (93 mg, 0.0803 mmol) were dissolved in dioxane: water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 65 mg of (S)-6-(2-hydroxy-2-methylpropoxy)-4-(6-(methyl(1-(6-(4-methyl-1H-pyrazol- 1-yl)pyridine)-3-yl)ethyl)amino)pyridin-3-yl)pyrazolo[1,5-a]pyridine-3-carbonitrile (compound 37). MS m/z (ESI): 523 $[M+H]^+$. $^1H$ NMR (400 MHz, DMSO-d6) δ 8.65 (d, J=2.1 Hz, 1H), 8.56 (s, 1H), 8.39-8.33 (m, 3H), 7.87-7.78 (m, 3H), 7.61 (s, 1H), 7.31 (d, J=2.1 Hz, 1H), 6.81 (d, J=8.8 Hz, 1H), 6.27 (q, J=7.0 Hz, 1H), 4.71 (s, 1H), 3.87 (s, 2H), 2.81 (s, 3H), 2.09 (s, 3H), 1.59 (d, J=7.0 Hz, 3H), 1.22 (s, 6H).

Example 38: Preparation of (S)-6-(1-ethyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile

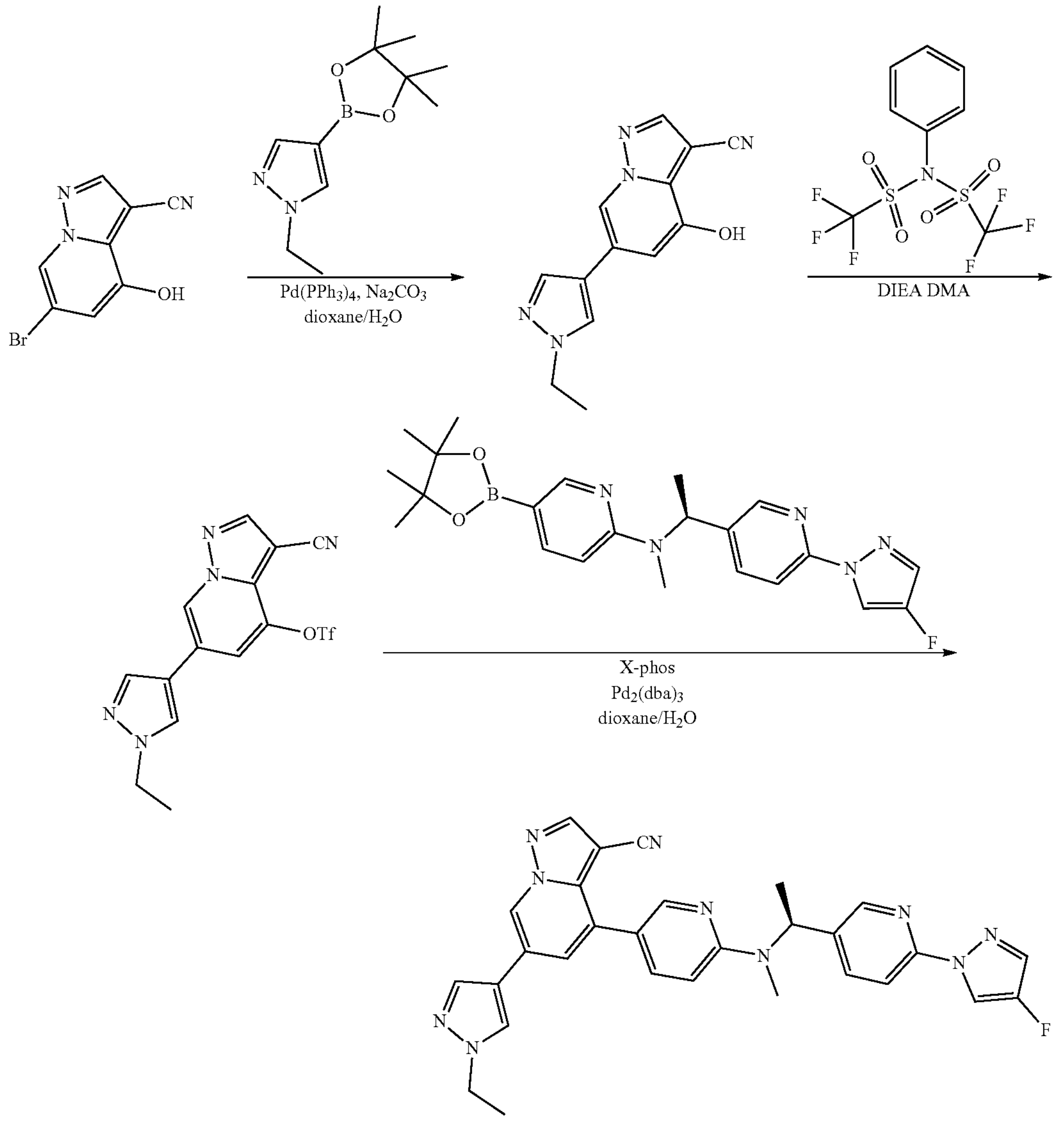

Step 1: Synthesis of 6-(1-ethyl-1H-pyrazol-4-yl)-4-hydroxypyrazolo[1,5-a]pyridine-3-carbonitrile 6-bromo-4-hydroxypyrazolo[1,5-a]pyridine-3-carbonitrile (300 mg, 1.26 mmol), sodium carbonate (402 mg, 3.79 mmol), 1-ethyl-1H-pyrazole-4-boronic acid pinacol ester (337 mg, 1.52 mmol) and tetrakis(triphenylphosphine)palladium (146 mg, 0.126 mmol) were dissolved in dioxane: water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 310 mg of 6-(1-ethyl-1H-pyrazol-4-yl)-4-hydroxypyrazolo[1,5-a]pyridine-3-carbonitrile. MS m/z (ESI): 254 $[M+H]^+$.

Step 2: 3-cyano-6-(1-ethyl-1H-pyrazol-4-yl)pyrazol[1,5-a]pyridin-4-yl trifluoromethanesulfonate 6-(1-ethyl-1H-pyrazol-4-yl)-4-hydroxypyrazolo[1,5-a]pyridine-3-carbonitrile (310 mg, 1.23 mmol), N-phenylbis(trifluoromethanesulfonyl)imide (539 mg, 1.47 mmol) and N,N-diisopropylethylamine (316 mg, 2.45 mmol) were dissolved in 30 mL of DMA. The mixed solution was stirred at room temperature for 16 h to react. After the reaction was found to be completed from the monitoring, water was added to quench the reaction, extraction with EA (30 mL*2) was then carried out, and the organic phase was washed with a NaCl solution and then dried, concentrated and subjected to column chromatography to obtain 325 mg of 3-cyano-6-(1-ethyl-1H-pyrazol-4-yl)pyrazol[1,5-a]pyridin-4-yl trifluoromethanesulfonate. MS m/z (ESI): 386 $[M+H]^+$.

Step 3: Synthesis of (S)-6-(1-ethyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile 3-cyano-6-(1-ethyl-1H-pyrazol-4-yl)pyrazol[1,5-a]pyridin-4-yl trifluoromethanesulfonate (325 mg, 0.84 mmol), tris(dibenzylideneacetone)dipalladium (49 mg, 0.084 m mol), 2-dicyclohexylphosphorus-2,4,6-triisopropylbiphenyl (80 mg, 0.168 mmol) and (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (426 mg, 1.01 mmol) were dissolved in dioxane:water (15 ml:5 ml). The mixed solution was stirred at 85° C. for 16 h to react. 10 mL of water was added to quench the reaction. Extraction with EA (20 mL*3) was then carried out, and the organic phase was washed with water and then dried, concentrated and subjected to column chromatography to obtain 100 mg of (S)-6-(1-ethyl-1H-pyrazol-4-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile (compound 38). MS m/z (ESI): 533 $[M+H]^+$. $^1H$ NMR (400 MHz, DMSO-d6) δ 9.22 (d, J=1.5 Hz, 1H), 8.66 (dd, J=4.6, 0.9 Hz, 1H), 8.64 (s, 1H), 8.46 (d, J=0.8 Hz, 1H), 8.42 (dd, J=2.6, 0.7 Hz, 1H), 8.40 (dd, J=2.0, 1.1 Hz, 1H), 8.13 (d, J=0.8 Hz, 1H), 7.94-7.83 (m, 4H), 7.81 (d, J=1.5 Hz, 1H), 6.87-6.82 (m, 1H), 6.30 (q, J=7.0 Hz, 1H), 4.15 (q, J=7.3 Hz, 2H), 2.84 (s, 3H), 1.62 (d, J=7.0 Hz, 3H), 1.41 (t, J=7.3 Hz, 3H).

Example 39: Preparation of (S)-4-(6-((1-(6-(4-fluoro-1H-pyrazol-1-yl)pyridin-3-yl)ethyl)(methyl)amino)pyridine-3-yl)-6-propoxypyrazolo[1,5-a]pyridine-3-carbonitrile

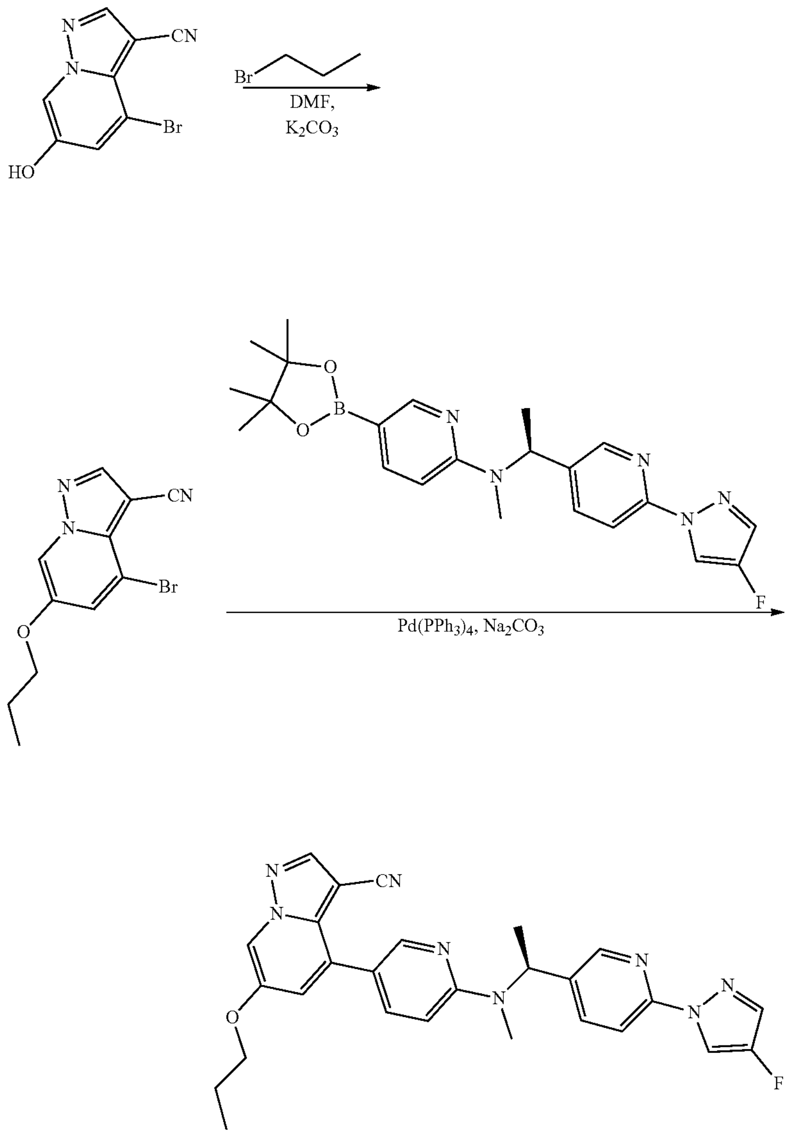

Step 1: Synthesis of 4-bromo-6-propoxypyrazolo[1,5-a]pyridine-3-carbonitrile 4-bromo-6-hydroxypyrazolo[1,5-a]pyridine-3-carbonitrile (300 mg, 1.26 mmol), potassium carbonate (523 mg, 3.79 mmol) and 1-bromopropane (187 mg, 1.52 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 210 mg of 4-bromo-6-propoxypyrazolo[1,5-a]pyridine-3-carbonitrile. MS m/z (ESI): 280 $[M+H]^+$.

Step 2: (S)-4-(6-((1-(6-(4-fluoro-1H-pyrazol-1-yl)pyridin-3-yl)ethyl)(methyl)amino)pyridine-3-yl)-6-propoxypyrazolo[1,5-a]pyridine-3-carbonitrile 4-bromo-6-propoxypyrazolo[1,5-a]pyridine-3-carbonitrile (210 mg, 0.75 mmol), sodium carbonate (239 mg, 2.26 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (381 mg, 0.9 mmol) and tetrakis (triphenylphosphine)palladium (87 mg, 0.075 mmol) were dissolved in dioxane:water (15 ml:5 ml). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 110 mg of (S)-4-(6-((1-(6-(4-fluoro-1H-pyrazol-1-yl)pyridin-3-yl)ethyl)(methyl)amino)pyridine-3-yl)-6-propoxypyrazolo[1,5-a]pyridine-3-carbonitrile (compound 39). MS m/z (ESI): 497 $[M+H]^+$. $^1H$ NMR (400 MHz, DMSO-d6) δ 8.64 (dd, J=4.6, 0.9 Hz, 1H), 8.63 (d, J=2.1 Hz, 1H), 8.56 (s, 1H), 8.40-8.38 (m, 1H), 8.36 (dd, J=2.5, 0.7 Hz, 1H), 7.93-7.84 (m, 3H), 7.79 (dd, J=8.8, 2.6 Hz, 1H), 7.29 (d, J=2.1 Hz, 1H), 6.81 (dd, J=8.9, 0.8 Hz, 1H), 6.27 (q, J=7.0 Hz, 1H), 4.05 (t, J=6.5 Hz, 2H), 2.81 (s, 3H), 1.76 (q, J=6.9 Hz, 2H), 1.60 (d, J=7.0 Hz, 3H), 0.99 (t, J=7.4 Hz, 3H).

Example 40: (S)-4-(6-((1-(6-(4-fluoro-1H-pyrazol-1-yl)pyridin-3-yl)ethyl)(methyl)amino)pyridine-3-yl)-6-methoxypyrazolo[1,5-a]pyridine-3-carbonitrile

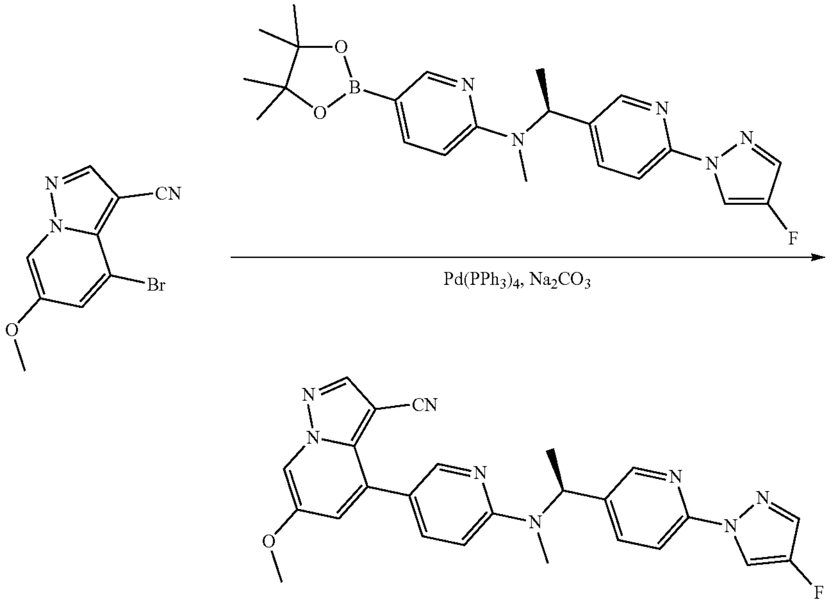

Step 1: (S)-4-(6-((1-(6-(4-fluoro-1H-pyrazol-1-yl)pyridin-3-yl)ethyl)(methyl)amino)pyridine-3-yl)-6-methoxypyrazolo[1,5-a]pyridine-3-carbonitrile 4-bromo-6-methoxypyrazolo[1,5-a]pyridine-3-carbonitrile (100 mg, 0.39 mmol), sodium carbonate (126 mg, 1.19 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (198 mg, 0.47 mmol) and tetrakis (triphenylphosphine)palladium (45 mg, 0.039 mmol) were dissolved in dioxane:water (15 mL:5 mL). The mixed solution reacted at 80° C. for 16 h. After the reaction was found to be completed from the monitoring, the reaction solution was cooled, and water was added to quench the reaction, ex traction with EA (20 mL*3) was then carried out, and the organic phase was washed with water and then dried, concentrated and subjected to column chromatography to obtain 110 mg of (S)-4-(6-((1-(6-(4-fluoro-1H-pyrazol-1-yl)pyridin-3-yl)ethyl)(methyl)amino)pyridine-3-yl)-6-methoxypyrazolo[1,5-a]pyridine-3-carbonitrile (compound 40). MS m/z (ESI): 469 $[M+H]^+$. $^1H$ NMR (400 MHz, DMSO-d6) δ 8.66-8.63 (m, 2H), 8.57 (s, 1H), 8.39 (dd, J=1.9, 1.1 Hz, 1H), 8.36 (dd, J=2.5, 0.7 Hz, 1H), 7.92-7.84 (m, 3H), 7.79 (dd, J=8.8, 2.6 Hz, 1H), 7.30 (d, J=2.1 Hz, 1H), 6.81 (dd, J=8.9, 0.8 Hz, 1H), 6.27 (q, J=7.0 Hz, 1H), 3.88 (s, 3H), 2.82 (s, 3H), 1.60 (d, J=7.1 Hz, 3H).

Example 41: Preparation of (S)-4-(6-((1-(6-(4-fluoro-1H-pyrazol-1-yl)pyridin-3-yl)ethyl)(methyl)amino)pyridine-3-yl)-6-(2-fluoroethoxy)pyrazolo[1,5-a]pyridine-3-carbonitrile

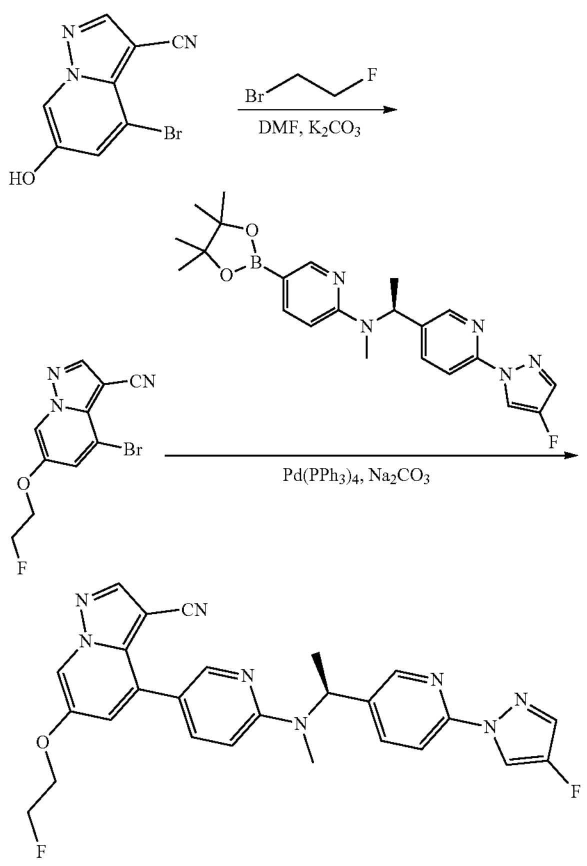

Step 1: Synthesis of 4-bromo-6-(2-fluoroethoxy)pyrazolo[1,5-a]pyridine-3-carbonitrile 4-bromo-6-hydroxypyrazolo[1,5-a]pyridine-3-carbonitrile (100 mg, 0.42 mmol), potassium carbonate (175 mg, 1.27 mmol) and 1-bromo-2-fluoroethane (64 mg, 0.50 mmol) were dissolved in DMF (20 ml). The mixed solution reacted at 60° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 103 mg of 4-bromo-6-(2-fluoroethoxy)pyrazolo[1,5-a]pyridine-3-carbonitrile. MS m/z (ESI): 284 $[M+H]^+$.

Step 2: (S)-4-(6-((1-(6-(4-fluoro-1H-pyrazol-1-yl)pyridin-3-yl)ethyl)(methyl)amino)pyridine-3-yl)-6-(2-fluoroethoxy)pyrazolo[1,5-a]pyridine-3-carbonitrile 4-bromo-6-(2-fluoroethoxy)pyrazolo[1,5-a]pyridine-3-carbonitrile (103 mg, 0.36 mmol), sodium carbonate (114 mg, 1.08 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (183 mg, 0.43 mmol) and tetrakis(triphenylphosphine)palladium (42 mg, 0.036 mmol) were dissolved in dioxane:water (15 mL:5 mL). The mixed solution reacted at 80° C. for 16 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 90 mg of (S)-4-(6-((1-(6-(4-fluoro-1H-pyrazol-1-yl)pyridin-3-yl)ethyl)(methyl)amino)pyridine-3-yl)-6-(2-fluoroethoxy)pyrazolo[1,5-a]pyridine-3-carbonitrile (compound 41). MS m/z (ESI): 501 $[M+H]^+$. $^1H$ NMR (500 MHz, DMSO-d6) δ 8.73 (d, J=2.2 Hz, 1H), 8.66 (d, J=4.5 Hz, 1H), 8.60 (s, 1H), 8.40 (d, J=2.3 Hz, 1H), 8.38 (d, J=2.5 Hz, 1H), 7.94-7.84 (m, 3H), 7.82 (dd, J=8.8, 2.6 Hz, 1H), 7.36 (d, J=2.0 Hz, 1H), 6.83 (d, J=8.8 Hz, 1H), 6.29 (d, J=7.2 Hz, 1H), 4.88-4.80 (m, 1H), 4.77-4.71 (m, 1H), 4.47-4.42 (m, 1H), 4.40-4.35 (m, 1H), 2.83 (s, 3H), 1.61 (d, J=6.9 Hz, 3H).

Example 42: Preparation of (S)-4-(6-((1-(6-(diethylamino)pyridin-3-yl)ethyl)(methyl)amino)pyridin-3-yl)-6-(2-hydroxy-2-methylpropoxy)pyrazolo[1,5-a]pyridine-3-carbonitrile

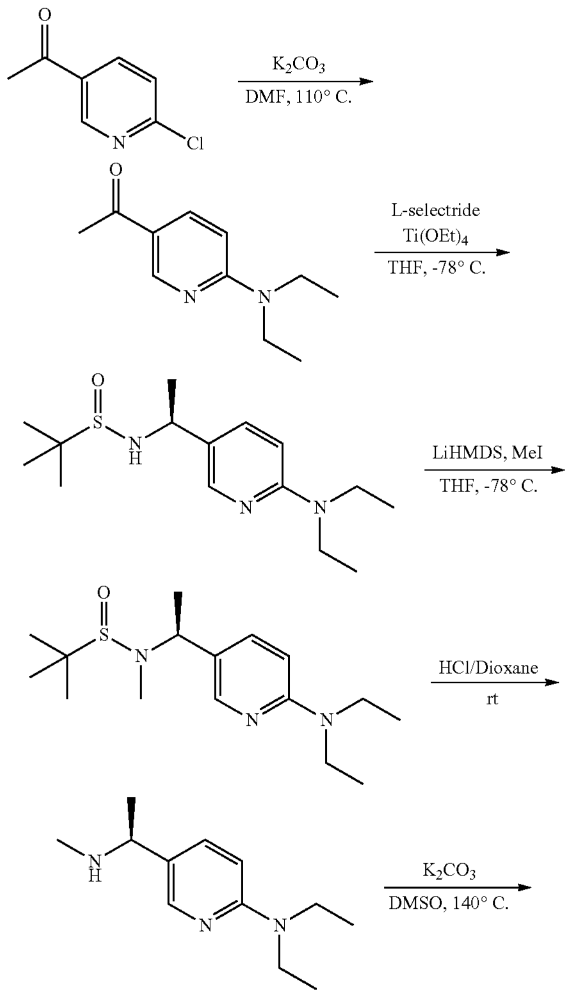

-continued

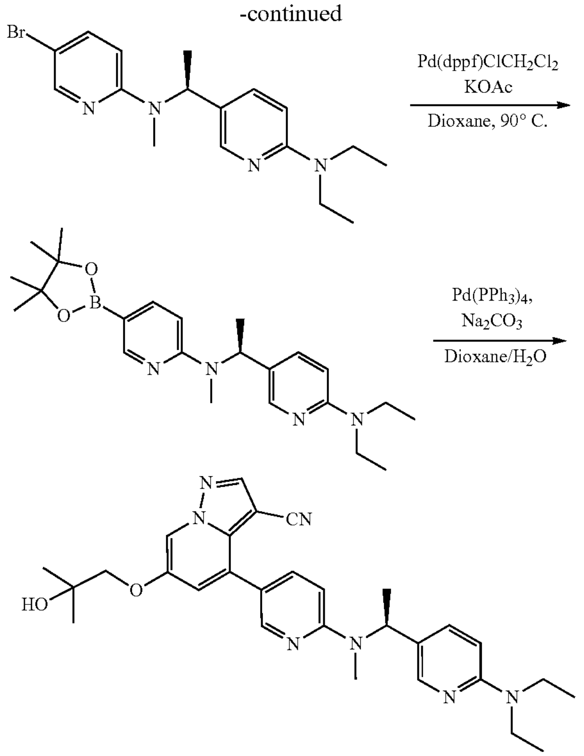

Step 1: 1-(6-(diethylamino)pyridin-3-yl)ethan-1-one

At room temperature, 2-chloro-5-acetylpyridine (2.1 g, 19.43 mmol), diethylamine (4.9 g, 7.48 mmol) and $K_2CO_3$ (5.5, g 4.47 mmol) were dissolved in DMF (20 mL). The mixed solution was stirred at 110° C. overnight. The reaction solution was cooled to room temperature, diluted with water (100 mL), extracted, and the organic phase was dried, filtered, concentrated and subjected to column chromatography to obtain 2.3 g of 1-(6-(diethylamino)pyridin-3-yl)ethan-1-one with a yield of 88% MS m/z (ESI): 193 $[M+H]^+$.

Step 2: N-((S)-1-(6-(diethylamino)pyridin-3-yl)ethyl)-2-methylpropane-2-sulfinamide At room temperature, (R)-2-methylpropane-2-sulfonimide (1.45 g, 11.98 mmol) and 1-(6-(diethylamino)pyridin-3-yl)ethan-1-one (2.3 g, 11.98 mmol), THF (50 mL) were added to a reaction flask, and then tetraethyl titanate (5.56 g, 24.4 mmol) was added dropwise. After addition was completed, the reaction solution was heated to 75° C. to react for 16 h, and then it was cooled to −78° C.; next, L-selectride (36 mL, 35.94 mmol) was added dropwise slowly, and the reaction solution was warmed to room temperature to react for 15 min, and then methanol was added at −50° C. to quench the reaction. The reaction solution was stirred adequacy with water (50 mL) and EA (200 mL), extracted, dried with anhydrous sodium sulfate, filtrated, concentrated to obtain a crude product. The crude product purified by column chromatography to obtain 2.5 g of N-((S)-1-(6-(diethylamino)pyridin-3-yl)ethyl)-2-methylpropane-2-sulfinamide with a yield of 71%. MS m/z (ESI): 298 $[M+H]^+$.

Step 3: N-((S)-1-(6-(diethylamino)pyridin-3-yl)ethyl)-N,2-dimethylpropane-2-sulfinamide At room temperature, N-((S)-1-(6-(diethylamino)pyridin-3-yl)ethyl)-2-methylpropane-2-sulfinamide (2.25 g, 7.5 mmol) was dissolved in THF (20 mL), and then MeI (1.17 g, 8.25 mmol) was added dropwise slowly at −78° C. The reaction was carried out at −78° C. to react for 1 h. The reaction solution was diluted with water (30 mL), extracted, and the organic phase was dried, filtered, concentrated and subjected to column chromatography to obtain 1.6 g of N-((S)-1-(6-(diethylamino)pyridin-3-yl)ethyl)-N,2-dimethylpropane-2-sulfinamide with a yield of 69%. MS m/z (ESI): 312 $[M+H]^+$.

Step 4: (S)—N,N-diethyl-5-(1-(methylamino)ethyl)pyridin-2-amine

At room temperature, N-((S)-1-(6-(diethylamino)pyridin-3-yl)ethyl)-N,2-dimethylpropane-2-sulfinamide (1.6 g, 5.14 mmol) was dissolved in MeOH (2 mL), and then HCl/dioxane (20 mL, 4M) was added, and the mixed solution reacted at room temperature for 1 h. The resulting reaction solution was concentrated in vacuum under reduced pressure to remove the solvent, and the reaction was quenched with $NaHCO_3$ solution. The reaction solution was extracted, dried, filtered, concentrated, and subjected to column chromatography to obtain 0.8 g of (S)—N,N-diethyl-5-(1-(methylamino)ethyl)pyridin-2-amine with a yield of 80%. MS m/z (ESI): 208 $[M+H]^+$.

Step 5: (S)-5-bromo-N-(1-(6-(diethylamino)pyridin-3-yl)ethyl)-N-methylpyridin-2-amine At room temperature, (S)—N,N-diethyl-5-(1-(methylamino)ethyl)pyridin-2-amine (0.7 g, 0.24 mmol), 5-bromo-2-fluoropyridine (4.76 g, 1.2 mmol) and $K_2CO_3$ (2.3 g, 0.72 mmol) were dissolved in DMSO (10 mL). The reaction was carried out at 140° C. to react for 24 h. The reaction solution was cooled to room temperature, diluted with water, extracted, and the organic phase was dried, filtered, concentrated and subjected to column chromatography to obtain 0.8 g of (S)-5-bromo-N-(1-(6-(diethylamino)pyridin-3-yl)ethyl)-N-methylpyridin-2-amine with a yield of 57%. MS m/z (ESI): 363 $[M+H]^+$.

Step 6: (S)—N-(1-(6-(diethylamino)pyridin-3-yl)ethyl)-N-methyl-5-(4,4,5,5-tetra methyl-1,3,2-dioxaborolane-2-yl)pyridin-2-amine At room temperature, (S)-5-bromo-N-(1-(6-(diethylamino)pyridin-3-yl)ethyl)-N-methylpyridin-2-amine (0.7 g, 0.13 mmol), pinacol biborate (1.4 g, 0.41 mmol), Pd(dppf)$ClCH_2Cl_2$ (140 mg, 0.013 mmol) and KOAc (560 mg, 0.041 mmol) were dissolved in dioxane (15 mL), and the mixed solution reacted at 90° C. for 6 h. The resulting reaction solution was concentrated in vacuum under reduced pressure to remove the solvent, and the reaction solution was diluted with $NaHCO_3$, extracted, dried, filtered, concentrated, and subjected to column chromatography to obtain 437 mg of (S)—N-(1-(6-(diethylamino)pyridin-3-yl)ethyl)-N-methyl-5-(4,4,5,5-tetramethyl-1,3,2-dioxaborolane-2-yl)pyridin-2-amine with a yield of 50.8%. MS m/z (ESI): 329 $[M+H]^+$.

Step 7: (S)-4-(6-((1-(6-(diethylamino)pyridin-3-yl)ethyl)(methyl)amino)pyridin-3-yl)-6-(2-hydroxy-2-methylpropoxy)pyrazolo[1,5-a]pyridine-3-carbonitrile At room temperature and under the protection of $N_2$, 4-bromo-6-(2-hydroxy-2-methylpropoxy)pyrazolo[1,5-a]pyridine-3-carbonitrile (240 mg, 0.77 mmol), (S)—N-(1-(6-

(diethylamino)pyridin-3-yl)ethyl)-N-methyl-5-(4,4,5,5-tetramethyl-1,3,2-dioxaborolane-2-yl)pyridin-2-amine (480 mg, 1.17 mmol), $Pd(PPh_3)_4$ (88 mg, 0.076 mmol) and $Na_2CO_3$ (324 mg, 3.05 mmol) were dissolved in 1,4-dioxane:$H_2O$=5:1 (12 mL). The mixed solution was stirred at 100° C. for 12 h to react. The reaction solution was cooled to room temperature, and water was added to quench the reaction, extraction was carried out, and the organic phase was washed with water and then dried, and subjected to column chromatography to obtain 92 mg of (S)4-(6-((1-(6-(diethylamino)pyridin-3-yl)ethyl)(methyl)amino)pyridin-3-yl)-6-(2-hydroxy-2-methylpropoxy)pyrazolo[1,5-a]pyridine-3-carbonitrile (compound 42) with a yield of 23%, as a white solid. MS m/z (ESI): 514 $[M+H]^{+1}$. $^1H$ NMR (400 MHz, DMSO) δ 8.64 (d, 1H), 8.56 (s, 1H), 8.34 (d, 1H), 8.00 (d, 1H), 7.74-7.77 (m, 1H), 7.29-7.38 (m, 1H), 7.36-7.38 (d, 1H), 6.73 (d, 1H), 6.56 (d, 1H), 4.68 (s, 1H), 3.84 (s, 2H), 3.41-3.46 (m, 4H), 2.73 (s, 3H), 1.37-1.48 (m, 3H), 1.20 (s, 6H).

Example 43: Preparation of (S)-6-(2-hydroxy-2-methylpropoxy)-4-(6-((1-(6-methoxypyridin-3-yl)ethyl)(methyl)amino)pyridin-3-yl)pyrazolo[1,5-a]pyridine-3-carbonitrile

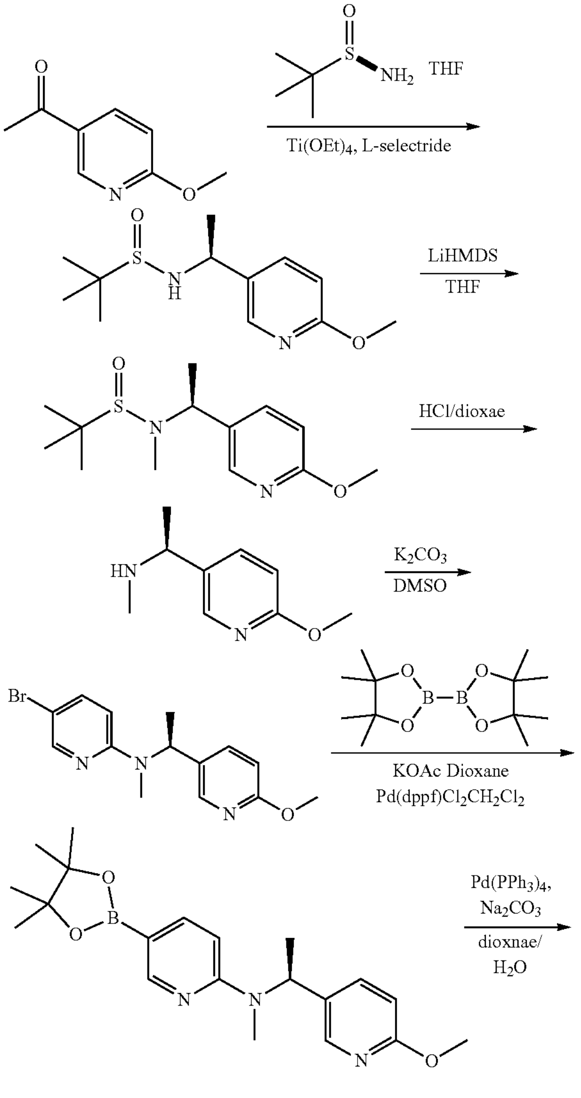

-continued

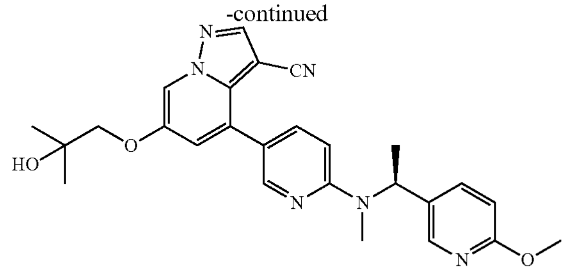

Step 1: N-((S)-1-(6-methoxypyridin-3-yl)ethyl)-2-methylpropane-2-sulfoxideamide

At room temperature, (R)-2-methylpropane-2-sulfonimide (4.8 g, 39.6 mmol) and 5-acetyl-2-methoxypyridine (4.0 g, 26 mmol), THF (50 mL) and tetraethyl titanate (11.86 g, 52 mmol) were added to a reaction flask. The reaction was carried out at 80° C. for 16 h, and then it was cooled to −78° C., next, L-selectride (18.8 mL, 188 mmol) was added dropwise slowly. After addition was completed, the reaction solution was warmed to room temperature to react for 15 min, and then methanol was added at −50° C. to quench the reaction. The reaction solution was stirred adequacy with 50 mL of water and EA (200 mL), and extracted, dried, filtered, concentrated. The crude product was purified by column chromatography to obtain 2.0 g of N-((S)-1-(6-methoxypyridin-3-yl)ethyl)-2-methylpropane-2-sulfoxideamide with a yield of 30%. MS m/z (ESI): 257 $[M+H]^+$.

Step 2: N-((S)-1-(6-methoxypyridin-3-yl)ethyl)-N,2-dimethylpropane-2-sulfinamide N-((S)-1-(6-methoxypyridin-3-yl)ethyl)-N,2-dimethylpropane-2-sulfinamide (2.0 g, 7.8 mmol) was dissolved in THF (20 mL); then, LiHMDS (15.6 mL, 15.6 mmol) was slowly added dropwise at −78° C., and the reaction was carried out at −78° C. for 1 h. Mel (1.22 g, 8.58 mmol) was added to the reaction system and the reaction was carried out at −78° C. for 3 h, and water was added to quench the reaction; then, extraction was carried out, and the organic phase was dried, filtered, concentrated and subjected to column chromatography to obtain 1.9 g of N-((S)-1-(6-methoxypyridin-3-yl)ethyl)-N,2-dimethylpropane-2-sulfinamide with a yield of 90%. MS m/z (ESI): 271 $[M+H]^+$.

Step 3: (S)-1-(6-methoxypyridin-3-yl)-N-methylethane-1-amine

N-((S)-1-(6-methoxypyridin-3-yl)ethyl)-N,2-dimethylpropane-2-sulfinamide (1.9 g, 7.0 mmol) was dissolved in DCM (10 mL), and then HCl/dioxane (20 mL, 4M) was added, and the mixed solution reacted at room temperature for 1 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.81 g of (S)-1-(6-methoxypyridin-3-yl)-N-methylethane-1-amine with a yield of 69%. MS m/z (ESI): 167 $[M+H]^+$.

Step 4: (S)-5-bromo-N-methyl-N-(1-(6-(methylamino)pyridin-3-yl)ethyl)pyridin-2-amine At room temperature, (S)-1-(6-methoxypyridin-3-yl)-N-methylethane-1-amine (0.8 g, 4.8 mmol), 5-bromo-2-fluoropyridine (6.8 g, 39 mmol) and $K_2CO_3$ (2.0 g, 14.6 mmol) were dissolved in DMSO (10 mL). The mixed solution reacted at 140° C. for 24 h, and then cooled to room temperature. The reaction solution was diluted with water, extracted, and the organic phase was dried, filtered, concentrated and subjected to column chromatography to obtain 860 mg of (S)-5-bromo-N-methyl-N-(1-(6-(methylamino) pyridin-3-yl)ethyl)pyridin-2-amine with a yield of 57%. MS m/z (ESI): 321 $[M+H]^+$.

Step 5: (S)—N-(1-(6-methoxypyridin-3-yl)ethyl)-N-methyl-5-(4,4,5,5-tetramethyl-1,3,2-dioxaborolane-2-yl)pyridin-2-amine (S)-5-bromo-N-methyl-N-(1-(6-(methylamino)pyridin-3-yl)ethyl)pyridin-2-amine (0.5 g, 1.5 mmol), pinacol biborate (1.18 g, 4.67 mmol), Pd(dppf)$ClCH_2Cl_2$ (122 mg, 0.15 mmol) and KOAc (460 mg, 4.67 mmol) were dissolved in dioxane (15 mL), and the mixed solution reacted at 90° C. for 12 h. The resulting reaction solution was concentrated in vacuum under reduced pressure to remove the solvent. The reaction solution was diluted with $NaHCO_3$, extracted, dried, filtered, concentrated, and subjected to column chromatography to obtain 770 mg of (S)—N-(1-(6-methoxypyridin-3-yl)ethyl)-N-methyl-5-(4,4,5,5-tetramethyl-1,3,2-dioxaborolane-2-yl)pyridin-2-amine with a yield of 100%. MS m/z (ESI): 288 $[M+H]^+$.

Step 6: (S)-6-(2-hydroxy-2-methylpropoxy)-4-(6-((1-(6-methoxypyridin-3-yl)ethyl)(methyl)amino) pyridin-3-yl)pyrazolo[1,5-a]pyridine-3-carbonitrile 4-bromo-6-(2-hydroxy-2-methylpropoxy)pyrazolo[1,5-a] pyridine-3-carbonitrile (140 mg 0.45 mmol), (S)—N-(1-(6-methoxypyridin-3-yl)ethyl)-N-methyl-5-(4,4,5,5-tetramethyl-1,3,2-dioxaborolane-2-yl)pyridin-2-amine (334 mg, 0.9 mmol), $Pd(PPh_3)_4$ (40 mg, 0.045 mmol) and $Na_2CO_3$ (143 mg, 1.35 mmol) were dissolved in 1,4-dioxane: $H_2O$=5:1 (12 mL). The mixed solution was stirred at 100° C. for 12 h to react under the protection of $N_2$. The reaction solution was cooled to room temperature, and water was added to quench the reaction, extraction was carried out, and the organic phase was washed with water and then dried, and subjected to column chromatography to obtain 66 mg of (S)-6-(2-hydroxy-2-methylpropoxy)-4-(6-((1-(6-methoxypyridin-3-yl)ethyl)(methyl)amino)pyridin-3-yl)pyrazolo[1,5-a]pyridine-3-carbonitrile (compound 43) with a yield of 31%, as a white solid. MS m/z (ESI): 473 $[M+H]^+$. $^1H$ NMR (400 MHz, DMSO) δ 8.65 (d, 1H), 8.57 (s, 1H), 8.35 (d, 1H), 8.10 (d, 1H), 7.75-7.80 (m, 1H), 7.59-7.63 (m, 2H), 7.30 (d, 1H), 6.72-6.79 (dd, 2H), 3.80 (s, 2H), 3.81 (s, 3H), 2.75 (s, 3H), 1.52 (d, 3H), 1.21 (s, 6H).

Example 44: Preparation of (S)-4-(6-((1-(6-(4-fluoro-1H-pyrazolyl)pyridin-3-yl)propyl)(methyl) amino)pyridin-3-yl)-6-(2-hydroxy-2-methylpropoxy) pyrazo[1,5-a]pyridine-3-carbonitrile

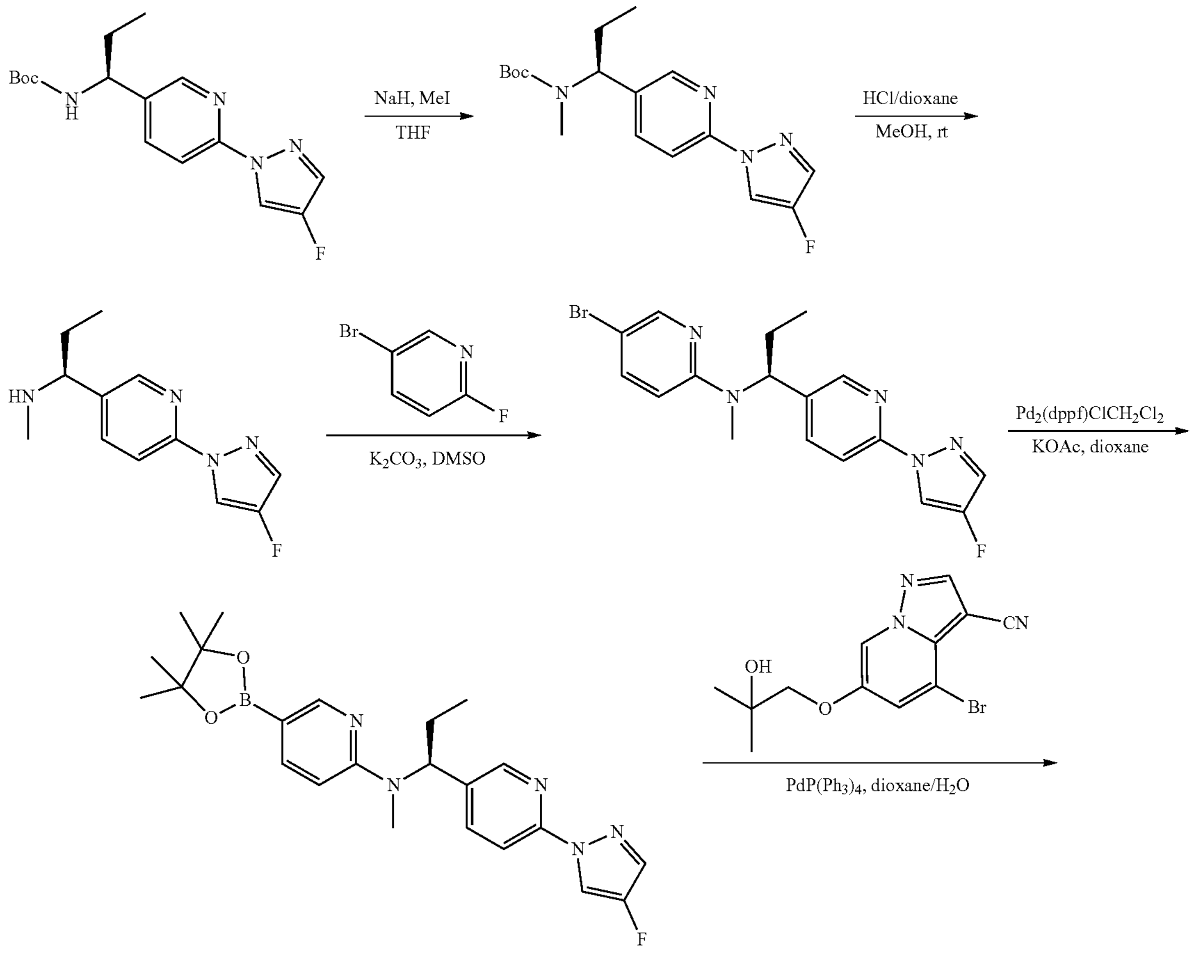

-continued

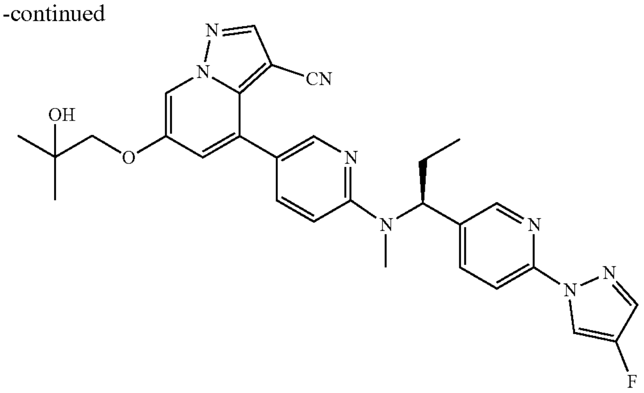

Step 1: tert-butyl (S)-(1-(6-(4-fluoro-1H-pyrazol-1-yl)pyridin-3-yl)propyl)(methyl)carbamate Tert-butyl (S)-(1-(6-(4-fluoro-1H-pyrazol-1-yl)pyridin-3-yl)propyl)carbamate (470 mg, 1.46 mmol) was dissolved in THF (20 mL), and sodium hydrogen (117 mg, 3.0 mmol) was added at 0° C. under the protection of $N_2$ to have thermal reaction for 0.5 h. Then, MeI (248 mg, 1.75 mmol) was added. The reaction was carried out at room temperature for 5 h. The reaction solution was diluted with water, extracted, and the organic phase was dried, filtered, concentrated and subjected to column chromatography to obtain 400 mg of tert-butyl (S)-(1-(6-(4-Fluoro-1H-pyrazol-1-yl) pyridin-3-yl)propyl)(methyl)carbamate with a yield of 81%. MS m/z (ESI): 335 $[M+H]^+$.

Step 2: (S)-1-(6-(4-fluoro-1H-pyrazol-1-yl)pyridin-3-yl)-N-methylpropan-1-amine

Tert-butyl (S)-(1-(6-(4-fluoro-1H-pyrazol-1-yl)pyridin-3-yl)propyl)(methyl)carbamate (400 mg, 1.19 mmol) was dissolved in MeOH (2 mL), and then HCl/dioxane (10 mL, 4M) was added; then, the mixed solution reacted at room temperature for 1 h. The resulting reaction solution was concentrated in vacuum under reduced pressure to remove the solvent. The reaction solution was diluted with $NaHCO_3$, extracted, dried, filtered, concentrated, and subjected to column chromatography to obtain 276 mg of (S)-1-(6-(4-fluoro-1H-pyrazol-1-yl)pyridin-3-yl)-N-methylpropan-1-amine with a yield of 100%. MS m/z (ESI): 225 $[M+H]^+$ Step 3: (S)-5-bromo-N-(1-(6-(4-fluoro-1H-pyrazolyl)pyridin-3-yl)propyl)-N-methylpyridin-2-amine (S)-1-(6-methoxypyridin-3-yl)-N-methylethane-1-amine (480 mg, 1.18 mmol), 5-bromo-2-fluoropyridine (1.25 g, 7.1 mmol) and $K_2CO_3$ (987 mg, 7.1 mmol) were dissolved in 10 mL of DMSO. The mixed solution reacted at 140° C. for 24 h, and then cooled to room temperature. The reaction solution was diluted with water, extracted, and the organic phase was dried, filtered, concentrated and subjected to column chromatography to obtain 160 mg of (S)-5-bromo-N-(1-(6-(4-fluoro-1H-pyrazolyl)pyridin-3-yl)propyl)-N-methylpyridin-2-amine with a yield of 19%. MS m/z (ESI): 390 $[M+H]^+$.

Step 4: (S)—N-(1-(6-(4-fluoro-1H-pyrazol-1-yl) pyridin-3-yl)propyl)-N-methyl-5-(4,4,5,5-tetramethyl-1,3,2-dioxaborolane-2-yl)pyridin-2-amine At room temperature, (S)-5-bromo-N-(1-(6-(4-fluoro-1H-pyrazolyl)pyridin-3-yl)propyl)-N-methylpyridin-2-amine (160 mg, 0.4 mmol), pinacol biborate (313 mg, 1.23 mmol), $Pd(dppf)ClCH_2Cl_2$ (32 mg, 0.04 mmol) and KOAc (121 mg, 1.23 mmol) were dissolved in dioxane (10 mL), and the mixed solution reacted at 90° C. for 12 h. The resulting reaction solution was concentrated in vacuum under reduced pressure to remove the solvent. The reaction solution was diluted with $NaHCO_3$, extracted, dried, filtered, concentrated, and subjected to column chromatography to obtain 160 mg of (S)—N-(1-(6-(4-fluoro-1H-pyrazol-1-yl)pyridin-3-yl)propyl)-N-methyl-5-(4,4,5,5-tetramethyl-1,3,2-dioxaborolane-2-yl)pyridin-2-amine with a yield of 89%. MS m/z (ESI): 456 $[M+H]^+$.

Step 5: (S)-4-(6-((1-(6-(4-fluoro-1H-pyrazolyl)pyridin-3-yl)propyl)(methyl)amino)pyridin-3-yl)-6-(2-hydroxy-2-methylpropoxy)pyrazo[1,5-a]pyridine-3-carbonitrile At room temperature and under the protection of $N_2$, 4-bromo-6-(2-hydroxy-2-m ethylpropoxy)pyrazolo[1,5-a]pyridine-3-carbonitrile (96 mg, 0.3 mmol), (S)—N-(1-(6-(4-fluoro-1H-pyrazol-1-yl)pyridin-3-yl)propyl)-N-methyl-5-(4,4,5,5-tetramethyl-1,3,2-dioxaborolane-2-yl)pyridin-2-amine (160 mg, 0.35 mmol), $Pd(PPh_3)_4$ (34 mg, 0.03 mmol) and $Na_2CO_3$ (95 mg, 0.9 mmol) were dissolved in 1,4-dioxane:$H_2O$=5:1 (12 mL), and the mixed reaction solution was stirred at 90° C. for 12 h to react. The reaction solution was cooled to room temperature, and water was added to quench the reaction, extraction was carried out, and the organic phase was washed with water, dried, and subjected to column chromatography to obtain 31 mg of (S)-4-(6-((1-(6-(4-fluoro-1H-pyrazolyl)pyridin-3-yl)propyl)(methyl) amino)pyridin-3-yl)-6-(2-hydroxy-2-methylpropoxy)pyrazo [1,5-a]pyridine-3-carbonitrile (compound 44) with a yield of 18%, as a white solid. MS m/z (ESI): 541 $[M+H]^+$. $^1H$ NMR (400 MHz, DMSO) δ 8.75 (s, 1H), 8.64 (s, 1H), 8.56 (s, 1H), 8.37 (d, 1H), 7.60-7.94 (m, 3H), 7.58-7.62 (m, 2H), 7.30 (s, 1H), 6.81 (d, 1H), 6.28 (d, 1H), 4.70 (s, 1H), 3.87 (s, 2H), 2.83 (s, 3H), 1.61 (s, 2H), 1.40 (s, 3H), 1.22 (s, 6H).

Example 45: Preparation of (S)-4-(6-((1-(6-(4-chloro-1H-pyrazol-1-yl)pyridin-3-yl)ethyl)(methyl)amino)pyridine-3-yl)-6-(2-hydroxy-2-methyl-propoxy)pyrazo[1,5-a]pyridine-3-carbonitrile
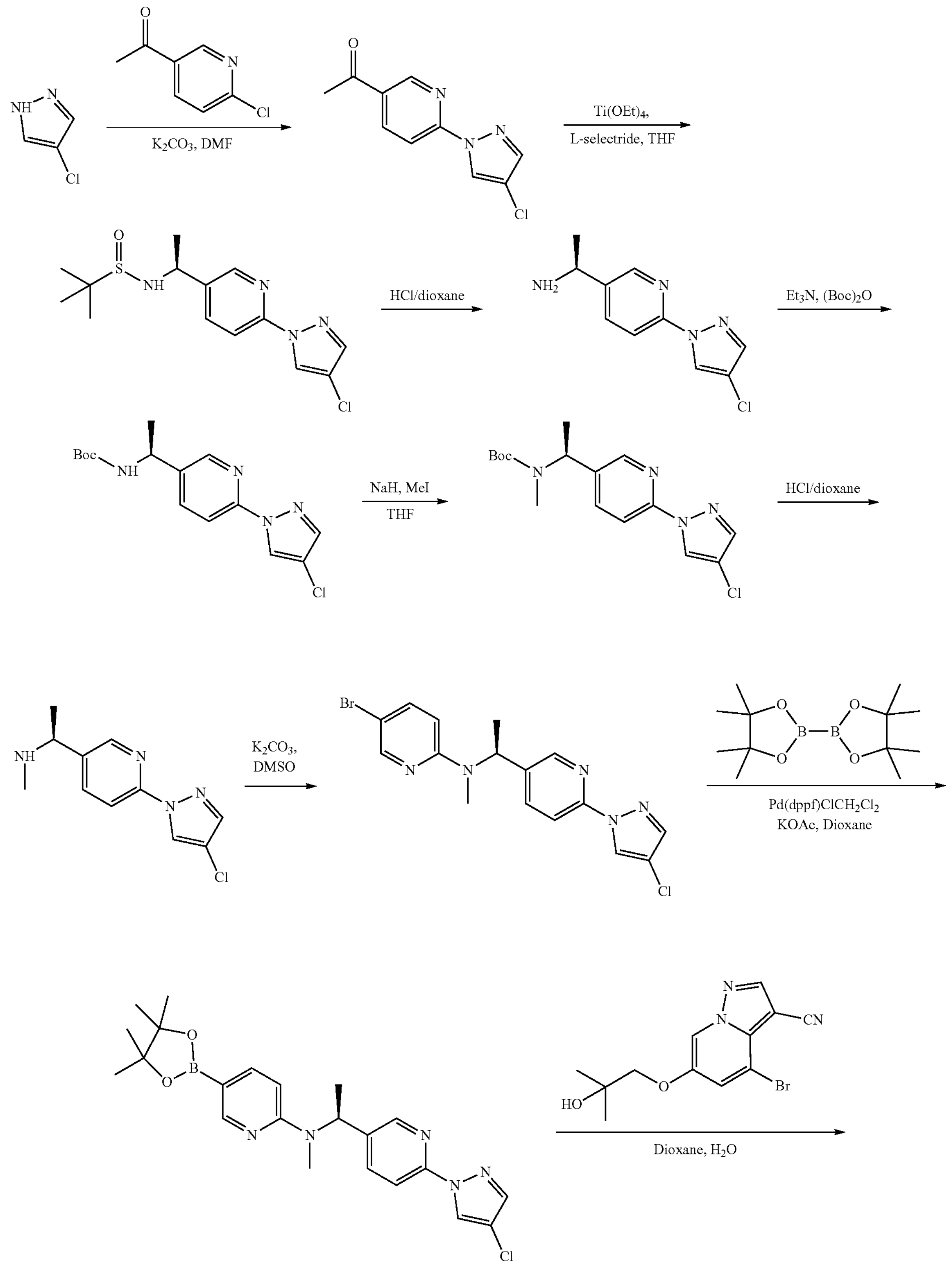

-continued

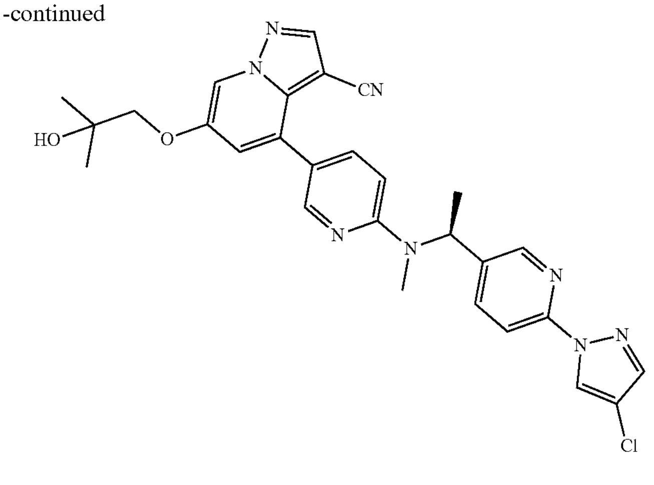

Step 1: 1-(6-(4-chloro-1H-pyrazol-1-yl)pyridin-3-yl) ethan-1-one 2-chloro-5-acetylpyridine (4.0 g, 29.26 mmol), 4-fluoro-1H-pyrazole (2.0 g, 19.50 mmol) and $K_2CO_3$ (8.1 g, 58.5 mmol) were dissolved in DMF (20 mL). The mixed solution was stirred at 110° C. overnight, and then cooled to room temperature. The reaction solution was diluted with water (50 mL), extracted, and the organic phase was dried, filtered, concentrated and subjected to column chromatography to obtain 4.0 g of 1-(6-(4-chloro-1H-pyrazol-1-yl)pyridin-3-yl) ethan-1-one with a yield of 93%. MS m/z (ESI): 222 $[M+H]^+$.

Step 2: N-((S)-1-(6-(4-chloro-1H-pyrazol-1-yl)pyridin-3-yl)ethyl)-2-methylpropane-2-sulfinamide At room temperature, (R)-2-methylpropane-2-sulfonimide (1.8 g, 14.89 mmol), 1-(6-(4-chloro-1H-pyrazol-1-yl) pyridin-3-yl)ethan-1-one (2.2 g, 9.9 mmol) and THF (50 mL) were added to a reaction flask, and then tetraethyl titanate (4.5 g, 19.8 mmol) was added. The reaction was carried out at 75° C. to react for 16 h, and then the reaction solution was cooled to −78° C.; next, L-selectride (20 mL, 19.8 mmol) was added dropwise slowly. After addition was completed, the reaction was carried out at −78° C. to react for 3 h. After the reaction solution was stirred adequacy with water (50 mL) and EA (200 mL), it was filtered, extracted, dried with anhydrous sodium sulfate, filtrated, concentrated to obtain a crude product. The crude product was purified by column chromatography to obtain 3.0 g of N-((S)-1-(6-(4-chloro-1H-pyrazol-1-yl)pyridin-3-yl)ethyl)-2-methylpropane-2-sulfinamide with a yield of 93%. MS m/z (ESI): 298 $[M+H]^+$.

Step 3: (S)-1-(6-(4-chloro-1H-pyrazol-1-yl)pyridin-3-yl)ethane-1-amine

N-((S)-1-(6-(4-chloro-1H-pyrazol-1-yl)pyridin-3-yl) ethyl)-2-methylpropane-2-sulfinamide (4.0 g, 12.26 mmol) was dissolved in DCM (20 mL), and then HCl/dioxane (50 mL, 4M) was added. The mixed solution reacted at room temperature for 1 h. Then, it was concentrated in vacuum under reduced pressure to remove the solvent, alkalized with $NaHCO_3$, extracted, dried, filtered, concentrated to obtain 2.28 g of (S)-1-(6-(4-chloro-1H-pyrazol-1-yl)pyridin-3-yl) ethane-1-amine with a yield of 89%. MS m/z (ESI): 223 $[M+H]^+$.

Step 4: tert-butyl (S)-(1-(6-(4-chloro-1H-pyrazol-1-yl)pyridin-3-yl)ethyl)carbamate (S)-1-(6-(4-chloro-1H-pyrazol-1-yl)pyridin-3-yl)ethane-1-amine (2.28 g, 10.2 mmol) and triethylamine (3.7 g, 36 mmol) were dissolved in DCM (20 mL), and then di-tert-butyl dicarbonate (3.0 g, 13.5 mmol) was added. The reaction solution was stirred at room temperature for 5 h. Extraction was carried out, and the organic phase was dried, filtered, concentrated and subjected to column chromatography to obtain 5 g of tert-butyl (S)-(1-(6-(4-chloro-1H-pyrazol-1-yl)pyridin-3-yl)ethyl)carbamate with a yield of 45%. MS m/z (ESI): 266 $[M-56]^+$.

Step 5: tert-butyl (S)-(1-(6-(4-chloro-1H-pyrazol-1-yl)pyridin-3-yl)ethyl)(methyl)carbamate Tert-butyl (S)-(1-(6-(4-chloro-1H-pyrazol-1-yl)pyridin-3-yl)ethyl)carbamate (1.5 g, 4.6 mmol) was dissolved in THF (20 mL), and then sodium hydrogen (276 mg, 6.9 mmol) was added to the resulting solution at 0° C. to have thermal reaction for 0.5 h. Then, MeI (0.85 g, 6.0 mmol) was added to the reaction system. The reaction was carried out at 0° C. for 1 h. The reaction solution was diluted with water (50 mL), extracted, and the organic phase was dried, filtered, concentrated and subjected to column chromatography to obtain 1.2 g of tert-butyl (S)-(1-(6-(4-chloro-1H-pyrazol-1-yl)pyridin-3-yl)ethyl)(methyl)carbamate with a yield of 77%. MS m/z (ESI): 337 $[M+H]^+$.

Step 6: (S)-1-(6-(4-chloro-1H-pyrazol-1-yl)pyridin-3-yl)-N-methylethane-1-amine

Tert-butyl (S)-(1-(6-(4-chloro-1H-pyrazol-1-yl)pyridin-3-yl)ethyl)(methyl)carbamate (1.2 g, 3.57 mmol) was dissolved in DCM (5 mL), and then HCl/dioxane (20 mL, 4M) was added, and the mixed solution reacted at room temperature for 1 h. The resulting reaction solution was concentrated in vacuum under reduced pressure to remove the solvent, diluted with $NaHCO_3$, extracted, dried, filtered, concentrated, and subjected to column chromatography to obtain 560 mg of (S)-1-(6-methoxypyridin-3-yl)-N-methylethane-1-amine with a yield of 66%. MS m/z (ESI): 237 $[M+H]^+$.

Step 7: (S)-5-bromo-N-(1-(6-(4-chloro-1H-pyrazol-1-yl)pyridin-3-yl)ethyl)-N-methyl pyridin-2-amine ((S)-1-(6-(4-chloro-1H-pyrazol-1-yl)pyridin-3-yl)-N-methylethane-1-amine (560 mg, 2.36 mmol), 5-bromo-2-fluoropyridine (2.5 g, 14 mmol) and $K_2CO_3$ (1.6 g, 11.8 mmol) were dissolved in DMSO (10 mL). The mixed solution reacted at 140° C. for 24 h, and then cooled to room temperature. The reaction solution was diluted with water, extracted, and the organic phase was dried, filtered, concentrated and subjected to column chromatography to obtain 300 mg of (S)-5-bromo-N-(1-(6-(4-chloro-1H-pyrazol-1-yl) pyridin-3-yl)ethyl)-N-methylpyridin-2-amine with a yield of 32%. MS m/z (ESI): 392 [M+H]$^+$.

Step 8: (S)—N-(1-(6-(4-chloro-1H-pyrazol-1-yl) pyridin-3-yl)ethyl)-N-methyl-5-(4,4,5,5-tetramethyl-1,3,2-dioxaborolane-2-yl)pyridin-2-amine (S)-5-bromo-N-(1-(6-(4-chloro-1H-pyrazol-1-yl)pyridin-3-yl)ethyl)-N-methylpyridin-2-amine (200 mg, 0.51 mmol), pinacol biborate (390 mg, 1.53 mmol), Pd(dppf)$ClCH_2Cl_2$ (41 mg, 0.051 mmol) and KOAc (150 mg, 1.53 mmol) were dissolved in dioxane (10 m L), and the mixed solution reacted at 0° C. for 12 h. The resulting reaction solution was concentrated in vacuum under reduced pressure to remove the solvent, diluted with $NaHCO_3$, extracted, dried, filtered, concentrated, and subjected to column chromatography to obtain 210 mg of (S)—N-(1-(6-(4-chloro-1H-pyrazol-1-yl) pyridin-3-yl)ethyl)-N-methyl-5-(4,4,5,5-tetramethyl-1,3,2-dioxaborolane-2-yl)pyridin-2-amine with a yield of 95%. MS m/z (ESI): 358 [M+H]$^+$.

Step 9: (S) 4-(6-((1-(6-(4-chloro-1H-pyrazol-1-yl) pyridin-3-yl)ethyl)(methyl)amino)pyridin-3-yl)-6-(2-hydroxy-2-methylpropoxy)pyrazo[1,5-a]pyridine-3-carbonitrile At room temperature and under the protection of $N_2$, 4-bromo-6-(2-hydroxy-2-m ethylpropoxy)pyrazolo[1,5-a] pyridine-3-carbonitrile (170 mg, 0.55 mmol), (S)—N-(1-(6-(4-chloro-1H-pyrazol-1-yl)pyridin-3-yl)ethyl)-N-methyl-5-(4,4,5,5-tetramethyl-1,3,2-dioxaborolane-2-yl)pyridin-2-amine (268 mg, 0.61 mmol), $Pd(PPh_3)_4$ (63 mg, 0.055 mmol) and $Na_2CO_3$ (175 mg, 1.65 mmol) were dissolved in 1,4-dioxane:$H_2O$=5:1 (12 mL), and the mixed reaction solution was stirred at 85° C. for 12 h to react. The reaction solution was cooled to room temperature, and water was added to quench the reaction, extraction was carried out, and the organic phase was washed with water, dried, and subjected to column chromatography to obtain 40 mg of (S) 4-(6-((1-(6-(4-chloro-1H-pyrazol-1-yl)pyridin-3-yl)ethyl) (methyl)amino)pyridin-3-yl)-6-(2-hydroxy-2-methyl-propoxy)pyrazo[1,5-a]pyridine-3-carbonitrile (compound 45) with a yield of 20%. MS m/z (ESI): 543 [M+H]$^+$. $^1$H NMR (400 MHz, DMSO) δ 8.76 (s, 1H), 8.65 (s, 1H), 8.57 (s, 1H), 8.38 (d, 1H), 7.60-7.94 (m, 3H), 7.59-7.62 (m, 2H), 7.31 (s, 1H), 6.81 (d, 1H), 6.28 (d, 1H), 4.70 (s, 1H), 3.87 (s, 2H), 2.83 (s, 3H), 1.61 (s, 3H), 1.22 (s, 6H).

Example 46: Preparation of (S)-4-(6-((1-(6-(4-fluoro-1H-pyrazolyl)pyridin-3-yl)ethyl)(methyl) amino)pyridin-3-yl)-6-((1-hydroxycyclopropyl) methoxy)pyrazolo[1,5-a]pyridine-3-carbonitrile

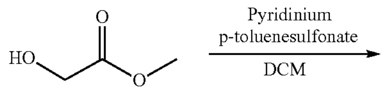

-continued

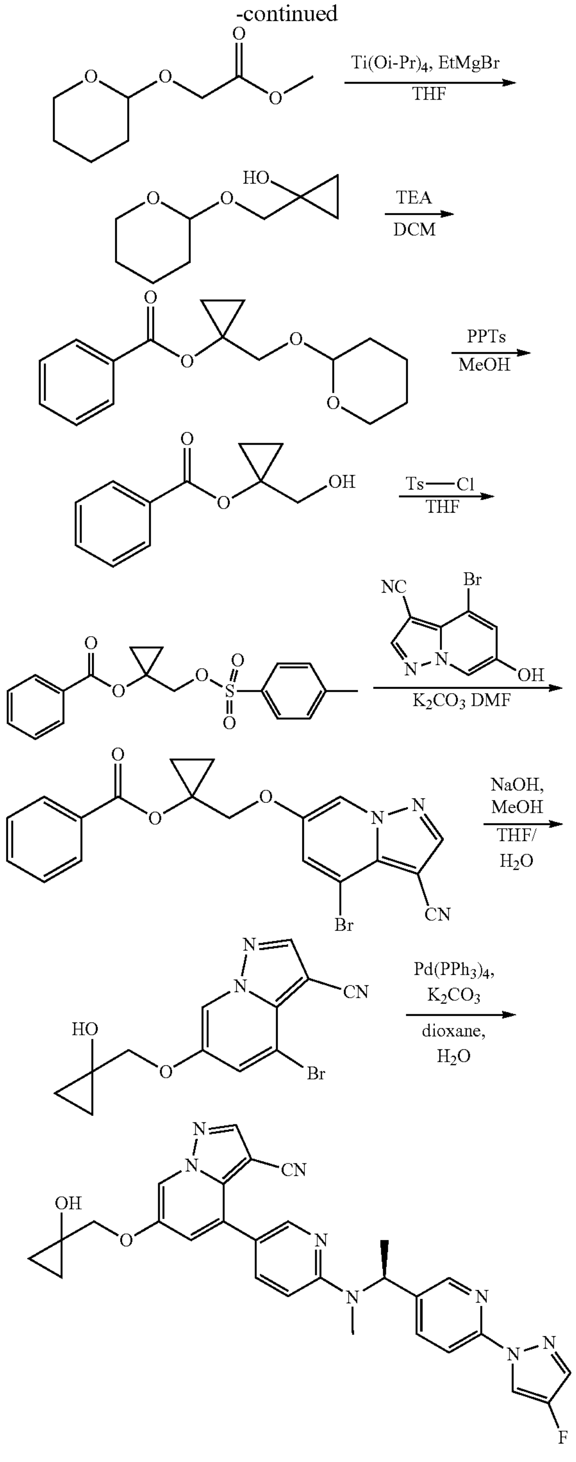

Step 1: Synthesis of methyl 2-((tetrahydro-2H-pyran-2-yl)oxy)acetate 3,4-dihydro-2H-pyran (6.0 g, 72 mmol), ethyl 2-hydroxy-acetate (5.0 g, 48 mmol) and PPTs (1.2 g, 4.8 mmol) were dissolved in DCM (30 mL). The reaction solution was stirred at room temperature overnight. After the reaction was completed, extraction was carried out, and the organic phase was dried, filtered, concentrated and subjected to column chromatography to obtain 6.0 g of 2-(tetrahydro-2H-pyran-2-yl)oxy)ethyl acetate with a yield of 66%.

Step 2: Synthesis of 1-((tetrahydro-2H-pyran-2-yl)oxy)methyl)cyclopropan-1-ol

Methyl 2-(tetrahydro-2H-pyran-2-yloxy)acetate (1.0 g, 5.32 mmol) and $Ti(Oi\text{-}Pr)_4$ (301 mg, 1.06 mmol) were dissolved in anhydrous ether (30 mL) at room temperature, and then ethylmagnesium bromide (6.6 mL, 2M) was added dropwise at 0° C. The mixed solution was stirred at 0° C. for 1 h to react, and 20 mL of water was added to quench the reaction, extraction with EA (30 mL*3) was then carried out, and the organic phases were combined, dried with $Na_2SO_4$, filtered, concentrated and subjected to column chromatography to obtain 870 mg of 1-((tetrahydro-2H-pyran-2-yl)oxy)methyl)cyclopropan-1-ol with a yield of 95%.

Step 3: Synthesis of 1-((tetrahydro-2H-pyran-2-yl)oxy)methyl)cyclopropylbenzoate 1-((tetrahydro-2H-pyran-2-yl)oxy)methyl)cyclopropan-1-ol (1.23 g, 2.9 mmol) and triethylamine (880 mg, 8.72 mmol) were dissolved in anhydrous DCM (10 mL), and then benzoyl chloride (490 mg, 3.48 mmol) was added dropwise at 0° C. The mixed solution was stirred at room temperature overnight, and 20 mL of water was added to quench the reaction, extraction with DCM (30 mL*3) was then carried out, and the organic phases were combined, dried with $Na_2SO_4$, filtered, concentrated and subjected to column chromatography to obtain 1.3 g of 1-((tetrahydro-2H-pyran-2-yl)oxy)methyl)cyclopropylbenzoate with a yield of 65%.

Step 4: Synthesis of 1-(hydroxymethyl)cyclopropylbenzoate 1-((tetrahydro-2H-pyran-2-yl)oxy)methyl)cyclopropylbenzoate (600 mg, 2.17 mmol) and PPTs (817 mg, 3.2 mmol) were dissolved in 10 mL of methanol. The reaction solution was stirred at room temperature for 2 h. Extraction was carried out, and the organic phase was dried, filtered, concentrated and subjected to column chromatography to obtain 230 mg of 1-(hydroxymethyl)cyclopropylbenzoate with a yield of 55%. MS m/z (ESI): 193 $[M+H]^+$.

Step 5: Synthesis of 1-((p-tolyloxy)methyl)cyclopropylbenzoate 1-(hydroxymethyl)cyclopropylbenzoate (230 mg, 1.2 mmol) and triethylamine (363 mg, 3.6 mmol) were dissolved in anhydrous THF (10 mL), and then p-toluenesulfonyl chloride (253 mg, 1.33 mmol) was added dropwise at 0° C. The mixed solution was stirred at room temperature overnight, and 10 mL of water was added to quench the reaction, extraction with EA (20 mL*3) was then carried out, and the organic phases were combined, dried with $Na_2SO_4$, filtered, concentrated and subjected to column chromatography to obtain 110 mg of 1-((p-tolyloxy)methyl)cyclopropylbenzoate with a yield of 27%. MS m/z (ESI): 369 $[M+Na]^+$.

Step 6: Synthesis of 1-((4-bromo-3-cyanopyrazolo[1,5-a]pyridin-6-yl)oxy)methyl)cyclopropylbenzoate 4-bromo-6-hydroxypyrazolo[1,5-a]pyridine-3-carbonitrile (60 mg, 0.21 mmol), 1-((p-tolyloxy)methyl)cyclopropylbenzoate (110 mg, 0.31 mmol) and potassium carbonate (86 mg, 0.63 mmol) were dissolved in 2 mL of anhydrous DMF. The mixed solution was stirred at 80° C. for 3 h to react. The reaction solution was cooled to room temperature and 10 mL of water was added to quench the reaction, extraction with EA (20 mL*3) was then carried out, and the organic phases were combined, dried with $Na_2SO_4$, filtered, concentrated and subjected to column chromatography to obtain 56 mg of 1-((4-bromo-3-cyanopyrazolo[1,5-a]pyridin-6-yl)oxy)methyl)cyclopropylbenzoate with a yield of 70%. MS m/z (ESI): 412 $[M+H]^+$.

Step 7: Synthesis of 4-bromo-6-((1-hydroxycyclopropyl)methoxy)pyrazolo[1,5-a]pyridine-3-carbonitrile 1-((4-bromo-3-cyanopyrazolo[1,5-a]pyridin-6-yl)oxy)methyl)cyclopropylbenzoate (120 mg, 0.29 mmol) was dissolved in 7 mL of a mixed solution of methanol:$H_2O$=2:1, and then sodium hydroxide (23 mg, 0.58 mmol) was added. Reaction was carried out at room temperature for 2 h, and 10 mL of water was added to quench the reaction, extraction with DCM (20 mL×3) was carried out, and the organic layers were combined, dried with $Na_2SO_4$, filtered, concentrated and subjected to column chromatography to obtain 35 mg of 4-bromo-6-((1-hydroxycyclopropyl)methoxy)pyrazolo[1,5-a]pyridine-3-carbonitrile, with a yield of 38%. MS m/z (ESI): 308 $[M+H]^+$.

Step 8: (S)-4-(6-((1-(6-(4-fluoro-1H-pyrazolyl)pyridin-3-yl)ethyl)(methyl)amino) pyridin-3-yl)-6-((1-hydroxycyclopropyl)methoxy)pyrazolo[1,5-a]pyridine-3-carbonitrile At room temperature, and under the protection of $N_2$, 4-bromo-6-((1-hydroxycyclopropyl)methoxy)pyrazolo[1,5-a]pyridine-3-carbonitrile (35 mg, 0.114 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (63 mg, 0.148 mmol) and $Pd(PPh_3)_4$ (15 mg, 0.0114 mmol) were dissolved in a mixed solution of 1,4-dioxane:$H_2O$=5:1 (6 mL), and then potassium carbonate (50 mg, 0.342 mmol) was added. The mixed solution was stirred at 90° C. overnight, and then it was cooled to room temperature, and water was added to quench the reaction. The organic phase was separated, washed with water, dried, and subjected to column chromatography (DCM:EA=10:1) to obtain 8 mg of (S)-4-(6-((1-(6-(4-fluoro-1H-pyrazolyl)pyridin-3-yl)ethyl)(methyl)amino)pyridin-3-yl)-6-((1-hydroxycyclopropyl)methoxy)pyrazolo[1,5-a]pyridine-3-carbonitrile (compound 46). MS m/z (ESI): 525 $[M+H]^+$. $^1H$ NMR (400 MHz, DMSO) δ 8.75 (s, 1H), 8.64 (s, 1H), 8.56 (s, 1H), 8.37 (d, 1H), 7.60-7.94 (m, 3H), 7.59-7.62 (m, 2H), 7.31 (s, 1H), 6.81 (d, 1H), 6.28 (d, 1H), 4.70 (s, 1H), 3.87 (s, 2H), 2.83 (s, 3H), 1.60 (s, 3H), 1.22 (m, 4H).

Example 47: Preparation of (S)-4-(6-((1-(6-(4-fluoro-1H-pyrazol-1-yl)pyridin-3-yl)ethyl)(methyl)amino)pyridine-3-yl)-6-(piperidin-1-yl)pyrazolo[1,5-a]pyridine-3-carbonitrile

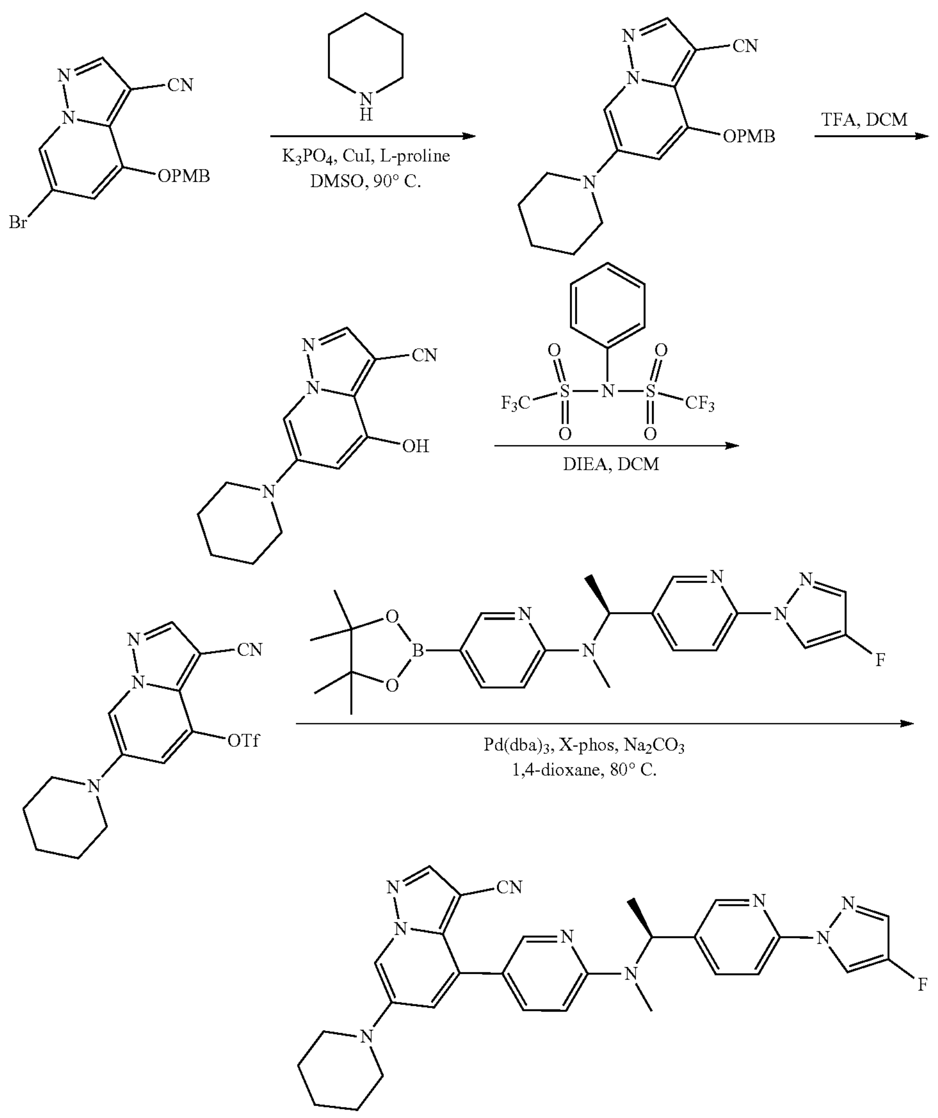

Step 1: Synthesis of 4-((4-methoxybenzyl)oxy)-6-(piperidin-1-yl)pyrazolo[1,5-a]pyridine-3-carbonitrile 6-bromo-4-((4-methoxybenzyl)oxy)pyrazolo[1,5-a]pyridine-3-carbonitrile (1.0 g, 2.79 mmol) was dissolved in DCM (5 mL), and then piperidine (0.96 g, 11.17 mmol), potassium phosphate (1.93 g, 8.37 mmol) and CuI (0.96 g, 11.17 mmol) were added. The reaction solution was heated to 90° C. to react for 5 h. After all the raw materials were consumed, the reaction system was poured into ice water. The reaction solution was extracted with EA, and the organic phases were combined, dried, spin-dried and subjected to column chromatography to obtain 0.15 g of 4-((4-methoxybenzyl)oxy)-6-(piperidin-1-yl)pyrazolo[1,5-a]pyridine-3-carbonitrile. MS m/z (ESI): 363.4 $[M+H]^+$.

Step 2: Synthesis of 4-hydroxy-6-(piperidin-1-yl)pyrazolo[1,5-a]pyridine-3-carbonitrile 4-((4-methoxybenzyl)oxy)-6-(piperidin-1-yl)pyrazolo[1,5-a]pyridine-3-carbonitrile (150 mg, 0.41 mmol) was dissolved in dichloromethane (5 mL), and then trifluoroacetic acid (5 mL) was added. The reaction solution was stirred at room temperature for 30 min. After the reaction was completed, the reaction system was spin-dried to obtain 0.1 g of a crude product of 4-hydroxy-6-(piperidin-1-yl)pyrazolo[1,5-a]pyridine-3-carbonitrile. MS m/z (ESI): 243.3 $[M+H]^+$.

Step 3: Synthesis of 3-cyano-6-(piperidin-1-yl)pyrazolo[1,5-a]pyridin-4-yl trifluoromethanesulfonate 4-hydroxy-6-(piperidin-1-yl)pyrazolo[1,5-a]pyridine-3-carbonitrile (100 mg, 0.41 mmol) was dissolved in dichloromethane (5 mL), and then 1,1,1-trifluoro-N-phenyl-N-

((trifluoromethyl)sulfonyl)methanesulfonamide (177 mg, 0.50 mmol) and DIEA (267 mg, 2.06 mmol) were added. The reaction solution was stirred at room temperature for 30 min. After the reaction was completed, the reaction system was washed with water, extracted with dichloromethane, and the organic phases were combined, dried, spin-dried and subjected to column chromatography to obtain 0.105 g of 3-cyano-6-(piperidin-1-yl)pyrazolo[1,5-a]pyridin-4-yl trifluoromethanesulfonate. MS m/z (ESI): 375.3 $[M+H]^+$.

Step 4: Synthesis of (S)-4-(6-((1-(6-(4-fluoro-1H-pyrazol-1-yl)pyridin-3-yl)ethyl)(methyl)amino)pyridine-3-yl)-6-(piperidin-1-yl)pyrazolo[1,5-a]pyridine-3-carbonitrile 3-cyano-6-(piperidin-1-yl)pyrazolo[1,5-a]pyridin-4-yl trifluoromethanesulfonate (0.15 g, 0.4 mmol) was dissolved in 4 mL of a mixed solution of dioxane:water=3:1, and then (S)—N-(1-(6-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (0.20 g, 0.48 mmol), $Pd_2(dba)_3$ (0.036 g, 0.04 mmol), X-Phos (0.038 g, 0.08 mmol) and sodium carbonate (0.212 g, 2.0 mmol) were added to the mixed solution. The reaction solution was heated to 80° C. to react overnight. After the reaction was completed, the reaction solution was washed with water, extracted with EA, and the organic phases were combined, dried, spin-dried and subjected to silica gel column chromatography to obtain 0.05 g of (S)-4-(6-((1-(6-(4-fluoro-1H-pyrazol-1-yl)pyridin-3-yl)ethyl)(methyl)amino)pyridine-3-yl)-6-(piperidin-1-yl)pyrazolo[1,5-a]pyridine-3-carbonitrile (compound 47). MS m/z (ESI): 522.6 $[M+H]^+$. $^1H$ NMR (500 MHz, DMSO) δ 8.65 (d, J=4.5 Hz, 1H), 8.49 (s, 1H), 8.39 (s, 1H), 8.36 (d, J=2.3 Hz, 1H), 8.25 (s, 1H), 7.91 (s, 1H), 7.90 (s, 1H), 7.86 (d, J=8.5 Hz, 1H), 7.79 (dd, J=8.8, 2.5 Hz, 1H), 7.46 (d, J=1.8 Hz, 1H), 6.80 (d, J=8.8 Hz, 1H), 3.15 (m, 4H), 1.97 (s, 1H), 1.62 (m, 3H), 1.60 (d, J=7.0 Hz, 3H), 1.53 (d, J=4.3 Hz, 2H), 1.21 (m, 4H).

Example 48: Preparation of ((S)-6-(4,4-difluoropiperidin-1-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile

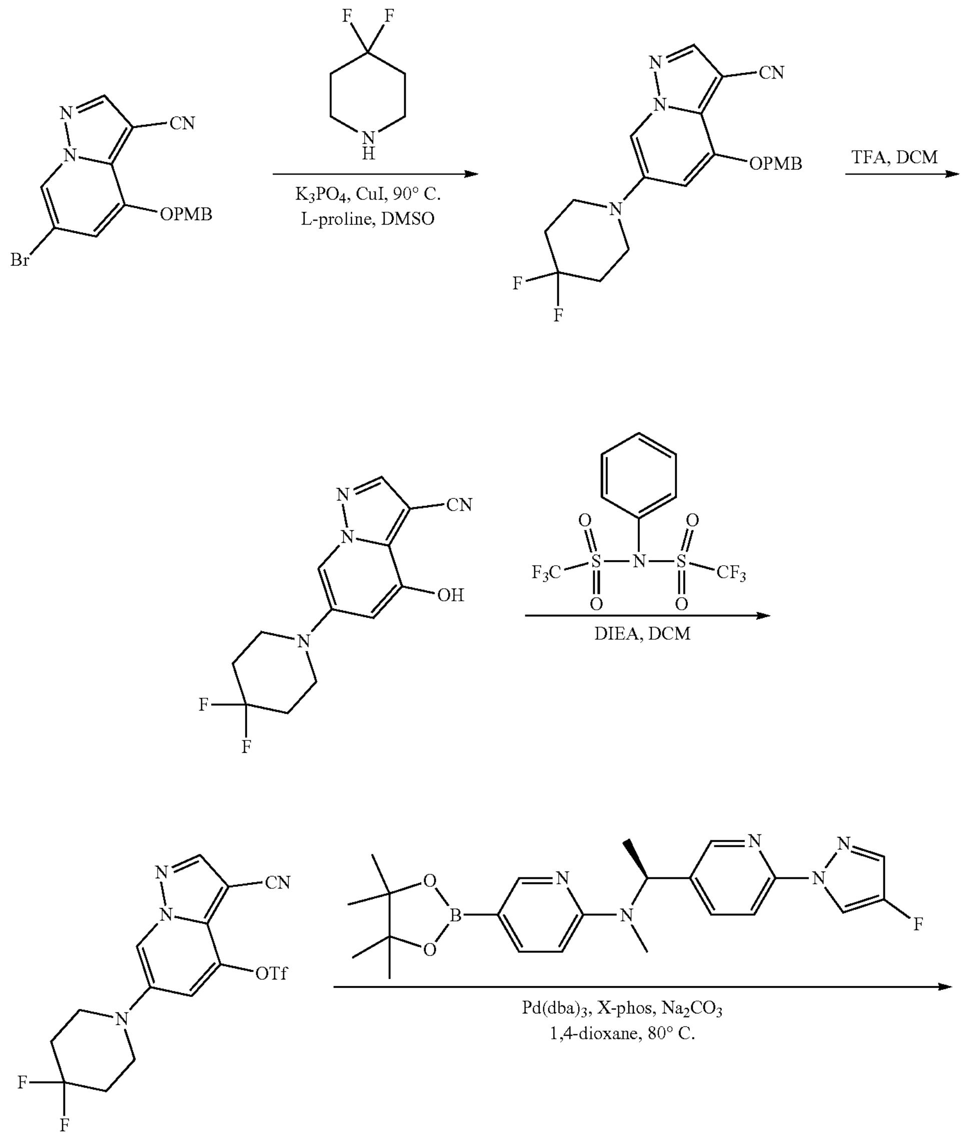

-continued

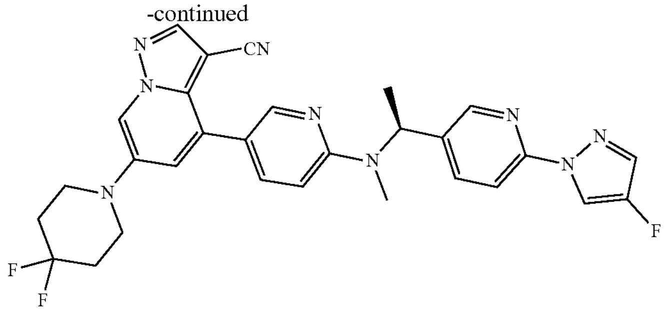

Step 1: Synthesis of 6-(4,4-difluoropiperidin-1-yl)-4-((4-methoxybenzyl)oxy)pyrazolo[1,5-a]pyridine-3-carbonitrile 6-bromo-4-((4-methoxybenzyl)oxy)pyrazolo[1,5-a]pyridine-3-carbonitrile (1.0 g, 2.79 mmol) was dissolved in DMSO (10 mL), and then 4,4-difluoropiperidine (1.35 g, 11.2 mmol), potassium phosphate (1.93 g, 8.37 mmol), CuI (0.53 g, 2.79 mmol) and L-proline (0.32 g, 2.79 mmol) were added. The reaction solution was heated to 90° C. to react for 5 h. After all the raw materials were consumed, the reaction system was lowered to an ice water. Extraction with EA was carried out, and the organic phases were combined, dried, spin-dried and subjected to column chromatography to obtain 0.14 g of 6-(4,4-difluoropiperidin-1-yl)-4-((4-methoxybenzyl)oxy)pyrazolo[1,5-a]pyridine-3-carbonitrile. MS m/z (ESI): 399.4 $[M+H]^+$.

Step 2: Synthesis of 6-(4,4-difluoropiperidin-1-yl)-4-hydroxypyrazolo[1,5-a]pyridine-3-carbonitrile 6-(4,4-difluoropiperidin-1-yl)-4-((4-methoxybenzyl)oxy)pyrazolo[1,5-a]pyridine-3-carbonitrile (200 mg, 0.50 mmol) was dissolved in dichloromethane (5 mL), and then trifluoroacetic acid (5 mL) was added. The reaction solution was stirred at room temperature for 30 min. After the reaction was completed, the reaction system was spin-dried to obtain 0.14 g of a crude product of 6-(4,4-difluoropiperidin-1-yl)-4-hydroxypyrazolo[1,5-a]pyridine-3-carbonitrile. MS m/z (ESI): 279.3 $[M+H]^+$.

Step 3: Synthesis of 3-cyano-6-(4,4-difluoropiperidin-1-yl)pyrazolo[1,5-a]pyridin-4-yl trifluoromethanesulfonate 6-(4,4-difluoropiperidin-1-yl)-4-hydroxypyrazolo[1,5-a]pyridine-3-carbonitrile (139 mg, 0.50 mmol) was dissolved in dichloromethane (5 mL), and then 1,1,1-trifluoro-N-phenyl-N-((trifluoromethyl)sulfonyl)methanesulfonamide (214 mg, 0.60 mmol) and DIEA (323 mg, 2.50 mmol) were added. The reaction solution was stirred at room temperature for 30 min. After the reaction was completed, the reaction system was washed with water, extracted with dichloromethane, and the organic phases were combined, dried, spin-dried and subjected to column chromatography to obtain 0.165 g of 3-cyano-6-(4,4-difluoropiperidin-1-yl)pyrazolo[1,5-a]pyridin-4-yl trifluoromethanesulfonate. MS m/z (ESI): 411.3 $[M+H]^+$.

Step 4: Synthesis of ((S)-6-(4,4-difluoropiperidin-1-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile 3-cyano-6-(4,4-difluoropiperidin-1-yl)pyrazolo[1,5-a]pyridin-4-yl trifluoromethanesulfonate (165 mg, 0.4 mmol) was dissolved in 4 mL of a mixed solution of 1,4-dioxane/water=3:1, and then (S)—N-(1-(6-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (204 mg, 0.48 mmol), $Pd_2(dba)_3$ (23 mg, 0.04 mmol), X-Phos (38 mg, 0.08 mmol) and sodium carbonate (213 mg, 2.0 mmol) were added. The reaction solution was heated to 80° C. to react overnight. After the reaction was completed, the reaction solution was washed with water, extracted with EA, and the organic phases were combined, dried, spin-dried and subjected to silica gel column chromatography to obtain 30 mg of ((S)-6-(4,4-difluoropiperidin-1-yl)-4-(6-((1-(6-(4-fluoro-1H-pyrazol-1-yl)pyridine-3-yl)ethyl)(methyl)amino)pyridin-3-yl)pyrazolo[1,5-a]pyridine-3-carbonitrile (compound 48). MS m/z (ESI): 558.6 $[M+H]^+$. $^1H$ NMR (500 MHz, DMSO) δ 8.65 (d, J=4.6 Hz, 1H), 8.52 (s, 1H), 8.42 (d, J=1.9 Hz, 1H), 8.39 (s, 1H), 8.37 (d, J=2.3 Hz, 1H), 7.91 (d, J=3.6 Hz, 1H), 7.90 (d, J=2.2 Hz, 1H), 7.86 (d, J=8.4 Hz, 1H), 7.80 (dd, J=8.8, 2.5 Hz 1H), 7.54 (d, J=2.0 Hz, 1H), 6.81 (d, J=8.9 Hz, 1H), 2.87 (s, 3H), 2.07 (m, 4H), 1.60 (d, J=7.0 Hz, 3H), 1.21 (m, 4H).

Example 49: Preparation of (S)-6-((cyclopropylmethyl)amino)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile

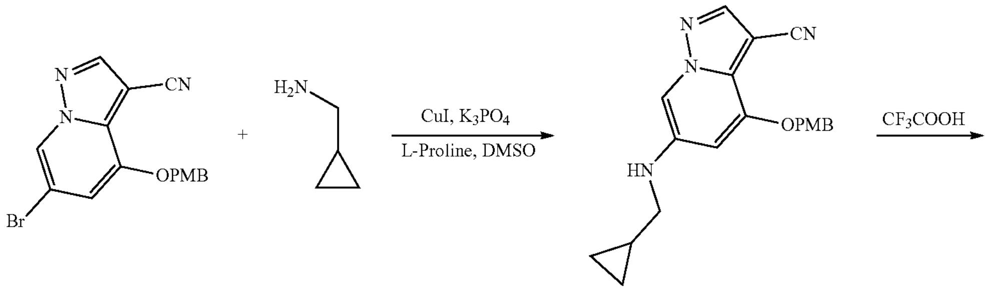

-continued

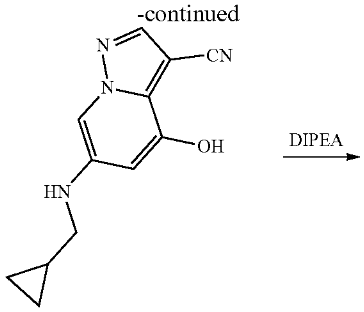

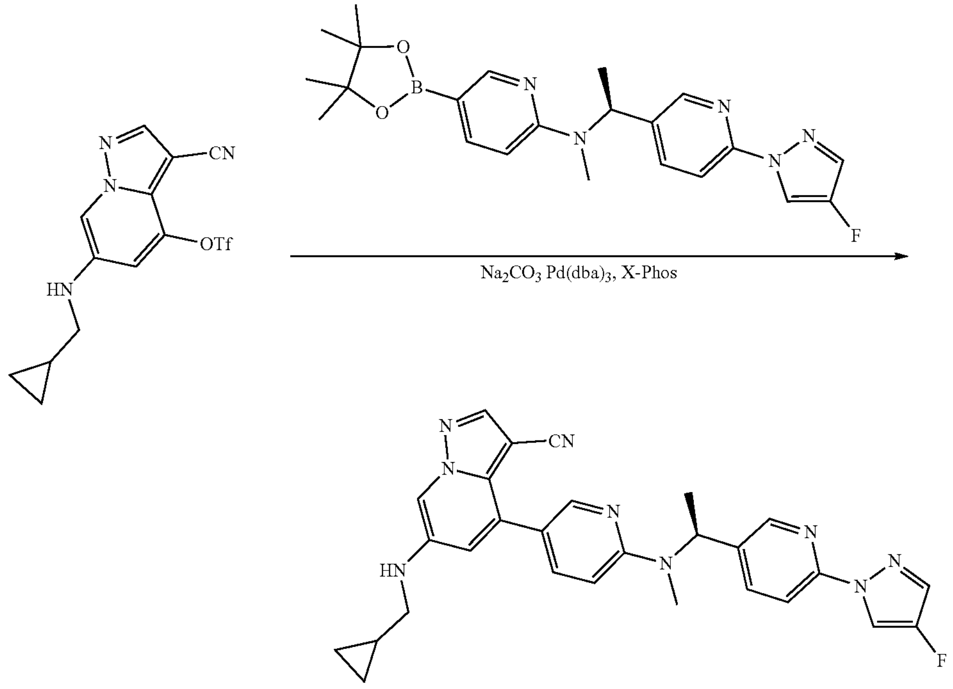

Step 1: Synthesis of 6-((cyclopropylmethyl)amino)-4-((4-methoxybenzyl)oxy)pyrazolo[1,5-a]pyridine-3-carbonitrile Under the protection of $N_2$, 6-bromo-4-((4-methoxybenzyl)oxy)pyrazolo[1,5-a]pyridine-3-carbonitrile (1.07 g, 3 mmol), cyclopropylmethylamine (640 mg, 9 mmol), CuI (57 mg, 0.3 mmol), potassium phosphate (1.27 g, 6 mmol) and L-proline (69 mg, 0.6 mmol) were scattered in 10 mL of dimethyl sulfoxide. The reaction solution was stirred at 120° C. for 4 h to react. After the reaction was completed, water (50 mL) was added, and extraction with EA (50 mL*3) was carried out. The organic phases were combined, washed with a saturated NaCl solution, dried with anhydrous sodium sulfate, concentrated and subjected to column chromatography to obtain 420 mg of 6-((cyclopropylmethyl)amino)-4-((4-methoxybenzyl)oxy)pyrazolo[1,5-a]pyridine-3-carbonitrile. MS m/z (ESI): 349.3 $[M+H]^+$.

Step 2: Synthesis of 6-((cyclopropylmethyl)amino)-4-hydroxypyrazolo[1,5-a]pyridine-3-carbonitrile 6-((cyclopropylmethyl)amino)-4-((4-methoxybenzyl)oxy)pyrazolo[1,5-a]pyridine-3-carbonitrile (420 mg, 1.2 mmol) was dissolved in dichloromethane (10 mL), and then trifluoroacetic acid (3 mL) was added in an ice water bath. The reaction solution reacted at room temperature for 30 min. After the reaction was completed, the reaction solution was spin-dried and proceed directly to the next step.

Step 3: Synthesis of 3-cyano-6-((cyclopropylmethyl)amino)pyrazolo[1,5-a]pyridin-4-yl trifluoromethanesulfonate 6-((cyclopropylmethyl)amino)-4-((4-methoxybenzyl)oxy)pyrazolo[1,5-a]pyridine-3-carbonitrile (420 mg, 1.2 mmol) was dissolved in dichloromethane (10 mL), and then DIPEA (311 mg, 2.4 mmol) and N-phenylbis(trifluoromethanesulfonyl)imide (515 mg, 1.44 mmol) were added in an ice water bath. The reaction solution reacted at room temperature for 1 h. After the reaction was completed, 30 mL of water was added to the mixed reaction solution, and the organic phase was extracted and separated. The aqueous layer was further extracted with DCM (30 mL×2). The organic phases were combined, washed with a saturated NaCl solution, dried with anhydrous sodium sulfate, concentrated and subjected to column chromatography to obtain 310 mg of 3-cyano-6-((cyclopropylmethyl)amino)pyrazolo[1,5-a]pyridin-4-yl trifluoromethanesulfonate. MS m/z (ESI): 361.2 $[M+H]^+$.

Step 4: Synthesis of (S)-6-((cyclopropylmethyl)amino)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile Under the protection of $N_2$, tris(dibenzylideneacetone)dipalladium (38.5 mg, 0.1 mol), 2-dicyclohexylphosphorus-2,4,6-triisopropylbiphenyl (40.1 mg, 0.2 mol), 3-cyano-6-((cyclopropylmethyl)amino)pyrazolo[1,5-a]pyridin-4-yl trifluoromethanesulfonate (150 mg, 1.0 mmol), (S)—N-(1-(6-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (211.7 mg, 1.2 mmol) and sodium carbonate (38.5 mg, 5 mmol) were scattered in a mixed solution of dioxane:water=6:1. The reaction solution reacted at 90° C. overnight. After the reaction was completed, water (50 mL) was added, and extraction with EA (50 mL*3) was carried out. The organic phases were combined, washed with a saturated NaCl solution, dried with anhydrous sodium sulfate, concentrated and subjected to column chromatography to obtain 35 mg of (S)-6-((cyclopropylmethyl)amino)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (compound 49). MS m/z (ESI): 508.5 $[M+H]^+$. $^1H$ NMR (400 MHz, DMSO-$d_6$) δ 8.66 (d, J=4.5 Hz, 1H), 8.40 (d, J=2.2 Hz, 1H), 8.37 (s, 1H), 8.31 (d, J=2.5 Hz, 1H), 7.95-7.89 (m, 3H), 7.86 (d, J=8.5 Hz, 1H), 7.74 (dd, J=8.8, 2.6 Hz, 1H), 7.12 (d, J=2.0 Hz, 1H), 6.81 (d, J=8.9 Hz, 1H), 6.28 (q, J=7.0 Hz, 1H), 6.02 (t, J=5.4 Hz, 1H), 2.92 (t, J=6.0 Hz, 2H), 2.81 (s, 3H), 1.60 (d, J=7.0 Hz, 3H), 1.06 (s, 1H), 0.55-0.46 (m, 2H), 0.29-0.20 (m, 2H).

Example 50: Preparation of (S)-4-(6-((1-(6-(4-fluoro-1H-pyrazol-1-yl)pyridin-3-yl)ethyl)(methyl)amino)pyridine-3-yl)-6-(isopropylamino)pyrazolo[1,5-a]pyridine-3-carbonitrile

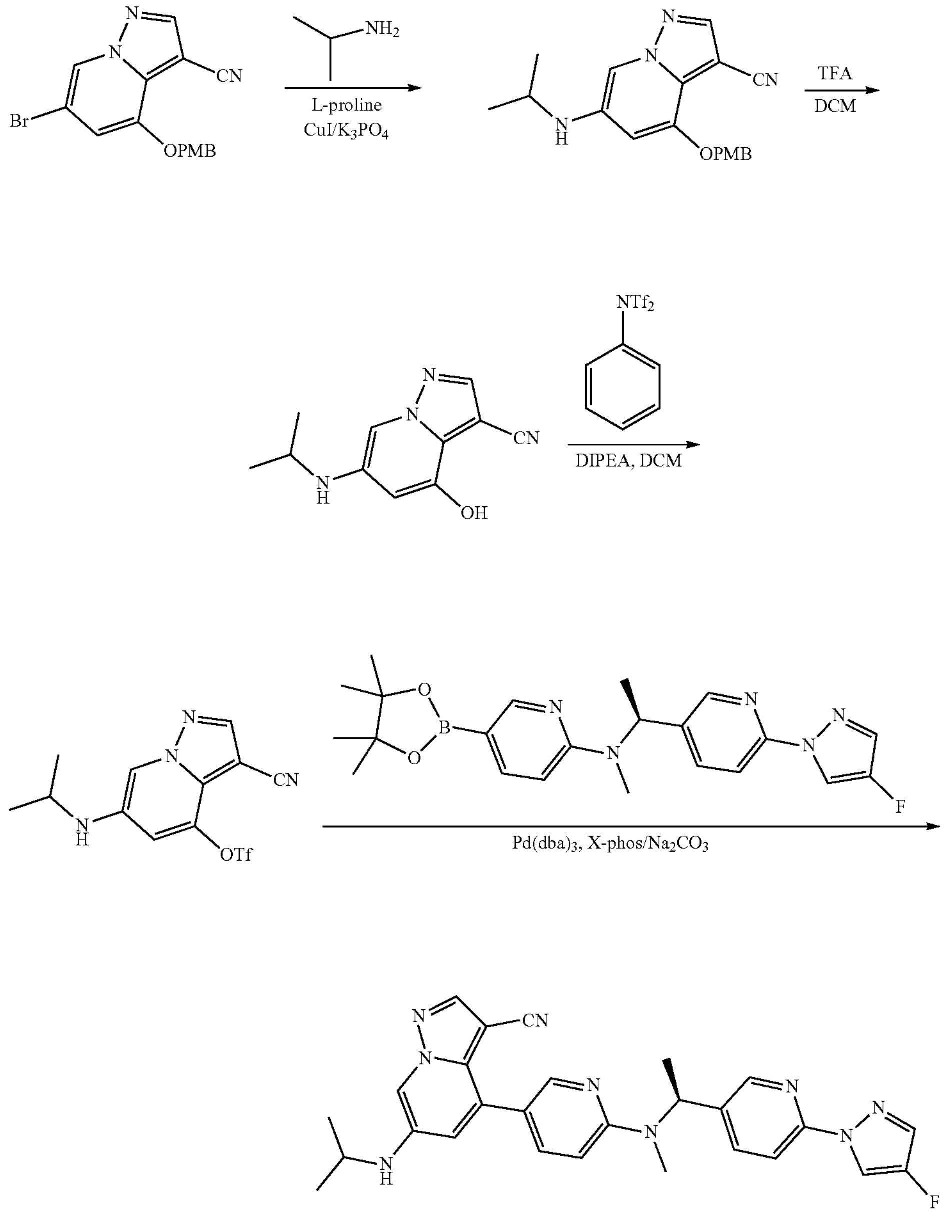

Step 1: Synthesis of 6-(isopropylamino)-4-((4-methoxybenzyl)oxy)pyrazolo[1,5-a]pyridine-3-carbonitrile 6-bromo-4-(4-methoxybenzyloxy)pyrazolo[1,5-a]pyridine-3-carbonitrile (400 mg, 1.12 mmol) was dissolved in DMSO (5 mL), isopropylamine (460 μL, 5.6 mmol), CuI (23 mg, 0.112 mmol), L-proline (26 mg, 0.224 mmol) and $K_3PO_4$ (480 mg, 2.24 mmol) were added in turn. After the reaction flask was replaced with $N_2$ three times, the reaction solution was heated to 115° C. under the protection of $N_2$ and stirred for 6 h. After the reaction was found to be completed from the monitoring of TLC, the reaction solution was poured into 20 mL of water, and extraction with ethyl acetate (20 mL*3) was carried out. The organic phases were combined, washed with a saturated NaCl solution (10 mL*2), dried with anhydrous sodium sulfate, filtrated, and rotary evaporated to obtain a crude product. The crude product was purified by a rapid column machine to obtain 4-(4-methoxybenzyloxy)-6-(isopropylamino)pyrazolo[1,5-a]pyridine-3-carbonitrile (220 mg). MS: m/z=337.1 $[M+1]^+$.

Step 2: Synthesis of 4-hydroxy-6-(isopropylamino)pyrazolo[1,5-a]pyridine-3-carbonitrile At room temperature, compound 4-(4-methoxybenzyloxy)-6-(isopropylamino)pyrazolo[1,5-a]pyridine-3-carbonitrile (220 mg, 0.651 mmol) was dissolved in dichloromethane (8 mL), and then TFA (2 mL) was added dropwise. The reaction solution was stirred at room temperature for 0.5 h. After the reaction was found to be completed from the monitoring of TLC (petroleum ether/ethyl acetate=1/1) and LCMS, the reaction solution was concentrated, pull-dried with oil pump to obtain a crude product of 4-hydroxy-6-(isopropylamino)pyrazolo[1,5-a]pyridine-3-carbonitrile. The crude product was directly used in the next step. MS: m/z=217.0 $[M+1]^+$.

Step 3: Synthesis of 3-cyano-6-(isopropylamino)pyrazolo[1,5-a]pyridin-4-yl trifluoromethanesulfonate The crude product of 4-hydroxy-6-(isopropylamino)pyrazolo[1,5-a]pyridine-3-carbonitrile, which was obtained from the previous step, was dissolved in DMF (3 mL). Then DIPEA (314 μL) and compound 1,1,1-trifluoro-N-phenyl-N-((trifluoromethyl)sulfonyl)methanesulfonamide (408 mg, 1.14 mmol) were added to the mixed solution. The reaction solution was stirred at room temperature for 1 h. After the reaction was found to be completed from the monitoring of TLC, the reaction solution was poured into 10 mL of water, and extraction with ethyl acetate (20 mL*2) was carried out. The organic phases were combined, washed with a saturated NaCl solution (10 mL*2), dried with anhydrous sodium sulfate, filtrated, and rotary evaporated to obtain a crude product. The crude product was purified by a rapid column machine to obtain 280 mg of 3-cyano-6-isopropylaminopyrazolo[1,5-a]pyridine-4-trifluoromethanesulfonate. LCMS: m/z=348.9 $[M+1]^+$.

Step 4: Synthesis of (S)-4-(6-((1-(6-(4-fluoro-1H-pyrazol-1-yl)pyridin-3-yl)ethyl)(methyl)amino)pyridine-3-yl)-6-(isopropylamino)pyrazolo[1,5-a]pyridine-3-carbonitrile 3-cyano-6-isopropylaminopyrazolo[1,5-a]pyridine-4-trifluoromethanesulfonate (280 mg, 0.603 mmol) was dissolved in a mixed solution of 1,4-dioxane (6 mL) and water (2 mL); then, compound (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (443 mg, 1.05 mmol), $Pd_2(dba)_3$ (160 mg, 0.17 mmol), X-Phos (333 mg, 0.70 mmol) and $Na_2CO_3$ (185 mg, 1.74 mmol) were added in turn at room temperature. After the reaction flask was replaced with $N_2$ three times, the reaction solution was heated to 85° C. under the protection of $N_2$ and stirred for 12 h. After the reaction was found to be completed from the monitoring of TLC, the reaction solution was poured into 10 mL of water, and extraction with ethyl acetate (20 mL*3) was carried out. The organic phases were combined, washed with a saturated NaCl solution (10 mL*2), dried with anhydrous sodium sulfate, filtrated, and rotary evaporated to obtain a crude product. The crude product was purified by a rapid column machine to obtain 50 mg of (S)—N-((1-(6-(4-fluoro-1H-pyrazol-1-yl)pyridin-3-yl)ethyl)(methyl)amine)-pyridin-3-yl)-6-isopropylamino-pyrazolo[1,5-a]pyridine-3-carbonitrile (compound 50). MS: m/z=496.2 $[M+1]^+$. $^1$HNMR (400 MHz, DMSO-$d_6$) δ: 8.81 (d, J=16.0 Hz, 1H), 8.51-8.32 (m, 3H), 7.93-7.81 (m, 4H), 7.77-7.74 (m, 1H), 6.83 (d, J=8.00 Hz, 1H), 6.51-6.36 (m, 1H), 3.50 (s, 1H), 3.2 (s, 1H), 2.82 (s, 3H), 1.86-1.58 (m, 3H), 0.97 (t, J=8.00 Hz, 6H).

Example 51: Preparation of (S)-4-(6-((1-(6-(4-fluoro-1H-pyrazol-1-yl)pyridin-3-yl)ethyl)(methyl)amino)pyridine-3-yl)-6-(ethylamino)pyrazolo[1,5-a]pyridine-3-carbonitrile

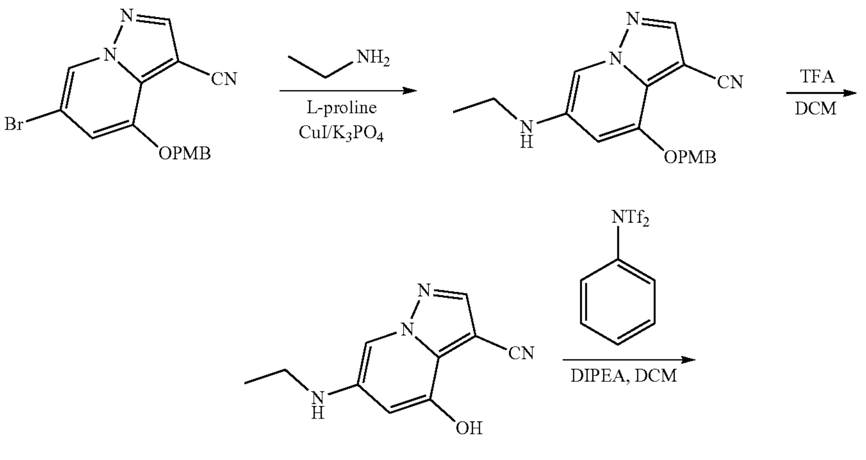

-continued

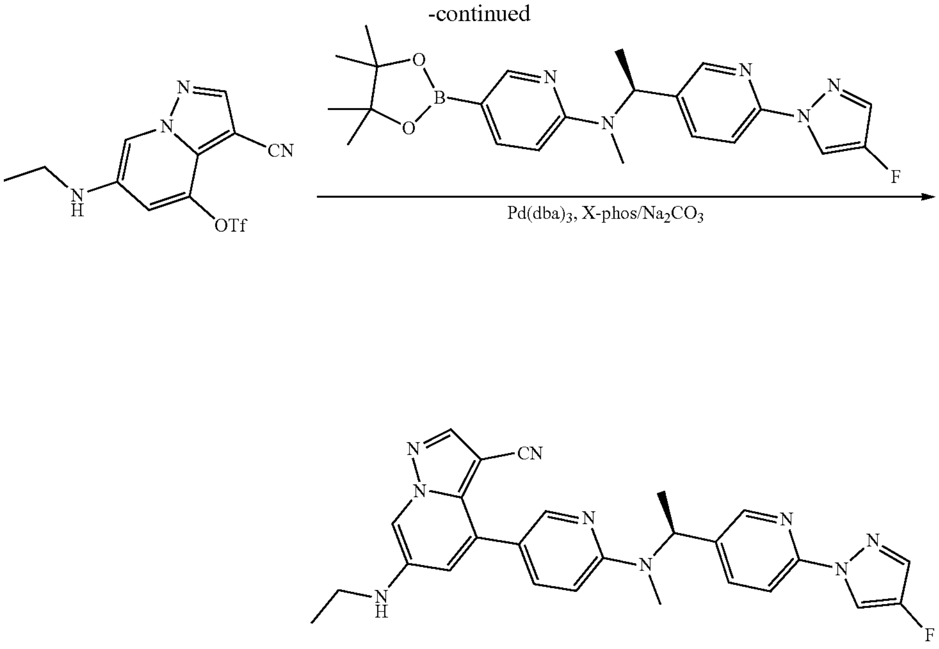

Step 1: Synthesis of 6-(ethylamino)-4-((4-methoxybenzyl)oxy)pyrazolo[1,5-a]pyridine-3-carbonitrile At room temperature, and under the protection of $N_2$, 6-bromo-4-((4-methoxybenzyl)oxy)pyrazolo[1,5-a]pyridine-3-carbonitrile (1.0 g, 2.8 mmol), CuI (53 mg, 0.28 mmol), L-proline (48 mg, 0.42 mmol) and potassium carbonate (3.8 g, 28 mmol) were dissolved in 15 mL of anhydrous DMSO, and ethylamine hydrochloride (2.28 g, 28 mmol) was added. Reaction was carried out at 100° C. overnight. After the reaction was completed, the reaction solution was cooled to room temperature and then diluted with EA (50 mL) and water (20 mL), stirred and filtered. Extraction was carried out, and the organic phase was dried, filtered, concentrated and subjected to column chromatography (PE:EA=3:1) to obtain 6-(ethylamino)-4-((4-methoxybenzyl)oxy)pyrazolo[1,5-a]pyridine-3-carbonitrile (470 mg). MS m/z (ESI): 323.1 $[M+H]^+$.

Step 2: 6-(ethylamino)-4-hydroxypyrazolo[1,5-a]pyridine-3-carbonitrile 6-(ethylamino)-4-((4-methoxybenzyl)oxy)pyrazolo[1,5-a]pyridine-3-carbonitrile (2.28 g, 7 mmol) was dissolved in 10 mL of DCM, and then 10 mL of trifluoroacetic acid was added at 0° C. The reaction was carried out for 0.5 h. After the reaction was completed, the reaction solution was concentrated and dried in vacuum at room temperature, and the product was directly used in the next step without further purification. MS m/z (ESI): 203.1 $[M+H]^+$.

Step 3: Synthesis of 3-cyano-6-(ethylamino)pyrazolo[1,5-a]pyridin-4-yl trifluoromethanesulfonate 6-(ethylamino)-4-hydroxypyrazolo[1,5-a]pyridine-3-carbonitrile (1.43 g, 7 mmol) and DIEA (2.7 g, 21 mmol) were dissolved in DMF (10 mL), and then N-phenylbis(trifluoromethanesulfonyl)imide (2.5 g, 7 mmol) was added at 0° C. The mixed solution was stirred at room temperature for 0.5 h. After the reaction was completed, water (10 mL) was added to quench the reaction, extraction with EA (20 mL*2) was carried out, and the organic phase was dried, filtered, concentrated and subjected to column chromatography (PE:EA=3:1) to obtain 3-cyano-6-(ethylamino)pyrazo[1,5-a]pyridin-4-yl trifluoromethanesulfonate (1.74 g). MS m/z (ESI): 335.1 $[M+H]^+$.

Step 4: Synthesis of (S)-6-(ethylamino)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile 3-cyano-6-(ethylamino)pyrazolo[1,5-a]pyridin-4-yl trifluoromethanesulfonate (300 mg, 0.89 mmol) was dissolved in a mixed solution of 1,4-dioxane (9 mL) and water (3 mL), and then (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (379 mg, 0.89 mmol), $Pd_2(dba)_3$ (91 mg, 0.1 mmol), X-Phos (127 mg, 0.26 mmol) and $Na_2CO_3$ (185 mg, 1.78 mmol) were added in turn. After the reaction flask was replaced with $N_2$ three times, the reaction solution was heated to 85° C. under the protection of $N_2$ and stirred for 12 h. After the reaction was found to be completed from the monitoring of TLC, the reaction solution was poured into water (10 mL), and extraction with ethyl acetate (20 mL*3) was carried out. The organic phases were combined, washed with a saturated NaCl solution (10 mL*2), dried with anhydrous sodium sulfate, filtrated, and rotary evaporated to obtain a crude product. The crude product was purified by a rapid column machine to obtain 80 mg of (S)-6-(ethylamino)-4-(6-((1-(6-(4-fluoro-1H-pyrazol-1-yl)pyridin-3-yl)ethyl)(methyl)amino)pyridin-3-yl)pyrazolo[1,5-a]pyridine-3-carbonitrile (compound 51). MS: m/z=482.2 $[M+1]^+$, $^1H$ NMR (400 MHz, DMSO) δ 8.64 (dd, J=4.6, 0.8 Hz, 1H), 8.40-8.34 (m, 2H), 8.32-8.26 (m, 1H), 7.88 (ddd, J=20.0, 11.9, 5.0 Hz, 4H), 7.72 (dd, J=8.8, 2.5 Hz, 1H), 7.02 (d, J=1.9 Hz, 1H), 6.79 (d, J=8.8 Hz, 1H), 6.25 (q, J=6.9 Hz, 1H), 5.88 (s, 1H), 3.03 (dd, J=6.8, 4.3 Hz, 2H), 2.79 (s, 3H), 1.58 (d, J=7.0 Hz, 3H), 1.08 (d, J=9.0 Hz, 3H).

Example 52: Preparation of (S)-4-(6-((1-(6-(4-fluoro-1H-pyrazol-1-yl)pyridin-3-yl)ethyl)(methyl)amino)pyridine-3-yl)-6-(methylamino)pyrazolo[1,5-a]pyridine-3-carbonitrile

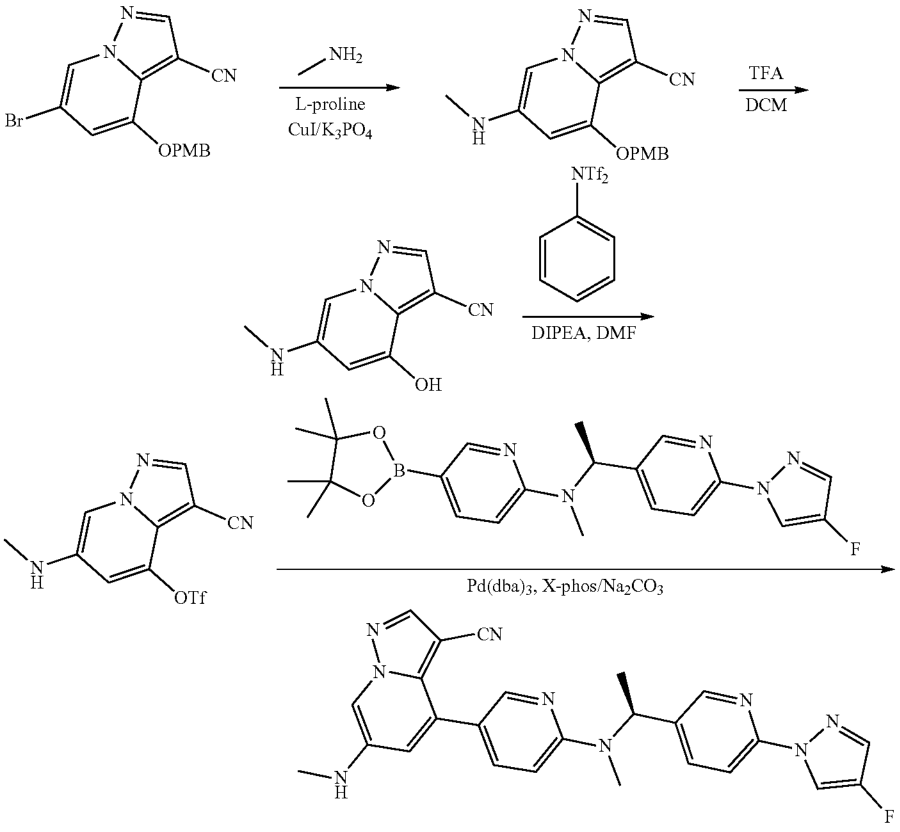

Step 1: Synthesis of 4-((4-methoxybenzyl)oxy)-6-(methylamino)pyrazolo[1,5-a]pyridine-3-carbonitrile At room temperature and under the protection of $N_2$, 6-bromo-4-((4-methoxybenzyl)oxy)pyrazolo[1,5-a]pyridine-3-carbonitrile (500 mg, 1.4 mmol), CuI (40 mg, 0.21 mmol), L-proline (32 mg, 0.28 mmol) and potassium carbonate (1.9 g, 14 mmol) were dissolved in anhydrous DMSO (15 mL), and then methylamine hydrochloride (940 mg, 14 mmol) was added. The resulting solution reacted at 100° C. for 10 h. After the reaction was completed, the reaction solution was cooled to room temperature and then extracted with EA (50 mL*2), diluted with water (50 mL), stirred, filtered, and separated; and the organic phase was extracted, dried, filtered, concentrated, and subjected to column chromatography (PE:EA=3:1) to obtain 4-((4-methoxybenzyl)oxy)-6-(methylamino)pyrazolo[1,5-a]pyridine-3-carbonitrile (150 mg). MS m/z (ESI): 309.1 $[M+H]^+$.

Step 2: Synthesis of 4-hydroxy-6-(methylamino)pyrazolo[1,5-a]pyridine-3-carbonitrile At room temperature, 4-((4-methoxybenzyl)oxy)-6-(methylamino)pyrazolo[1,5-a]pyridine-3-carbonitrile (150 mg, 0.48 mmol) was dissolved in DCM (3 mL), and then trifluoroacetic acid (1 mL) was added at 0° C., and the reaction was carried out for 0.5 h. After the reaction was completed, the reaction solution was concentrated and dried in vacuum at room temperature, and the product was directly used in the next step without further purification. MS m/z (ESI): 189.1 $[M+H]^+$.

Step 3: Synthesis of 3-cyano-6-(methylamino)pyrazolo[1,5-a]pyridin-4-yl trifluoromethanesulfonate 4-hydroxy-6-(methylamino)pyrazolo[1,5-a]pyridine-3-carbonitrile (150 mg, 0.8 mmol) and DIEA (307 mg, 2.4 mmol) were dissolved in 5 mL of DMF, and N-phenylbis(trifluoromethanesulfonyl)imide (286 mg, 0.8 mmol) was added at 0° C. The mixed solution was stirred at room temperature for 0.5 h to react until the reaction was completed. Extraction was carried out, and the organic phase was dried, filtered, concentrated and subjected to column chromatography (PE:EA=3:1) to obtain 3-cyano-6-(methylamino)pyrazolo[1,5-a]pyridin-4-yl trifluoromethanesulfonate (180 mg). MS m/z (ESI): 321.3 $[M+H]^+$.

Step 4: Synthesis of (S)-4-(6-((1-(6-(4-fluoro-1H-pyrazol-1-yl)pyridin-3-yl)ethyl)(methyl)amino)pyridine-3-yl)-6-(methylamino)pyrazolo[1,5-a]pyridine-3-carbonitrile At room temperature, 3-cyano-6-(methylamino)pyrazolo[1,5-a]pyridin-4-yl trifluoromethanesulfonate (300 mg, 0.93 mmol) was dissolved in a mixed solution of 1,4-dioxane (9 mL) and water (3 mL); then, compound (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (385 mg, 0.93 mmol), $Pd_2(dba)_3$ (91 mg, 0.1 mmol), X-Phos (127 mg, 0.26 mmol) and $Na_2CO_3$ (190 mg, 1.86 mmol) were added in turn at room temperature. After the reaction flask was replaced with $N_2$ three times, the reaction solution was heated to 85° C. under the protection of $N_2$ and stirred for 12 h. After the reaction was found to be completed from the monitoring of TLC, the reaction solution was poured into water (10 mL), and then extraction with ethyl acetate (20 mL*3) was carried out. The organic phases were combined, washed with a saturated NaCl solution (10 mL*2), dried with anhydrous sodium sulfate, filtrated, and rotary evaporated to obtain a crude product. The crude product was purified by a rapid column machine to obtain 60 mg of (S)-4-(6-((1-(6-(4-fluoro-1H-pyrazol-1-yl)pyridin-3-yl)ethyl)(methyl)amino)pyridine-3-yl)-6-(methylamino)pyrazolo[1,5-a]pyridine-3-carbonitrile (compound 52). MS m/z (ESI): 468.3 $[M+H]^+$. $^1$H NMR (400 MHz, DMSO) δ 8.64 (dd, 1H), 8.40-8.34 (m, 2H), 8.32-8.28 (m, 1H), 7.88 (s, 4H), 7.72 (dd, J=8.8, 2.5 Hz, 1H), 7.02 (d, J=1.9 Hz, 1H), 6.79 (d, J=8.8 Hz, 1H), 6.25 (q, J=6.9 Hz, 1H), 5.89 (s, 1H), 2.89 (s, 3H), 1.88 (s, 3H), 1.28 (s, 3H).

Example 53: Preparation of (S)-4-(6-((1-(6-(4-fluoro-1H-pyrazol-1-yl)pyridin-3-yl)ethyl)(methyl)amino)pyridine-3-yl)-6-(prop-2-yn-1-yloxy)pyrazolo[1,5-a]pyridine-3-carbonitrile

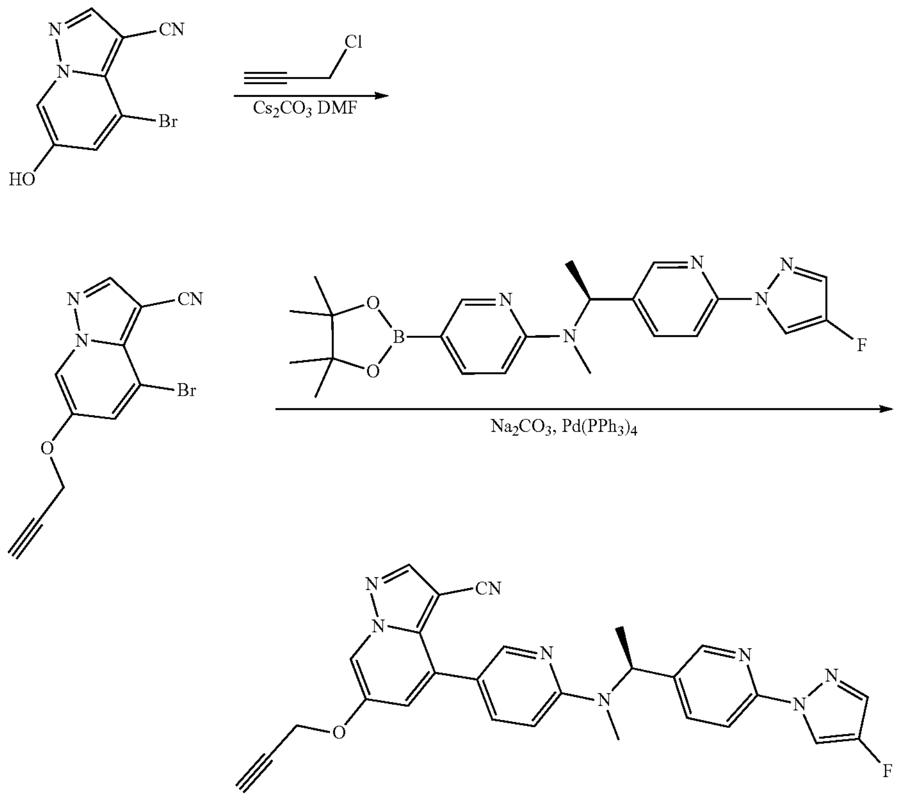

Step 1: Synthesis of 4-bromo-6-(prop-2-yn-1-yloxy)pyrazolo[1,5-a]pyridine-3-carbonitrile 4-bromo-6-hydroxypyrazolo[1,5-a]pyridine-3-carbonitrile (200 mg, 0.84 mmol), 3-chloropropyne (189 mg, 2.52 mmol) and cesium carbonate (554.4 mg, 1.68 mmol) were dissolved in 3 mL of DMF, and the mixed solution was stirred at 60° C. overnight to react. After the reaction was found to be completed from the monitoring, the reaction solution was cooled, and water was added to quench the reaction, extraction with EA (30 mL*2) was then carried out, and the organic phase was washed with water, dried, concentrated and subjected to column chromatography to obtain 150 mg of 4-bromo-6-(prop-2-yn-1-yloxy)pyrazolo[1,5-a]pyridine-3-carbonitrile. MS m/z (ESI): 277.2 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(prop-2-yn-1-yloxy)pyrazolo[1,5-a]pyridine-3-carbonitrile Under the protection of $N_2$, 4-bromo-6-(prop-2-yn-1-yloxy)pyrazolo[1,5-a]pyridine-3-carbonitrile (150 mg, 0.54 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (230 mg, 0.54 mmol), sodium carbonate (172 mg, 1.62 mmol) and tetrakistriphenylphosphine palladium (63 mg, 0.054 mmol) were dissolved in 6 mL of dioxane and 2 mL of water, and the resulting reaction solution was stirred at 90° C. overnight. After the reaction was found to be completed from the monitoring, the reaction solution was cooled, water was added to quench the reaction, extraction with EA (30 mL*2) was then carried out, and the organic phase was washed with water, dried, concentrated and subjected to column chromatography to obtain 60 mg of (S)-4-(6-((1-(6-(4-fluoro-1H-pyrazol-1-yl)pyridin-3-yl)ethyl)(methyl)amino)pyridine-3-yl)-6-(prop-2-yn-1-yloxy)pyrazolo[1,5-a]pyridine-3-carbonitrile (compound 53). MS m/z (ESI): 493.2 $[M+H]^+$. $^1$H NMR (400 MHz, DMSO-d6) δ 8.93 (s 1H), 8.71-8.64 (m, 2H), 8.43-8.38 (m, 2H), 7.95-7.86 (m, 3H), 7.83 (s, 1H), 7.47 (d, J=2.2 Hz, 1H), 6.86-6.81 (m, 1H), 5.34 (s, 1H), 4.14 (s, 1H), 2.83 (s, 3H), 1.61 (d, J=7.0 Hz, 3H).

Example 54: Preparation of (S)-4-(6-((1-(6-(4-fluoro-1H-pyrazol-1-yl)pyridin-3-yl)ethyl)(methyl)amino)pyridine-3-yl)-6-(2-methoxyethoxy)pyrazolo[1,5-a]pyridine-3-carbonitrile

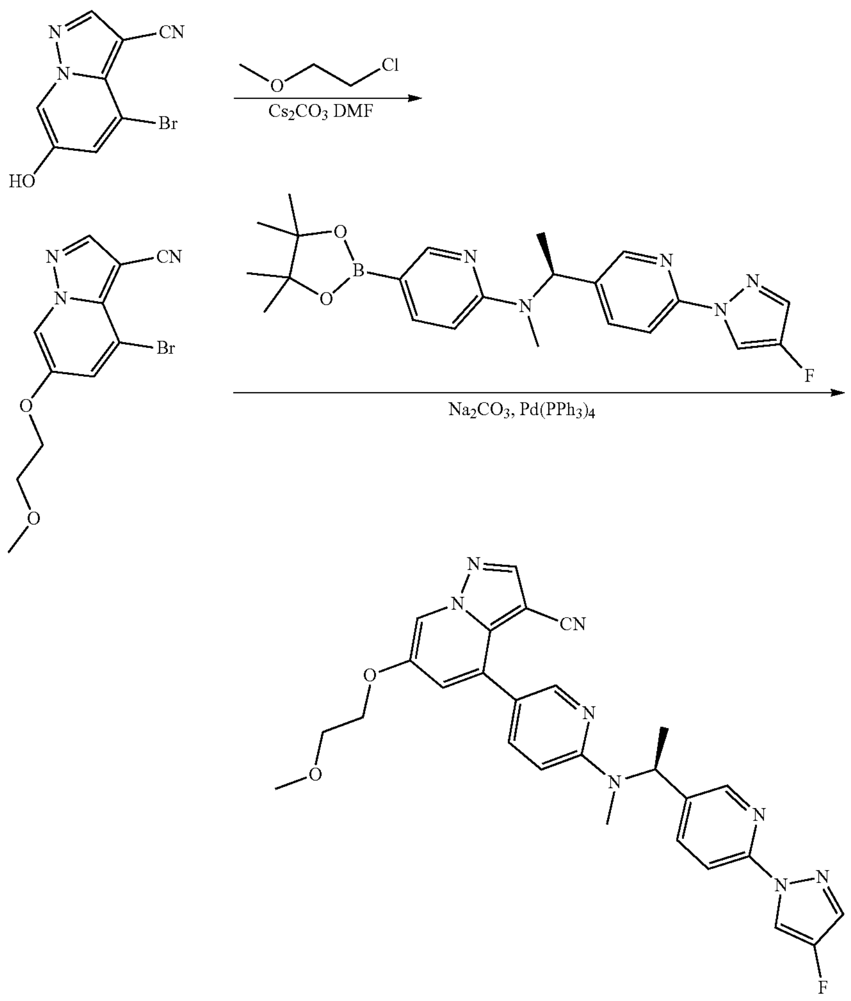

Step 1: Synthesis of 4-bromo-6-(2-methoxyethoxy)pyrazolo[1,5-a]pyridine-3-carbonitrile 4-bromo-6-hydroxypyrazolo[1,5-a]pyridine-3-carbonitrile (200 mg, 0.84 mmol), 2-chloroethyl methyl ether (239 mg, 2.52 mmol) and cesium carbonate (554.4 mg, 1.68 mmol) were dissolved in 3 mL of DMF, and the mixed solution was stirred at 60° C. overnight to react. After the reaction was found to be completed from the monitoring, the reaction solution was cooled, and water was added to quench the reaction, extraction with EA (30 mL*2) was then carried out, and the organic phase was washed with water, dried, concentrated and subjected to column chromatography to obtain 180 mg of 4-bromo-6-(2-methoxyethoxy)pyrazolo[1,5-a]pyridine-3-carbonitrile. MS m/z (ESI): 297.1 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(2-methoxyethoxy)pyrazolo[1,5-a]pyridine-3-carbonitrile Under the protection of $N_2$, 4-bromo-6-(2-methoxyethoxy)pyrazolo[1,5-a]pyridine-3-carbonitrile (180 mg, 0.61 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (256 mg, 0.61 mmol), sodium carbonate (129 mg, 1.22 mmol) and tetrakistriphenylphosphine palladium (70 mg, 0.061 mmol) were dissolved in 6 mL of dioxane and 2 mL of water, and the resulting reaction solution was stirred at 90° C. overnight to react. After the reaction was found to be completed from the monitoring, the reaction solution was cooled, water was added to quench the reaction, extraction with EA (30 mL*2) was then carried out, and the organic phase was washed with water and then dried, concentrated and subjected to column chromatography to obtain 75 mg of (S)-4-(6-((1-(6-(4-fluoro-1H-pyrazol-1-yl)pyridin-3-yl)ethyl)(methyl)amino)pyridine-3-yl)-6-(2-methoxyethoxy)pyrazolo[1,5-a]pyridine-3-carbonitrile (compound 54). MS m/z (ESI): 513.5 $[M+H]^+$. $^1H$ NMR (500 MHz, DMSO) δ 8.66 (dd, J=11.5, 3.3 Hz, 2H), 8.57 (s, 1H), 8.38 (dd, J=9.9, 2.3 Hz, 2H), 7.84 (ddd, J=13.3, 11.3, 3.0 Hz, 4H), 7.31 (d, J=2.0 Hz, 1H), 6.81 (d, J=8.9 Hz, 1H), 6.28 (d, J=7.0 Hz, 1H), 4.27-4.17 (m, 2H), 3.69 (dd, J=5.2, 3.5 Hz, 2H), 3.31 (s, 3H), 2.82 (s, 3H), 1.60 (d, J=7.0 Hz, 3H).

Example 55: Preparation of (S)-4-(6-((1-(6-(4-fluoro-1H-pyrazol-1-yl)pyridin-3-yl)ethyl)(methyl)amino)pyridine-3-yl)-6-(methoxymethoxy)pyrazolo[1,5-a]pyridine-3-carbonitrile

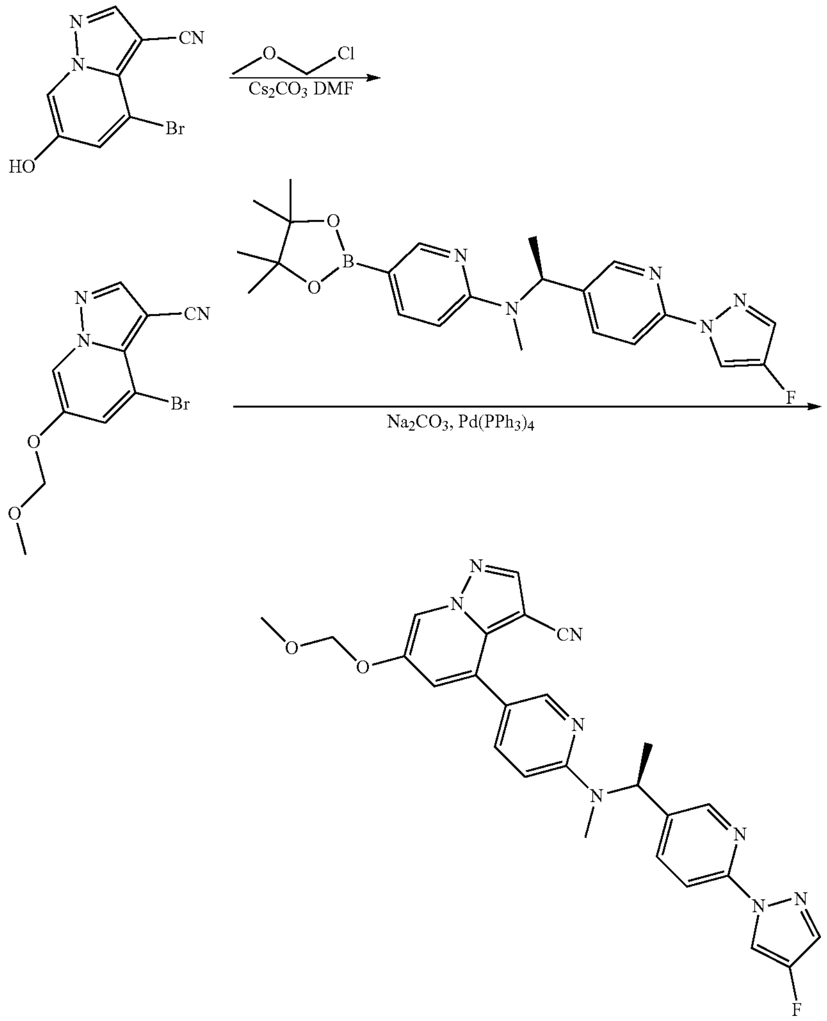

Step 1: Synthesis of 4-bromo-6-(methoxymethoxy)pyrazolo[1,5-a]pyridine-3-carbonitrile 4-bromo-6-hydroxypyrazolo[1,5-a]pyridine-3-carbonitrile (200 mg, 0.84 mmol), 2-chloromethyl methyl ether (201 mg, 2.52 mmol) and cesium carbonate (554.4 mg, 1.68 mmol) were dissolved in 3 mL of DMF, and the mixed solution was stirred at 60° C. overnight. After the reaction was found to be completed from the monitoring, the reaction solution was cooled, and water was added to quench the reaction, extraction with EA (30 mL*2) was then carried out, and the organic phase was washed with water, dried, concentrated and subjected to column chromatography to obtain 170 mg of 4-bromo-6-(methoxymethoxy)pyrazolo[1,5-a]pyridine-3-carbonitrile. MS m/z (ESI): 283.1 $[M+H]^+$.

Step 2: Synthesis of (S)-4-(6-((1-(6-(4-fluoro-1H-pyrazol-1-yl)pyridin-3-yl)ethyl)(methyl)amino)pyridine-3-yl)-6-(methoxymethoxy)pyrazolo[1,5-a]pyridine-3-carbonitrile Under the protection of $N_2$, 4-bromo-6-(methoxymethoxy)pyrazolo[1,5-a]pyridine-3-carbonitrile (170 mg, 0.61 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (256 mg, 0.61 mmol), sodium carbonate (129 mg, 1.22 mmol) and tetrakistriphenylphosphine palladium (70 mg, 0.061 mmol) were dissolved in dioxane (6 mL) and water (2 mL), and the resulting reaction solution was stirred at 90° C. overnight to react. After the reaction was found to be completed from the monitoring, the reaction solution was cooled, water was added to quench the reaction, extraction with EA (30 mL*2) was then carried out, and the organic phase was washed with water and then dried, concentrated and subjected to column chromatography to obtain 55 mg of (S)-4-(6-((1-(6-(4-fluoro-1H-pyrazol-1-yl)pyridin-3-yl)ethyl)(methyl)amino)pyridine-3-yl)-6-(methoxymethoxy)pyrazolo[1,5-a]pyridine-3-carbonitrile (compound 55). MS m/z (ESI): 499.4 $[M+H]^+$. $^1H$ NMR (500 MHz, DMSO) δ 8.66 (dd, J=11.5, 3.3 Hz, 2H), 8.57 (s, 1H), 8.38 (dd, J=9.9, 2.3 Hz, 2H), 7.84 (ddd, J=13.3, 11.3, 3.0 Hz, 4H), 7.31 (d, J=2.0 Hz, 1H), 6.81 (d, J=8.9 Hz, 1H), 6.28 (d, J=7.0 Hz, 1H), 4.27-4.17 (m, 2H), 3.35 (s, 3H), 2.92 (s, 3H), 1.65 (d, J=7.0 Hz, 3H).

organic phase was washed with water, dried and spin-dried to obtain 1.5 g of tert-butyl ((6-(4-(4-fluoro-1H-pyrazol-1-yl)pyridin-3-yl)methyl)carbamate. MS m/z (ESI): 293.4 $[M+H]^+$.

Example 56: Preparation of 4-(6-(((6-(4-fluoro-1H-pyrazol-1-yl)pyridin-3-yl) methyl)(methyl)amino) pyridin-3-yl)-6-(2-hydroxy-2-methylpropoxy)pyrazolo[1,5-a]pyridine-3-carbonitrile

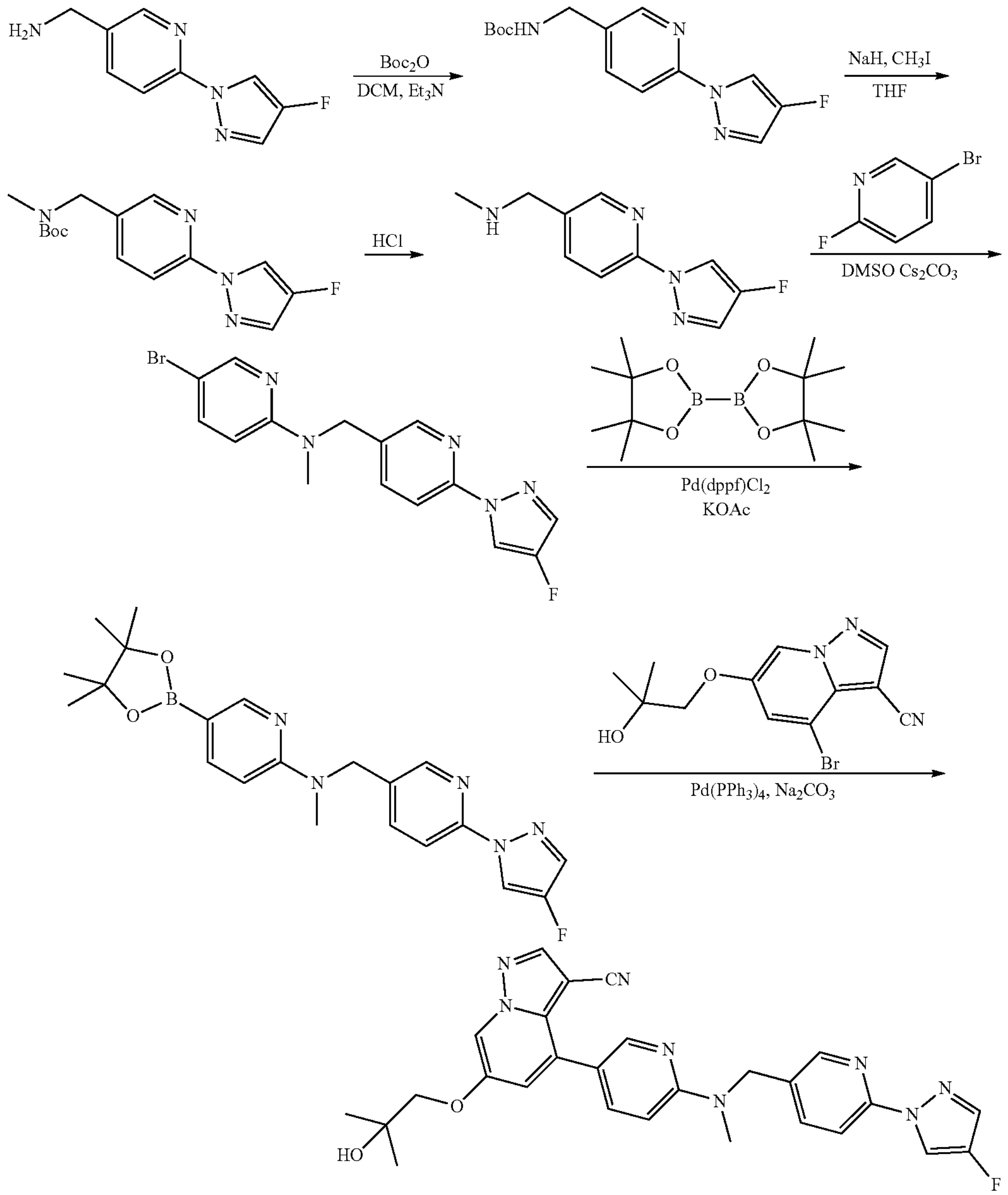

Step 1: Synthesis of tert-butyl ((6-(4-(4-fluoro-1H-pyrazol-1-yl)pyridin-3-yl)methyl)carbamate (6-(4-fluoro-1H-pyrazol-1-yl)pyridin-3-yl)methanamine (1.5 g, 7.8 mmol) and triethylamine (1.58 g, 15.6 mmol) were dissolved in DCM (20 mL), and then Boc-anhydride (1.6 g, 7.8 mmol) was added. The reaction solution was stirred at room temperature for 4 h. After the reaction was completed, water (10 mL) was added to quench the reaction, extraction with DCM (20 mL*2) was carried out, and the

Step 2: Synthesis of tert-butyl(((6-(4-fluoro-1H-pyrazol-1-yl)pyridin-3-yl)methyl)(methyl)carbamate Tert-butyl ((6-(4-(4-fluoro-1H-pyrazol-1-yl)pyridin-3-yl) methyl)carbamate (1.5 g, 5.1 mmol) was dissolved in THF (20 mL), and the mixed solution was cooled to 0° C., and then NaH (0.25 g, 10.2 mmol) was slowly added. The reaction solution was stirred at low temperature to react for 0.5 h, and then iodomethane (0.94 g, 6.6 mmol) was added. After the addition was completed, the reaction was further carried out at low temperature for 5 h. After the reaction was completed, methanol was added at low temperature to quench the reaction, extraction with EA (30 mL*2) was carried out, and the organic phase was washed, dried, spin-dried and subjected to column chromatography (PE: DCM=1:1) to obtain 1.7 g of tert-butyl(((6-(4-fluoro-1H-pyrazol-1-yl)pyridin-3-yl)methyl)(methyl)carbamate. MS m/z (ESI): 307.3 $[M+H]^+$.

Step 3: Synthesis of 1-(6-(4-fluoro-1H-pyrazol-1-yl)pyridin-3-yl)-N-methylmethanamine Tert-butyl (((6-(4-fluoro-1H-pyrazol-1-yl)pyridin-3-yl)methyl)(methyl)carbamate (1.7 g, 5.5 mmol) was dissolved in a small amount of dichloromethane. Then, 4N HCl/dioxane (6 mL) was added at low temperature, and the reaction solution was stirred at room temperature to react for 2 h. After the reaction was completed, the reaction solution was spin-dried, and petroleum ether was added and stirred to precipitate a solid, which was filtered, and then 0.9 g of 1-(6-(4-fluoro-1H-pyrazol-1-yl)pyridin-3-yl)-N-methylmethanamine was obtained. MS m/z (ESI): 207.2 $[M+H]^+$.

Step 4: Synthesis of 5-bromo-N-(((6-(4-fluoro-1H-pyrazol-1-yl)pyridin-3-yl)methyl)-N-methylpyridin-2-amine 1-(6-(4-fluoro-1H-pyrazol-1-yl)pyridin-3-yl)-N-methylmethanamine (0.9 g, 4.3 mmol), 2-fluoro-5-bromopyridine (3.8 g, 21.7 mmol) and cesium carbonate (4.1 g, 12.9 mmol) were added to a single-mouth flask, and DMSO (25 mL) was added. The mixed solution was heated to 130° C. to react for about 40 h. After the reaction was completed, water (10 mL) was added to quench the reaction, extraction with DCM (30 mL*2) was then carried out, and the organic phase was washed with water, dried, spin-dried and subjected to column chromatography (PE:DCM=1:1) to obtain 0.6 g of 5-bromo-N-(((6-(4-fluoro-1H-pyrazol-1-yl)pyridin-3-yl)methyl)-N-methylpyridin-2-amine. MS m/z (ESI): 363.2 $[M+H]^+$.

Step 5: Synthesis of N-(((6-(4-fluoro-1H-pyrazol-1-yl)pyridin-3-yl)methyl)-N-methyl-5-(4,4,5,5-tetramethyl)-1,3,2-dioxaborolane-2-yl)pyridin-2-amine 5-bromo-N-(((6-(4-fluoro-1H-pyrazol-1-yl)pyridin-3-yl)methyl)-N-methylpyridin-2-amine (0.6 g, 1.65 mmol), pinacol biborate (0.84 g, 3.3 mmol), $Pd(dppf)Cl_2CH_2Cl_2$ (0.13 g, 0.1 mmol) and KOAc (0.97 g, 9.9 mmol) were dissolved in dioxane (15 mL), and the mixed solution reacted at 90° C. for 6 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.45 g of N-(((6-(4-fluoro-1H-pyrazol-1-yl)pyridin-3-yl)methyl)-N-methyl-5-(4,4,5,5-tetramethyl)-1,3,2-dioxaborolane-2-yl)pyridin-2-amine. MS m/z (ESI): 410.1 $[M+H]^+$.

Step 6: Synthesis of 4-(6-(((6-(4-fluoro-1H-pyrazol-1-yl)pyridin-3-yl)methyl)(methyl)amino)pyridin-3-yl)-6-(2-hydroxy-2-methylpropoxy)pyrazolo[1,5-a]pyridine-3-carbonitrile At room temperature, and under the protection of $N_2$, 4-bromo-6-(2-hydroxy-2-m ethylpropoxy)pyrazolo[1,5-a]pyridine-3-carbonitrile (0.24 g, 0.77 mmol), N-(((6-(4-fluoro-1H-pyrazol-1-yl)pyridin-3-yl)methyl)-N-methyl-5-(4,4,5,5-tetramethyl)-1,3,2-dioxaborolane-2-yl)pyridin-2-amine (0.48 g, 1.17 mmol), $Pd(PPh_3)_4$ (0.01 g, 0.076 mmol) and $Na_2CO_3$ (0.33 g, 3.05 mmol) were dissolved in dioxane (15 mL) and water (5 mL), and the resulting reaction solution was stirred at 100° C. for 5 h to react. The reaction solution was cooled to room temperature, and water was added to quench the reaction, extraction was carried out, and the organic phase was washed, dried, and subjected to column chromatography to obtain 90 mg of 4-(6-(((6-(4-fluoro-1H-pyrazol-1-yl)pyridin-3-yl)methyl)(methyl)amino)pyridin-3-yl)-6-(2-hydroxy-2-methylpropoxy)pyrazolo[1,5-a]pyridine-3-carbonitrile (compound 56). MS m/z (ESI): 513.3 $[M+H]^+$ $^1H$ NMR (500 MHz, DMSO) δ 8.68-8.61 (m, 2H), 8.55 (s, 1H), 8.37 (dd, J=18.8, 2.0 Hz, 2H), 7.97-7.81 (m, 3H), 7.78 (dd, J=8.8, 2.5 Hz, 1H), 7.30 (d, J=2.0 Hz, 1H), 6.82 (d, J=8.8 Hz, 1H), 4.94 (s, 2H), 3.86 (s, 2H), 3.11 (s, 3H), 1.22 (s, 6H).

Example 57: Preparation of 4-(6-(ethyl((6-(4-(4-fluoro-1H-pyrazol-1-yl)pyridin-3-yl)methyl)amino)pyridin-3-yl)-6-(2-hydroxy-2-methylpropoxy)pyrazolo[1,5-a]pyridine-3-carbonitrile

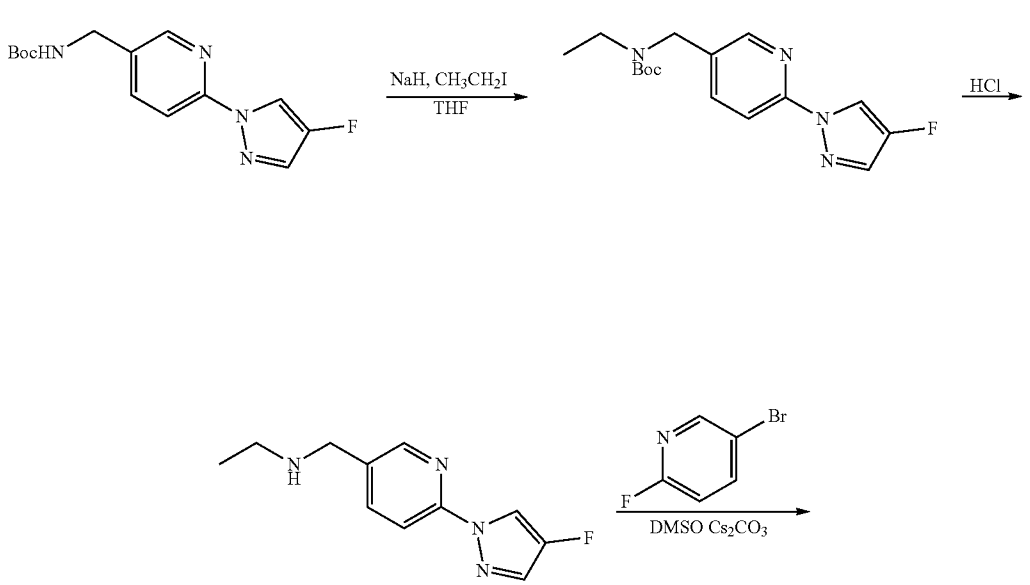

-continued

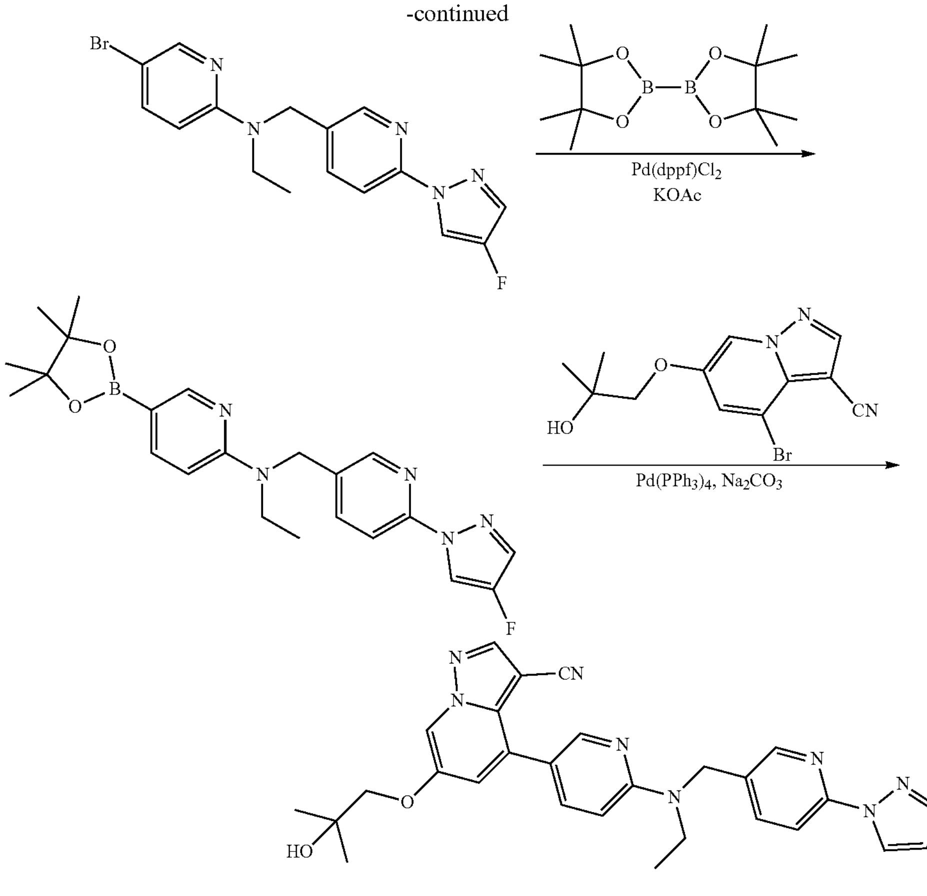

Step 1: Synthesis of tert-butylethyl ((6-(4-fluoro-1H-pyrazol-1-yl)pyridin-3-yl)methyl)carbamate Tert-butyl ((6-(4-(4-fluoro-1H-pyrazol-1-yl)pyridin-3-yl) methyl)carbamate (2.0 g, 6.8 mmol) was dissolved in THF (20 mL), and the mixed solution was cooled to 0° C., and then NaH (0.33 g, 13.6 mmol) was slowly added. The reaction solution was stirred at low temperature to react for 0.5 h, and then iodomethane (1.3 g, 8.8 mmol) was added. After the addition was completed, the reaction was further carried out at low temperature for 5 h. After the reaction was completed, methanol was added at low temperature to quench the reaction, extraction with EA (30 mL*2) was carried out, and the organic phase was washed, dried, spin-dried and subjected to column chromatography (PE: DCM=1:1) to obtain 1.8 g of tert-butylethyl ((6-(4-fluoro-1H-pyrazol-1-yl)pyridin-3-yl)methyl)carbamate. MS m/z (ESI): 321.5 [M+H]$^+$.

Step 2: Synthesis of N-((6-(4-fluoro-1H-pyrazol-1-yl)pyridin-3-yl)methylethylamine Tert-butylethyl ((6-(4-fluoro-1H-pyrazol-1-yl)pyridin-3-yl)methyl)carbamate (1.8 g, 5.6 mmol) was dissolved in a small amount of dichloromethane. Then, 4N HCl/dioxane (6 mL) was added at low temperature, and the reaction solution was stirred at room temperature to react for 2 h. After the reaction was completed, the reaction solution was spin-dried, and petroleum ether was added and stirred to precipitate a solid, which was filtered, and then 1.1 g of N-((6-(4-fluoro-1H-pyrazol-1-yl)pyridin-3-yl)methylethylamine was obtained. MS m/z (ESI): 221.2 [M+H]$^+$.

Step 3: Synthesis of 5-bromo-N-ethyl-N-(((6-(4-fluoro-1H-pyrazol-1-yl)pyridin-3-yl)methyl)pyridin-2-amine N-((6-(4-fluoro-1H-pyrazol-1-yl)pyridin-3-yl)methylethylamine (0.9 g, 5.0 mmol), 2-fluoro-5-bromopyridine (4.4 g, 25.0 mmol) and cesium carbonate (4.9 g, 15.0 mmol) were added to a single-mouth flask, and then DMSO (25 mL) was added. The mixed solution was heated to 130° C. to react for 40 h. After the reaction was completed, water (10 mL) was added to quench the reaction, extraction with DCM (30 mL*2) was carried out and the organic phase was washed with water, dried, spin-dried and subjected to column chromatography (PE:DCM=1:1) to obtain 0.8 g of 5-bromo-N-ethyl-N-(((6-(4-fluoro-1H-pyrazol-1-yl)pyridin-3-yl) methyl)pyridin-2-amine. MS m/z (ESI): 377.2 [M+H]$^+$.

Step 4: Synthesis of N-ethyl-N-(((6-(4-fluoro-1H-pyrazol-1-yl)pyridin-3-yl)methyl)-5-(4,4,5,5-tetramethyl)-1,3,2-dioxaborolane-2-yl)pyridin-2-amine 5-bromo-N-ethyl-N-(((6-(4-fluoro-1H-pyrazol-1-yl)pyridin-3-yl)methyl)pyridin-2-amine (0.8 g, 2.1 mmol), pinacol biborate (1.0 g, 4.2 mmol), Pd(dppf)$Cl_2CH_2Cl_2$ (0.26 g, 0.2 mmol) and KOAc (0.97 g, 9.9 mmol) were dissolved in dioxane (20 mL), and the mixed solution reacted at 90° C. for 6 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.5 g of N-ethyl-N-(((6-(4-fluoro-1H-pyrazol-1-yl)pyridin-3-yl)methyl)-5-(4,4,5,5-tetramethyl)-1,3,2-dioxaborolane-2-yl)pyridin-2-amine. MS m/z (ESI): 424.1 $[M+H]^+$.

Step 5: Synthesis of 4-(6-(ethyl((6-(4-(4-fluoro-1H-pyrazol-1-yl)pyridin-3-yl)methyl)amino)pyridin-3-yl)-6-(2-hydroxy-2-methylpropoxy)pyrazolo[1,5-a]pyridine-3-carbonitrile At room temperature and under the protection of $N_2$, 4-bromo-6-(2-hydroxy-2-methylpropoxy)pyrazolo[1,5-a]pyridine-3-carbonitrile (0.3 g, 0.97 mmol), N-ethyl-N-(((6-(4-fluoro-1H-pyrazol-1-yl)pyridin-3-yl)methyl)-5-(4,4,5,5-tetramethyl)-1,3,2-dioxaborolane-2-yl)pyridin-2-amine (0.5 g, 1.2 mmol), $Pd(PPh_3)_4$ (0.015 g, 0.1 mmol) and $Na_2CO_3$ (0.32 g, 3.0 mmol) were dissolved in dioxane (15 mL) and water (5 mL), and the resulting reaction solution was stirred at 100° C. for 5 h to react. The reaction solution was cooled to room temperature, and water was added to quench the reaction, extraction was carried out, and the organic phase was washed, dried, and subjected to column chromatography to obtain 70 mg of 4-(6-(ethyl((6-(4-(4-fluoro-1H-pyrazol-1-yl)pyridin-3-yl)methyl)amino)pyridin-3-yl)-6-(2-hydroxy-2-methylpropoxy)pyrazolo[1,5-a]pyridine-3-carbonitrile (compound 57). MS m/z (ESI): 527.5 $[M+H]^+$ $^1H$ NMR (500 MHz, DMSO) δ 8.65 (dd, J=6.8, 1.4 Hz, 2H), 8.56 (s, 1H), 8.40 (d, J=1.7 Hz, 1H), 8.34 (d, J=2.4 Hz, 1H), 7.96-7.86 (m, 2H), 7.85 (s, 1H), 7.76 (dd, J=8.8, 2.5 Hz, 1H), 7.30 (d, J=2.1 Hz, 1H), 6.80 (d, J=8.8 Hz, 1H), 4.89 (s, 2H), 3.86 (s, 2H), 3.62 (d, J=7.0 Hz, 2H), 1.21 (s, 6H), 1.14 (t, J=7.0 Hz, 3H).

Example 58: Preparation of (S)-4-(6-((1-(6-(1H-pyrazol-1-yl)pyridin-3-yl)ethyl)(methyl)amino)pyridin-3-yl)-6-(2-hydroxy-2-methylpropoxy)pyrazolo[1,5-a]pyridine-3-carbonitrile

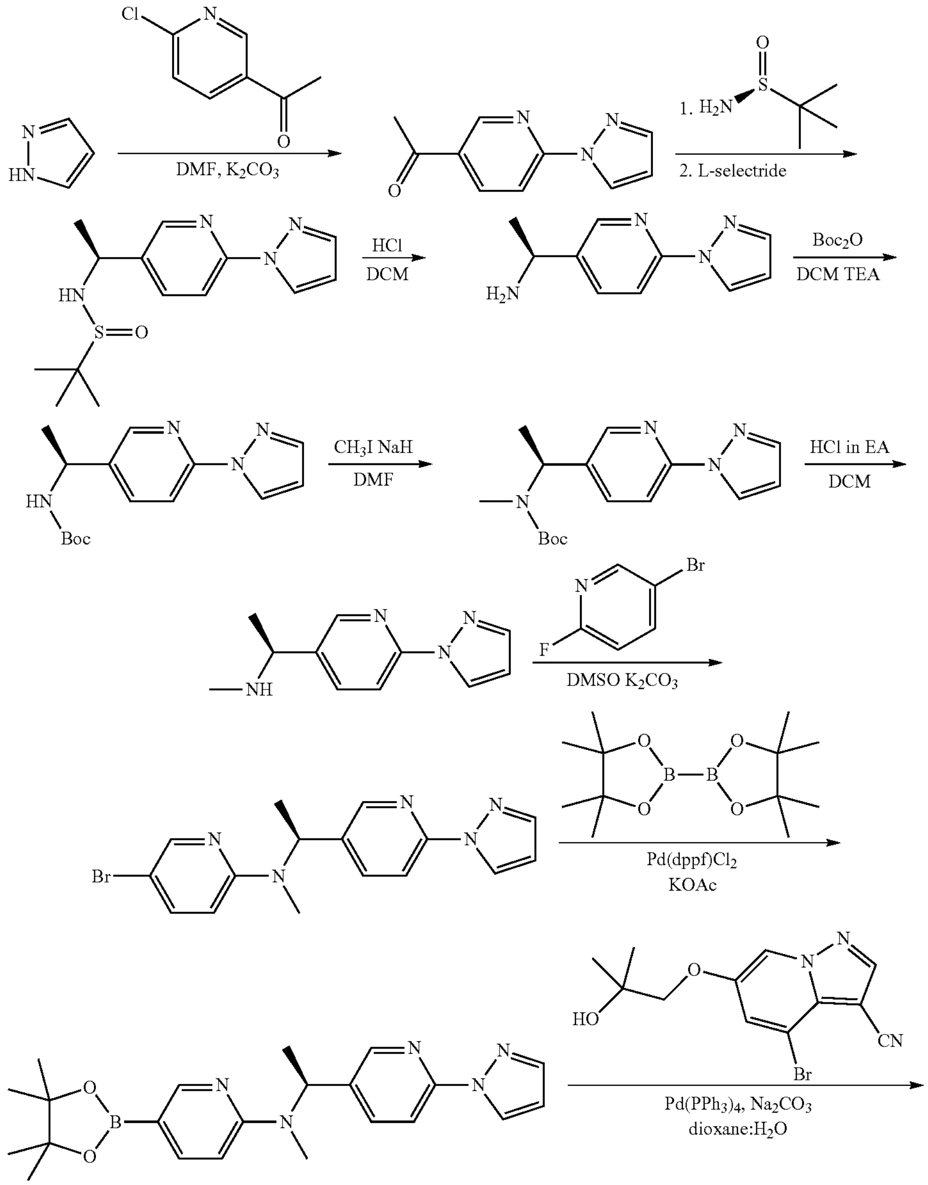

-continued

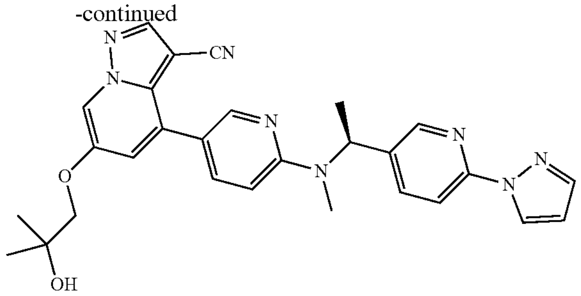

Step 1: Synthesis of 1-(6-(1H-pyrazol-1-yl)pyridin-3-yl)ethan-1-one 2-chloro-5-acetylpyridine (4.0 g, 25.8 mmol), pyrazole (1.75 g, 25.8 mmol) and $K_2CO_3$ (7.1 g, 51.6 mmol) were dissolved in DMF (40 mL), and the mixed solution was stirred at 90° C. overnight. The reaction solution was cooled to room temperature, diluted with water (50 mL), extracted, and the organic phase was dried, filtered, concentrated and subjected to column chromatography to obtain 4.1 g of 1-(6-(1H-pyrazol-1-yl)pyridin-3-yl)ethan-1-one. MS m/z (ESI): 188.2 $[M+H]^+$.

Step 2: Synthesis of (R)-N-((S)-1-(6-(1H-pyrazol-1-yl)pyridin-3-yl)ethyl)-2-methylpropane-2-sulfinamide At room temperature, (R)-2-methylpropane-2-sulfonimide (1.6 g, 12.7 mmol) and 1-(6-(1H-pyrazol-1-yl)pyridin-3-yl)ethan-1-one (2.0 g, 10.6 mmol) and THF (50 mL) were added to the reaction flask. Then, tetraethyl titanate (4.9 g, 21.2 mmol) was added dropwise to the reaction solution. The mixed solution reacted at 75° C. for 16 h. After addition was completed, the reaction was carried out at −78° C. to react for 3 h. The reaction solution was stirred adequacy with water (50 mL) and EA (200 mL), filtered, extracted, dried with anhydrous sodium sulfate, filtrated, concentrated to obtain a crude product. The crude product was purified by column chromatography to obtain 2.5 g of (R)-N-((S)-1-(6-(1H-pyrazol-1-yl)pyridin-3-yl)ethyl)-2-methylpropane-2-sulfinamide. MS m/z (ESI): 293.3 $[M+H]^+$.

Step 3: Synthesis of (S)-1-(6-(1-(1-H-pyrazol-1-yl)pyridin-3-yl)ethan-1-amine

At room temperature, (R)-N-((S)-1-(6-(1H-pyrazol-1-yl)pyridin-3-yl)ethyl)-2-methylpropane-2-sulfinamide (4.0 g, 13.6 mmol) was dissolved in DCM (20 mL), HCl/dioxane (20 mL, 4M) was then added, and the mixed solution reacted at room temperature for 1 h. The resulting reaction solution was concentrated in vacuum under reduced pressure to remove the solvent. The reaction solution was alkalized with $NaHCO_3$, extracted, dried, filtered, concentrated to obtain 2.3 g of (S)-1-(6-(1-(1-H-pyrazol-1-yl)pyridin-3-yl)ethan-1-amine. MS m/z (ESI): 189.5 $[M+H]^+$.

Step 4: Synthesis of tert-butyl (S)-(1-(1-(6-(1H-pyrazol-1-yl)pyridin-3-yl)ethyl)carbamate (S)-1-(6-(1-(1H-pyrazol-1-yl)pyridin-3-yl)ethan-1-amine (2.3 g, 12.2 mmol) and triethylamine (2.5 g, 24.4 mmol) were dissolved in 20 mL of DCM, and di-tert-butyl dicarbonate (3.0 g, 13.5 mmol) was added. The mixed solution was stirred at room temperature for 5 h to react. Extraction was carried out, and the organic phase was dried, filtered, concentrated and subjected to column chromatography to obtain 4.6 g of tert-butyl (S)-(1-(1-(6-(1H-pyrazol-1-yl)pyridin-3-yl)ethyl)carbamate. MS m/z (ESI): 289.4 $[M+H]^+$.

Step 5: Synthesis of tert-butyl (S)-(1-(6-(1-(6-H-pyrazol-1-yl)pyridin-3-yl)ethyl)(methyl)carbamate Tert-butyl (S)-(1-(1-(6-(1H-pyrazol-1-yl)pyridin-3-yl)ethyl)carbamate (2.0 g, 6.9 mmol) was dissolved in THF (20 mL), and then sodium hydrogen (0.32 g, 13.8 mmol) was added to the resulting solution at 0° C. to have thermal reaction for 0.5 h. Then, iodomethane (1.3 g, 9.0 mmol) was added. The reaction was further carried out at 0° C. for 4 h. After the reaction was completed, water (20 mL) was added to quench the reaction, extraction was carried out, and the organic phase was dried, filtered, concentrated and subjected to column chromatography to obtain 1.8 g of tert-butyl (S)-(1-(6-(1-(6H-pyrazol-1-yl)pyridin-3-yl)ethyl)(methyl)carbamate.

Step 6: Synthesis of (S)-1-(6-(1H-pyrazol-1-yl)pyridin-3-yl)-N-methyl-1-amine

Tert-butyl (S)-(1-(6-(1-(6H-pyrazol-1-yl)pyridin-3-yl)ethyl)(methyl)carbamate (1.8 g, 6.0 mmol) was dissolved in DCM (5 mL), and then HCl/dioxane (10 mL, 4M) was added. The mixed solution reacted at room temperature for 1 h. After the reaction was completed, the resulting reaction solution was concentrated in vacuum under reduced pressure to remove the solvent. The reaction solution was diluted with $NaHCO_3$, extracted, dried, filtered, concentrated, and subjected to column chromatography to obtain 0.9 g of (S)-1-(6-(1H-pyrazol-1-yl)pyridin-3-yl)-N-methyl-1-amine. MS m/z (ESI): 203.6 $[M+H]^+$.

Step 7: Synthesis of (S)—N-(1-(6-(6-(1H-pyrazol-1-yl)pyridin-3-yl)ethyl)-5-bromo-N-methylpyridin-2-amine (S)-1-(6-(1H-pyrazol-1-yl)pyridin-3-yl)-N-methyl-1-amine (0.9 g, 4.5 mmol), 5-bromo-2-fluoropyridine (3.9 g, 22.5 mmol) and $K_2CO_3$ (1.9 g, 13.5 mmol) were dissolved in DMSO (10 mL). The mixed solution reacted at 140° C. for 30 h. The reaction solution was cooled to room temperature, diluted with water, extracted, and the organic phase was dried, filtered, concentrated and subjected to column chromatography to obtain 0.5 g of (S)—N-(1-(6-(6-(1H-pyrazol-1-yl)pyridin-3-yl)ethyl)-5-bromo-N-methylpyridin-2-amine. MS m/z (ESI): 359.3 $[M+H]^+$.

Step 8: Synthesis of (S)—N-(1-(6-(6-(1H-pyrazol-1-yl)pyridin-3-yl)ethyl)-N-methyl-5-(4,4,5,5-tetramethyl-1,3,2-dioxaboran-2-yl)pyridin-2-amine (S)—N-(1-(6-(6-(1H-pyrazol-1-yl)pyridin-3-yl)ethyl)-5-bromo-N-methylpyridin-2-amine (0.5 g, 1.4 mmol), pinacol biborate (0.7 g, 2.8 mmol), Pd(dppf)$ClCH_2Cl_2$ (90 mg, 0.14 mmol) and KOAc (0.27 g, 2.8 mmol) were dissolved in dioxane (15 mL), and the mixed solution reacted at 90° C. for 12 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.3 g of (S)—N-(1-(6-(6-(1H-pyrazol-1-yl)pyridin-3-yl)ethyl)-N-methyl-5-(4,4,5,5-tetramethyl-1,3,2-dioxaborolane-2-yl)pyridin-2-amine. MS m/z (ESI): 406.1 $[M+H]^+$.

Step 9: Synthesis of (S)-4-(6-((1-(6-(1H-pyrazol-1-yl)pyridin-3-yl)ethyl)(methyl)amino)pyridin-3-yl)-6-(2-hydroxy-2-methylpropoxy)pyrazolo[1,5-a]pyridine-3-carbonitrile At room temperature and under the protection of $N_2$, 4-bromo-6-(2-hydroxy-2-methylpropoxy)pyrazolo[1,5-a]pyridine-3-carbonitrile (0.2 g, 0.65 mmol), (S)—N-(1-(6-(6-(1H-pyrazol-1-yl)pyridin-3-yl)ethyl)-N-methyl-5-(4,4,5,5-tetramethyl-1,3,2-dioxaborolane-2-yl)pyridin-2-amine (0.27 g, 0.65 mmol), $Pd(PPh_3)_4$ (0.07 g, 0.065 mmol) and $Na_2CO_3$ (0.18 g, 1.65 mmol) were dissolved in a mixed solution of dioxane:water=5:1 (12 mL), and the mixed reaction solution was stirred at 85° C. for 12 h to react. The reaction solution was cooled to room temperature, and water was added to quench the reaction, extraction was carried out, and the organic phase was washed with water, dried, and subjected to column chromatography to obtain 65 mg of (S)-4-(6-((1-(6-(1H-pyrazol-1-yl)pyridin-3-yl)ethyl)(methyl)amino)pyridin-3-yl)-6-(2-hydroxy-2-methylpropoxy)pyrazolo[1,5-a]pyridine-3-carbonitrile (compound 58). MS m/z (ESI): 509.2 $[M+H]^+$. $^1H$ NMR (400 MHz, DMSO) δ 8.78 (s, 1H), 8.65 (s, 1H), 8.50 (s, 1H), 8.18 (d, 1H), 7.80-7.90 (m, 3H), 7.50-7.66 (m, 2H), 7.32 (s, 1H), 6.81 (d, 1H), 6.28 (d, 1H), 6.03 (d, 1H), 5.57 (s, 1H), 3.87 (s, 2H), 2.83 (s, 3H), 1.61 (s, 3H), 1.23 (s, 6H).

Example 59: Preparation of (S)—N-((1-(6-(4-fluoro-1H-pyrazol-1-yl)pyridin-3-yl)ethyl)(methyl)amine)-pyridin-3-yl)-6-(pyrrolidin-1-yl)pyrazolo[1,5-a]pyridine-3-carbonitrile

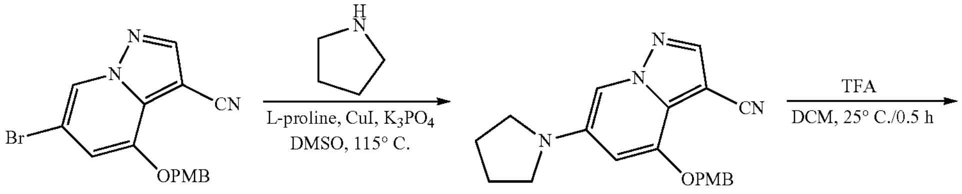

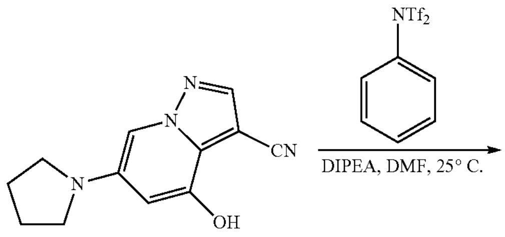

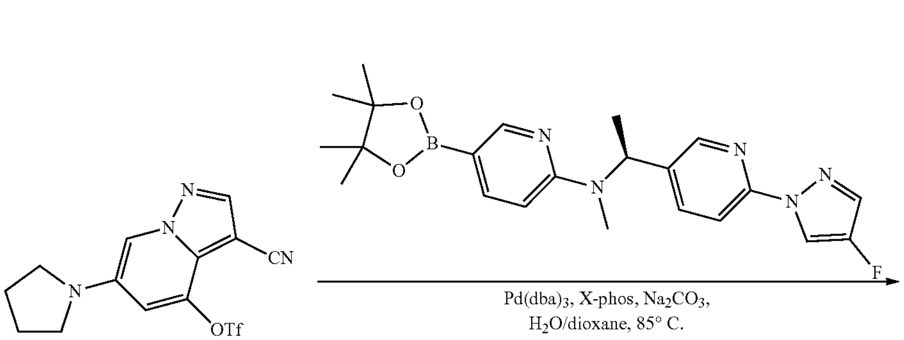

-continued

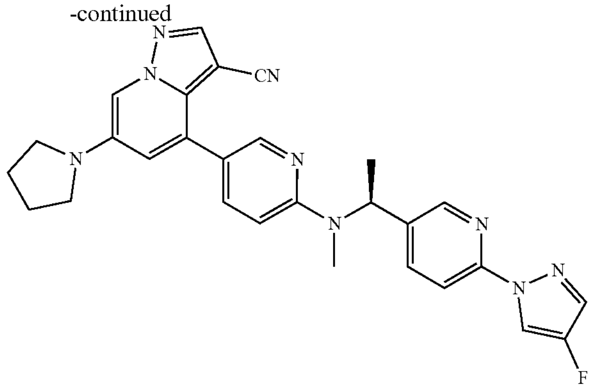

Step 1. Synthesis of 4-(4-methoxybenzyloxy)-6-(pyrrolidin-1-yl)pyrazolo[1,5-a]pyridine-3-carbonitrile 6-bromo-4-(4-methoxybenzyloxy)pyrazolo[1,5-a]pyridine-3-carbonitrile (800 mg, 2.23 mmol) was dissolved in DMSO (5 mL), and then tetrahydropyrrole (900 uL, 11.6 mmol), CuI (43 mg, 0.223 mmol), L-proline (52 mg, 0.446 mmol) and $K_3PO_4$ (958 mg, 4.86 mmol) were added in turn. After the reaction flask was replaced with $N_2$ three times, the reaction solution was heated to 115° C. under the protection of $N_2$ and stirred for 12 h. After the reaction was found to be completed from the monitoring of TLC (petroleum ether/ethyl acetate=5/1, $R_{f1}$=0.55, $R_{f2}$=0.25), the reaction solution was poured into water (100 mL), and then extraction with ethyl acetate (80 mL*2) was carried out. The organic phases were combined, washed with a saturated NaCl solution (50 mL*2), dried with anhydrous sodium sulfate, filtrated, and rotary evaporated to obtain a crude product. The crude product was purified by a rapid column machine (petroleum ether:ethyl acetate=20/1~5/1) to obtain 4-(4-methoxybenzyloxy)-6-(pyrrolidin-1-yl)pyrazolo[1,5-a]pyridine-3-carbonitrile (155 mg) with a yield of 19.1%. MS: m/z=349.1 $[M+1]^+$.

Step 2. Synthesis of 4-hydroxy-6-(pyrrolidin-1-yl)pyrazolo[1,5-a]pyridine-3-carbonitrile 4-(4-methoxybenzyloxy)-6-(pyrrolidin-1-yl)pyrazolo[1,5-a]pyridine-3-carbonitrile (155 mg, 0.445 mmol) was dissolved in dichloromethane (2 mL), and then TFA (0.5 mL) was added dropwise. The reaction solution was stirred at room temperature for 0.5 h. After the reaction was found to be completed from the monitoring of TLC (petroleum ether/ethyl acetate=2/1, $R_{f1}$=0.80, $R_{f2}$=0.1) and LCMS, the reaction solution was concentrated, pull-dried with oil pump to obtain a crude product of 4-hydroxy-6-(pyrrolidin-1-yl)pyrazolo[1,5-a]pyridine-3-carbonitrile, and the crude product was directly used in the next step. MS: m/z=229.0 $[M+1]^+$.

Step 3. Synthesis of 3-cyano-6-(pyrrolidin-1-yl)pyrazolo[1,5-a]pyridine-4-trifluoromethanesulfonate The crude product of 4-hydroxy-6-(pyrrolidin-1-yl)pyrazolo[1,5-a]pyridine-3-carbonitrile, which was obtained from the previous step, was dissolved in DMF (3 mL). Then, DIPEA (400 μL) and 1,1,1-trifluoro-N-phenyl-N-((trifluoromethyl)sulfonyl)methanesulfonamide (344 mg, 0.963 mmol) were added to the reaction solution. The reaction solution was stirred at room temperature for 1 h. After the reaction was found to be completed from the monitoring of TLC (petroleum ether/ethyl acetate=5/1, $R_{f1}$=0.15, $R_{f2}$=0.6), the reaction solution was poured into water (50 mL), and extraction with ethyl acetate (30 mL*2) was carried out. The organic phases were combined, washed with a saturated NaCl solution (30 mL*2), dried with anhydrous sodium sulfate, filtrated, and rotary evaporated to obtain a crude product. The crude product was purified by a rapid column machine (petroleum ether:ethyl acetate=20/1~5/1) to obtain 3-cyano-6-(pyrrolidin-1-yl)pyrazolo[1,5-a]pyridine-4-trifluoromethanesulfonate (95 mg, 0.246 mmol, with a two-step yield of 59.3%). MS: m/z=360.9 $[M+1]^+$.

Step 4. Synthesis of (S)—N-((1-(6-(4-fluoro-1H-pyrazol-1-yl)pyridin-3-yl)ethyl)(methyl)amine)-pyridin-3-yl)-6-(pyrrolidin-1-yl)pyrazolo[1,5-a]pyridine-3-carbonitrile 3-cyano-6-(pyrrolidin-1-yl)pyrazolo[1,5-a]pyridine-4-trifluoromethanesulfonate (130 mg, 0.361 mmol) was dissolved in a mixed solution of 1,4-dioxane (3 mL) and water (0.6 mL), and then (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (230 mg, 0.541 mmol), $Pd_2(dba)_3$ (66 mg, 0.072 mmol), X-Phos (138 mg, 0.289 mmol) and $Na_2CO_3$ (76.5 mg, 0.722 mmol) were added in turn at room temperature. After the reaction flask was replaced with $N_2$ three times, the reaction solution was heated to 85° C. under the protection of $N_2$ and stirred for 12 h. After the reaction was found to be completed from the monitoring of TLC (petroleum ether/ethyl acetate=5/1, $R_{f1}$=0.7, $R_{f2}$=0.45) and LCMS, the reaction solution was poured into water (50 mL), and then extraction with ethyl acetate (30 mL*2) was carried out. The organic phases were combined, washed with a saturated NaCl solution (30 mL*2), dried with anhydrous sodium sulfate, filtrated, and rotary evaporated to obtain a crude product. The crude product was purified by a rapid column machine (petroleum ether:ethyl acetate=20/1~5/1) to obtain 8 mg of (S)—N-((1-(6-(4-fluoro-1H-pyrazol-1-yl)pyridin-3-yl)ethyl)(methyl)amine)-pyridin-3-yl)-6-(pyrrolidin-1-yl)pyrazolo[1,5-a]pyridine-3-carbonitrile (compound 59) (with a purity of 92.5%). MS: m/z=508.1 $[M+1]^+$, $^1$HNMR (400 MHz, DMSO-$d_6$) δ: 8.67 (d, J=4.00 Hz, 1H), 8.43-8.38 (m, 3H), 8.07-8.02 (m, 1H), 7.94-7.87 (m, 3H), 7.83-7.80 (m, 1H), 7.18-7.14 (m, 1H), 6.84 (d, J=8.00 Hz, 1H), 6.30-6.28 (m, 1H), 2.84 (s, 3H), 2.0-1.96 (m, 4H), 1.63 (d, J=8.00 Hz, 3H), 1.33-1.23 (m, 4H).

Example 60: Preparation of (S)—N-((1-(6-(4-fluoro-1H-pyrazol-1-yl)pyridin-3-yl)ethyl)(methyl)amine)-pyridin-3-yl)-6-propylamino-pyrazolo[1,5-a]pyridine-3-carbonitrile

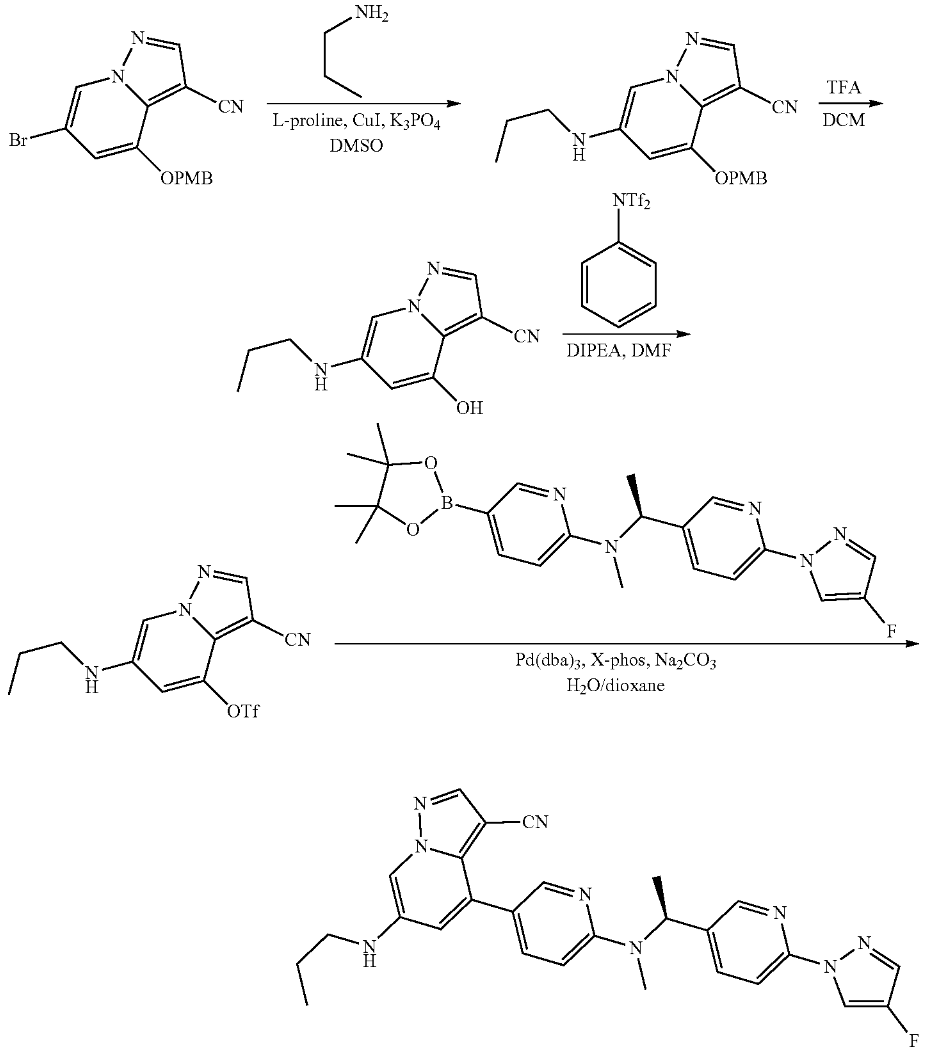

Step 1. Synthesis of 4-(4-methoxybenzyloxy)-6-(propylamino)pyrazolo[1,5-a]pyridine-3-carbonitrile 6-bromo-4-(4-methoxybenzyloxy)pyrazolo[1,5-a]pyridine-3-carbonitrile (800 mg, 2.23 mmol) was dissolved in DMSO (5 mL); then, propylamine (918 μL, 11.2 mmol), CuI (43 mg, 0.223 mmol), L-proline (52 mg, 0.446 mmol) and $K_3PO_4$ (950 mg, 4.27 mmol) were added in turn. After the reaction flask was replaced with $N_2$ three times, the reaction solution was heated to 115° C. under the protection of $N_2$ and stirred for 12 h. After the reaction was found to be completed from the monitoring of TLC (petroleum ether/ethyl acetate=5/1, $R_{f1}$=0.55, $R_{f2}$=0.3), the reaction solution was poured into water (100 mL), and then extraction with ethyl acetate (50 mL*3) was carried out. The organic phases were combined, washed with a saturated NaCl solution (50 mL*2), dried with anhydrous sodium sulfate, filtrated, and rotary evaporated to obtain a crude product. The crude product was purified by a rapid column machine (petroleum ether:ethyl acetate=20/1~5/1) to obtain 4-(4-methoxybenzyloxy)-6-(propylamino)pyrazolo[1,5-a]pyridine-3-carbonitrile (320 mg, 0.951 mmol, with a yield of 42.6%). MS: m/z=337.0 $[M+1]^+$.

Step 2. Synthesis of 4-hydroxy-6-(propylamino)pyrazolo[1,5-a]pyridine-3-carbonitrile Compound 4-(4-methoxybenzyloxy)-6-(propylamino)pyrazolo[1,5-a]pyridine-3-carbonitrile (320 mg, 0.951 mmol) was dissolved in dichloromethane (8 mL), and then TFA (2 mL) was added dropwise. The reaction solution was stirred at room temperature for 0.5 h. After the reaction was found to be completed from the monitoring of TLC (petroleum ether/ethyl acetate=1/1, $R_{f2}$=0.5, $R_{f3}$=0.1) and LCMS, the reaction solution was concentrated, pull-dried with oil pump to obtain the crude product of 4-hydroxy-6-(propylamino)pyrazolo[1,5-a]pyridine-3-carbonitrile. The crude product was directly used in the next step. MS: m/z=217.0 $[M+1]^+$.

Step 3. Synthesis of 3-cyano-6-propylaminopyrazolo[1,5-a]pyridine-4-trifluoro methanesulfonate The crude product of 4-hydroxy-6-(propylamino)pyrazolo[1,5-a]pyridine-3-carbonitrile, which was obtained from the previous step, was dissolved in DMF (3.00 mL). Then DIPEA (314 μL) and compound 1,1,1-trifluoro-N-phenyl-N-((trifluoromethyl)sulfonyl)methanesulfonamide (408 mg, 1.14 mmol) were added to the reaction solution. The reaction solution was stirred at room temperature for 1 h. After the reaction was found to be completed from the monitoring of TLC (petroleum ether/ethyl acetate=5/1, $R_{f3}$=0.1, $R_{f4}$=0.5), the reaction solution was poured into water (100 mL), and extraction with ethyl acetate (50 mL*2) was carried out. The organic phases were combined, washed with a saturated NaCl solution (100 mL*2), dried with anhydrous sodium sulfate, filtrated, and rotary evaporated to obtain a crude product. The crude product was purified by a rapid column machine (petroleum ether:ethyl acetate=20/1~5/1) to obtain 280 mg (with a purity of 75.0% and a two-step of yield of 63.3%) 3-cyano-6-propylaminopyrazolo[1,5-a]pyridine-4-trifluoromethanesulfonate. LCMS: m/z=348.9 $[M+1]^+$.

Step 4. Synthesis of (S)—N-((1-(6-(4-fluoro-1H-pyrazol-1-yl)pyridin-3-yl)ethyl)(methyl)amine)-pyridin-3-yl)-6-propylamino-pyrazolo[1,5-a]pyridine-3-carbonitrile 3-cyano-6-propylaminopyrazolo[1,5-a]pyridine-4-trifluoromethanesulfonate (280 mg, 0.603 mmol) was dissolved in a mixed solution of 1,4-dioxane (6 mL) and water (2 mL); then, (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (443 mg, 1.05 mmol), $Pd_2(dba)_3$ (160 mg, 0.17 mmol), X-Phos (333 mg, 0.70 mmol) and $Na_2CO_3$ (185 mg, 1.74 mmol) were added in turn at room temperature. After the reaction flask was replaced with $N_2$ three times, the reaction solution was heated to 85° C. under the protection of $N_2$ and stirred for 12 h. After the reaction was found to be completed from the monitoring of TLC (petroleum ether/ethyl acetate=3/1, $R_{f4}$=0.7, $R_{f7}$=0.3) and LCMS, the reaction solution was poured into water (100 mL), and then extraction with ethyl acetate (50 mL*3) was carried out. The organic phases were combined, washed with a saturated NaCl solution (100 mL*2), dried with anhydrous sodium sulfate, filtrated, and rotary evaporated to obtain a crude product. The crude product was purified by a rapid column machine (petroleum ether:ethyl acetate=10/1~2/1) to obtain 80 mg of (S)—N-((1-(6-(4-fluoro-1H-pyrazol-1-yl)pyridin-3-yl)ethyl)(methyl)amine)-pyridin-3-yl)-6-propylamino-pyrazolo[1,5-a]pyridine-3-carbonitrile (compound 60) (with a yield of 26.8% and a purity of 93.45%). MS: m/z=496.1 $[M+1]^+$. $^1$HNMR (400 MHz, DMSO-$d_6$) δ: 8.71 (d, J=16.0 Hz, 1H), 8.41-8.32 (m, 3H), 7.93-7.88 (m, 4H), 7.77-7.74 (m, 1H), 6.83 (d, J=8.00 Hz, 1H), 6.31-6.26 (m, 1H), 3.00 (t, J=8.00 Hz, 2H), 2.82 (s, 3H), 1.86-1.58 (m, 5H), 0.97 (t, J=8.00 Hz, 3H).

Example 61: Preparation of (S)-4-(6-((1-(6-(4-fluoro-1H-pyrazol-1-yl)pyridin-3-yl)ethyl)(methyl)amino)pyridine-3-yl)-6-(2-hydroxy-2-methylpropoxy)pyrazolo[1,5-a]pyridine-3-carbonitrile

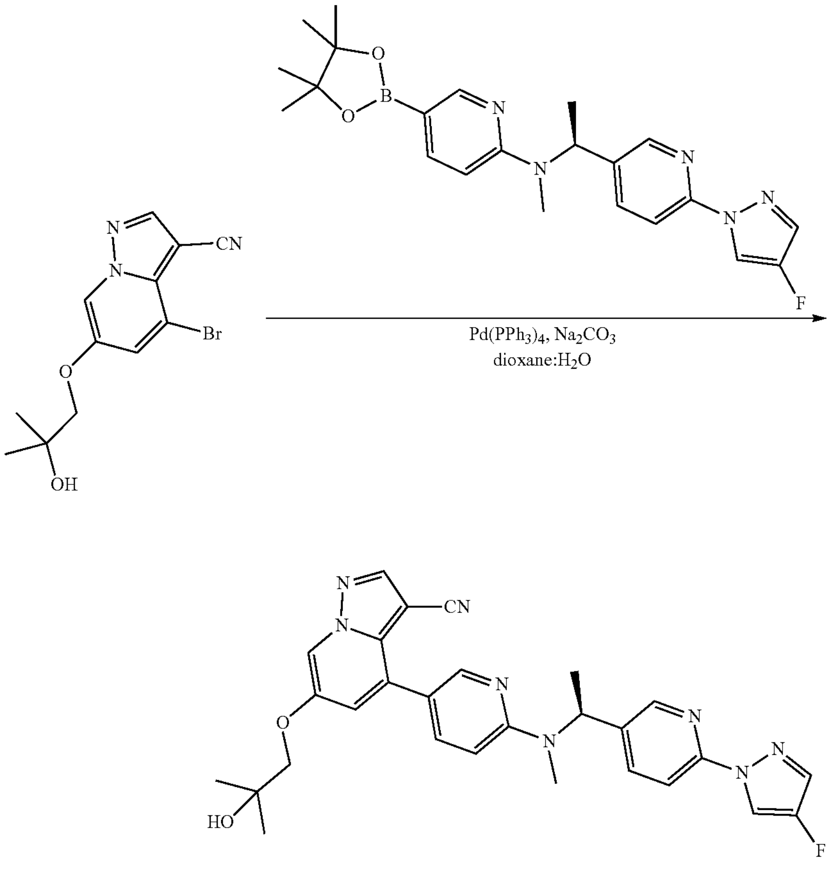

Step 1: Synthesis of (S)-4-(6-((1-(6-(4-fluoro-1H-pyrazol-1-yl)pyridin-3-yl)ethyl)(methyl)amino)pyridine-3-yl)-6-(2-hydroxy-2-methylpropoxy)pyrazolo[1,5-a]pyridine-3-carbonitrile 4-bromo-6-(2-hydroxy-2-methylpropoxy)pyrazolo[1,5-a]pyridine-3-carbonitrile (200 mg, 0.65 mmol), sodium carbonate (205 mg, 1.93 mmol), (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (409 mg, 0.97 mmol) and tetrakis(triphenylphosphine)palladium (115 mg, 0.1 mmol) were dissolved in dioxane:water (15 mL:5 mL). The mixed solution reacted at 90° C. for 6 h. After the reaction was found to be completed from the monitoring, the reaction solution was cooled, and water was added to quench the reaction, extraction with EA (20 mL*3) was then carried out, and the organic phase was washed with water and then dried, concentrated and subjected to column chromatography to obtain 50 mg of (S)-4-(6-((1-(6-(4-fluoro-1H-pyrazol-1-yl)pyridin-3-yl)ethyl)(methyl)amino)pyridine-3-yl)-6-(2-hydroxy-2-methylpropoxy)pyrazolo[1,5-a]pyridine-3-carbonitrile (compound 61). MS m/z (ESI): 527.3 $[M+H]^+$. $^1H$ NMR (400 MHz, DMSO) δ 8.70-8.61 (m, 2H), 8.57 (s, 1H), 8.38 (dd, J=8.0, 2.3 Hz, 2H), 7.84 (ddd, J=12.8, 11.4, 3.4 Hz, 4H), 7.31 (d, J=2.0 Hz, 1H), 6.81 (d, J=8.9 Hz, 1H), 6.29 (d, J=6.9 Hz, 1H), 3.86 (s, 2H), 2.81 (s, 3H), 1.60 (d, J=7.0 Hz, 3H), 1.21 (s, 6H).

Example 62: Preparation of (S)-6-(2-hydroxy-2-methylpropoxy)-4-(6-(methyl(1-(6-(pyrrolidin-1-yl)pyridin-3-yl)ethyl)yl)amino)pyridin-3-yl)pyrazolo[1,5-a]pyridine-3-carbonitrile

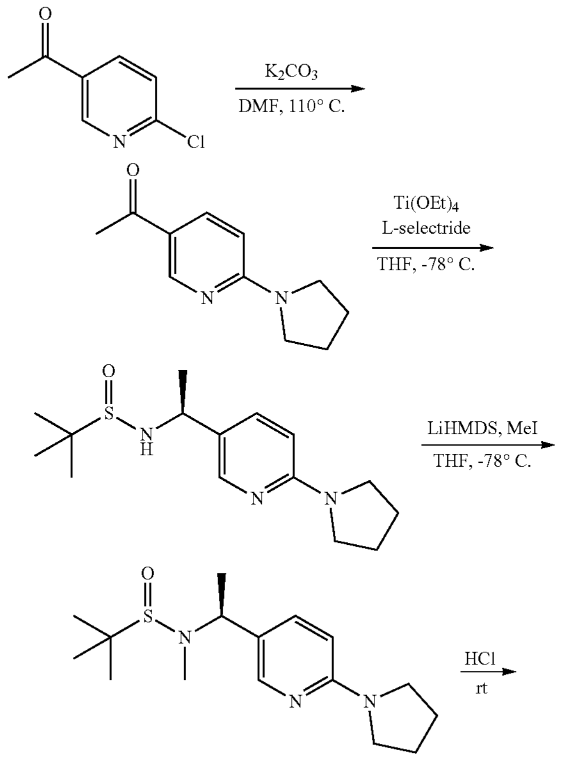

-continued

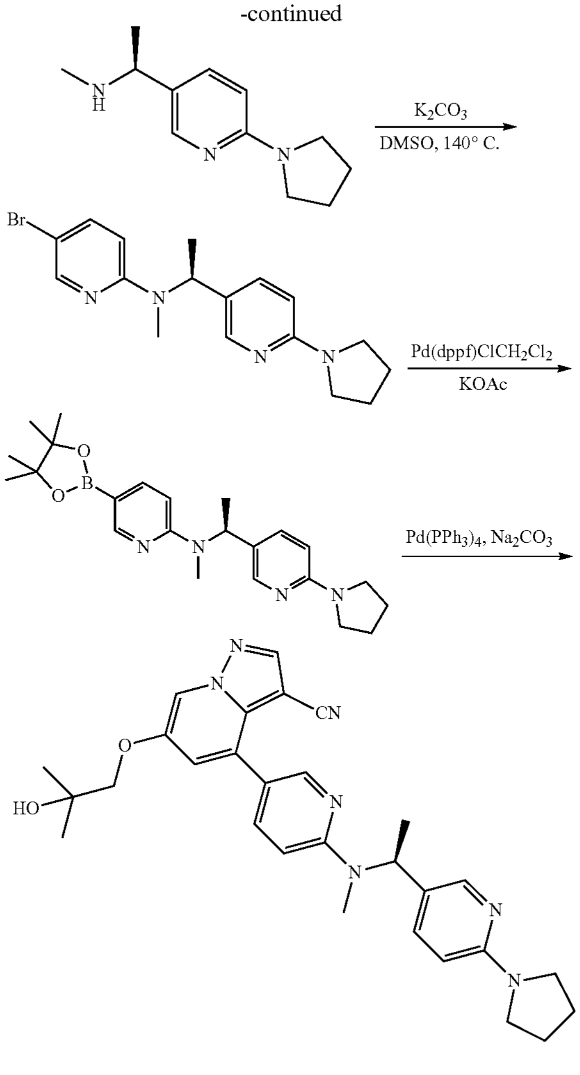

Step 1: Synthesis of 1-(6-(pyrrolidin-1-yl)pyridin-3-yl)ethan-1-one

At room temperature, 2-chloro-5-acetylpyridine (2.0 g, 12.9 mmol), tetrahydropyrrole (2.7 g, 38.7 mmol) and $K_2CO_3$ (3.6 g, 25.8 mmol) were dissolved in DMF (20 mL), and the mixed solution was stirred at 80° C. overnight. After the reaction was completed, the reaction solution was cooled to room temperature, and quenched with water (20 mL). Extraction was carried out, and the organic phase was dried, filtered, concentrated and subjected to column chromatography to obtain 1.8 g of 1-(6-(pyrrolidin-1-yl)pyridin-3-yl)ethan-1-one. MS m/z (ESI): 191.4 $[M+H]^+$.

Step 2: Synthesis of 2-methyl-N-((S)-1-(6-(pyrrolidin-1-yl)pyridin-3-yl)ethyl)propane-2-sulfinamide At room temperature, (R)-2-methylpropane-2-sulfonimide (1.2 g, 9.4 mmol) and 1-(6-(pyrrolidin-1-yl)pyridin-3-yl)ethan-1-one (1.8 g, 9.4 mmol) and THF (20 mL) were added to the reaction flask, and tetraethyl titanate (4.3 g, 18.8 mmol) was added dropwise. After addition was completed, the reaction solution was heated to 75° C. to react for 16 h, then it was cooled to −78° C. Next, L-selectride (18.8 mL, 18.8 mmol) was slowly added dropwise. After addition was completed, the reaction solution was warmed to room temperature to react for 15 min, then methanol was added at −50° C. to quench the reaction. The reaction solution was stirred adequacy with water (20 mL) and EA (60 mL), extracted, dried with anhydrous sodium sulfate, filtrated, concentrated to obtain a crude product, and the crude product was purified by column chromatography to obtain 2.0 g of 2-methyl-N-((S)-1-(6-(pyrrolidin-1-yl)pyridin-3-yl)ethyl)propane-2-sulfinamide. MS m/z (ESI): 296.1 $[M+H]^+$.

Step 3: Synthesis of N,2-dimethyl-N-((S)-1-(6-(pyrrolidin-1-yl)pyridin-3-yl)ethyl)propane-2-sulfinamide 2-methyl-N-((S)-1-(6-(pyrrolidin-1-yl)pyridin-3-yl)ethyl)propane-2-sulfinamide (2.0 g, 6.75 mmol) was dissolved in THF (20 mL), and the mixed solution was cooled to −78° C., and then lithium bistrimethylsilylamide (8.25 mmol) was slowly added dropwise to the reaction system. The reaction solution was stirred at low temperature for 0.5 h, and then MeI (1.17 g, 8.25 mmol) was slowly added dropwise. The reaction was carried out at −78° C. for 1 h, and water (30 mL) was added to quench the reaction, extraction was carried out, and the organic phase was dried, filtered, concentrated and subjected to column chromatography to obtain 1.5 g of N,2-dimethyl-N-((S)-1-(6-(pyrrolidin-1-yl)pyridin-3-yl)ethyl)propane-2-sulfinamide. MS m/z (ESI): 310.2 $[M+H]^+$.

Step 4: Synthesis of (S)—N-methyl-1-(6-(pyrrolidin-1-yl)pyridin-3-yl)ethan-1-amine At room temperature, N,2-dimethyl-N-((S)-1-(6-(pyrrolidin-1-yl)pyridin-3-yl)ethyl)propane-2-sulfinamide (1.5 g, 4.8 mmol) was dissolved in MeOH (2 mL), HCl/dioxane (6 mL, 4M) was then added, and the mixed solution reacted at room temperature for 1 h. The resulting reaction solution was concentrated in vacuum under reduced pressure to remove the solvent. The reaction was quenched with $NaHCO_3$ solution, and the reaction solution was extracted, dried, filtered, concentrated, and subjected to column chromatography to obtain 0.8 g of (S)—N-methyl-1-(6-(pyrrolidin-1-yl)pyridin-3-yl)ethan-1-amine. MS m/z (ESI): 206.3 $[M+H]^+$.

Step 5: Synthesis of (S)-5-bromo-N-methyl-N-(1-(6-(pyrrolidin-1-yl)pyridin-3-yl)ethyl)pyridin-2-amine At room temperature, (S)—N-methyl-1-(6-(pyrrolidin-1-yl)pyridin-3-yl)ethan-1-amine (0.8 g, 3.8 mmol), 5-bromo-2-fluoropyridine (3.4 g, 19 mmol) and $K_2CO_3$ (1.6 g, 11.4 mmol) were dissolved in DMSO (10 mL). The mixed solution reacted at 140° C. for 24 h, and then cooled to room temperature. The reaction solution was diluted with water, extracted, and the organic phase was dried, filtered, concentrated and subjected to column chromatography to obtain 0.7 g of (S)-5-bromo-N-methyl-N-(1-(6-(pyrrolidin-1-yl)pyridin-3-yl)ethyl)pyridin-2-amine. MS m/z (ESI): 362 $[M+H]^+$.

Step 6: Synthesis of (S)—N-methyl-N-(1-(6-(pyrrolidin-1-yl)pyridin-3-yl)ethyl)-5-(4,4,5,5-tetramethyl-1,3,2-dioxaborolane-2-yl)pyridin-2-amine (S)-5-bromo-N-methyl-N-(1-(6-(pyrrolidin-1-yl)pyridin-3-yl)ethyl)pyridin-2-amine (0.7 g, 1.9 mmol), pinacol biborate (0.74 g, 2.9 mmol), $Pd(dppf)ClCH_2Cl_2$ (155 mg, 0.19 mmol) and KOAc (559 mg, 5.7 mmol) were dissolved in dioxane (15 mL), and the mixed solution reacted at 90° C. for 6 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.4 g of (S)—N-methyl-N-(1-(6-(pyrrolidin-1-yl)pyridin-3-yl)ethyl)-5-(4,4,5,5-tetramethyl-1,3,2-dioxaborolane-2-yl)pyridin-2-amine. MS m/z (ESI): 409.2 $[M+H]^+$.

Step 7: Synthesis of (S)-6-(2-hydroxy-2-methylpropoxy)-4-(6-(methyl(1-(6-(pyrrolidin-1-yl)pyridin-3-yl)ethyl)yl)amino)pyridin-3-yl)pyrazolo[1,5-a]pyridine-3-carbonitrile At room temperature, and under the protection of $N_2$, 4-bromo-6-(2-hydroxy-2-methylpropoxy)pyrazolo[1,5-a]pyridine-3-carbonitrile (200 mg, 0.65 mmol), (S)—N-methyl-N-(1-(6-(pyrrolidin-1-yl)pyridin-3-yl)ethyl)-5-(4,4,5,5-tetramethyl-1,3,2-dioxaborolane-2-yl)pyridin-2-amine (400 mg, 0.97 mmol), $Pd(PPh_3)_4$ (76 mg, 0.065 mmol) and $Na_2CO_3$ (207 mg, 1.95 mmol) were dissolved in 1,4-dioxane:$H_2O$=5:1 (12 mL). The mixed solution was stirred at 90° C. for 8 h to react. The reaction solution was cooled to room temperature, and water was added to quench the reaction, extraction was carried out, and the organic phase was washed with water and then dried, and subjected to column chromatography to obtain 80 mg of (S)-6-(2-hydroxy-2-methylpropoxy)-4-(6-(methyl(1-(6-(pyrrolidin-1-yl)pyridin-3-yl)ethyl)yl)amino)pyridin-3-yl) pyrazolo[1,5-a]pyridine-3-carbonitrile (compound 62). $^1H$ NMR (300 MHz, DMSO) δ 8.64 (d, J=1.9 Hz, 1H), 8.56 (s, 1H), 8.35 (d, J=2.3 Hz, 1H), 8.01 (d, J=2.1 Hz, 1H), 7.76 (dd, J=8.8, 2.5 Hz, 1H), 7.38 (dd, J=8.7, 2.3 Hz, 1H), 7.29 (d, J=1.9 Hz, 1H), 6.75 (d, J=8.9 Hz, 1H), 6.37 (d, J=8.7 Hz, 1H), 6.07 (d, J=6.8 Hz, 1H), 3.86 (s, 2H), 3.32 (d, J=6.3 Hz, 4H), 2.71 (s, 3H), 1.90 (t, J=6.4 Hz, 4H), 1.47 (d, J=6.9 Hz, 3H), 1.21 (s, 6H).

Example 63: Preparation of (S)-6-(2-hydroxy-2-methylpropoxy)-4-(6-(methyl(1-(6-(6-methylpyridin-3-yl)ethyl)amino)pyridin-3-yl)pyrazolo[1,5-a]pyridine-3-carbonitrile

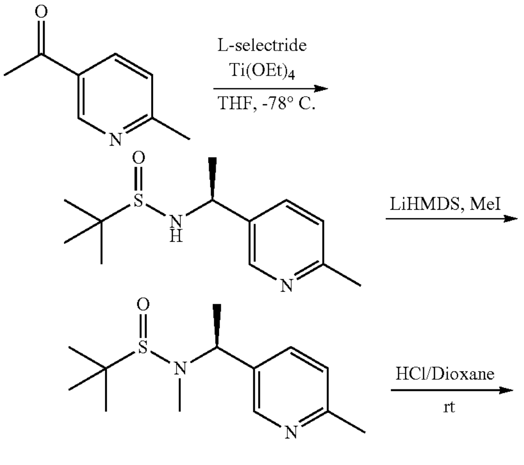

-continued

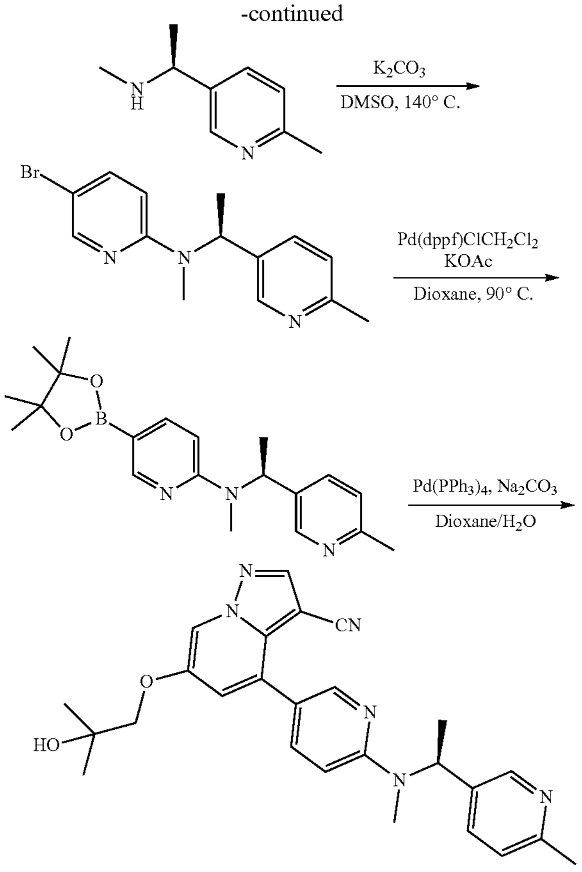

Step 1: Synthesis of 2-methyl-N-((S)-1-(6-methylpyridin-3-yl)ethyl)propane-2-sulfinamide At room temperature, (R)-2-methylpropane-2-sulfonimide (1.8 g, 14.8 mmol), 2-methyl-5-acetylpyridine (2.0 g, 14.8 mmol) and THF (20 mL) were added to the reaction flask, and tetraethyl titanate (6.7 g, 29.6 mmol) was added dropwise. After addition was completed, the reaction solution was heated to 75° C. to react for 16 h, then it was cooled to −78° C. Next, L-selectride (30 mL, 29.6 mmol) was slowly added dropwise. After addition was completed, the reaction solution was warmed to room temperature to react for 15 min, then methanol was added at −50° C. to quench the reaction. The reaction solution was stirred adequacy with water (20 mL) and EA (60 mL), extracted, dried with anhydrous sodium sulfate, filtrated, concentrated to obtain a crude product, and the crude product was purified by column chromatography to obtain 2.6 g of 2-methyl-N-((S)-1-(6-methylpyridin-3-yl)ethyl)propane-2-sulfinamide. MS m/z (ESI): 241.1 $[M+H]^+$.

Step 2: Synthesis of N,2-dimethyl-N-((S)-1-(6-methylpyridin-3-yl)ethyl)propane-2-sulfinamide 2-methyl-N-((S)-1-(6-methylpyridin-3-yl)ethyl)propane-2-sulfinamide (2.6 g, 10.8 mmol) was dissolved in THF (20 mL), and the mixed solution was cooled to −78° C., and then lithium bistrimethylsilylamide (10.8 mmol) was slowly added dropwise. The reaction solution was stirred at low temperature for 0.5 h, and then MeI (1.5 g, 10.8 mmol) was slowly added dropwise. The reaction was carried out at −78° C. for 1 h, and water (30 mL) was added to quench the reaction, extraction was carried out, and the organic phase was dried, filtered, concentrated and subjected to column chromatography to obtain 2.0 g of N,2-dimethyl-N-((S)-1-(6-methylpyridin-3-yl)ethyl)propane-2-sulfinamide. MS m/z (ESI): 255.2 $[M+H]^+$.

Step 3: Synthesis of (S)—N-methyl-1-(6-methylpyridin-3-yl)ethan-1-amine

At room temperature, N,2-dimethyl-N-((S)-1-(6-methylpyridin-3-yl)ethyl)propane-2-sulfinamide (2.0 g, 7.8 mmol) was dissolved in MeOH (4 mL), and then HCl/dioxane (6 mL, 4M) was added, and the mixed solution reacted at room temperature for 1 h. The resulting reaction solution was concentrated in vacuum under reduced pressure to remove the solvent. The reaction was quenched with $NaHCO_3$ solution, and the reaction solution was extracted, dried, filtered, concentrated, and subjected to column chromatography to obtain 1.2 g of (S)—N-methyl-1-(6-methylpyridin-3-yl)ethan-1-amine. MS m/z (ESI): 151.3 $[M+H]^+$.

Step 4: Synthesis of (S)-5-bromo-N-methyl-N-(1-(6-methylpyridin-3-yl)ethyl)pyridin-2-amine (S)—N-methyl-1-(6-methylpyridin-3-yl)ethan-1-amine (1.2 g, 7.9 mmol), 5-bromo-2-fluoropyridine (6.9 g, 40 mmol) and $K_2CO_3$ (3.2 g, 23.7 mmol) were dissolved in DMSO (20 mL). The mixed solution reacted at 140° C. for 24 h, and then cooled to room temperature. The reaction solution was diluted with water, extracted, and the organic phase was dried, filtered, concentrated and subjected to column chromatography to obtain 1.0 g of (S)-5-bromo-N-methyl-N-(1-(6-methylpyridin-3-yl)ethyl)pyridin-2-amine. MS m/z (ESI): 306.5 $[M+H]^+$.

Step 5: Synthesis of (S)—N-methyl-N-(1-(6-methylpyridin-3-yl)ethyl)-5-(4,4,5,5-tetramethyl-1,3,2-Dioxaborolane-2-yl)pyridin-2-amine At room temperature, (S)-5-bromo-N-methyl-N-(1-(6-methylpyridin-3-yl)ethyl)pyridin-2-amine (1.0 g, 3.3 mmol), pinacol biborate (1.3 g, 4.9 mmol), Pd(dppf)$ClCH_2Cl_2$ (266 mg, 0.33 mmol) and KOAc (970 mg, 9.9 mmol) were dissolved in dioxane (15 mL), and the mixed solution reacted at 90° C. for 6 h. The resulting reaction solution was concentrated in vacuum under reduced pressure to remove the solvent. The reaction solution was diluted with $NaHCO_3$, extracted, dried, filtered, concentrated, and subjected to column chromatography to obtain 0.6 g of (S)—N-methyl-N-(1-(6-methylpyridin-3-yl)ethyl)-5-(4,4,5,5-tetramethyl-1,3,2-dioxaborolane-2-yl)pyridin-2-amine. MS m/z (ESI): 354.2 $[M+H]^+$.

Step 6: Synthesis of (S)-6-(2-hydroxy-2-methylpropoxy)-4-(6-(methyl(1-(6-(6-methylpyridin-3-yl)ethyl)amino)pyridin-3-yl)pyrazolo[1,5-a]pyridine-3-carbonitrile At room temperature, and under the protection of $N_2$, 4-bromo-6-(2-hydroxy-2-methylpropoxy)pyrazolo[1,5-a]pyridine-3-carbonitrile (200 mg, 0.65 mmol), (S)—N-methyl-N-(1-(6-methylpyridin-3-yl)ethyl)-5-(4,4,5,5-tetramethyl-1,3,2-dioxaborolane-2-yl)pyridin-2-amine (360 mg, 0.97 mmol), $Pd(PPh_3)_4$ (76 mg, 0.065 mmol) and $Na_2CO_3$ (207 mg, 1.95 mmol) were dissolved in 1,4-dioxane:$H_2O$=5:1 (12 mL). The mixed solution was stirred at 90° C. for 8 h to react. The reaction solution was cooled to room temperature, and water was added to quench the reaction, extraction was carried out, and the organic phase was washed with water and then dried, and subjected to column chromatography to obtain 100 mg of (S)-6-(2-hydroxy-2-methylpropoxy)-4-(6-(methyl(1-(6-(6-methylpyridin-3-yl)ethyl)amino)pyridin-3-yl)pyrazolo[1,5-a]pyridine-3-carbonitrile (compound 63). MS m/z (ESI): 457.2 $[M+H]^+$. $^1H$ NMR (300 MHz, DMSO) δ 8.66 (d, J=2.0 Hz, 1H), 8.57 (s, 1H), 8.37 (dd, J=7.0, 2.2 Hz, 2H), 7.79 (dd, J=8.8, 2.5 Hz, 1H), 7.58 (dd, J=8.0, 2.3 Hz, 1H), 7.30 (d, J=2.0 Hz, 1H), 7.20 (d, J=8.0 Hz, 1H), 6.78 (d, J=8.8 Hz, 1H), 6.20 (q, J=6.8 Hz, 1H), 3.86 (s, 2H), 2.76 (s, 3H), 2.43 (s, 3H), 1.55 (d, J=7.0 Hz, 3H), 1.21 (s, 6H).

Example 64: N-(5-(3-cyano-6-(2-hydroxy-2-methylpropoxy)pyrazolo[1,5-a]pyridin-4-yl)pyridin-2-yl)-N-methyl-6-(pyrrolidone-1-yl)nicotinamide

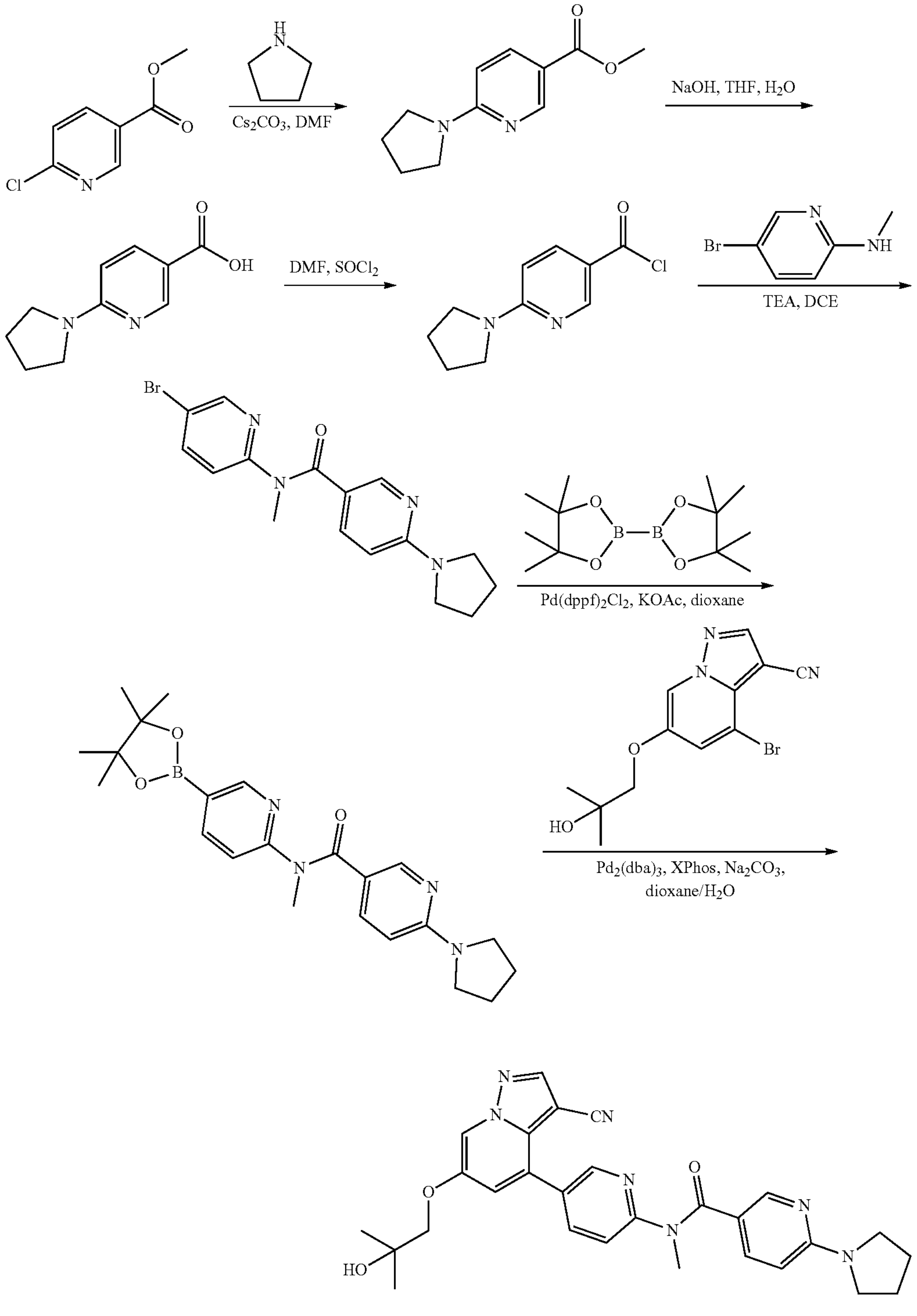

Step 1: Synthesis of methyl 6-(pyrrolidin-1-yl)nicotinate

Methyl 6-chloronicotinate (2 g, 11.66 mmol), pyrrolidine (1.95 mL, 23.31 mmol) and cesium carbonate (11 g, 34.97 mmol) were dissolved in 20 mL of DMF. The reaction solution was stirred at 65° C. overnight. After the reaction was found to be completed from the monitoring, water was added to quench the reaction. Extraction with dichloromethane was carried out, and the organic phase was washed, dried, concentrated, and subjected to column chromatography to obtain 2.4 g of methyl 6-(pyrrolidin-1-yl)nicotinate with a yield of 99.85%. MS m/z (ESI): 207.1 $[M+H]^+$.

Step 2: Synthesis of 6-(pyrrolidin-1-yl)nicotinic acid

Methyl 6-(pyrrolidin-1-yl)nicotinate (2.4 g, 11.64 mmol) was dissolved in THF (12 mL) and water (12 mL), and then sodium hydroxide (1.4 g, 34.92 mmol) was added. The reaction solution was stirred at room temperature overnight. After the reaction was found to be completed from the monitoring, the reaction solution was concentrated. Water and concentrated hydrochloric acid were added to adjust pH to neutrality or slight acidity, and then filtrated to obtain 1.6 g of 6-(pyrrolidin-1-yl)nicotinic acid with a yield of 71.51%. MS m/z (ESI): 191.0 $[M-H]^-$.

Step 3: Synthesis of 6-(pyrrolidin-1-yl)nicotinyl chloride 6-(pyrrolidin-1-yl)nicotinic acid (0.6 g, 3.12 mmol) was dissolved in $SOCl_2$ (10 mL); then, 2 drops of DMF was added. The reaction solution was reflexed at 85° C. for 2 h. After the reaction was found to be completed from the monitoring, the reaction solution was concentrated to obtain a crude product, and the product was directly used in the next step.

Step 4: Synthesis of N-(5-bromopyridin-2-yl)-N-methyl-6-(pyrrolidin-1-yl)nicotinamide Under the protection of $N_2$, 5-bromo-N-methylpyridin-2-amine (0.35 g, 1.87 mmol) were dissolved in DME (4 mL); then, TEA (0.78 mL, 5.61 mmol) was added, and the crude product obtained from the previous step was added at 0° C. The mixed solution was stirred at 70° C. overnight. After the reaction was found to be completed from the monitoring, an appropriate amount of water was then added, extraction with ethyl acetate was then carried out. The organic phase was dried, concentrated, and column chromatography and separation were carried out to obtain 0.52 g of N-(5-bromopyridin-2-yl)-N-methyl-6-(pyrrolidin-1-yl)nicotinamide with a yield of 76.93%. MS m/z (ESI): 360.9 $[M+H]^+$.

Step 5: Synthesis of N-methyl-6-(pyrrolidin-1-yl)-N-(5-(4,4,5,5-tetramethyl-1,3,2-dioxaborolane-2-yl)pyridin-2-yl)nicotinamide Under the protection of $N_2$, N-(5-bromopyridin-2-yl)-N-methyl-6-(pyrrolidin-1-yl)nicotinamide (0.3 g, 0.83 mmol), biboron pinacol ester (0.42 g, 1.66 mmol), potassium acetate (0.25 g, 2.49 mmol) and [1,1'-bis(diphenylphosphino)ferrocene]dichloropalladium dichloromethane complex (69 mg, 0.08 mmol) were dissolved in dioxane (5 mL). The mixed solution was stirred at 90° C. overnight. After the reaction was found to be completed from the monitoring, the reaction solution was cooled to room temperature, and an appropriate amount of water was added. Extraction with ethyl acetate was then carried out, and the organic phase was concentrated and then column chromatography and separation were carried out to obtain 0.20 g of N-methyl-6-(pyrrolidin-1-yl)-N-(5-(4,4,5,5-tetramethyl-1,3,2-dioxaborolane-2-yl)pyridin-2-yl)nicotinamide with a yield of 59%. MS m/z (ESI): 327.0 $[M+H]^+$.

Step 6: Synthesis of N-(5-(3-cyano-6-(2-hydroxy-2-methylpropoxy)pyrazolo[1,5-a]pyridin-4-yl)pyridin-2-yl)-N-methyl-6-(pyrrolidone-1-yl)nicotinamide Under the protection of $N_2$, N-methyl-6-(pyrrolidin-1-yl)-N-(5-(4,4,5,5-tetramethyl-1,3,2-dioxaborolane-2-yl)pyridin-2-yl)nicotinamide (60 mg, 0.15 mmol), 4-bromo-6-(2-hydroxy-2-methylpropoxy)pyrazolo[1,5-a]pyridine-3-carbonitrile (55 mg, 0.18 mmol), $Pd_2(dba)_3$ (14 mg, 0.01 mmol), X-phos (14 mg, 0.03 mmol) and sodium carbonate (78 mg, 0.74 mmol) were dissolved in dioxane (3 mL) and water (1 mL), and the resulting reaction solution was stirred at 90° C. overnight until the reaction was found to be completed from the monitoring. After the reaction solution was cooled to room temperature, the reaction solution was concentrated, water was then added. Extraction with dichloromethane was carried out, and the organic phase was washed with water, and then dried, concentrated, and subjected to column chromatography to obtain 16 mg of N-(5-(3-cyano-6-(2-hydroxy-2-methylpropoxy)pyrazolo[1,5-a]pyridin-4-yl)pyridin-2-yl)-N-methyl-6-(pyrrolidone-1-yl)nicotinamide (compound 64) with a yield of 21%. MS m/z (ESI): 512.1 $[M+H]^+$. $^1H$ NMR (500 MHz, DMSO) δ 8.75 (d, J=2.1 Hz, 1H), 8.64 (d, J=2.5 Hz, 1H), 8.59 (s, 1H), 8.19 (d, J=2.0 Hz, 1H), 7.93 (dd, J=8.3, 2.5 Hz, 1H), 7.42 (d, J=2.0 Hz, 1H), 7.26 (t, J=9.2 Hz, 2H), 6.24 (d, J=9.0 Hz, 1H), 4.70 (s, 1H), 3.87 (s, 2H), 3.47 (s, 3H), 3.36 (s, 4H), 1.90 (s, 4H), 1.22 (s, 6H).

Example 65: Preparation of (S)—N-((1-(6-(4-fluoro-1H-pyrazol-1-yl)pyridin-3-yl)ethyl)methylamine)-pyridin-3-yl)-6-ethynyl-pyrazolo[1,5-a]pyridine-3-carbonitrile

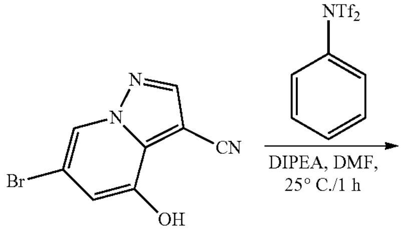

-continued

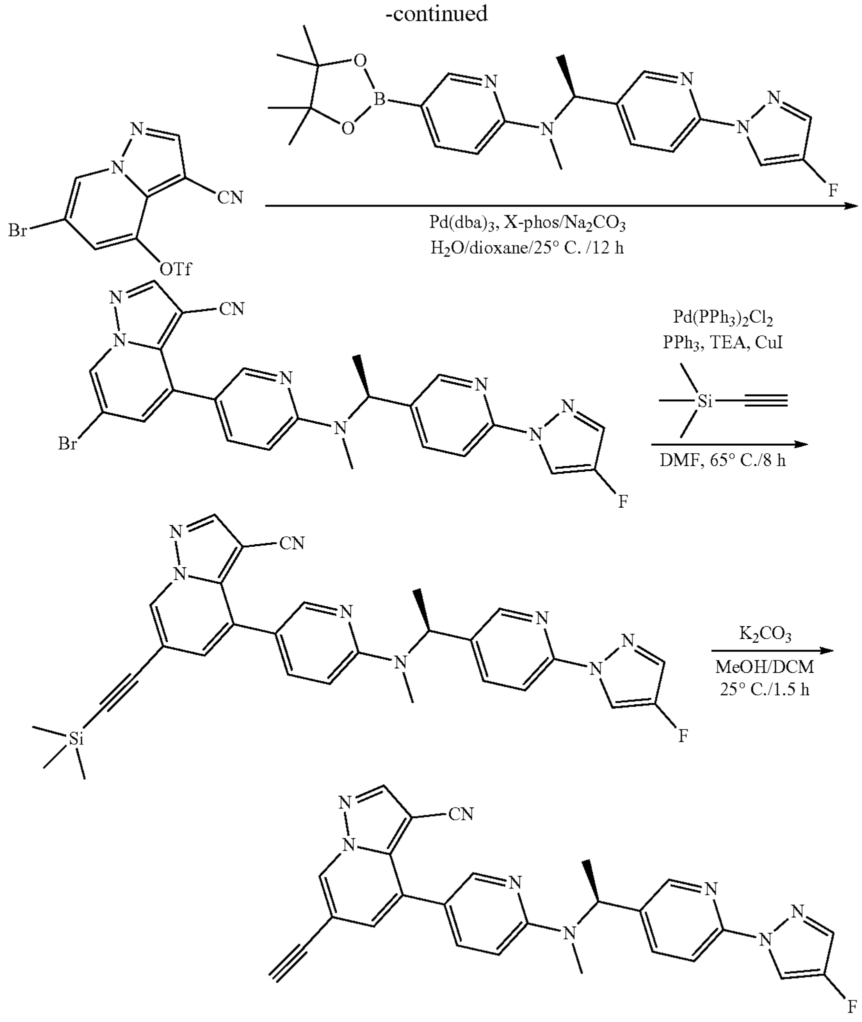

Step 1. Synthesis of 6-bromo-3-cyanopyrazolo[1,5-a]pyridine-4-trifluoromethanesulfonate At room temperature, 6-bromo-4-hydroxypyrazolo[1,5-a]pyridine-3-carbonitrile (1.00 g, 4.20 mmol) was dissolved in DMF (10.0 mL), and then DIPEA (1.46 mL, 8.40 mmol) and 1,1,1-trifluoro-N-phenyl-N-(trifluoromethylsulfonyl)methanesulfonamide (1.80 g, 5.04 mmol) were added in turn while stirring. The reaction solution was stirred at room temperature for 1 h. After the reaction was found to be completed from the monitoring of TLC (petroleum ether/ethyl acetate=10/1, $R_{f\ T1}$=0.25, $R_{f\ T2}$=0.4), the reaction solution was poured into 100 mL of water, and extraction with ethyl acetate (50 mL*3) was carried out. The organic phases were combined, washed with a saturated NaCl solution (50 mL*2), dried with anhydrous sodium sulfate, filtrated, and rotary evaporated to obtain a crude product. The crude product was purified by a rapid column machine (petroleum ether:ethyl acetate=100/1~10/1) to obtain 6-bromo-3-cyanopyrazolo[1,5-a]pyridine-4-trifluoromethanesulfonate (1.13 g, 3.05 mmol, with a yield of 72.7%). MS m/z: 370.0 $[M+1]^+$.

Step 2. Synthesis of (S)-6-bromo-N-((1-(6-(4-fluoro-1H-pyrazol-1-yl)pyridin-3-yl)ethyl)(methyl)amine)-pyridine-3-yl)pyrazolo[1,5-a]pyridine-3-carbonitrile At room temperature, 6-bromo-3-cyanopyrazolo[1,5-a]pyridine-4-trifluoromethanesulfonate (400 mg, 1.08 mmol) was dissolved in a mixed solution of 1,4-dioxane (8 mL) and water (0.8 mL), and then (S)—N-(1-(6-(4-fluoro-1H-pyrazol-1-yl)pyridin-3-yl)ethyl)-N-methyl-5-(4,4,5,5-tetramethyl-1,3,2-dioxaborolane-2-yl)pyridin-2-amine (503 mg, 1.19 mmol), $Pd_2(dba)_3$ (18 mg, 0.216 mmol), X-Phos (412 mg, 0.864 mmol) and $Na_2CO_3$ (229 mg, 2.16 mmol) were added in turn. After the reaction flask was replaced with $N_2$ three times, the reaction solution was stirred at room temperature for 12 h under the protection of $N_2$. After the reaction was found to be completed from the monitoring of TLC (petroleum ether/ethyl acetate=3/1, $R_{fT2}$=0.65, $R_{fT3}$=0.4) and LCMS, the reaction solution was poured into water (100 mL), and then extraction with ethyl acetate (50 mL*2) was carried out. The organic phases were combined, washed with a saturated NaCl solution (50 mL*2), dried with anhydrous sodium sulfate, filtrated, and rotary evaporated to obtain a crude product. The crude product was purified by a rapid column machine (petroleum ether:ethyl acetate=10/1~3/1) to obtain 128 mg (22.9%) of (S)-6-bromo-N-((1-(6-(4-fluoro-1H-pyrazol-1-yl)pyridin-3-yl)ethyl)(methyl)amine)-pyridine-3-yl)pyrazolo[1,5-a]pyridine-3-carbonitrile. MS m/z: 517.0 $[M+1]^+$.

Step 3. Synthesis of (S)—N-((1-(6-(4-fluoro-1H-pyrazol-1-yl)pyridin-3-yl)ethyl)methylamine)-pyridin-3-yl)-6-((trimethylsilyl)ethynyl)-pyrazolo[1,5-a]pyridine-3-carbonitrile At room temperature, compound (S)-6-bromo-N-((1-(6-(4-fluoro-1H-pyrazol-1-yl)pyridin-3-yl)ethyl)methylamine)-pyridin-3-yl)pyrazolo[1,5-a]pyridine-3-carbonitrile (400 mg, 1.08 mmol) was dissolved in DMF (2.00 mL), and then compound trimethylsilylacetylene (49 mg, 70 μL, 0.494 mmol), $Pd(PPh_3)_2Cl_2$ (17.3 mg, 0.025 mmol), $PPh_3$ (3.24 mg, 0.012 mmol) and TEA (75 mg, 103 μL, 0.74 mmol) were added in turn. After the reaction flask was replaced with $N_2$ three times, the reaction solution was heated to 65° C. and stirred for 3 h under the protection of $N_2$. After the reaction was found to be completed from the monitoring of TLC (petroleum ether/ethyl acetate=5/1, $R_{fT3}$=0.3, $R_{fT4}$=0.4) and LCMS, the reaction solution was poured into water (50 mL), and then extraction with ethyl acetate (30 mL*2) was carried out. The organic phases were combined, washed with a saturated NaCl solution (30 mL*2), dried with anhydrous sodium sulfate, filtrated, and rotary evaporated to obtain a crude product. The crude product was purified by a rapid column machine to obtain 109 mg (82.4%) of (S)—N-((1-(6-(4-fluoro-1H-pyrazol-1-yl)pyridin-3-yl)ethyl)methylamine)-pyridin-3-yl)-6-((trimethylsilyl)ethynyl)-pyrazolo[1,5-a]pyridine-3-carbonitrile. MS: m/z=535.1 $[M+1]^+$.

Step 4. Synthesis of (S)—N-((1-(6-(4-fluoro-1H-pyrazol-1-yl)pyridin-3-yl)ethyl)methylamine)-pyridin-3-yl)-6-ethynyl-pyrazolo[1,5-a]pyridine-3-carbonitrile At room temperature, (S)—N-((1-(6-(4-fluoro-1H-pyrazol-1-yl)pyridin-3-yl)ethyl)methylamine)-pyridin-3-yl)-6-((trimethylsilyl)ethynyl)-pyrazolo[1,5-a]pyridine-3-carbonitrile (109 mg, 0.203 mmol) was dissolved in DCM/MeOH (2/1, 5 mL), and then $K_2CO_3$ (10.0 mg, 0.073 mmol) was added. The reaction solution was stirred at room temperature for 2 h. After the reaction was found to be completed from the monitoring of TLC (petroleum ether/ethyl acetate=5/1, $R_{fT4}$=0.4, $R_{fT3}$=0.3) and LCMS, the reaction solution was spin-dried to obtain a crude product. The crude product was purified by a rapid column machine (petroleum ether:ethyl acetate=50/1~5/1) to obtain (S)—N-((1-(6-(4-fluoro-1H-pyrazol-1-yl)pyridin-3-yl)ethyl)methylamine)-pyridin-3-yl)-6-ethynyl-pyrazolo[1,5-a]pyridine-3-carbonitrile (compound 65) (89 mg, 0.192 mmol; with a purity of 96.96% and a yield of 94.6%). MS m/z: 463.0 $[M+1]^+$. $^1$HNMR (400 MHz, DMSO-$d_6$) δ: 9.23 (d, J=1.08 Hz, 1H), 8.75 (s, 1H), 8.67-8.65 (m, 1H), 8.40-8.38 (m, 2H), 7.93-7.86 (m, 3H), 7.83-7.80 (m, 1H), 7.51 (d, J=4.00 Hz, 1H), 6.30-6.26 (m, 1H), 4.47 (s, 1H), 2.83 (s, 3H), 1.62 (d, J=8.00 Hz, 3H).

Example 66: Preparation of (S)—N-((1-(6-(4-fluoro-1H-pyrazol-1-yl)pyridin-3-yl)ethyl methylamine)-pyridin-3-yl-6-ethyl-pyrazolo[1,5-a]pyridine-3-carbonitrile

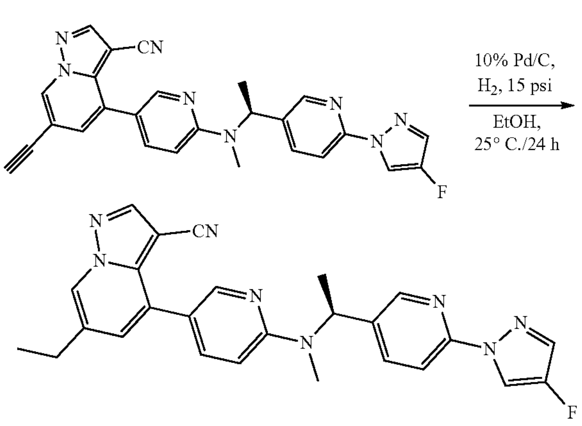

Step 1. Synthesis of (S)—N-((1-(6-(4-fluoro-1H-pyrazol-1-yl)pyridin-3-yl)ethyl)methylamine)-pyridin-3-yl)-6-ethyl-pyrazolo[1,5-a]pyridine-3-carbonitrile At room temperature, (S)—N-((1-(6-(4-fluoro-1H-pyrazol-1-yl)pyridin-3-yl)ethyl)methylamine)-pyridin-3-yl)-6-ethynyl-pyrazolo[1,5-a]pyridine-3-carbonitrile (70 mg, 0.151 mmol) was dissolved in EtOH (3.00 mL), and then 10% Pd/C (8 mg) was added. After the reaction system was replaced with $H_2$ (15 psi) three times, the reaction solution was stirred at room temperature in $H_2$ (15 psi) atmosphere for 24 h. After the reaction was found to be completed from the monitoring of LCMS and TLC (petroleum ether/ethyl acetate=4/1, $R_{fT4}$=0.5, $R_{f3}$=0.3), the reaction solution was filtrated with diatomite and washed with EtOH (20 mL*3). The filtrate was spin-dried to obtain a crude product. Then the crude product was purified by a rapid column machine (petroleum ether:ethyl acetate=50/1~5/1) to obtain (S)—N-((1-(6-(4-fluoro-1H-pyrazol-1-yl)pyridin-3-yl)ethyl)methylamine)-pyridin-3-yl)-6-ethyl-pyrazolo[1,5-a]pyridine-3-carbonitrile (compound 66) (13.4 mg, 0.029 mmol; with a purity of 98.6% and a yield of 19.0%). MS: m/z=467.1 $[M+1]^+$, $^1$HNMR (400 MHz, DMSO-$d_6$) δ: 8.77 (d, J=4.00 Hz, 1H), 8.66 (d, J=4.00 Hz, 3H), 8.61 (s, 1H), 8.40-8.37 (m, 2H), 7.93-7.86 (m, 3H), 7.82-7.79 (m, 1H), 7.46 (s, 2H), 2.83 (s, 3H), 2.74-2.70 (m, 2H), 2.02-1.95 (m, 1H), 1.28 (t, J=4.00 Hz, 3H).

Biological Activity Test Example 1

(a) In Vitro Screening Experiment-HTRF Method for Testing the Inhibitory Activity of Compounds Against RET Experimental Procedure:

1. Preparation of 1× kinase buffer: 5× enzyme buffer was mixed with distilled water at a ratio of 1:4, the final concentration: 5 mM $MgCl_2$; 1 mM dithiothreitol.

2. The test compound (5 mM stock solution) was diluted 5 folds to 1 mM with 100% dimethyl sulfoxide; the compound was diluted into 10 concentrations at an equal ratio of 1:3 in a 384-well dilution plate.

3. 0.2 μL of the serially diluted compound was added to a 384-well plate using an Echo 550 pipetting system, 2 replicate wells for each concentration, and the final concentration of dimethyl sulfoxide was 0.5% (v/v). The gradient concentrations of the test compound were 5000, 1666.7, 555.5, 185.18, 61.72, 20.57, 6.858, 2.286, 0.764, and 0.254 nM.

4. 2×RET (0.1 ng/μl) was prepared using the 1× kinase buffer.

5. 5 μL of 2×RET was added to a 384-well plate, and then centrifuged at 1000 g for 30 s, and incubated at room temperature for 10 min.

6. A mixed solution of 2× tyrosine kinase-biotinylated substrate (2 μM) and adenosine triphosphate (20 μM) was prepared using the 1× kinase buffer.

7. 5 μL of the mixed solution of tyrosine kinase-biotinylated substrate and adenosine triphosphate was added to start the reaction. The reaction solution was centrifuged at 1000 g for 30 s, and then sealed, and incubated at room temperature for 30 min.

8. A mixed solution of 2×Sa-XL 665 (a reagent) (125 μM) and a tyrosine kinase-antibody-cryptate was prepared using a homogeneous time-resolved fluorescence immunoassay buffer.

9. 10 μL of mixed solution of the Sa-XL 665 and the tyrosine kinase-antibody-cryptate was added to each well, and then centrifuged at 1000 g for 30 s, and incubated at room temperature for 1 h.

10. The plate was read at 615 nm and 665 nm on an Envision 2104 microplate reader and the ratio was calculated (665/615 nm).

11. The inhibition rate was calculated as follows:

$$\text{inhibition rate} = \left[1 - \frac{R1 - R2}{R0 - R2}\right] \times 100\%$$

wherein

R0 refers to the average ratio of the microplate reader plate of the vehicle blank group R1 refers to the ratio of the test compound on the microplate reader plate.

R2 refers to the average ratio on the microplate reader plate in the case of 100% inhibitory activity against RET.

$IC_{50}$ was calculated with software GraphPad 6.0 by fitting inhibition values and logarithms of compound concentrations to a nonlinear regression (dose response–variable slope).

(b) In Vitro Screening Experiment—HTRF Method for Testing the Inhibitory Activity of Compounds Against VEGFR2

Experimental Procedure:

1. Preparation of 1× kinase buffer: 5× enzyme buffer was mixed with distilled water at a ratio of 1:4, the final concentration: 5 mM $MgCl_2$; 1 mM dithiothreitol; 1 mM MnCl.

2. The test compound (5 mM stock solution) was diluted 5 folds to 1 mM with 100% dimethyl sulfoxide; the compound was diluted into 10 concentrations at an equal ratio of 1:3 in a 384-well dilution plate.

3. 0.2 μL of the serially diluted compound was added to a 384-well cell culture plate (Corning, 3570) using an Echo 550 pipetting system, 2 replicate wells for each concentration, and the final concentration of dimethyl sulfoxide was 0.5% (v/v). The gradient concentrations of the test compound were 5000, 1666.7, 555.5, 185.18, 61.72, 20.57, 6.858, 2.286, 0.764, and 0.254 nM.

4. 2×VEGFR2 (0.02 ng/μl) was prepared using the 1× kinase buffer.

5. 5 μl of 2×VEGFR2 was added to a 384-well plate, and then centrifuged at 1000 g for 30 s, and incubated at room temperature for 10 min.

6. A mixed solution of 2× tyrosine kinase-biotinylated substrate (2 μM) and ATP (8 μM) was prepared using the 1× kinase buffer.

7. 5 μL of the mixed solution of tyrosine kinase-biotinylated substrate and adenosine triphosphate was added to start the reaction. The reaction solution was centrifuged at 1000 g for 30 s, and then sealed, and incubated at room temperature for 40 min.

8. A mixed solution of 2×Sa-XL 665 (125 μM) and a tyrosine kinase-antibody-cryptate was prepared using a homogeneous time-resolved fluorescence immunoassay buffer.

9. 10 μL of mixed solution of Sa-XL 665 and the tyrosine kinase-antibody-cryptate was added to each well, and then centrifuged at 1000 g for 30 s, and incubated at room temperature for 1 h.

10. The plate was read at 615 nm and 665 nm on an Envision 2104 microplate reader and the ratio was calculated (665/615 nm).

11. The inhibition rate was calculated as follows:

$$\text{inhibition rate} = \left[1 - \frac{R1 - R2}{R0 - R2}\right] \times 100\%$$

wherein

R0 refers to the average ratio of the microplate reader plate of the vehicle blank group R1 refers to the ratio of the test compound on the microplate reader plate.

R2 refers to the average ratio on the microplate reader plate in the case of 100% inhibitory activity against RET.

12. $IC_{50}$ was calculated with software GraphPad 6.0 by fitting inhibition values and logarithms of compound concentrations to a nonlinear regression (dose response–variable slope).

(c) In Vitro Screening Experiment—CellTiter-Glo Luminescence Assay for Testing the Inhibitory Activity of Compounds Against Ba/F3-KIF5B-RET Cell Experimental Procedure:

1. The mammalian cell expression vector containing human KIF5B-RET cDNA was introduced into Ba/F3 cells using the Neon® transfection system method, and the surviving clones screened by puromycin were subjected to cell growth inhibitory function experiments and Western blotting to verify cell lines with stable and high expression of RET.

2. Cells were cultured in RPMI 1640 medium containing 10% fetal bovine serum, 1% penicillin-streptomycin, and 2 μg/mL puromycin, and then placed in a 37° C., 5% carbon dioxide cell incubator.

3. The test compound (5 mM stock) was diluted 2.5 folds to 2 mM with 100% dimethyl sulfoxide; and the compound was diluted into 10 concentrations at an equal ratio of 1:3 in a 384-well dilution plate.

4. 0.2 μL of the serially diluted compound was added to a 384-well cell culture plate (Corning, 3570) using an Echo 550 pipetting system, 2 replicate wells for each concentration, and the final concentration of dimethyl sulfoxide was 0.5% (v/v). The gradient concentrations of the test compound were 5000, 1666.7, 555.5, 185.18, 61.72, 20.57, 6.858, 2.286, 0.764, 0.254 nM.

5. 40 μL of Ba/F3-KIF5B-RET cell suspension containing 800 cells was added to each well, and incubated for 72 h in a 5% $CO_2$ cell incubator.

6. 20 μL of Cell Titer-Glo reagent was added to each well of the cell culture plate, and the culture system was then shaken and mixed thoroughly for 2 min to lyse the cells, the cells were then incubated at room temperature for 30 min, and the fluorescence signal values were then read with an Envision 2104 microplate reader.

7. By fitting the data with XLFit 5.0 based on the parameters formula, the $IC_{50}$ value was calculated as:

$$Y=\text{Bottom}+(\text{Top}-\text{Bottom})/(1+10\hat{}((\text{Log }IC_{50}-X)*\text{HillSlope})).$$

The activity of the compounds is summarized in Table 1 below.

TABLE 1

| Compound | RET kinase activity (nM) | Cell activity (nM) | VEGFR2 kinase activity (nM) |
|---|---|---|---|
| Cabozantinib | 22.51 | — | 12.26 |
| Vandetinib | 7.67 | — | 69.18 |
| 1 | 0.34 | 13.87 | 7.37 |
| 2 | 0.46 | 10.66 | 3.51 |
| 3 | 0.19 | 17.99 | 1.078 |
| 4 | 0.18 | 12.01 | 0.31 |
| 5 | 6.3 | 85.1 | 44.72 |
| 6 | 1.2 | 50.53 | 11.79 |
| 7 | 7.14 | 203.4 | 72.09 |
| 8 | 9.4 | 68.5 | 170.5 |
| 9 | 19.6 | 145.4 | 116 |
| 10 | 2.08 | 7.3 | 90.80 |
| 11 | 12.54 | 613.1 | 110.2 |
| 12 | 12.83 | 75.5 | 106.7 |
| 13 | 5.17 | 50.78 | 136.2 |
| 14 | 16.58 | 219.9 | 346.8 |
| 15 | 0.58 | 10.37 | 2.95 |
| 16 | 1.63 | 35.47 | 15.57 |
| 17 | 18.41 | 184 | 1208 |
| 18 | 0.40 | 40.01 | 135.1 |
| 19 | 0.42 | 40.97 | 41.14 |
| 20 | 0.25 | 13.46 | 10.06 |
| 21 | 1.17 | 22.39 | >5000 |
| 22 | 0.40 | 44.2 | 41.88 |
| 23 | 0.82 | 18.08 | 74.94 |
| 24 | 0.99 | 5.85 | 64.64 |
| 25 | 0.54 | 14.68 | 61.06 |
| 26 | 0.245 | 7.40 | 32.98 |
| 27 | 1.33 | 43.77 | 21.88 |
| 28 | 2.25 | 177 | 1194 |
| 29 | 0.36 | 0.75 | 3.285 |
| 30 | 0.47 | 15.05 | 175.1 |
| 31 | 269.4 | — | >5000 |
| 32 | 4.23 | 223.6 | >5000 |
| 33 | 3.04 | 413.1 | >5000 |
| 34 | 1.55 | 119 | 128.2 |
| 35 | 6.94 | 395.6 | 818.6 |
| 36 | 2.76 | 19.91 | 46.98 |
| 37 | — | 18.57 | 270.4 |
| 38 | 0.56 | 5.142 | 7.39 |
| 39 | 1.93 | 181.7 | >5000 |
| 40 | 0.83 | — | 48.28 |
| 41 | 0.34 | — | 49.74 |
| 42 | 17.97 | — | 199.4 |
| 43 | 2.05 | 34.95 | 245.4 |
| 44 | 0.26 | 18.62 | 17.99 |
| 45 | — | 39.33 | 1976 |
| 46 | 0.73 | 13.63 | 80.52 |
| 47 | 5.45 | 236.4 | >5000 |
| 48 | 4.32 | 141.6 | 5436 |
| 49 | 1.25 | 30.66 | >5000 |
| 50 | 1.67 | 104.1 | 155.8 |

TABLE 1-continued

| Compound | RET kinase activity (nM) | Cell activity (nM) | VEGFR2 kinase activity (nM) |
|---|---|---|---|
| 51 | 0.47 | 5.024 | 4.139 |
| 52 | 0.29 | — | 5.62 |
| 53 | 5.52 | 431.8 | 293.4 |
| 54 | 0.30 | — | 21.14 |
| 55 | 3.79 | 379.7 | >5000 |
| 56 | 0.68 | 13.87 | 30.17 |
| 57 | 1.30 | 40.72 | 59.18 |
| 58 | 0.50 | 42.77 | 26.52 |
| 59 | 3.49 | — | 64.27 |
| 60 | 0.98 | 11.62 | 43.95 |
| 61 | 0.48 | 1.53 | 25.49 |
| 62 | 1.85 | 1030 | 175.5 |
| 63 | 4.56 | — | 361.3 |
| 64 | >500 | 1121 | 2477 |
| 65 | 2.66 | — | 779.8 |
| 66 | 4.35 | — | 240.7 |

Note:
'—' means no test.

From the results, it can be seen that: compared with the existing known compounds (Cabozantinib and Vandetinib), the compounds designed in the disclosure have good RET kinase activity. Meanwhile, the compounds also have good selectivity for VEGFR2 kinase, and the selectivity of some compounds can reach more than 1000 times. In addition, the compounds have good activities against RET kinase-sensitive cells.

All documents mentioned herein are incorporated by reference in this application as if each document was individually incorporated by reference. In addition, it should be understood that after reading the above teaching content of this disclosure, those skilled in the art can make various changes or modifications to this disclosure, and these equivalent forms also fall within the scope defined by the appended claims of this application.

The invention claimed is:

1. A compound of formula (I) or a pharmaceutically acceptable salt, hydrate, solvate, stereoisomer, isotopic compound or prodrug thereof, (I)

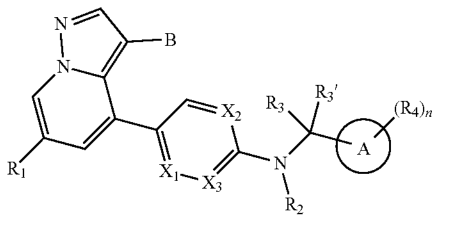

wherein $R_1$ is selected from a group consisting of halogen, nitro, cyano, C1-C6 alkyl, C3-C8 cycloalkyl, 3- to 8-membered heterocyclyl, C1-C6 heteroalkyl, C2-C6 alkenyl, C2-C6 alkynyl, C6-C14 aryl, 5- to 14-membered heteroaryl, —$OR_5$, —O(C1-C6 alkylene)$R_5$, —$SR_5$, —N($R_5$)($R_6$), —S(O)$_2R_5$, —S(O)$R_5$, —C(O)$R_5$, —OC(O)$R_5$, —C(O)O$R_5$, —OC(O)O—(C1-C6 alkylene)-C(O)$R_5$, —C(O)—N($R_5$)($R_6$), —N($R_5$)—C(O)$R_6$, —N($R_5$)—C(O)O$R_6$, —N($R_5$)—C(O)N($R_5$)($R_6$), —(C1-C6 alkylene)-N($R_5$)—C(O)$R_6$, —N($R_5$)S(O)$_2R_6$, and —P(O)($R_5$)($R_6$);

wherein the heteroalkyl contains one or more carbon atoms on an alkyl carbon chain that is replaced substituted by a divalent linking group selected from a group consisting of —O—, —S—, —NH— and —C(O)—;

B is independently selected from a group consisting of H, halogen, cyano, $CHF_2$, $CF_3$, —C(O)$OR_5$, C1-C6 alkyl, and C3-C8 cycloalkyl;

$X_1$, $X_2$ and $X_3$ are each independently CR or N; wherein each R is independently selected from a group consisting of H, substituted or unsubstituted C1-C6 alkyl, halogen, and cyano, wherein the term "substituted" means "substituted with one or more groups independently selected from a group consisting of halogen, cyano, hydroxyl, and amino; and 0, 1, 2 or 3 of $X_1$, $X_2$ and $X_3$ are N";

$R_2$ is independently selected from a group consisting of H, C1-C6 alkyl, C3-C8 cycloalkyl, C1-C6 heteroalkyl, 3- to 8-membered cycloheteroalkyl; wherein the alkyl, cycloalkyl, heteroalkyl, or cycloheteroalkyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

$R_3$ and $R_3$' are each independently selected from a group consisting of H, halogen, cyano, hydroxyl, mercapto, amino, $CHF_2$, $CF_3$, C1-C6 alkyl, C1-C6 alkoxy, C3-C8 cycloalkyl, C1-C6 heteroalkyl, and 3- to 8-membered cycloheteroalkyl; wherein the alkyl, alkoxy, cycloalkyl, heteroalkyl, or cycloheteroalkyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

alternatively, $R_3$ and $R_3$' together with the C atom to which they are attached form C3-C8 cycloalkyl, 3- to 8-membered heterocyclyl, or carbonyl; wherein the cycloalkyl or heterocyclyl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

A is independently selected from a group consisting of C3-C8 cycloalkyl, 3- to 8-membered heterocyclyl, C6-C14 aryl and 5- to 14-membered heteroaryl;

each $R_4$ is independently selected from a group consisting of H, halogen, nitro, cyano, hydroxyl, carboxyl, mercapto, C1-C6 alkyl, C3-C8 cycloalkyl, 3- to 8-membered heterocyclyl, C1-C6 heteroalkyl, C2-C6 alkenyl, C2-C6 alkynyl, C6-C14 aryl, 5- to 14-membered heteroaryl, —$OR_5$, —$SR_5$, —N($R_5$)($R_6$), —S(O)$_2R_5$, —S(O)$R_5$, —C(O)$R_5$, —OC(O)$R_5$, —C(O)$OR_5$, —OC(O)O—(C1-C6 alkylene)-C(O)$R_5$, —C(O)—N($R_5$)($R_6$), —N($R_5$)—C(O)$R_6$, —N($R_5$)—C(O)$OR_6$, —N($R_5$)—C(O)N($R_5$)($R_6$), —(C1-C6 alkylene)-N($R_5$)—C(O)$R_6$, —N($R_5$)S(O)$_2R_6$, and —P(O)($R_5$)($R_6$); wherein the alkyl, cycloalkyl, heteroalkyl, heterocyclyl, alkenyl, alkynyl, aryl, or heteroaryl is unsubstituted or substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl;

$R_5$ and $R_6$ are each independently selected from a group consisting of substituted or unsubstituted groups: H, C1-C6 alkyl, C3-C8 cycloalkyl, 3- to 8-membered monoheterocyclyl, C6-C10 aryl, 5- to 10-membered heteroaryl, C5-C12 fused bicyclic group, 5- to 12-membered fused heterobicyclic group, C5-C12 spirobicyclic group and 5- to 12-membered spiro heterobicyclic group; wherein the term "substituted" means "substituted with one or more groups independently selected from a group consisting of C1-C6 alkyl, C1-C6 alkoxy, C3-C8 cycloalkyl, C3-C8 cycloalkoxy, C1-C6 heteroalkyl, 3- to 8-membered cycloheteroalkyl, $CHF_2$, $CF_3$, halogen, cyano, carboxyl, carbonyl, hydroxyl, mercapto, amino, methyl ester group, amido, methyl sulfone group, sulfonamido, and dimethylphosphoryl";

alternatively, $R_5$ and $R_6$ together with the N or P atom to which they are attached form 3- to 8-membered heterocyclyl;

unless otherwise specified, the alkyl, alkylene, cycloalkyl, heteroalkyl, alkenyl, alkynyl, aryl, heteroaryl, or heterocyclyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl;

n is 0, 1, 2 or 3.

2. The compound of formula I or the pharmaceutically acceptable salt, hydrate, solvate, stereoisomer, isotopic compound or prodrug thereof according to claim 1, wherein $R_2$ is selected from a group consisting of H, C1-C6 alkyl, and C3-C8 cycloalkyl; wherein the alkyl or cycloalkyl is unsubstituted or substituted with one or more groups independently selected from a group consisting of C1-C6 alkyl, $CHF_2$, $CF_3$, halogen, cyano, hydroxyl, carboxyl, methyl ester group, amido, sulfonamido, carbonyl, mercapto, amino and dimethylphosphoryl.

3. The compound of formula (I) or the pharmaceutically acceptable salt, hydrate, solvate, stereoisomer, isotopic compound or prodrug thereof according to claim 1, wherein $R_3$ and $R_3$' are each independently selected from a group consisting of H, halogen, cyano, hydroxyl, $CHF_2$, $CF_3$, C1-C6 alkyl, C1-C6 alkoxy, C3-C8 cycloalkyl, and C1-C6 heteroalkyl;

alternatively, $R_3$ and $R_3$' together with the C atom to which they are attached form C3-C8 cycloalkyl, 3- to 8-membered heterocyclyl, or carbonyl;

wherein the alkyl, alkoxy, cycloalkyl, heteroalkyl, or heterocyclyl is unsubstituted or substituted with one or more groups independently selected from a group consisting of C1-C6 alkyl, $CHF_2$, $CF_3$, halogen, cyano, hydroxyl, carboxyl, methyl ester group, amido, sulfonamido, carbonyl, mercapto, amino and dimethylphosphoryl.

4. The compound of formula (I) or the pharmaceutically acceptable salt, hydrate, solvate, stereoisomer, isotopic compound or prodrug thereof according to claim 1, wherein $R_1$ is independently selected from a group consisting of —$OR_5$, —OC(O)$R_5$, —N($R_5$)($R_6$), —C(O)—N($R_5$)($R_6$), —N($R_5$)—C(O)$R_6$, —N($R_5$)—C(O)O$R_6$, and —N($R_5$)S(O)$_2$ $R_6$; wherein $R_5$ and $R_6$ are each independently selected from a group consisting of substituted or unsubstituted groups: H, C1-C6 alkyl, C3-C8 cycloalkyl, 3- to 8-membered monoheterocyclyl, C6-C10 aryl, and 5- to 10-membered heteroaryl;

wherein the term "substituted" means "substituted with one or more groups independently selected from a group consisting of C1-C6 alkyl, cyano, halogen, hydroxyl, C3-C8 cycloalkyl, and 3- to 8-membered cycloheteroalkyl".

5. The compound of formula (I) or the pharmaceutically acceptable salt, hydrate, solvate, stereoisomer, isotopic compound or prodrug thereof according to claim 1, wherein A is independently selected from a group consisting of C6-C10 aryl or 5- to 10-membered heteroaryl, wherein the aryl or heteroaryl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, mercapto, amino and dimethylphosphoryl.

6. The compound of formula (I) or the pharmaceutically acceptable salt, hydrate, solvate, stereoisomer, isotopic compound or prodrug thereof according to claim 1, wherein $R_4$ is independently selected from a group consisting of H, C1-C6 alkyl, C3-C8 cycloalkyl, C1-C6 heteroalkyl, C6-C10 aryl, 5- to 10-membered heteroaryl, 3- to 8-membered heterocyclyl, —O$R_5$, —OC(O)$R_5$, —N($R_5$)($R_6$), —C(O)—N($R_5$)($R_6$), —N($R_5$)—C(O)$R_6$, —N($R_5$)—C(O)O$R_6$, and —N($R_5$)S(O)$_2R_6$;

wherein $R_5$ and $R_6$ are each independently selected from a group consisting of substituted or unsubstituted groups of: H, C1-C6 alkyl, C3-C8 cycloalkyl, 3- to 8-membered monoheterocyclyl, C6-C10 aryl, and 5- to 10-membered heteroaryl, wherein the term "substituted" means "substituted with one or more groups selected from a group consisting of C1-C6 alkyl, cyano, halogen, hydroxyl, C3-C8 cycloalkyl, and 3- to 8-membered cycloheteroalkyl";

unless otherwise specified, the alkyl, cycloalkyl, heteroalkyl, heterocyclyl, aryl, or heteroaryl is unsubstituted or substituted with one or more groups independently selected from a group consisting of C1-C6 alkyl, halogen, cyano, hydroxyl, carboxyl, ester group, amido, sulfonamido, carbonyl, mercapto, amino and dimethylphosphoryl.

7. The compound or the pharmaceutically acceptable salt, hydrate, solvate, stereoisomer, isotopic compound or prodrug thereof according to claim 1, wherein the compound has a structure of formula (II):

(II)

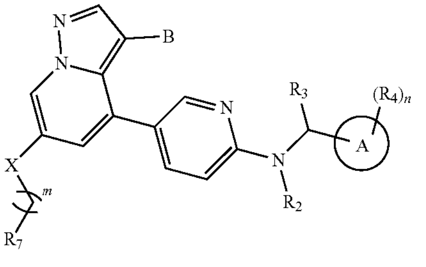

wherein

X is selected from a group consisting of O, S, and $NR_8$;

m is 0;

$R_7$ and $R_8$ are each a substituted or unsubstituted group selected from a group consisting of H, C1-C6 alkyl, C3-C8 cycloalkyl, 3- to 8-membered monoheterocyclyl, C6-C10 aryl, 5- to 10-membered heteroaryl, C5-C12 fused bicyclic group, 5- to 12-membered fused heterobicyclic group, C5-C12 spirobicyclic group, and 5- to 12-membered spiro heterobicyclic group;

wherein the term "substituted" means "substituted with one or more groups independently selected from a group consisting of C1-C6 alkyl, cyano, halogen, hydroxyl, C3-C8 cycloalkyl, and 3- to 8-membered cycloheteroalkyl";

B, $R_2$, $R_3$, A, $R_4$, and n are defined as in claim 1.

8. The compound or the pharmaceutically acceptable salt, hydrate, solvate, stereoisomer, isotopic compound or prodrug thereof according to claim 1, wherein the compound has a structure of formula (III):

(III)

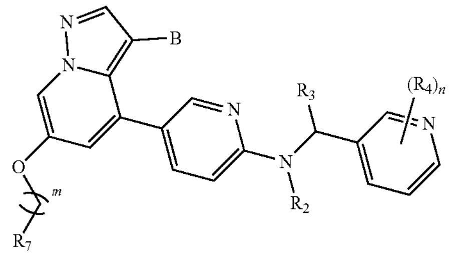

wherein B, $R_2$, $R_3$, $R_4$, $R_7$, m, and n are defined as in claim 7.

9. The compound or the pharmaceutically acceptable salt, hydrate, solvate, stereoisomer, isotopic compound or prodrug thereof according to claim 1, wherein the compound has a structure of formula (IV):

(IV)

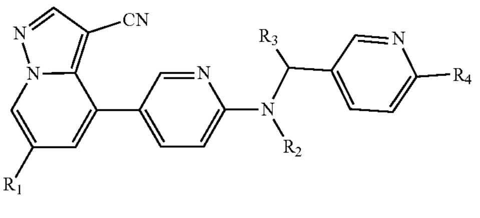

wherein $R_1$ is selected from a group consisting of —O$R_5$, —N($R_5$)($R_6$), C3-C8 cycloalkyl, 3- to 8-membered heterocyclyl, C2-C6 alkenyl, C2-C6 alkynyl, C6-C14 aryl, and 5- to 14-membered heteroaryl;

$R_2$ is selected from a group consisting of H and C1-C6 alkyl;

$R_3$ is selected from a group consisting of H, halogen, cyano, hydroxyl, $CHF_2$, $CF_3$, C1-C6 alkyl, and C1-C6 alkoxy;

$R_4$ is independently selected from a group consisting of C3-C8 cycloalkyl, C6-C10 aryl, 5- to 10-membered heteroaryl, 3- to 8-membered heterocyclyl, —O$R_5$, —OC(O)$R_5$, —N($R_5$)($R_6$), —C(O)—N($R_5$)($R_6$), —N($R_5$)—C(O)$R_6$, —N($R_5$)—C(O)O$R_6$, and —N($R_5$)S(O)$_2R_6$;

wherein $R_5$ and $R_6$ are each independently selected from a group consisting of substituted or unsubstituted groups of: H, C1-C6 alkyl, C3-C8 cycloalkyl, 3- to 8-membered monoheterocyclyl, C6-C10 aryl, and 5- to 10-membered heteroaryl, wherein the term "substituted" means "substituted with one or more groups independently selected from a group consisting of C1-C6 alkyl, cyano, halogen, hydroxyl, C3-C8 cycloalkyl, and 3- to 8-membered cycloheteroalkyl";

and unless otherwise specified, the alkyl, alkenyl, alkynyl, cycloalkyl, aryl, heteroaryl, or heterocyclyl is unsubstituted or substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto, amino and dimethylphosphoryl.

10. The prodrug or the pharmaceutically acceptable salt of the compound according to claim 1, having a structure of formula (V):

(V)

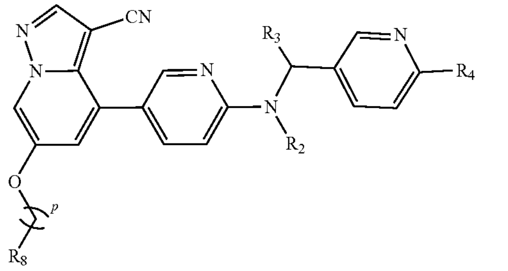

wherein $R_8$ is selected from a group consisting of

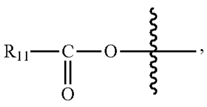, 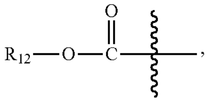, 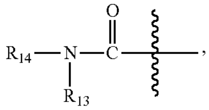, and 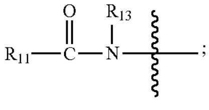;

$R_{11}$ and $R_{12}$ are each independently selected from substituted or unsubstituted C1-C6 alkyl, substituted or unsubstituted C6-C10 aryl, substituted or unsubstituted 5- to 10-membered heteroaryl;

$R_{13}$ and $R_{14}$ are each independently selected from substituted or unsubstituted C1-C6 alkyl, substituted or unsubstituted C6-C10 aryl, substituted or unsubstituted 5- to 10-membered heteroaryl;

p is 1, 2 or 3;

wherein the term "substituted" means "substituted with one or more groups independently selected from a group consisting of C1-C6 alkyl, C1-C6 alkoxy, C3-C8 cycloalkyl, 3- to 8-membered heterocyclyl, C1-C6 heteroalkyl, C2-C6 alkenyl, C2-C6 alkynyl, nitro, halogen, cyano, hydroxyl, carboxyl, ester group, amido, sulfonamido, carbonyl, mercapto and amino";

$R_2$, $R_3$ and $R_4$ are defined as in claim 1.

11. A compound or the pharmaceutically acceptable salt, hydrate, solvate, stereoisomer, isotopic compound or prodrug thereof, wherein the compound is selected from:

1

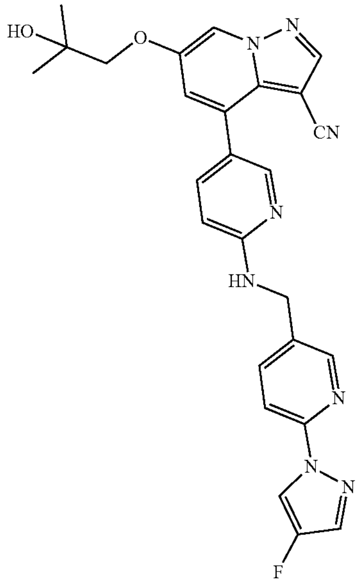

2

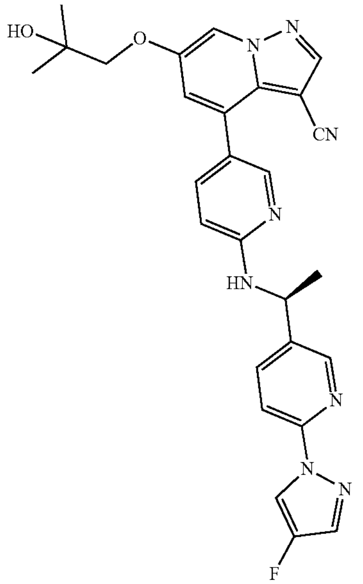

-continued
3
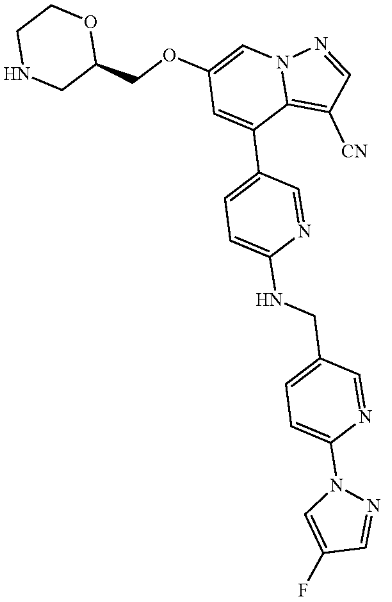
4
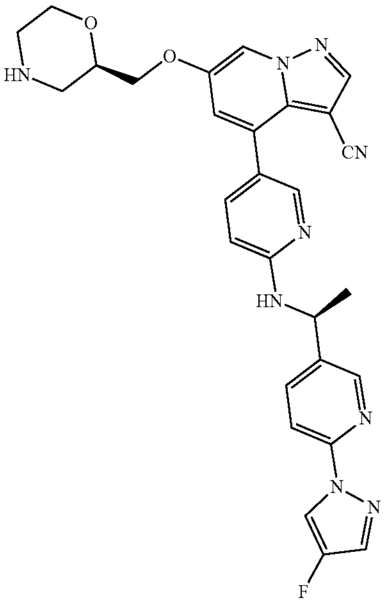
-continued
5
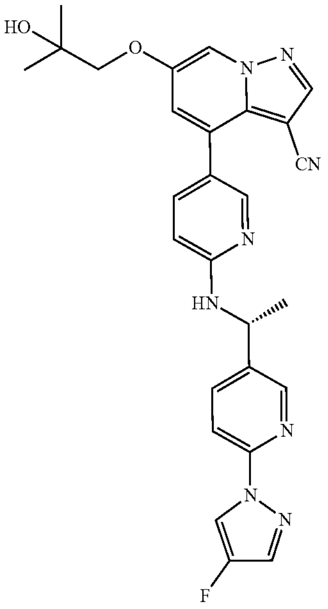
6
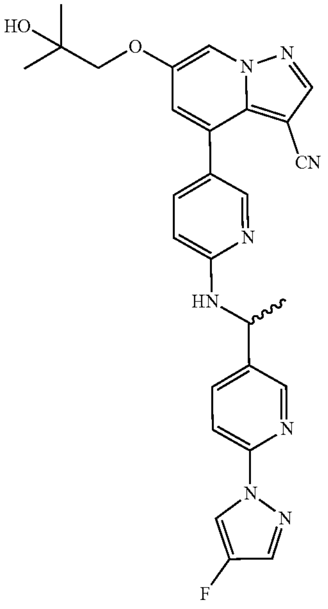

-continued
7
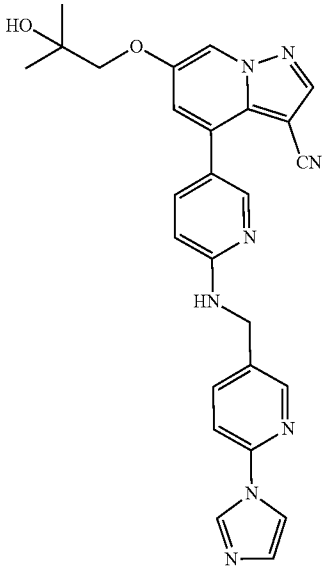
8
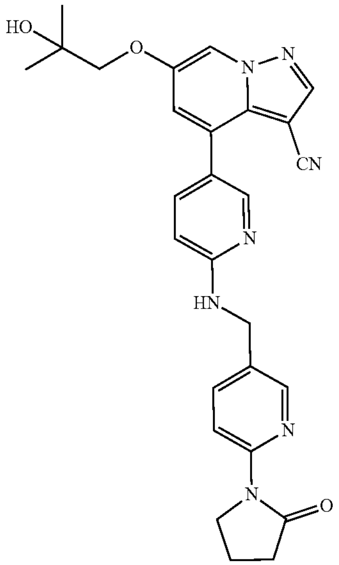
-continued
9
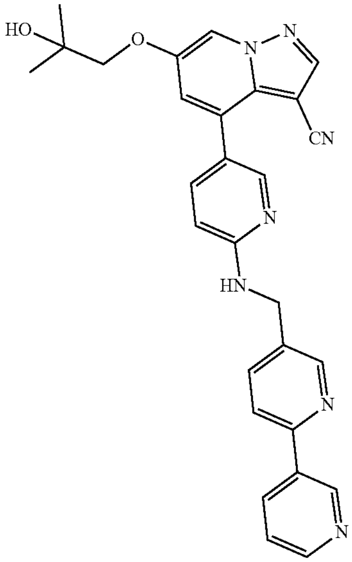
10
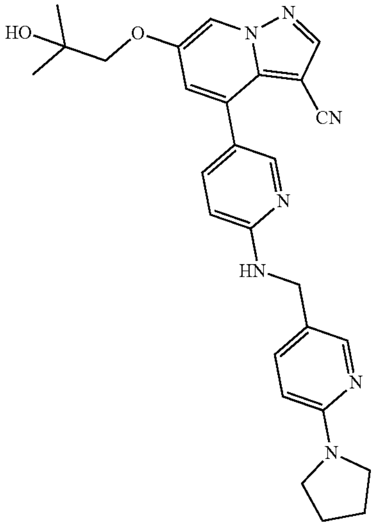
11
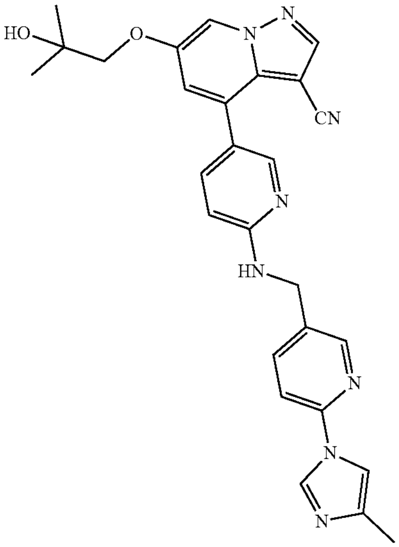

-continued
12
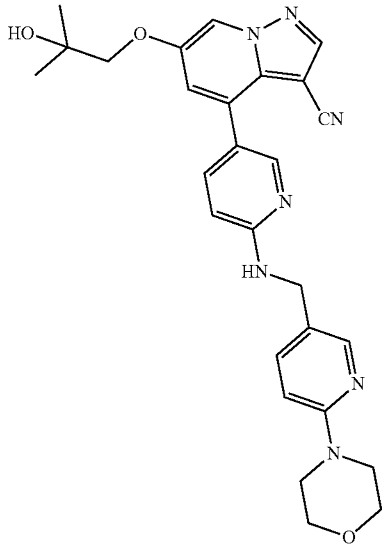
13
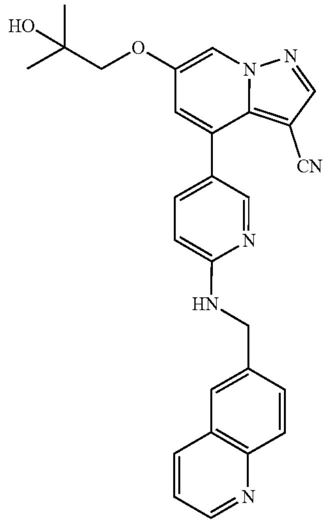
14
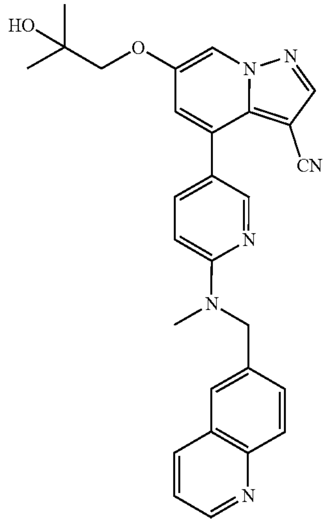
-continued
15
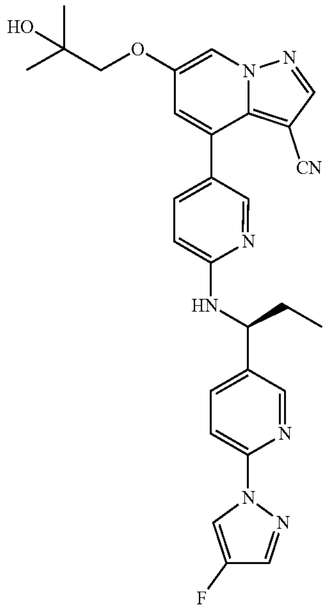
16
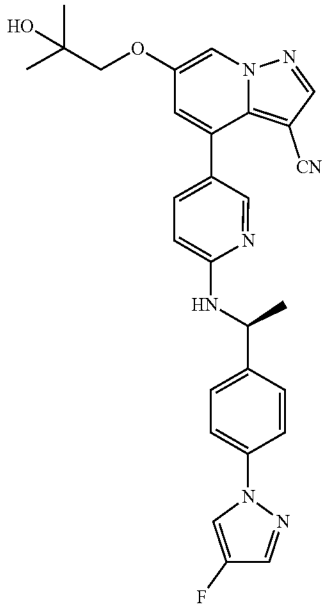

-continued
17
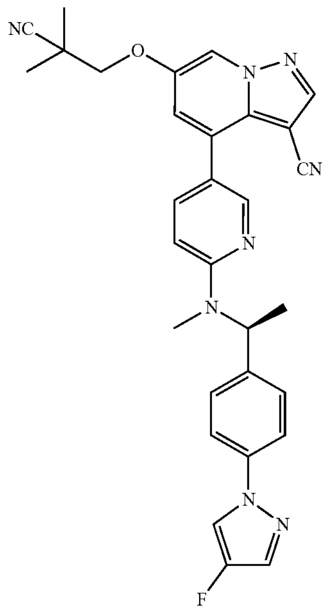
18
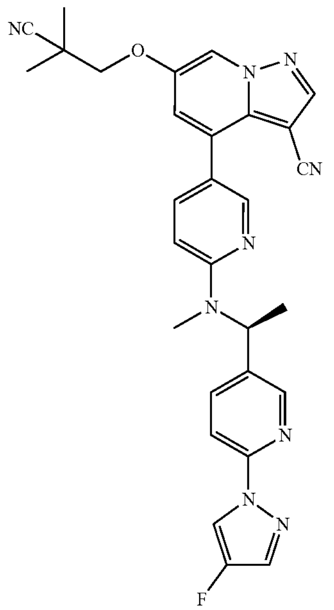
-continued
19
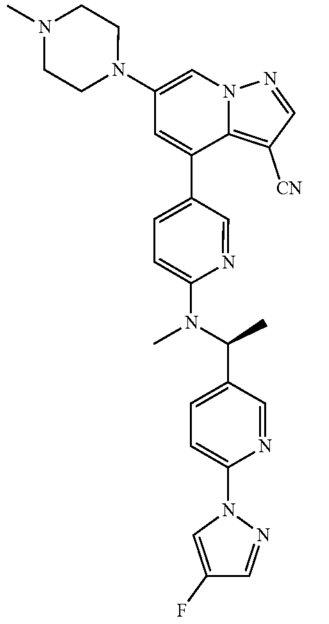
20
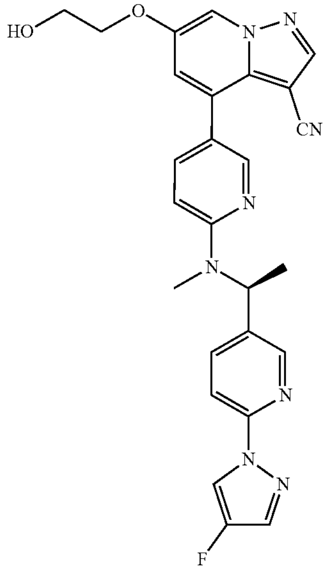

-continued
21
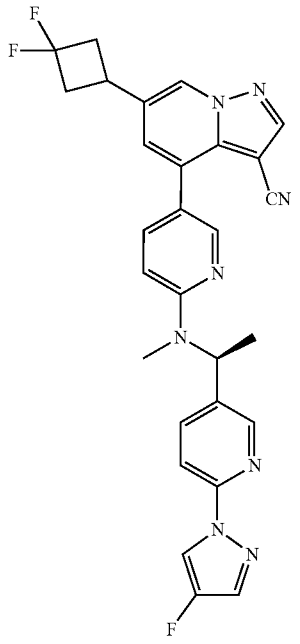
-continued
23
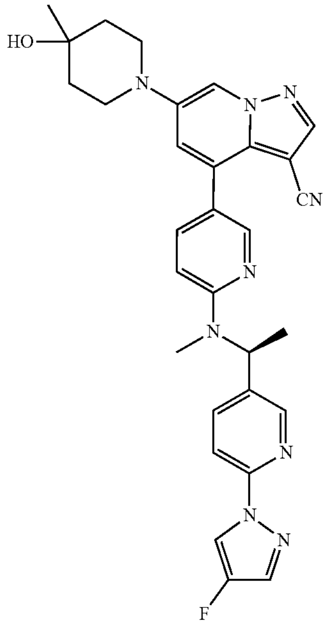
22
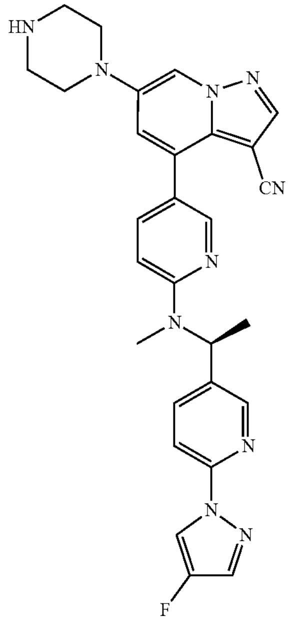
24
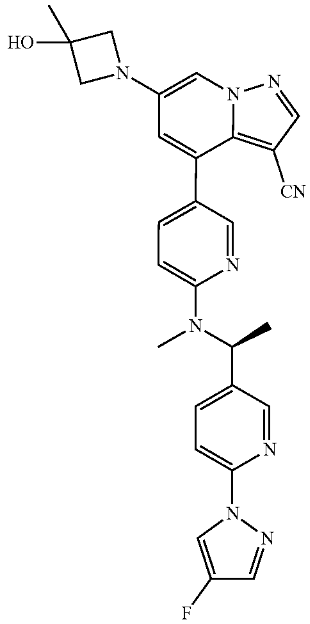

-continued
25
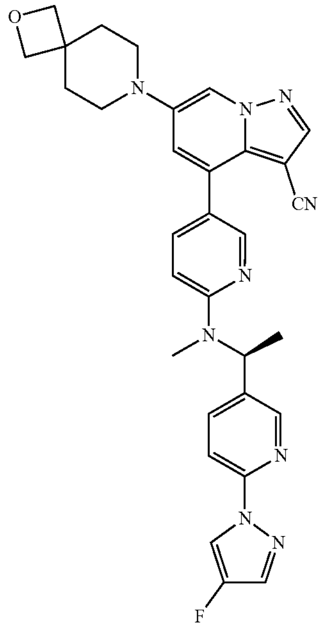
26
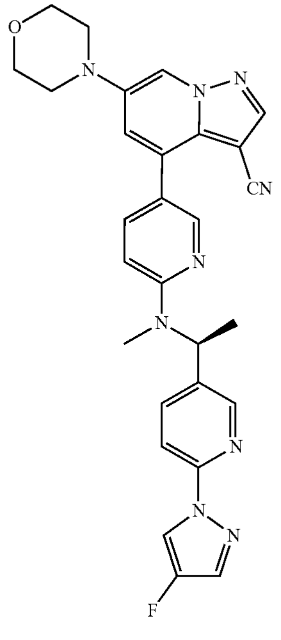
-continued
27
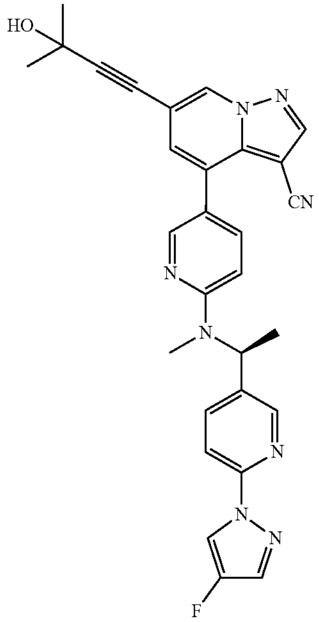
28
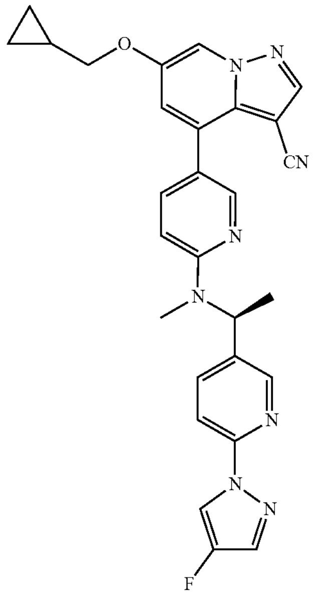

-continued
29
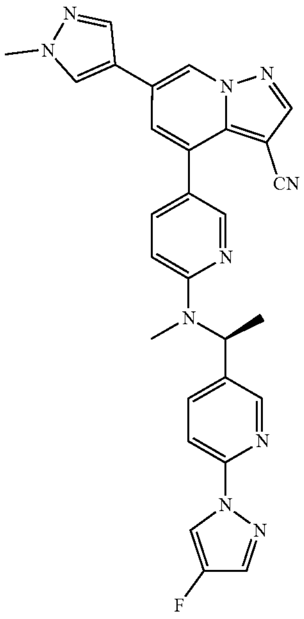
30
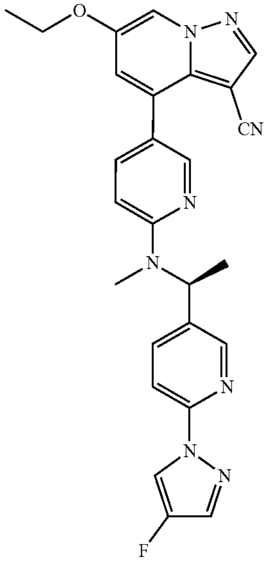
-continued
31
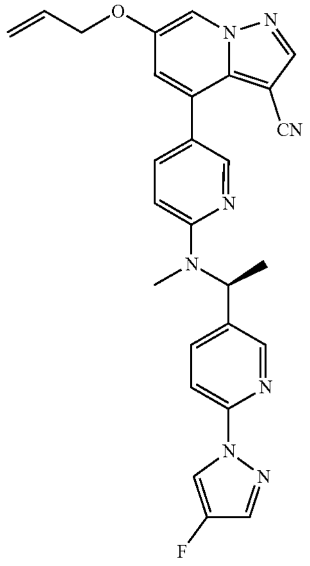
32
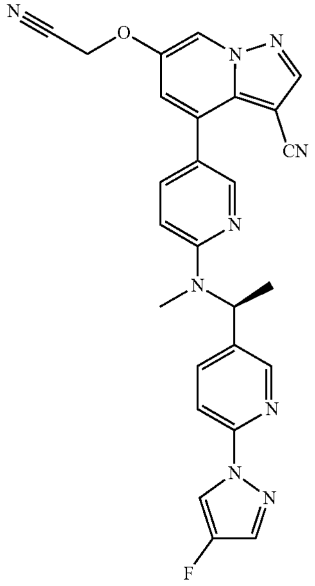

-continued
33
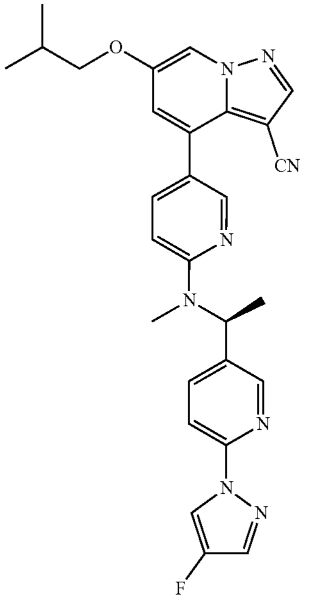
34
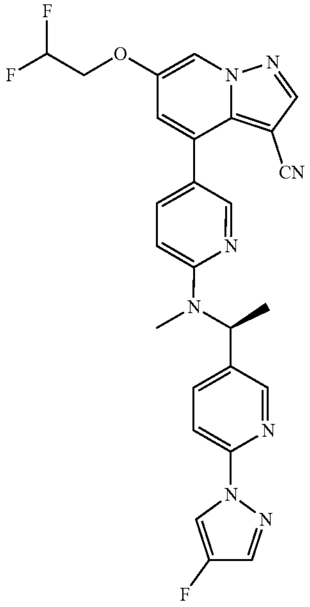
-continued
35
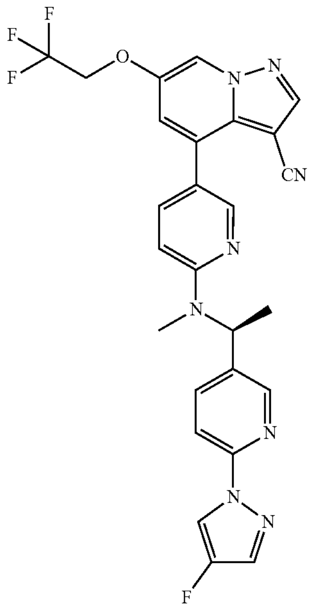
36
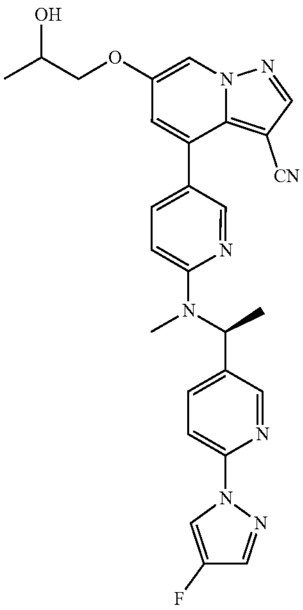

-continued
37
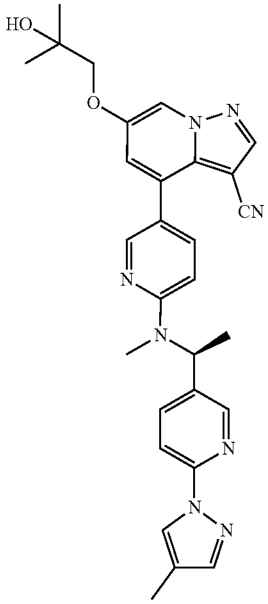
38
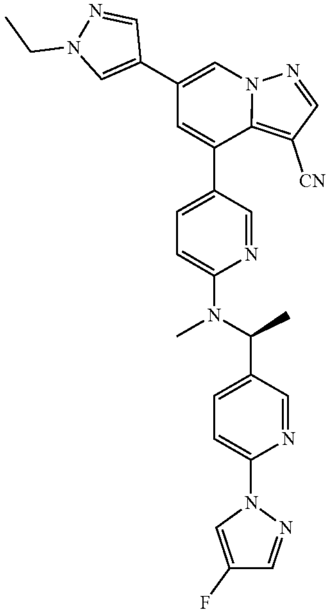
-continued
39
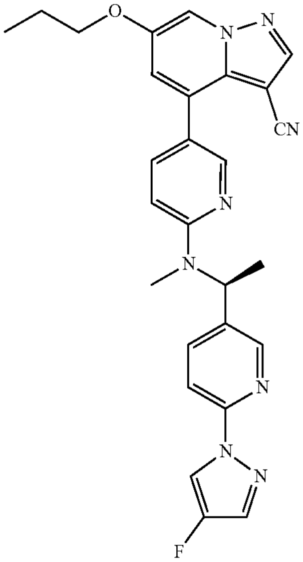
40
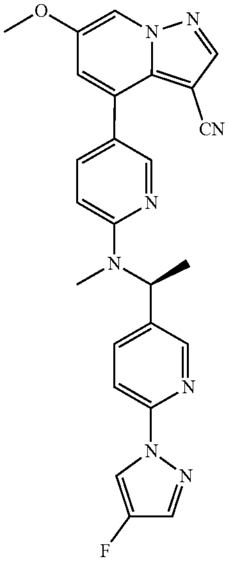

-continued
41
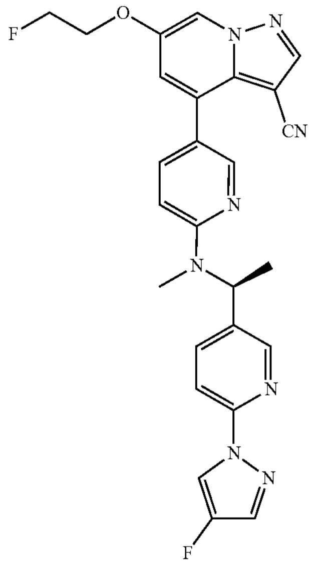
-continued
43
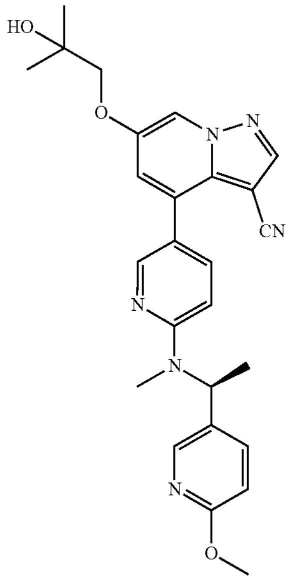
42
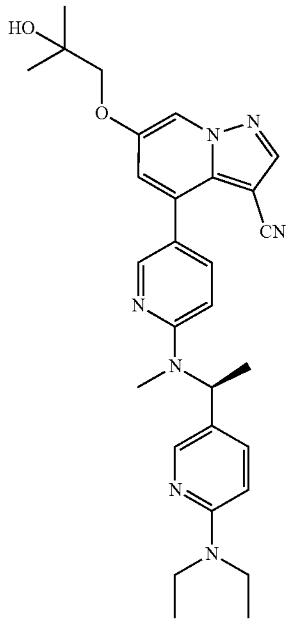
44
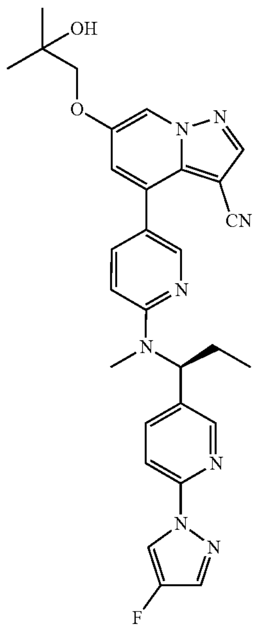

-continued
45
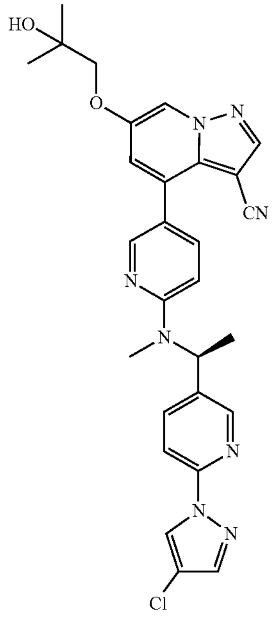
46
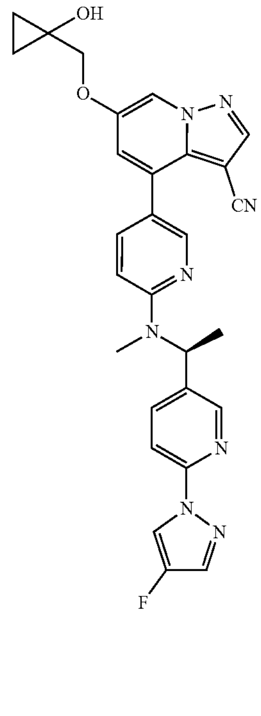
-continued
47
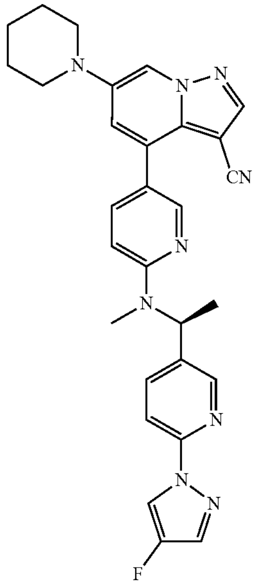
48
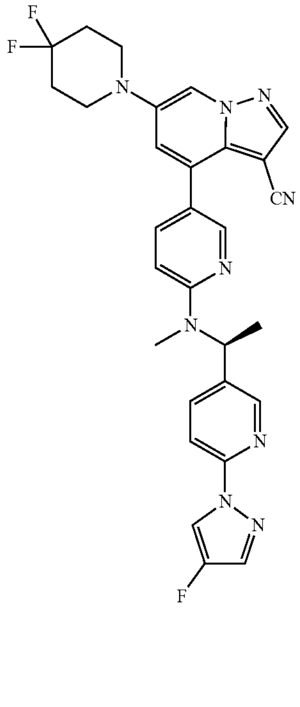

-continued
49
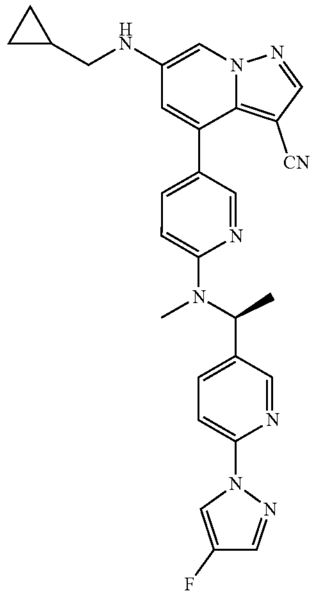
50
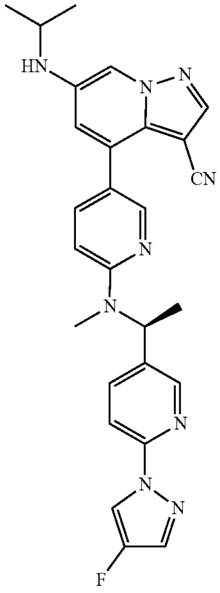
-continued
51
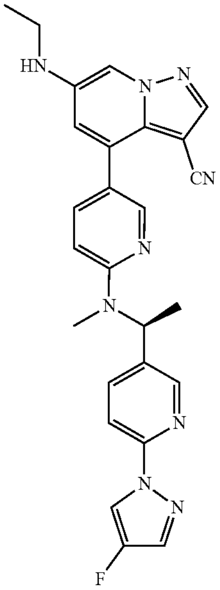
52
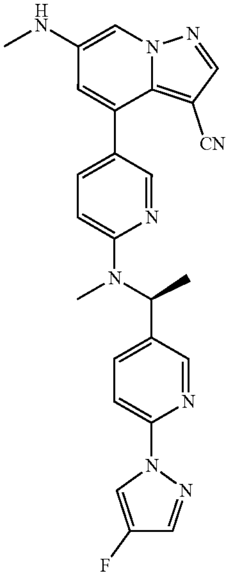

-continued
53
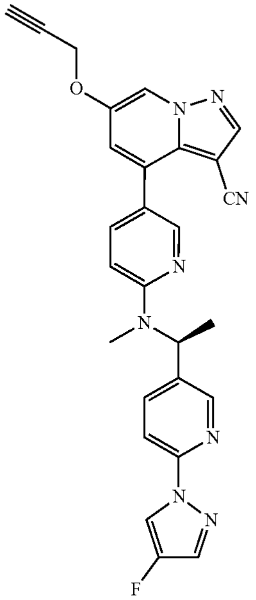
54
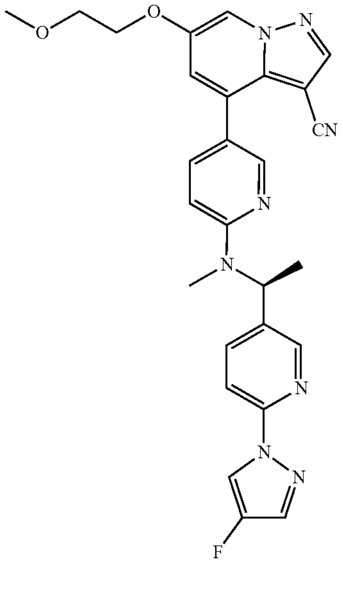
-continued
55
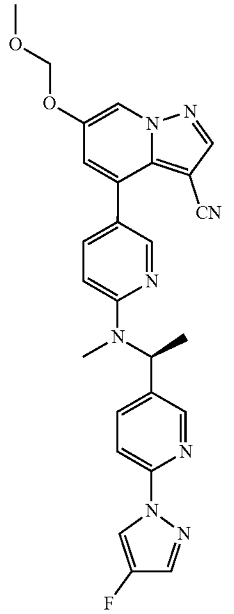
56
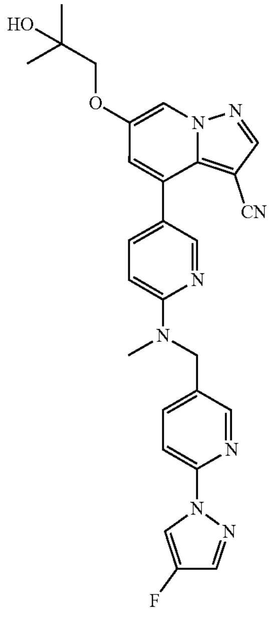

-continued
57
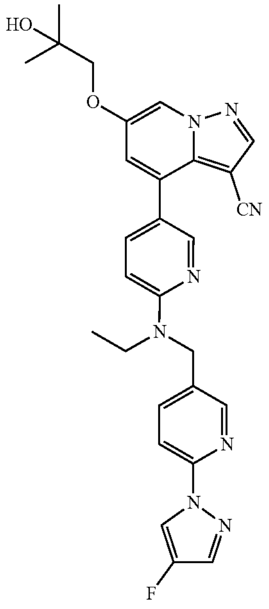
58
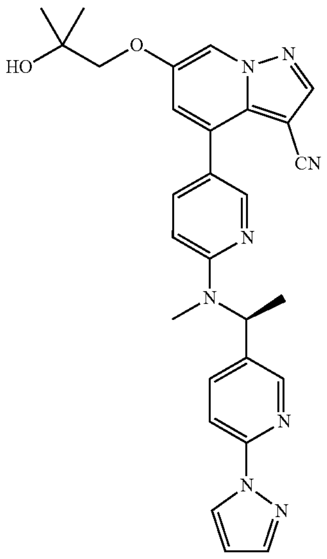
-continued
59
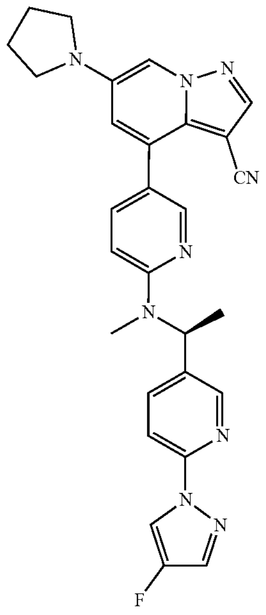
60
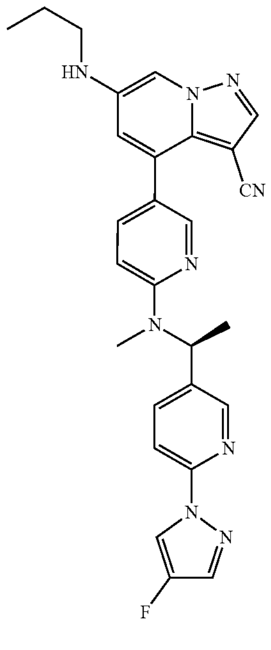

-continued
61
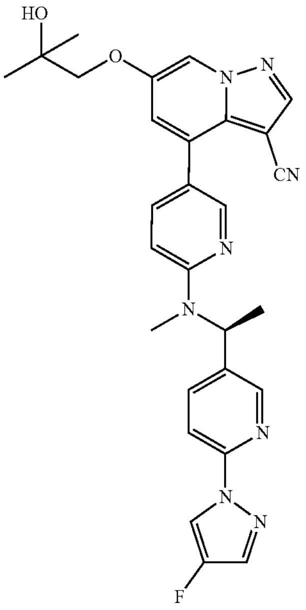
62
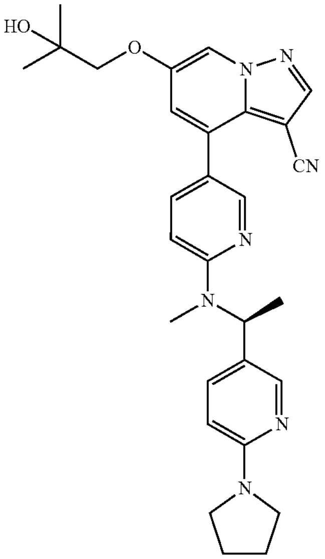
63
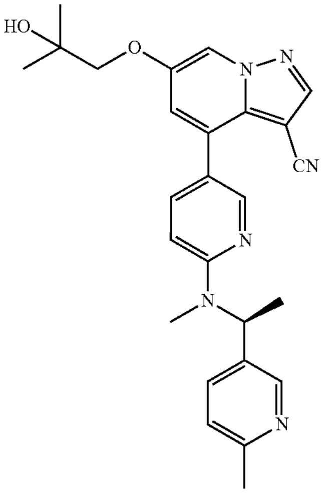
-continued
64
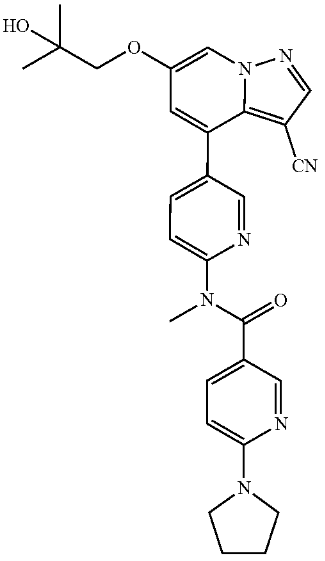
65
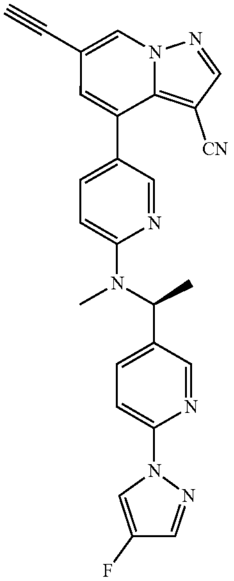

-continued

66

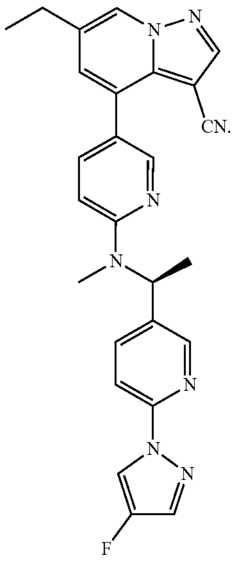

12. A pharmaceutical composition, comprising the compound or the pharmaceutically acceptable salt, hydrate, solvate, stereoisomer, isotopic compound or prodrug thereof according to claim 1 and a pharmaceutically acceptable carrier or diluent.

13. The pharmaceutical composition according to claim 12, wherein the pharmaceutical composition further comprises a second therapeutic agent for a cancer.

14. A method of treating an RET-related disease, comprising administering to a subject identified or diagnosed as having an RET-related disease a therapeutically effective dose of the compound, or the pharmaceutically acceptable salt, hydrate, solvate, stereoisomer, isotopic compound or prodrug thereof according to claim 1, or a pharmaceutical composition comprising the compound or the pharmaceutically acceptable salt, hydrate, solvate, stereoisomer, isotopic compound or prodrug thereof according to claim 1 and a pharmaceutically acceptable carrier or diluent, wherein the RET-related disease is selected from irritable bowel syndrome, lung cancer, papillary thyroid cancer, medullary thyroid cancer, differentiated thyroid cancer, recurrent thyroid cancer, refractory differentiated thyroid cancer, type 2A or 2B multiple endocrine tumor, pheochromocytoma, parathyroid hyperplasia, breast cancer, colorectal cancer, papillary renal cell carcinoma, gangliomatosis of the gastrointestinal mucosa, or cervical cancer.

15. A method for inhibiting activity of an RET kinase in a cell or a subject, the method including a step of allowing the cell to contact the compound or the pharmaceutically acceptable salt, hydrate, solvate, stereoisomer, isotopic compound or prodrug thereof according to claim 1 or a pharmaceutical composition or administering to the subject the compound or the pharmaceutically acceptable salt, hydrate, solvate, stereoisomer, isotopic compound or prodrug thereof according to claim 1 or a pharmaceutical composition, wherein the pharmaceutical composition comprising the compound or the pharmaceutically acceptable salt, hydrate, solvate, stereoisomer, isotopic compound or prodrug thereof according to claim 1 and a pharmaceutically acceptable carrier or diluent.

16. A method for preparing the compound according to claim 1, wherein the method is selected from the following Method 1, Method 2 and Method 3:

Method 1:

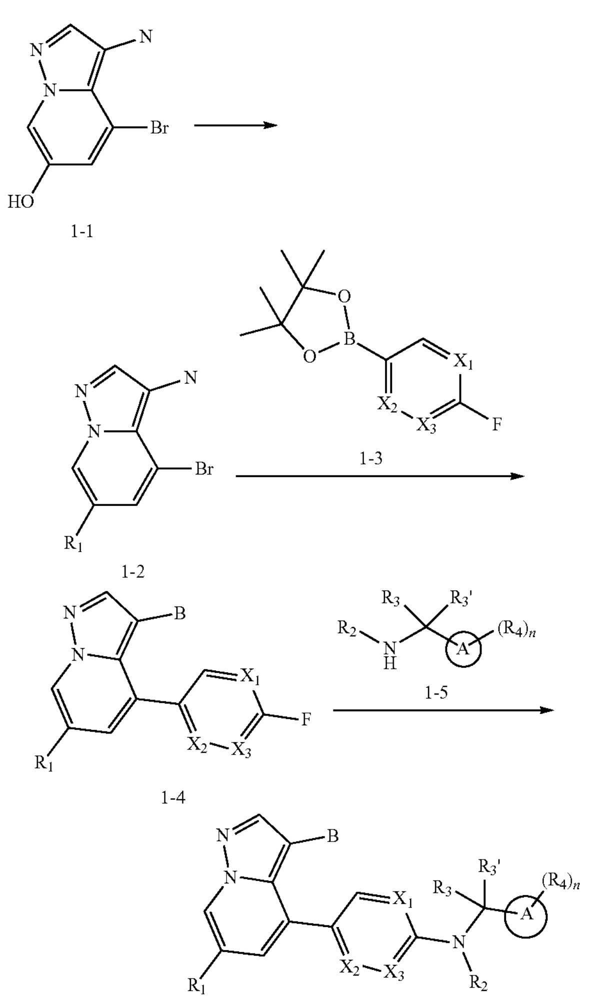

1-1

1-2

1-3

1-4

1-5

1-6

$X_1$, $X_2$, $X_3$, A, B, $R_1$, $R_2$, $R_3$, $R_3'$, n and $R_4$ are defined as in claim 1;

the method includes the following steps:

(i) causing compound 1-1 to react in an inert solvent under an alkaline condition to obtain compound 1-2;

(ii) causing compound 1-2 to have a coupling reaction with compound 1-3 under an alkaline condition in the presence of a catalyst, to obtain compound 1-4; and (iii) causing compound 1-4 to react with compound 1-5 in an inert solvent under an alkaline condition at a high temperature to obtain compound 1-6;

Method 2:

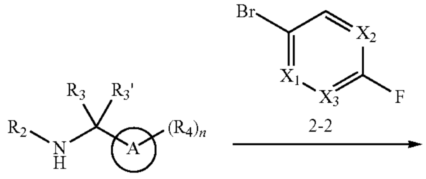

2-2

2-1

-continued

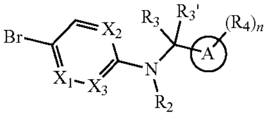

2-3

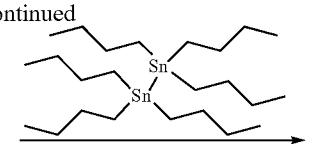

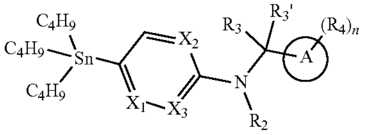

2-4

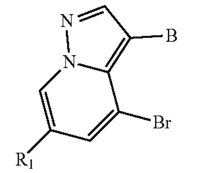

2-5

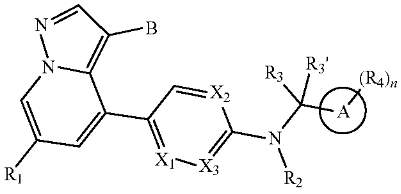

2-6

$X_1$, $X_2$, $X_3$, A, B, $R_1$, $R_2$, $R_3$, $R_3$', n and $R_4$ are defined as in claim 1;

the method includes the following steps:

(i') causing compound 2-1 to react with compound 2-2 in an inert solvent under an alkaline condition at a high temperature to obtain compound 2-3;

(ii') causing compound 2-3 to react with $Sn_2(Bu\text{-}n)_6$ in an inert solvent in the presence of a catalyst to obtain a tin reagent compound 2-4; and (iii') causing the tin reagent compound 2-4 to have a coupling reaction with compound 2-5 in an inert solvent in the presence of a catalyst to obtain compound 2-6;

Method 3:

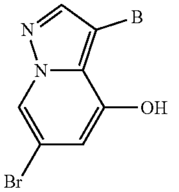

3-1

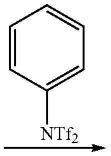

-continued

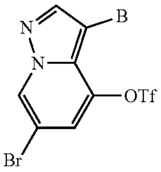

3-2

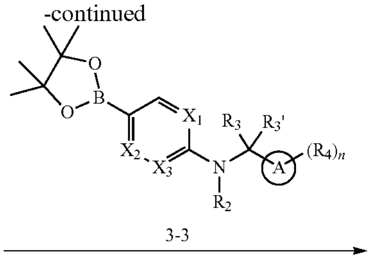

3-3

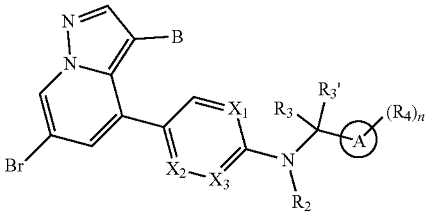

3-4

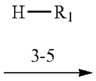

3-5

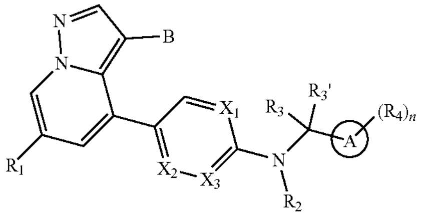

3-6

$X_1$, $X_2$, $X_3$, A, B, $R_1$, $R_2$, $R_3$, $R_3$, n and $R_4$ are defined as in claim 1;

the method includes the following steps:

(i) causing compound 3-1 to react with N-phenylbis(trifluoromethanesulfonyl)imide in an inert solvent under an alkaline condition to obtain compound 3-2;

(ii) causing the compound 3-2 to have a coupling reaction with compound 3-3 in a mixed solvent in the presence of a catalyst to obtain compound 3-4;

(ii) causing compound 3-4 to react with compound 3-5 under an alkaline condition in the presence of a catalyst to obtain compound 3-6.

* * * * *